(12) United States Patent
Yu et al.

(10) Patent No.: US 9,028,874 B2
(45) Date of Patent: May 12, 2015

(54) ANTIOXIDANT NANOSPHERE COMPRISING [1,2]-DITHIOLANE MOIETIES

(75) Inventors: John S. Yu, Los Angeles, CA (US); Bong Seop Lee, Torrance, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 841 days.

(21) Appl. No.: 12/811,197

(22) PCT Filed: Dec. 30, 2008

(86) PCT No.: PCT/US2008/088541
§ 371 (c)(1),
(2), (4) Date: Jun. 29, 2010

(87) PCT Pub. No.: WO2009/086547
PCT Pub. Date: Jul. 9, 2009

(65) Prior Publication Data
US 2010/0291222 A1    Nov. 18, 2010

Related U.S. Application Data

(60) Provisional application No. 61/018,749, filed on Jan. 3, 2008.

(51) Int. Cl.
| | | |
|---|---|---|
| A61K 9/14 | (2006.01) | |
| C07D 409/12 | (2006.01) | |
| A61K 31/497 | (2006.01) | |
| A61K 38/02 | (2006.01) | |
| C07D 339/04 | (2006.01) | |
| A61K 9/107 | (2006.01) | |
| A61K 9/51 | (2006.01) | |
| A61K 47/24 | (2006.01) | |
| A61K 9/00 | (2006.01) | |

(52) U.S. Cl.
CPC ............ *C07D 339/04* (2013.01); *A61K 9/0014* (2013.01); *A61K 9/1075* (2013.01); *A61K 9/5146* (2013.01); *A61K 47/24* (2013.01)

(58) Field of Classification Search
CPC ... A61K 47/24; A61K 9/0014; A61K 9/1075; A61K 9/5146; C07D 339/04
USPC ............ 424/489; 506/16, 9; 514/1.1, 252.13, 514/283; 544/374; 549/39
See application file for complete search history.

(56) References Cited

U.S. PATENT DOCUMENTS

| | | |
|---|---|---|
| 3,963,771 A | 6/1976 | Robson et al. |
| 5,122,526 A | 6/1992 | Wall et al. |
| 5,543,158 A | 8/1996 | Gref et al. |
| 5,962,520 A | 10/1999 | Smith et al. |
| 6,013,663 A | 1/2000 | Fujita et al. |
| 6,090,842 A | 7/2000 | Packer et al. |
| 6,117,899 A | 9/2000 | Wessel et al. |
| 6,127,394 A | 10/2000 | Pershadsingh et al. |
| 6,150,358 A | 11/2000 | Goldstein et al. |
| 6,204,288 B1 | 3/2001 | Pershadsingh et al. |
| 6,235,772 B1 | 5/2001 | Packer et al. |
| 6,288,106 B1 | 9/2001 | Pearson et al. |
| 6,353,011 B1 | 3/2002 | Pershadsingh et al. |
| 6,369,098 B1 | 4/2002 | Pershadsingh et al. |
| 6,380,405 B1 | 4/2002 | Ekwuribe et al. |
| 6,387,945 B2 | 5/2002 | Packer et al. |
| 6,572,888 B2 | 6/2003 | Byrd |
| 6,605,637 B1 | 8/2003 | Harnett et al. |
| 6,629,995 B1 | 10/2003 | Wrenn et al. |
| 6,664,287 B2 | 12/2003 | Avery et al. |
| 6,821,529 B2 | 11/2004 | Nelson |
| 6,878,374 B2 | 4/2005 | Yu et al. |
| 6,887,891 B2 | 5/2005 | Harnett et al. |
| 6,900,337 B2 * | 5/2005 | Manzer et al. ................ 548/554 |
| 6,900,338 B1 * | 5/2005 | Haj-Yehia ....................... 549/20 |
| 6,936,715 B2 | 8/2005 | Harnett et al. |
| 6,998,115 B2 | 2/2006 | Langer et al. |
| 7,048,925 B2 | 5/2006 | Van et al. |
| 7,056,901 B2 | 6/2006 | Frechet et al. |
| 7,157,444 B2 | 1/2007 | Nelson |
| 7,220,414 B2 | 5/2007 | Brocchini et al. |

(Continued)

FOREIGN PATENT DOCUMENTS

| | | |
|---|---|---|
| EP | 2125775 | 12/2009 |
| JP | 2010-520333 | 6/2010 |

(Continued)

OTHER PUBLICATIONS

Gruzman et al., Bioorganic & Medicinal Chemistry,12(2004)1183-1190.*
Gruzman et al. (Bioorganic & Medicinal Chemistry, 12(2004)1183-1190).*
International PCT Search Report and Written Opinion dated Jul. 1, 2008 for PCT/US2008/055465.
International Preliminary Report on Patentability dated Sep. 1, 2009 for PCT/US2008/055465.
European publication No. 2125775 published Dec. 2, 2009, abstract corresponds to WO/2008/106640.
International PCT Search Report and Written Opinion dated Jun. 10, 2009 for PCT/US2009/039956.
International Preliminary Report on Patentability dated Dec. 6, 2010 for PCT/US2009/039956.
International PCT Search Report and Written Opinion dated Jan. 21, 2010 for PCT/US2009/065776.
International Preliminary Report on Patentability dated May 24, 2011 for PCT/US2009/065776.

(Continued)

*Primary Examiner* — Janet Epps-Smith
*Assistant Examiner* — Courtney Brown
(74) *Attorney, Agent, or Firm* — Seth D. Levy; Nixon Peabody LLP

(57) ABSTRACT

The present invention is directed to multiple a-lipoic acid-containing hydrophobic compounds (mALAs) capable of acting as scavengers of free radicals, metals and reactive oxygen species (ROS). Methods of synthesizing novel antioxidant mALAs, spontaneous emulsification or nanoprecipitaion thereof to produce antioxidant nanospheres and their use in preventing or treating diseases or conditions caused by oxidative stress and other free radical mediated conditions are also described. Another aspect of this invention is the use of these antioxidant nanospheres for the preparation of antioxidant particulate delivery system of therapeutic agents.

26 Claims, 33 Drawing Sheets

(56) References Cited

U.S. PATENT DOCUMENTS

| | | | |
|---|---|---|---|
| 8,318,795 | B2 | 11/2012 | Yu et al. |
| 2004/0053989 | A1 | 3/2004 | Prendergast et al. |
| 2005/0043493 | A1 | 2/2005 | Smith et al. |
| 2005/0065194 | A1 | 3/2005 | Shankar et al. |
| 2006/0013882 | A1 | 1/2006 | Kohn et al. |
| 2007/0148196 | A1 | 6/2007 | Haas et al. |
| 2007/0208134 | A1 | 9/2007 | Hunter et al. |
| 2007/0281047 | A1* | 12/2007 | Henry et al. ............ 424/776 |
| 2010/0098653 | A1 | 4/2010 | Yu et al. |
| 2011/0086073 | A1 | 4/2011 | Yu et al. |
| 2011/0300187 | A1 | 12/2011 | Yu et al. |

FOREIGN PATENT DOCUMENTS

| | | | |
|---|---|---|---|
| JP | 2012-509901 A | | 4/2012 |
| WO | 9743274 A1 | | 11/1997 |
| WO | 9801440 A2 | | 1/1998 |
| WO | WO 99/38881 | | 8/1999 |
| WO | WO 01/29221 | | 4/2001 |
| WO | WO 01/53312 | | 7/2001 |
| WO | WO 02/046465 A3 | | 6/2002 |
| WO | WO 2004/050795 | | 6/2004 |
| WO | WO 2007/027559 A2 | | 3/2007 |
| WO | WO 2008/012365 A2 | | 1/2008 |
| WO | WO 2008/106640 A1 | | 9/2008 |
| WO | 2009/086547 A1 | | 7/2009 |
| WO | WO 20091148698 A1 | | 12/2009 |
| WO | WO 20101060098 A1 | | 5/2010 |
| WO | WO 2013/016696 | | 1/2013 |

OTHER PUBLICATIONS

Di Stefano, et al., Antiparkinson Prodrugs, Molecules, Jan. 16, 2008, vol. 13, pp. 46-68.

Colman, P.M., Effects of amino acid sequence changes on antibody-antigen interactions, Biomolecular Research Institute, 343 Royale Parade, Parkville, 3052 (Australia), Research in Immunology, No. 1, vol. 145, 1994, pp. 33-35.

Lederman et al., A single amino acid substitution in a common african allele of the CD4 molecule ablates binding of the monoclonal antibody, OKT4, Molecur Immunology, vol. 28, No. 11, pp. 1171-1181, 1991.

Van Regenmortel, Marc H.V., Mapping epitope structure and activity: from one-dimensional prediction to four-dimensional description of antigenic specifity, Methods: A Companion to Methods in Enzymology 9, (1996), pp. 465-472.

Abaza et al., Effects of amino acid substitutions outside and antigenic site on protein binding to monoclonal antibodies of predetermined specificity obtained by peptide immunization: demonstration with region 94-100 (antigenic site 3) of myoglobin, Journal of Protein Chemistry, vol. 11, No. 5, 1992, pp. 433-444.

Pham et al., Thermodynamic and structural characterization of 2-nitrogen-modified RNA duplexes, Nucleic Acids Research, 2004, vol. 32, No. 11, pp. 3446-3455.

Conklin, Cancer chemotherapy and antioxidants, J. Nutri., 2004, vol. 134, pp. 3201A-3204A.

European Application No. 08731097.5 Extended Search Report dated Jun. 15, 2011.

Casolaro et al. Redox-active Polymers: Sythesis and Exchange Reaction of Amino Compounds Containing a Cyclic Disulfide. Polymer (1994). 35(2): pp. 360-366.

Fujimoto et al. Synthesis of a Polymer Containing the Cyclic Disulfide (1, 2-Dithiolane) Structure. Die Makromolekulare Chemie (1974). 175: pp. 3597-3602.

Sieczkowska et al. Sythesis and Characterization of Photolabile Aminoterpolymers for Covalent Attachment onto Gold Substrates. Designed Monomers and Polymers (2005). 8(6): pp. 629-644.

Sun et al. Ultrathin Self-Assembled Polymeric Films on Solid Surfaces. I. Synthesis and Characterization of Acrylate Copolymers Containing Alkyl Disulfide Side Chains. Journal of Polymer Science: Part A: Polymer Chemistry. (1993). 31: pp. 1729-1740.

Sun et al. Ultrathin Self-Assembled Polymeric Films on Solid Surfaces. III. Influence of Acrylate Dithioalkyl Side Chain Length on Polymeric Monolayer Formation of Gold. J. Vac. Sci. Technol. A (1994). 12(4): pp. 2499-2506.

Japanese Application No. 2009-551871 Official Action dated Dec. 21, 2011.

Rice et al. Inhibition of multiple phases of human immunodeficiency virus type 1 replication by a dithiane compound that attacks the conserved zinc fingers of retroviral nucleocapsid proteins. Antimicrob Agents Chemother. (1997). 41 (2): pp. 419-426.

Kalyuzhny et al. Ligand effects on optical properties of CdSe nanocrystals. Journal of Physical Chemistry B. (2005). 109(15): pp. 7012-7021. Abstract.

Kieller et al. The Five-membered Disulfide Ring System. III. Antineoplastic Potentialities. Acta Biochimica Polonica (1964). 11(2-3): pp. 279-291.

Lee et al. Nereistoxin and Cartap Neurotoxicity Attributable to Direct Block of the Insect Nicotinic Receptor/Channel. Journal of Agricultrual and Food Chemistry. (2003). 51(9): pp. 2646-2652. Abstract.

Povalyaeva et al. Synthesis and Properties of N-substituted 4-amino-1,2, dithiolanes and Related Compounds. Zhurnal Organicheskoi Khimii. (2004). 20(4): pp. 849-860.

U.S. Appl. No. 12/528,067 Non-Final Office Action dated Jan. 4, 2012.

Hsu et al. Synthesis of functionalized 1,3-propanedithiols as derivatizing reagent for organoarsenic (III) compounds. Proceed. ERDEC Sci. Conf. Clin. Biol. Defense Res., Aberdeen Proving Ground. Nov. 17-20, 1998. Abstract.

Schotte et al. Five-membered Disulfide Ring System. I. General Chemistry and Therapeutic Aspects. Biochemical Pharmacology. (1962). 11. Abstract.

Thomas et al. Campthotecin: Current Perspectives. Bioorg Med Chem. (2004): 12: pp. 1585-1604. Abstract.

U.S. Appl. No. 12/995,125 Restriction Requirement dated Jun. 7, 2012.

U.S. Appl. No. 13/114,539 Restriction Requirement dated May 25, 2012.

PCT/US2012/048703 International Search Report dated Dec. 7, 2012.

PCT/US2012/048703 Written Opinion dated Dec. 7, 2012.

U.S. Appl. No. 12/528,067 Notice of Allowance dated Jul. 16, 2012.

U.S. Appl. No. 12/995,125 Non-Final Office Action dated Oct. 12, 2012.

U.S. Appl. No. 13/114,539 Non-Final Office Action dated Oct. 2, 2012.

EP Application No. 09828387.2 Supplemental Search Report dated Aug. 10, 2012.

Kunii et al. Preparation and antitumor characteristics of PLA/(PEG-PPG-PEG) nanoparticles loaded with camptothecin. European Journal of Pharmaceuticals and Biopharmaceuticals. (2007) 67(1):9-17.

Moon et al. Antibody Conjugates of 7-Ethyl-10-hydroxycamptothecin (SN-38) for Targeted Cancer Chemotherapy. J. Med. Chem (2008). 51(21):6916-6926.

U.S. Appl. No. 12/995,125 Final Office Action dated May 9, 2013.

U.S. Appl. No. 12/995,125 Notice of Allowance dated Aug. 13, 2013, Jan. 25, 2014.

U.S. Appl. No. 13/114,539 Final Office Action dated Apr. 23, 2013.

U.S. Appl. No. 13/114,539 Notice of Allowance dated Aug. 27, 2013.

International Preliminary Report on Patentability mailed Jul. 15, 2010 for PCT/US2008/088541.

\* cited by examiner

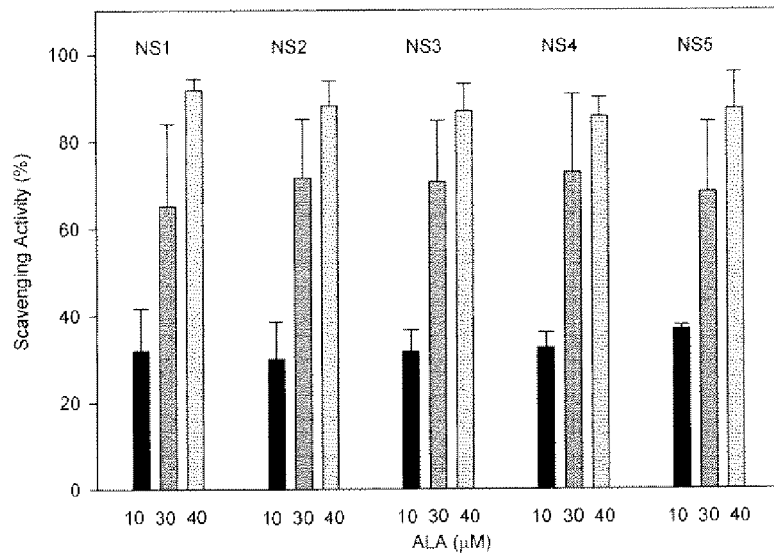
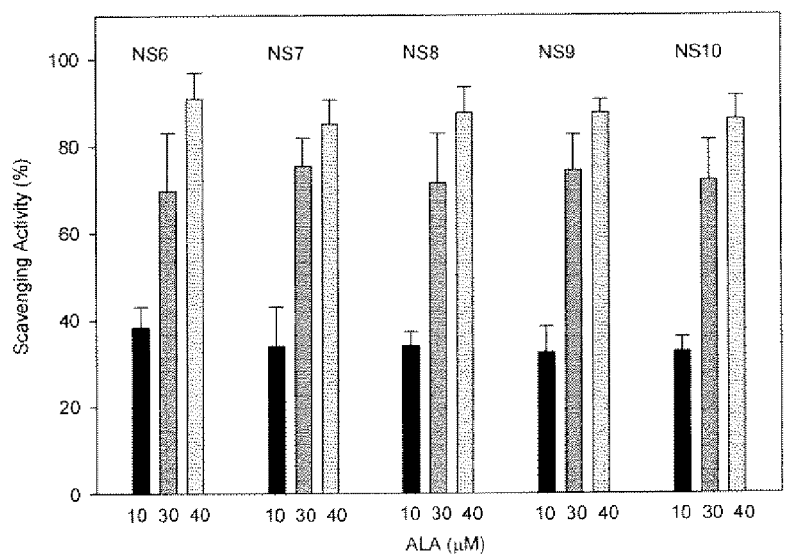

DPPH    A    B    C    D    E    Toco
             LipoToco1

DPPH  25 µM   50 µM  100 µM  250 µM   50 µM  100 µM  250 µM
      LipoToco4C       LipoToco4E              Toco DPPH    t = 1 min    20 min    40 min    t = 0    20 min    40 min
            LipoToco4A (25 µM)            Toco (25 µM)

DPPH    t = 0    20 min    40 min    t = 0    20 min    40 min
            LipoToco4A (25 µM)            LipoToco4E (25 µM)

DPPH    t = 0    20 min    40 min    t = 0    20 min    40 min
            Trolox (25 µM)            Ascorbic acid (25 µM)

ANTIOXIDANT NANOSPHERE COMPRISING [1,2]-DITHIOLANE MOIETIES

CROSS-REFERENCE TO RELATED APPLICATIONS

This application is the National Phase of International Application PCT/US08/88541, filed Dec. 30, 2008, which designated the U.S. and that International Application was published under PCT Article 21(2) in English. This application also includes a claim of priority under 35 U.S.C. §119(e) to U.S. provisional patent application No. 61/018,749, filed Jan. 3, 2008.

FIELD OF INVENTION

This invention relates to antioxidant molecules capable of scavenging free radicals, metals and reactive oxygen species, to antioxidant nanospheres comprising the antioxidant molecules, to methods for their preparation and to methods of using the antioxidant molecules and nanospheres.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Molecules containing a dithiolane moiety are widely investigated due to their antioxidant properties. α-Lipoic acid (thioctic acid, 1,2-dithiolane-3-pentanoic acid), which has dithiolane ring in its molecule, is a widely distributed natural substance which was originally discovered as a growth factor. Physiologically, it acts as a coenzyme of the oxidative decarboxylation of α-keto carboxylic acid (e.g., pyruvates) and as an antioxidant, and it is able to regenerate vitamin C, vitamin E, glutathione and coenzyme Q10. In pathological conditions, lipoic acid is applied in the treatment of diabetic polyneuropathy, liver cirrhosis and metal intoxications.

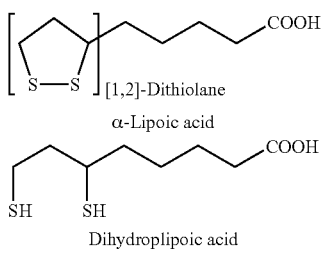

Lipoic acid and dihydrolipoic acid are capable of trapping a number of radicals both in a lipid and in an aqueous environment. Lipoic acid and dihydrolipoic acid act as antioxidants not only by direct radical trapping and/or metal chelation but also by recycling other antioxidants (e.g., vitamin C, vitamin E, etc.) and by reducing glutathione, which in turn recycles vitamin E. The two thiol groups present in [1,2]-dithiolane ring system confer it a unique antioxidant potential. The disulfides with a cyclic five-member ring such as lipoic acid have been found to be more effective in reductive and/or nucleophilic attack than open-chain derivatives such as cystine or glutathione.

The antioxidant potential of a compound may be evaluated based on the properties such as (1) specificity of free radical scavenging, (2) interaction with other antioxidants, (3) metal-chelating activity, (4) effects on gene expression, (5) absorption and bioavailability, (6) location (in aqueous or membrane domains, or both), and (7) ability to repair oxidative damage (Packer et al., Free Radical Biology & Medicine. Vol. 19, No. 2, pp. 227-250, 1995). According to the above criteria, the [1,2]-dithiolane containing lipoic acid/dihydrolipoic acid redox system has been regarded as a universal antioxidant.

There have been many attempts to develop lipoic acid derivatives or complexes having antioxidant activity. U.S. Pat. Nos. 6,090,842; 6,013,663; 6,117,899; 6,127,394; 6,150,358; 6,204,288, 6,235,772; 6,288,106; 6,353,011; 6,369,098; 6,387,945; 6,605,637; 6,887,891; 6,900,338; and 6,936.715 are some examples.

In many other U.S. patents, the natural and synthetic lipoic acid derivatives and their metabolites are disclosed for use in preventing skin aging and in the treatment of free radical mediated diseases, including inflammatory, proliferative, neurodegenerative, metabolic and infectious diseases.

A. Inhibitory Activity on NO-Synthase and Trapping the Reactive Oxygen Species (ROS)

Various conditions or disease conditions have demonstrated a potential role of nitric oxide (NO) and the ROS's and the metabolism of glutathione in their physiopathology. These conditions and disease conditions are characterized by an excessive production or a dysfunction of nitrogen monoxide and/or the metabolism of glutathione and of the redox status of the thiol groups (Duncan and Heales, NITRIC OXIDE AND NEUROLOGICAL DISORDERS, *Molecular Aspects of Medicine.* 26, 67-96, 2005; Kerwin et al., NITRIC OXIDE: A NEW PARADIGM FOR SECOND MESSENGERS, *J. Med. Chem.* 38, 4343-4362, 1995; Packer et al., Free Radical Biology & Medicine. 19, 227-250, 1995). U.S. Pat. Nos. 6,605,637, 6,887,891, and 6,936.715 disclose that lipoic acid derivatives inhibit the activity of NO-synthase enzymes producing nitrogen monoxide NO and regenerate endogenous antioxidants which trap the ROS and which intervene in a more general fashion in the redox status of thiol groups. U.S. Pat. Nos. 5,693,664, 5,948,810, and 6,884,420 disclose the use of racemic alpha-lipoic acid or their metabolites, salts, amides or esters for the synthesis of drugs for the treatment of diabetes mellitus of types I and II. U.S. Pat. No. 5,925,668 discloses a method of treating free radical mediated diseases, and/or reducing the symptoms associated with such diseases whereby the compounds with antioxidant activity contain 1,2-dithiolane, reduced or oxidized forms. U.S. Pat. No. 6,251,935 discloses methods for the prevention or treatment of migraine comprising the administration of an active ingredient selected from the group consisting of racemic alpha-lipoic acid, enantiomers and pharmaceutically acceptable salts, amides, esters or thioesters thereof. U.S. Pat. Nos. 6,472,432 and 6,586,472 disclose the treatment of a chronic inflammatory disorder, rosacea, by application of a composition containing lipoic acid and/or lipoic acid derivatives. There is also strong evidence that the neuroprotective effects of lipoic acid and dihydrolipoic acid are mediated by antioxidant and free radical scavenging mechanisms (Packer et al., Free Radical Biology & Medicine. Vol. 22, pp. 359-378, 1997).

B. Topical Application and Cosmetic Preparation

Ultraviolet light can produce reactive oxygen species (ROS) that damage the skin leading to the premature aging of the skin. ROS are a collection of reactive free radicals produced from the oxygen molecules, including singlet oxygen, the superoxide radical, hydrogen peroxide, and the hydroxyl radical, as well as the reaction products produced by these free radicals. These ROS react with other molecules and generate a cascade of harmful free radical reactions in the skin.

U.S. Pat. Nos. 5,709,868 and 6,752,999 disclose methods for the prevention and/or treatment of skin damage, particularly inflammation and aging whereby a composition containing lipoic acid and/or lipoic acid derivatives are topically applied to affected skin areas. U.S. Pat. Nos. 5,965,618 and 6,955,816 disclose compositions and methods for the treatment and inhibition of scar tissue based on topical application of compositions containing lipoic acid and/or lipoic acid derivatives to scars and to injured skin sites. U.S. Pat. No. 6,365,623 discloses the treatment of active acne and acne-form scars by topical application of a composition containing lipoic acid and/or a lipoic acid derivative.

C. Cancer Therapy

U.S. Pat. Nos. 5,035,878 and 5,294,430 disclose that dithiocarbamates, which have antioxidant properties, can reverse the damage to the blood-forming function of the bone marrow (myelesuppression) caused by treatment with antineoplastic agents. U.S. Pat. Nos. 6,284,786, 6,448,287, and 6,951,887 disclose methods of cancer therapy using lipoic acid as a therapeutic agent administered in combination with ascorbic acid. U.S. Pat. No. 7,071,158 discloses that antioxidants increase the cytotoxicity of antineoplastic agents to abnormally proliferating cells and decrease the toxicity of antineoplastic agents to normal cells.

However, many of the currently available oral formulations have a critical bioavailability due to incomplete absorption and first-pass metabolism. Rapid degradation of antioxidants in the body fluid and elimination of antioxidants from the body further decreases the beneficial effects of antioxidants. Further, some antioxidants may be limited by their stoichiometric quantities; for example, it has been postulated that antioxidant potency of vitamins such as C and E is limited because they work as scavengers of existing excess reactive species. (Johanse et al., OXIDATIVE STRESS AND THE USE OF ANTIOXIDANTS IN DIABETES: LINKING BASIC SCIENCE TO CLINICAL PRACTICE. *Cardiovascular Diabetology* 2005 4:5) Thus, there is a need in the art to overcome one or more of these limitations. There is also a need for useful compounds for the treatment of conditions or disease conditions wherein the potential role of NO and the ROS's and the metabolism of glutathione has been demonstrated in their physiopathology.

SUMMARY OF THE INVENTION

The following embodiments and aspects thereof are described and illustrated in conjunction with compositions and methods which are meant to be exemplary and illustrative, not limiting in scope.

One embodiment of the present invention provides an antioxidant molecule represented by Formula I

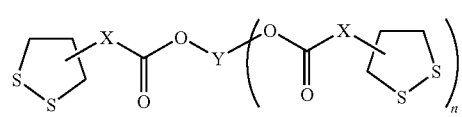

(I)

wherein X may be selected from the group consisting of a substituted, unsubstituted, branched or unbranched chain of carbon atoms, and may optionally contain a heteroatom; Y may be selected from the group consisting of a branched and unbranched alkyl, branched and unbranched alkenyl, branched and unbranched alkynyl, heteroatom-containing branched and unbranched alkyl, heteroatom-containing branched and unbranched alkenyl, heteroatom-containing branched and unbranched alkynyl, aryl, cyclic aliphatic, cyclic aromatic, heterocyclic, and aromatic heterocyclic group; and n may be an integer of at least one. In particular embodiments, n may be an integer from 1 to 4; and X may be an unsubstituted, unbranched chain of 1 to 6 carbon atoms. In various embodiments, the [1,2]-dithiolane moiety is α-lipoic acid and thus, the antioxidant molecule is represented by formula II

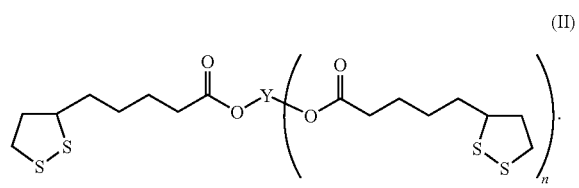

(II)

In various embodiments, Y may be a moiety formed by esterification of the hydroxyl groups of a polyol selected from the group consisting of

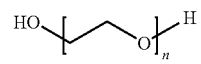

wherein n is an integer between 1 and 4 and

wherein n is an integer between 3 and 16. In various embodiments, Y may be a moiety formed by esterification of the hydroxyl groups of a polyol selected from Table 11.

Another embodiment of the present invention provides an antioxidant molecule selected from Table 12.

Another embodiment of the present invention provides a method of synthesizing the antioxidant molecule of the present invention, comprising: providing at least two [1,2]-dithiolane moieties; providing a polyol to conjugate the at least two [1,2]-dithiolane moieties; and reacting the at least two [1,2]-dithiolane moieties with the polyol to produce the antioxidant molecule.

Another embodiment of the present invention provides an antioxidant nanosphere, comprising: an antioxidant molecule of the present invention.

Another embodiment of the present invention provides a method of producing an antioxidant nanosphere, comprising: providing a quantity of an antioxidant molecule of the present invention; dissolving the quantity of the antioxidant molecule in an organic solvent to produce an organic solution; stirring the organic solution into an aqueous solution; and removing the organic solvent to produce the antioxidant nanosphere. The method may further comprise a step selected from the group consisting of filtering the nanosphere, purifying the nanosphere and combinations thereof. In one embodiment, the organic solvent is acetone. In another embodiment, the aqueous solution comprises a quantity of poloxamers.

Another embodiment of the present invention provides a method of treating a disease or disease condition in a subject in need thereof, comprising: providing a composition comprising an antioxidant molecule of the present invention and/or an antioxidant nanosphere of the present invention; and administering a therapeutically effective amount of the composition to the subject. The disease or disease condition may be selected from the group consisting of: a disease or disease condition caused by oxidative stress, inflammation of the skin mediated by free radicals, aging of the skin mediated by free radicals, and combinations thereof.

Another embodiment of the present invention provides a method of increasing the toxicity of an antineoplastic agent to abnormally proliferating cells and/or decreasing the toxicity of an antineoplastic agent to normal cells, in a subject in need thereof comprising: providing a composition comprising an antioxidant molecule of the present invention and/or an antioxidant nanosphere of the present invention; and administering a therapeutically effective amount of the composition and the antineoplastic agent to the subject. In various embodiments, the antineoplastic agent may be selected from the group consisting of temozolomide, paclitaxel and camptothecin and combinations thereof.

Another embodiment of the present invention provides a delivery vehicle composition, comprising: an antioxidant molecule of the present invention or an antioxidant nanosphere of the present invention; and a therapeutic agent. In various embodiments, the therapeutic agent may be selected from the group consisting of genetic molecule, peptide, protein, chemotherapeutic agent and combinations thereof.

Another embodiment of the present invention provides a method of delivering a therapeutic agent to a location in or on the body, comprising: providing a composition comprising a therapeutic agent, and an antioxidant molecule the present invention and/or an antioxidant nanosphere of the present invention; and administering a therapeutically effective amount of the composition to the subject. In various embodiments, the therapeutic agent may be selected from the group consisting of a genetic molecule, a peptide, a protein and combinations thereof. In a particular embodiment, the therapeutic agent may be an antineoplastic drug.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 4 depicts HOCl scavenging activity of the nanospheres in accordance with an embodiment of the present invention. The results are expressed as a percent scavenging activity, where 100% activity is measured with 50 µM of α-lipoic acid and 0% activity with PBS. The percent scavenging activity was calculated from the elastase activity measured after 120 s incubation. Error bar represents ±SD above and below the average activity determined in triplicate.

DESCRIPTION OF THE INVENTION

Figure 1:
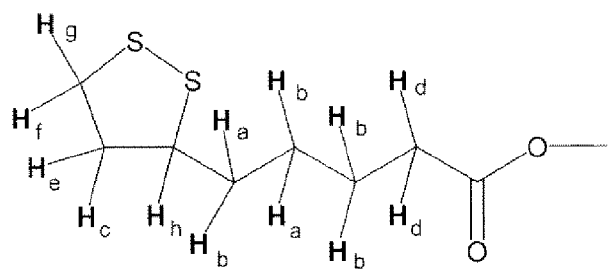
FIG. 1 depicts NMR active protons in the α-lipoic acid unit in accordance with an embodiment of the present invention.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); and March, *Advanced Organic Chemistry Reactions, Mechanisms and Structure* 5$^{th}$ ed., J. Wiley & Sons (New York, N.Y. 2001) provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Antineoplastic agent," as used herein, refers to a substance that decreases abnormal cell proliferation.

"Beneficial results" may include, but are in no way limited to, lessening or alleviating the severity of the disease condition, preventing the disease condition from worsening, curing the disease condition and prolonging a patient's life or life expectancy. The disease conditions may relate to or may be modulated by the central nervous system.

"Conditions" and "disease conditions," as used herein may include, but are in no way limited to conditions or disease conditions wherein the potential role of nitric oxide ("NO"), reactive oxygen species ("ROS") or the metabolism of glutathione have been demonstrated in their physiopathology, conditions or disease conditions caused by oxidative damage, or any form of neoplastic cell growth and proliferation, whether malignant or benign, pre-cancerous and cancerous cells and tissues.

Examples of conditions or disease conditions wherein the potential role of nitric oxide ("NO"), reactive oxygen species ("ROS") or the metabolism of glutathione have been demonstrated in their physiopathology and conditions or disease conditions caused by oxidative damage include but are not limited to cardiovascular and cerebrovasular disorders (e.g., atherosclerosis, migraine, arterial hypertension, septic shock, ischemic or hemorrhagic cardiac or cerebral infarctions, ischemias and thromboses); disorders of the central or peripheral nervous system (e.g., neurodegenerative nervous system); neurodegenerative diseases including cerebral infarctions, sub-arachnoid hemorrhaging, ageing, senile dementias (e.g., Alzheimer's disease), Huntington's chorea, Parkinson's disease, prion disease (e.g., Creutzfeld Jacob disease), amyotrophic lateral sclerosis, pain, cerebral and spinal cord traumas, addiction to opiates, alcohol and addictive substances, erective and reproductive disorders, cognitive disorders, encephalopathies, encephalopathies of viral or toxic origin, depression, anxiety, schizophrenia, epilepsy, sleeping disorders, eating disorders (e.g., anorexia, bulimia); disorders of the skeletal muscle and neuromuscular joints (e.g., myopathy, myositis), cutaneous diseases; proliferative and inflammatory diseases (e.g., atherosclerosis), pulmonary hypertension, respiratory distress, glomerulonephritis, cataracts, portal hypertension, psoriasis and rheumatoid arthritis, fibroses, amyloidoses, inflammations of the gastro-intestinal system (e.g., colitis, Crohn's disease) or of the pulmonary system and airways (e.g., asthma, sinusitis, rhinitis) as well as contact or delayed hypersensitivities; organ transplantation; auto-immune and viral diseases (e.g., lupus, AIDS, parasitic and viral infections), diabetes and its complications (e.g., retinopathies, nephropathies and polyneuropathies, multiple sclerosis, myopathies); cancer; autosomal genetic diseases (e.g., Unverricht-Lundborg disease); neurological diseases associated with intoxications (e.g., cadmium poisoning, inhalation of n-hexane, pesticides, herbicides), associated with treatments (e.g., radiotherapy) or disorders of genetic origin (e.g., Wilson's disease); and impotence linked to diabetes.

"Cancer" and "cancerous" refer to or describe the physiological condition in mammals that is typically characterized by unregulated cell growth. Examples of cancer include, but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer; including, but not limited to, gliomas, glioblastomas, glioblastoma multiforme (GBM), oligodendrogliomas, primitive neuroectodermal tumors, low, mid and high grade astrocytomas, ependymomas (e.g., myxopapillary ependymoma papillary ependymoma, subependymoma, anaplastic ependymoma), oligodendrogliomas, medulloblastomas, meningiomas, pituitary carcinomas, neuroblastomas, and craniopharyngiomas.

"Therapeutically effective amount" as used herein refers to an amount which is capable of achieving beneficial results in a patient with a condition or a disease condition in which treatment is sought. A therapeutically effective amount can be determined on an individual basis and will be based, at least in part, on consideration of the physiological characteristics of the mammal, the type of delivery system or therapeutic technique used and the time of administration relative to the progression of the disease.

"Therapeutic agent" as used herein refers to any substance used internally or externally as a medicine for the treatment, cure, prevention, slowing down, or lessening of a disease or disorder, even if the treatment, cure, prevention, slowing down, or lessening of the disease or disorder is ultimately unsuccessful.

"Treatment" and "treating," as used herein refer to both therapeutic treatment and prophylactic or preventative measures, wherein the object is to prevent, slow down and/or lessen the disease even if the treatment is ultimately unsuccessful.

"Polyol" as used herein refers to a compound that contains at least two free esterifiable hydroxyl groups.

"Nanosphere" as used herein refers to a particle with a size, in at least one dimension, between about 10 nm to about 1000 nm; and may also include a nanoemulsion.

Various embodiments of the present invention provide for antioxidant molecules, antioxidant nanospheres comprising the antioxidant molecules, methods of preparing these antioxidant molecules and nanospheres, and methods of therapeutic treatment with these antioxidant molecules and nanospheres.

One embodiment of the present invention provides an antioxidant molecule represented by Formula I

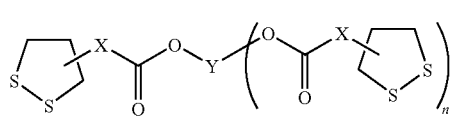

wherein X may be selected from the group consisting of a substituted, unsubstituted, branched or unbranched chain of carbon atoms and may optionally contain a heteroatom; Y may be selected from the group consisting of branched and unbranched alkyl, branched and unbranched alkenyl, branched and unbranched alkynyl, heteroatom-containing branched and unbranched alkyl, heteroatom-containing branched and unbranched alkenyl, heteroatom-containing branched and unbranched alkynyl, aryl, cyclic aliphatic, cyclic aromatic, heterocyclic, and aromatic heterocyclic groups; and n may be an integer and is at least one, and in particular embodiments n may be an integer from 1-4. In one embodiment, X may be an unsubstituted, unbranched chain of 4 carbon atoms. In various embodiments, Y is a moiety that is formed by esterification of least two free esterifiable hydroxyl groups on a polyol.

In one embodiment, the [1,2]-dithiolane moieties are from α-lipoic acid, and the antioxidants molecules are generally represented by the formula II:

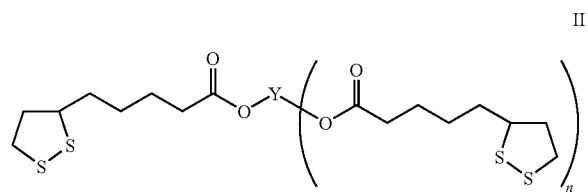

In this embodiment, at least two α-lipoic acids are linked to a polyol via ester bonds.

In various embodiments, polyols that are useful in the present invention include commercially available diols as follows:

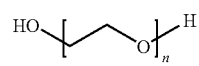

wherein n is an integer between 1 and 4.

wherein n is an integer between 3 and 16.

Thus, the hydrophobic antioxidant molecule in various embodiment may be one as shown below:

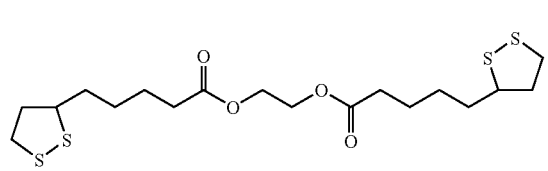

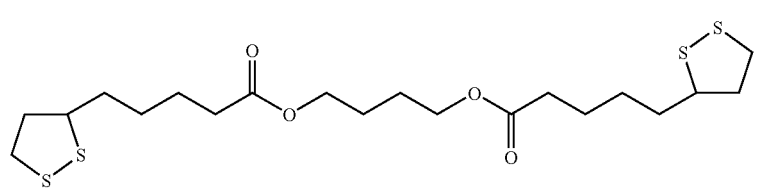

-continued
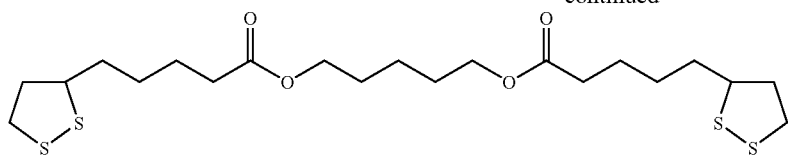
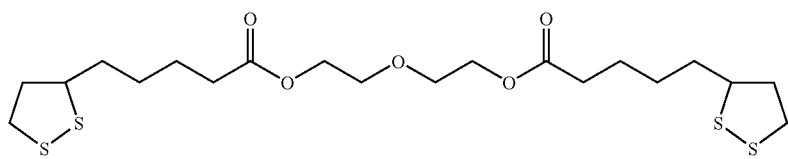
2a
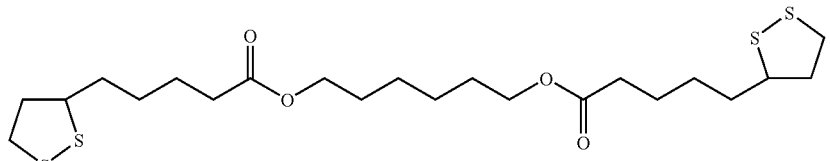
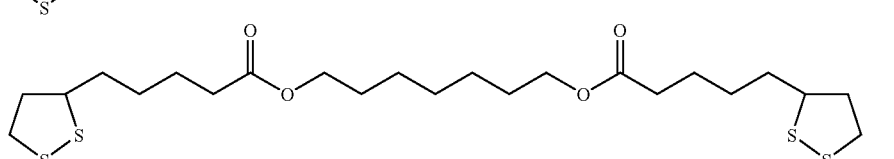
5a
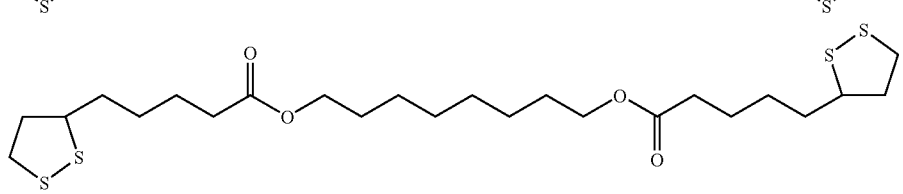
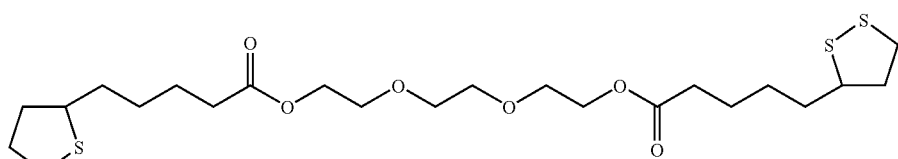
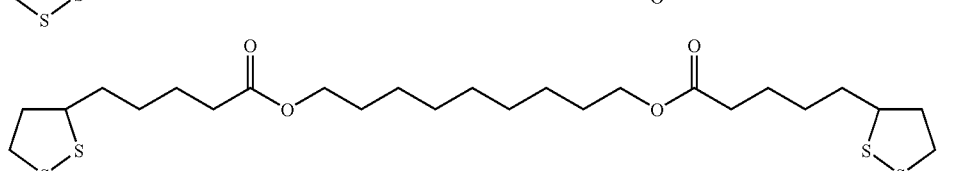
3a
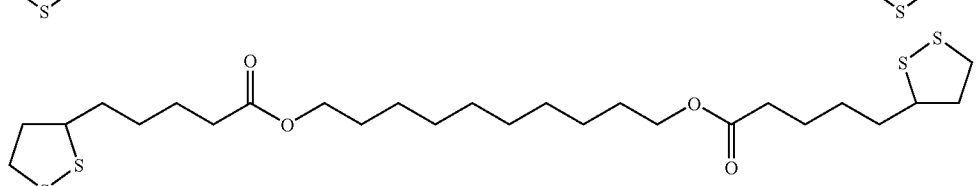
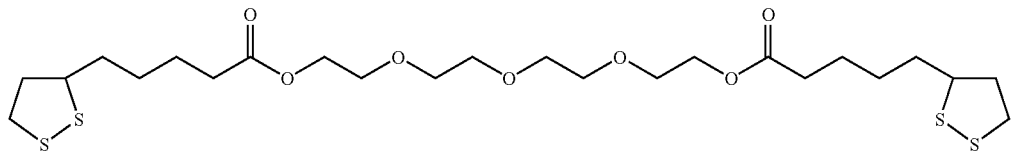
4a
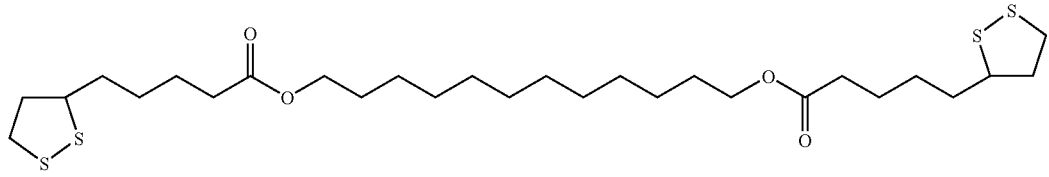

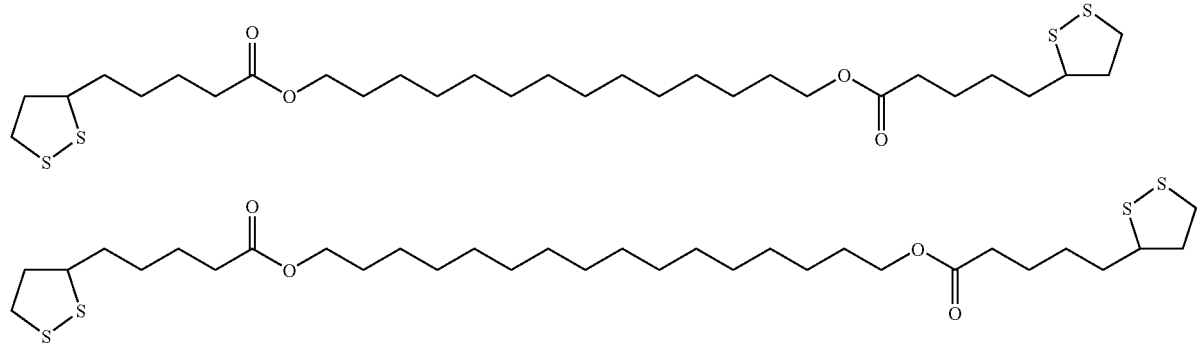
In other embodiments, the polyols may be selected from the commercial available polyols as shown below:
TABLE 11
| Compound | Structure |
|---|---|
| 1 | HOCH$_2$CH$_2$OH (ethylene glycol) |
| 2 | diethylene glycol |
| 3 | triethylene glycol |
| 4 | tetraethylene glycol |
| 5 | 1,6-hexanediol |
| 6 | 1,4-benzenedimethanol |
| 7 | N,N'-bis(2-hydroxyethyl)piperazine |
| 8 | glycerol |
| 9 | triethanolamine |
| 10 | triisopropanolamine |
| 11 | pentaerythritol |

TABLE 11-continued

| Compound | Structure |
|---|---|
| 12 | 2-[(hydroxymethyl)]-2-(2-hydroxyethyl)-1,3-propanediol with additional hydroxyethyl (dipentaerythritol-like polyol) |
| 13 | 2,3-butanediol |
| 14 | 1,2-butanediol |
| 15 | 1,3-butanediol |
| 16 | 2,4-pentanediol |
| 17 | 1,4-pentanediol |
| 18 | 2,2-dimethyl-1,3-propanediol (neopentyl glycol) |
| 19 | 1,2-pentanediol |
| 20 | 1,2-hexanediol |
| 21 | 2,5-hexanediol |
| 22 | 3-methyl-1,5-pentanediol |
| 23 | 1,5-hexanediol |
| 24 | 2-ethyl-1,3-hexanediol |

TABLE 11-continued

| Compound | Structure |
|---|---|
| 25 | 2-ethyl-2-propylpropane-1,3-diol structure (2-butyl-2-ethylpropane-1,3-diol) |
| 26 | hexane-1,4,5-triol |
| 27 | octane-1,2-diol (2-hydroxymethyl heptanol) |
| 28 | dodecane-1,2-diol |
| 29 | hexadecane-1,2-diol |
| 30 | 2-(hydroxymethyl)-2-methylpropane-1,3-diol |
| 31 | 2-(hydroxymethyl)propane-1,3-diol |
| 32 | hexane-1,5,6-triol |
| 33 | 2-ethyl-2-(hydroxymethyl)propane-1,3-diol |
| 34 | butane-1,2,3,4-tetraol |
| 35 | octane-1,2,7,8-tetraol |
| 36 | bis(3-hydroxy-2-(hydroxymethyl)-2-ethylpropyl) ether |
| 37 | 1,1-bis(hydroxymethyl)cyclopropane |

TABLE 11-continued

| Compound | Structure |
|---|---|
| 38 | cyclopentane-1,2-diol |
| 39 | cyclopentane-1,3-diol |
| 40 | cyclohexane-1,2-diol |
| 41 | cyclohexane-1,3-diol |
| 42 | cyclohexane-1,4-diol |
| 43 | cyclohexane-1,3,5-triol |
| 44 | 1,2-bis(hydroxymethyl)cyclohexane |
| 45 | 1,4-bis(hydroxymethyl)cyclohexane |
| 46 | cyclooctane-1,2-diol |
| 47 | cyclooctane-1,5-diol |
| 48 | 1,3-benzenedimethanol |

TABLE 11-continued

| Compound | Structure |
|---|---|
| 49 | 1-phenyl-1,2-ethanediol |
| 50 | 1,2-benzenedimethanol |
| 51 | 2-phenyl-1,3-propanediol |
| 52 | 3-(2-methylphenoxy)-1,2-propanediol |
| 53 | 2-(benzyloxy)-1,3-propanediol |
| 54 | (4-methoxy-1,3-phenylene)dimethanol |
| 55 | (5-methoxy-1,3-phenylene)dimethanol |
| 56 | 1,2-diphenyl-1,2-ethanediol |

TABLE 11-continued

| Compound | Structure |
| --- | --- |
| 57 | 9,9-bis(hydroxymethyl)fluorene |
| 58 | N-methyldiethanolamine |
| 59 | N-ethyldiethanolamine |
| 60 | N-tert-butyldiethanolamine |
| 61 | 1-(diethylamino)-2,3-propanediol |
| 62 | N-butyldiethanolamine |
| 63 | N-phenyldiethanolamine |
| 64 | N,N-bis(2-hydroxyethyl)-p-toluidine |
| 65 | complex aminoalcohol (see structure) |

Thus, in specific embodiments, the antioxidant molecule may be ones as shown below.

TABLE 12

| Compound | Structure |
| --- | --- |
| 1a | 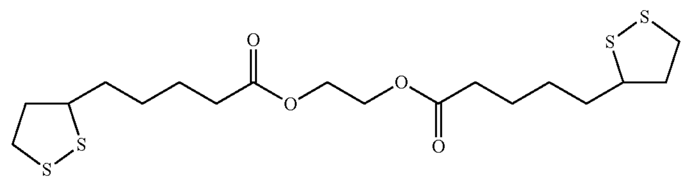 [SMILES: O=C(CCCCC1CCSS1)OCCOC(=O)CCCCC1CCSS1] |
| 2a | 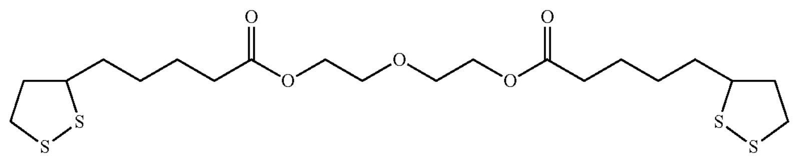 |
| 3a | 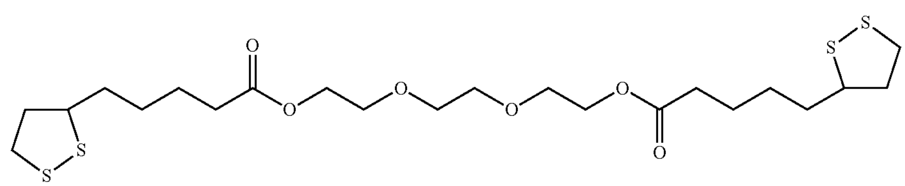 [SMILES: O=C(CCCCC1CCSS1)OCCOCCOCCOC(=O)CCCCC1CCSS1] |
| 4a | 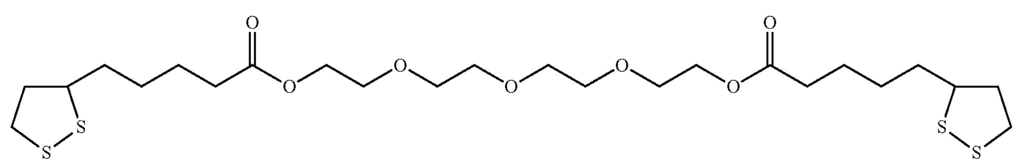 [SMILES: O=C(CCCCC1CCSS1)OCCOCCOCCOCCOC(=O)CCCCC1CCSS1] |
| 5a | 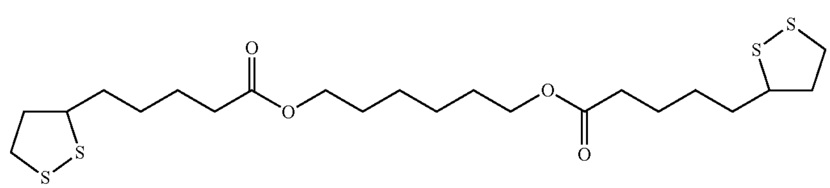 [SMILES: O=C(CCCCC1CCSS1)OCCCCCCOC(=O)CCCCC1CCSS1] |
| 6a | 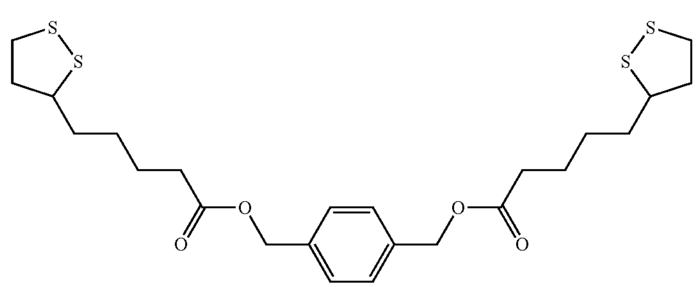 [SMILES: O=C(CCCCC1CCSS1)OCc1ccc(COC(=O)CCCCC2CCSS2)cc1] |
| 7a | 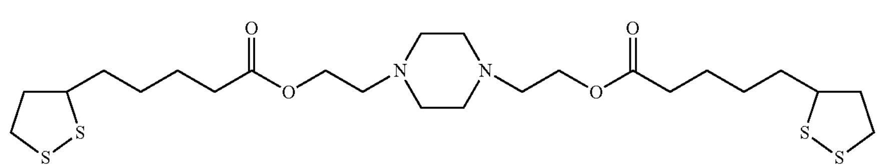 [SMILES: O=C(CCCCC1CCSS1)OCCN1CCN(CCOC(=O)CCCCC2CCSS2)CC1] |

TABLE 12-continued
| Compound | Structure |
|---|---|
| 8a | 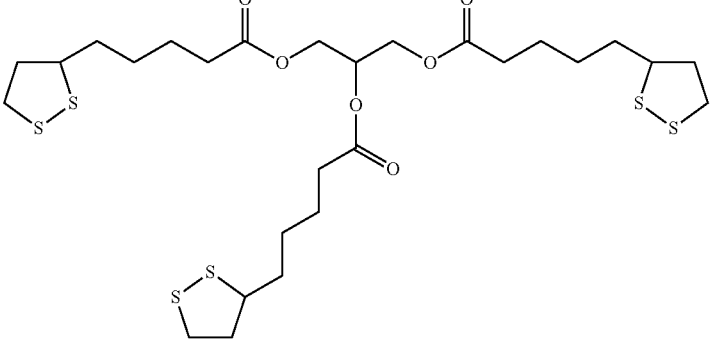 |
| 9a | 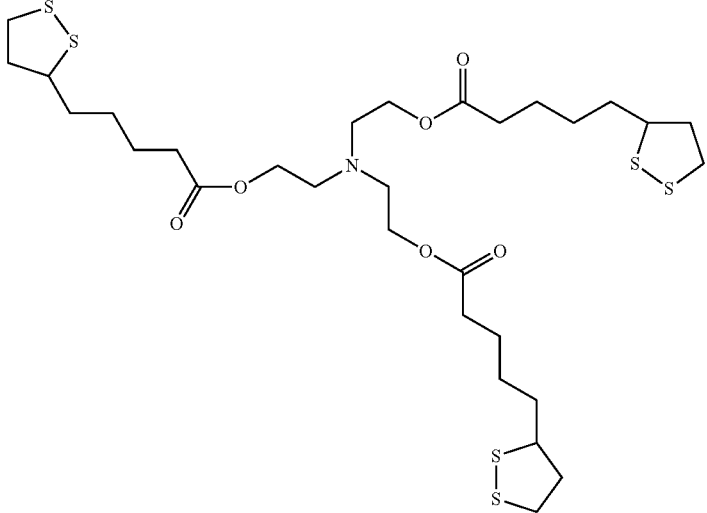 [SMILES: O=C(CCCCC1CCSS1)OCCN(CCOC(=O)CCCCC1CCSS1)CCOC(=O)CCCCC1CCSS1] |
| 10a | 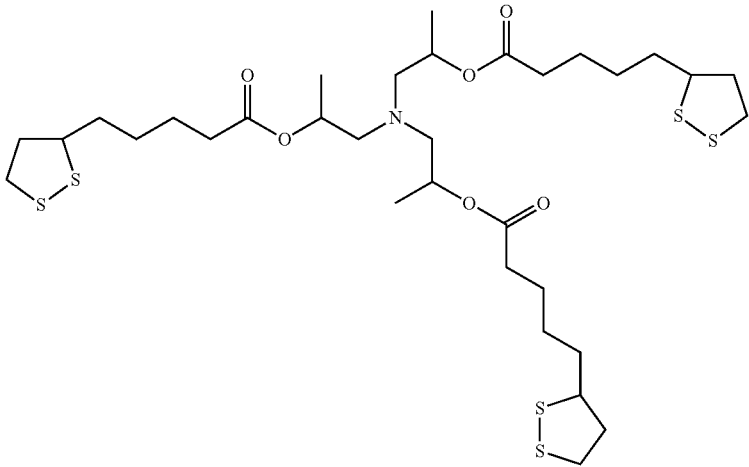 [SMILES: CC(CN(CC(C)OC(=O)CCCCC1CCSS1)CC(C)OC(=O)CCCCC1CCSS1)OC(=O)CCCCC1CCSS1] |

TABLE 12-continued

| Compound | Structure |
|---|---|
| 11a | 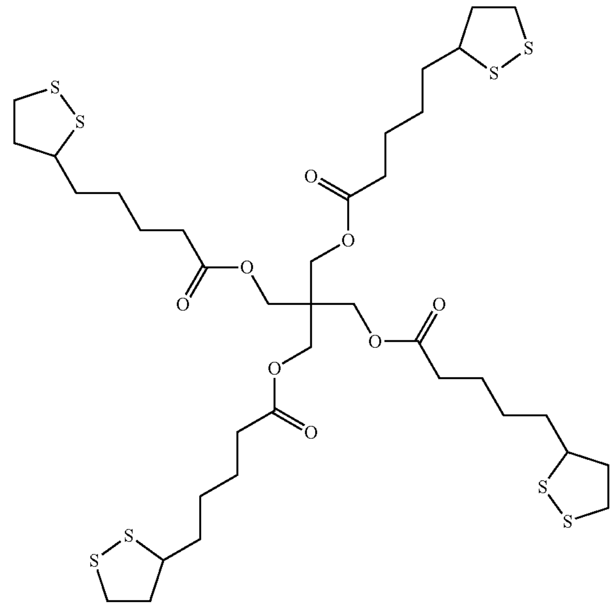 [SMILES: O=C(CCCCC1CCSS1)OCC(COC(=O)CCCCC1CCSS1)(COC(=O)CCCCC1CCSS1)COC(=O)CCCCC1CCSS1] |
| 12a | 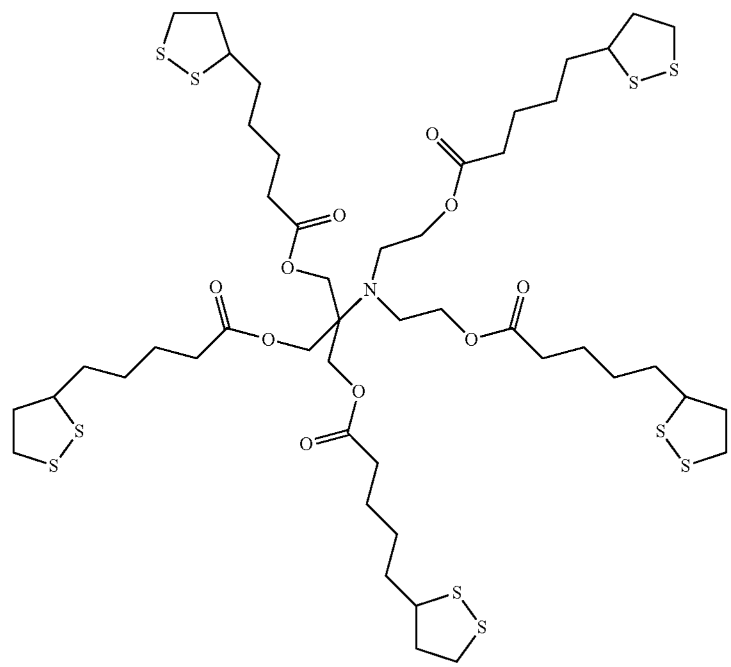 [SMILES: O=C(CCCCC1CCSS1)OCCN(CCOC(=O)CCCCC1CCSS1)C(COC(=O)CCCCC1CCSS1)(COC(=O)CCCCC1CCSS1)COC(=O)CCCCC1CCSS1] |
| 13a | 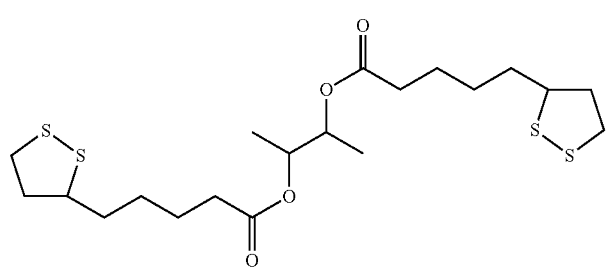 [SMILES: CC(OC(=O)CCCCC1CCSS1)C(C)OC(=O)CCCCC1CCSS1] |

TABLE 12-continued

| Compound | Structure |
| --- | --- |
| 14a | 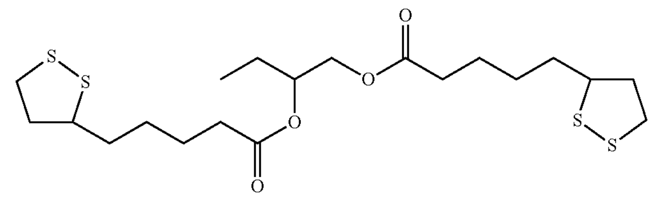 [SMILES: CCC(COC(=O)CCCCC1CCSS1)OC(=O)CCCCC1CCSS1] |
| 15a | 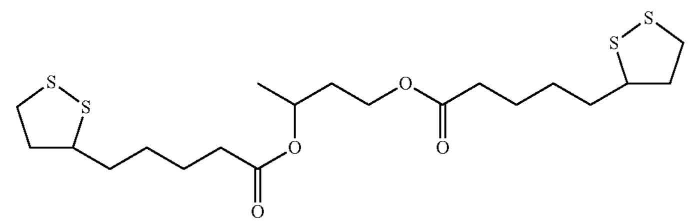 [SMILES: CC(CCOC(=O)CCCCC1CCSS1)OC(=O)CCCCC1CCSS1] |
| 16a | 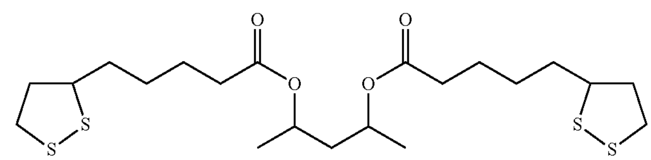 [SMILES: CC(CC(C)OC(=O)CCCCC1CCSS1)OC(=O)CCCCC1CCSS1] |
| 17a | 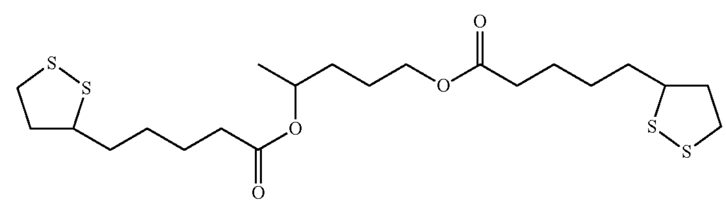 [SMILES: CC(CCCOC(=O)CCCCC1CCSS1)OC(=O)CCCCC1CCSS1] |
| 18a | 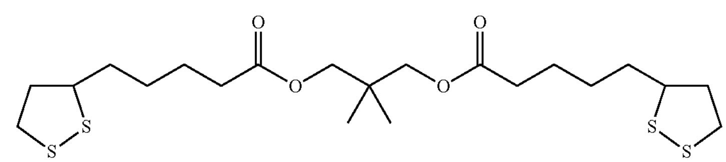 [SMILES: CC(C)(COC(=O)CCCCC1CCSS1)COC(=O)CCCCC1CCSS1] |
| 19a | 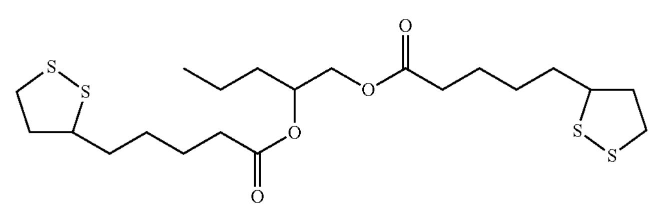 [SMILES: CCCC(COC(=O)CCCCC1CCSS1)OC(=O)CCCCC1CCSS1] |
| 20a | 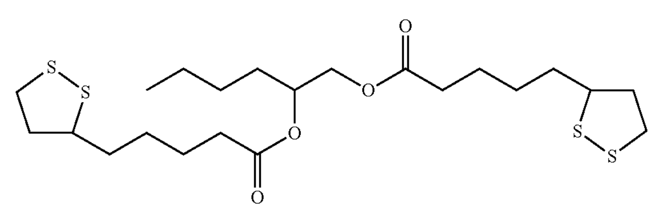 [SMILES: CCCCC(COC(=O)CCCCC1CCSS1)OC(=O)CCCCC1CCSS1] |

TABLE 12-continued
| Compound | Structure |
|---|---|
| 21a | 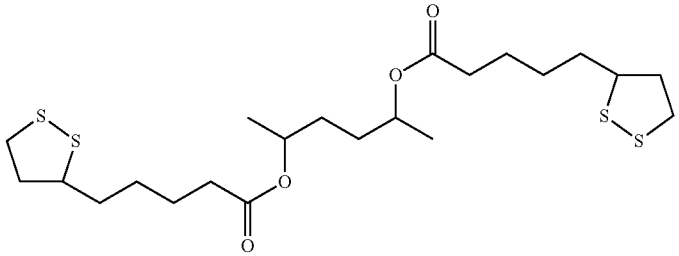 [SMILES: CC(CCC(C)OC(=O)CCCCC1CCSS1)OC(=O)CCCCC1CCSS1] |
| 22a | 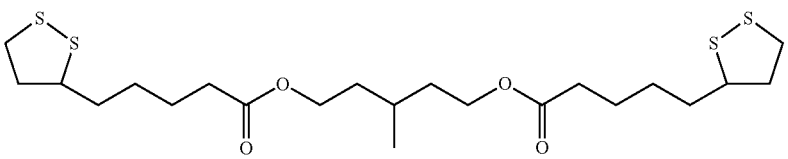 [SMILES: CC(CCOC(=O)CCCCC1CCSS1)CCOC(=O)CCCCC1CCSS1] |
| 23a | 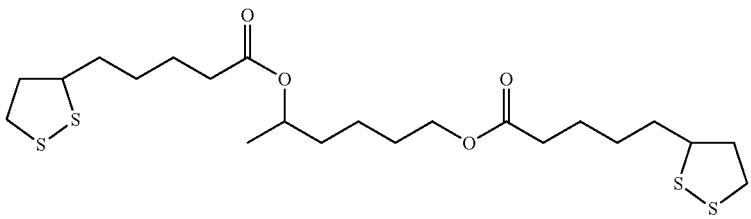 [SMILES: CC(CCCCOC(=O)CCCCC1CCSS1)OC(=O)CCCCC1CCSS1] |
| 24a | 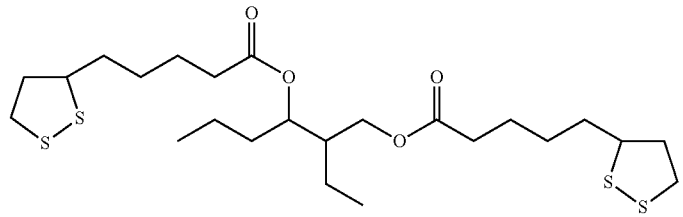 [SMILES: CCCC(OC(=O)CCCCC1CCSS1)C(CC)COC(=O)CCCCC1CCSS1] |
| 25a | 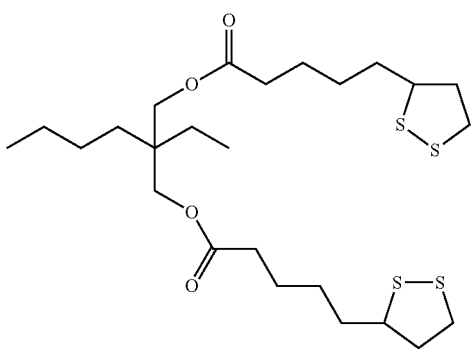 [SMILES: CCCCC(CC)(COC(=O)CCCCC1CCSS1)COC(=O)CCCCC1CCSS1] |

TABLE 12-continued

| Compound | Structure |
|---|---|
| 26a | 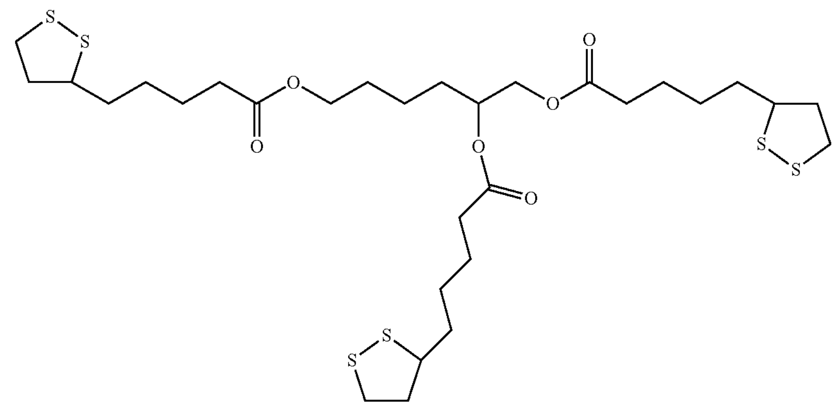 [SMILES: O=C(CCCCC1CCSS1)OCCCCC(COC(=O)CCCCC1CCSS1)OC(=O)CCCCC1CCSS1] |
| 27a | 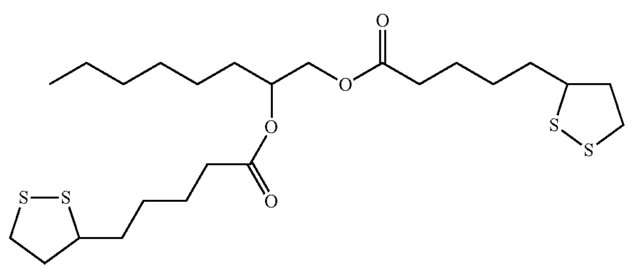 [SMILES: CCCCCCC(COC(=O)CCCCC1CCSS1)OC(=O)CCCCC1CCSS1] |
| 28a | 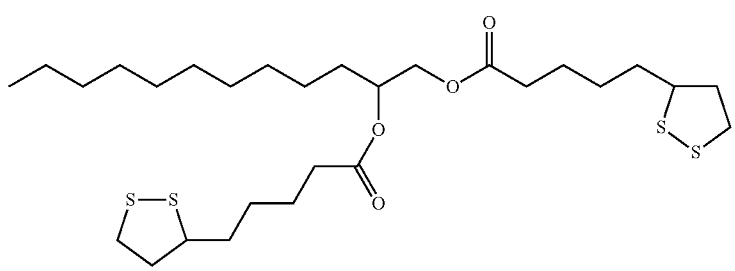 [SMILES: CCCCCCCCCCC(COC(=O)CCCCC1CCSS1)OC(=O)CCCCC1CCSS1] |
| 29a | 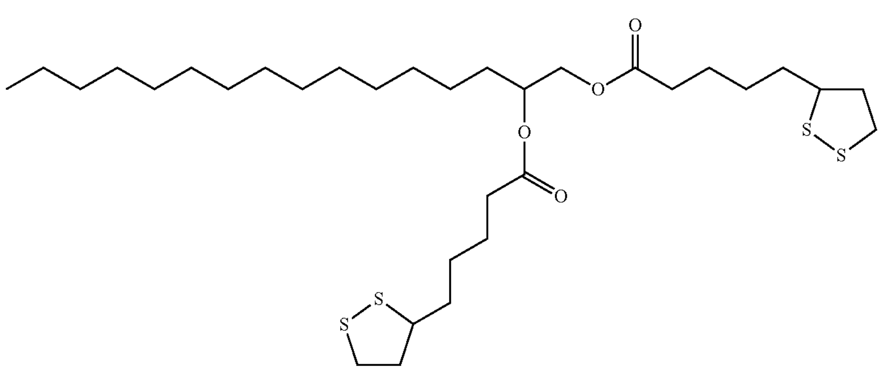 [SMILES: CCCCCCCCCCCCCCC(COC(=O)CCCCC1CCSS1)OC(=O)CCCCC1CCSS1] |

TABLE 12-continued
| Compound | Structure |
|---|---|
| 30a | 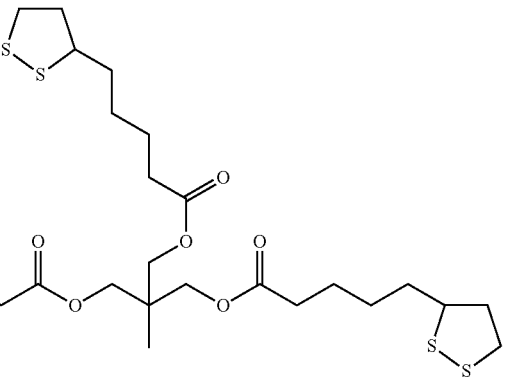 |
| 31a | 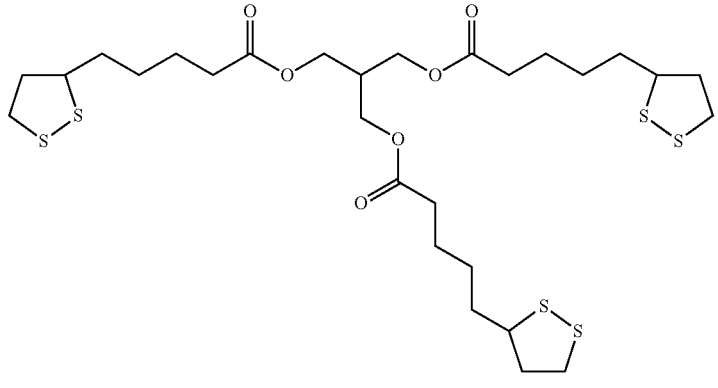 [SMILES: O=C(CCCCC1CCSS1)OCC(COC(=O)CCCCC1CCSS1)COC(=O)CCCCC1CCSS1] |
| 32a | 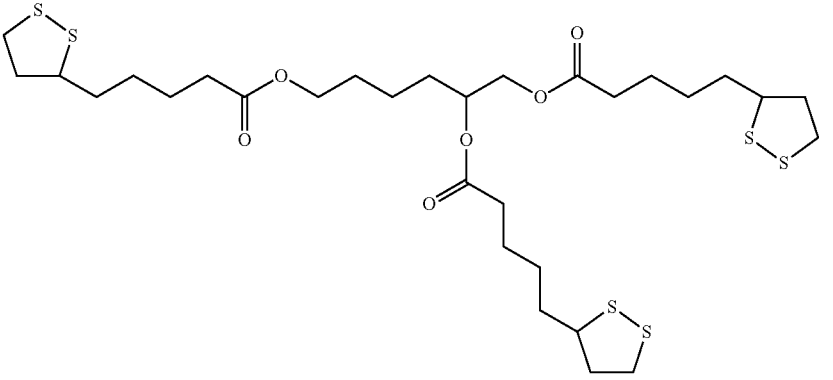 [SMILES: O=C(CCCCC1CCSS1)OCCCCC(COC(=O)CCCCC1CCSS1)OC(=O)CCCCC1CCSS1] |

TABLE 12-continued

| Compound | Structure |
|---|---|
| 33a | 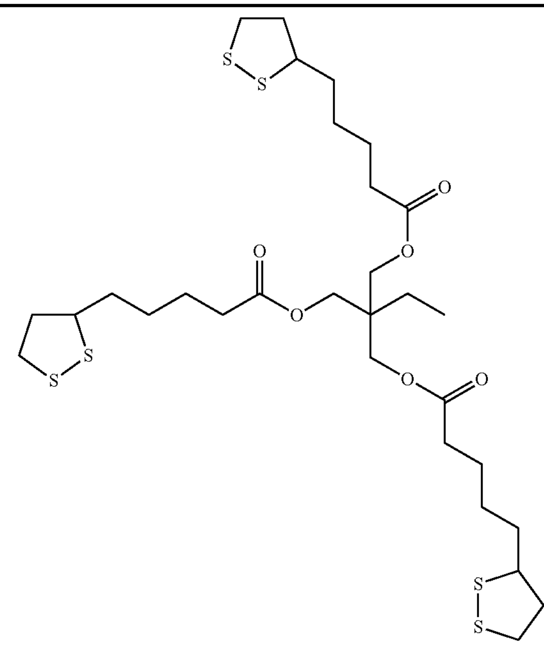 |
| 34a | 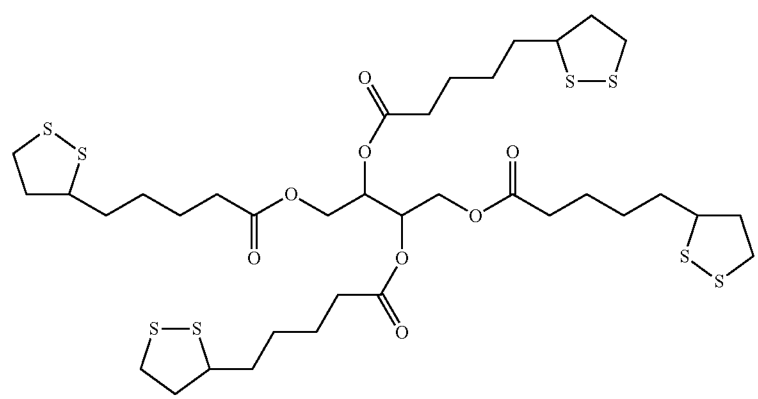 [SMILES: O=C(CCCCC1CCSS1)OCC(OC(=O)CCCCC1CCSS1)C(COC(=O)CCCCC1CCSS1)OC(=O)CCCCC1CCSS1] |
| 35a | 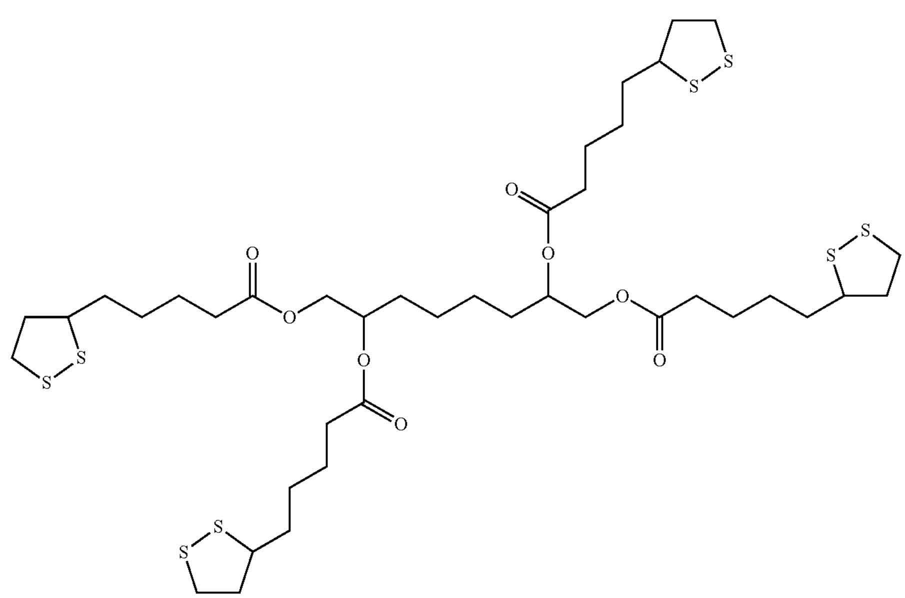 [SMILES: O=C(CCCCC1CCSS1)OCC(CCCCC(COC(=O)CCCCC1CCSS1)OC(=O)CCCCC1CCSS1)OC(=O)CCCCC1CCSS1] |

TABLE 12-continued
| Compound | Structure |
|---|---|
| 36a | 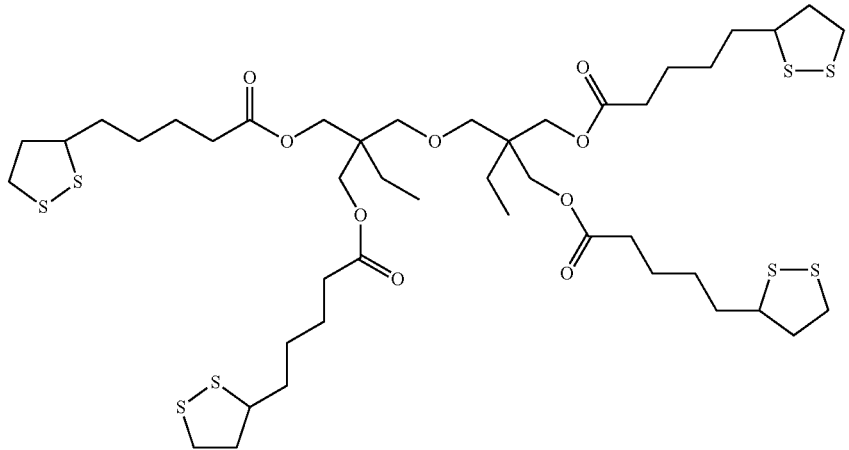 [SMILES: CCC(COCC(CC)(COC(=O)CCCCC1CCSS1)COC(=O)CCCCC1CCSS1)(COC(=O)CCCCC1CCSS1)COC(=O)CCCCC1CCSS1] |
| 37a | 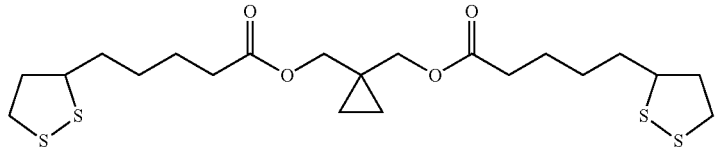 [SMILES: O=C(CCCCC1CCSS1)OCC1(COC(=O)CCCCC2CCSS2)CC1] |
| 38a | 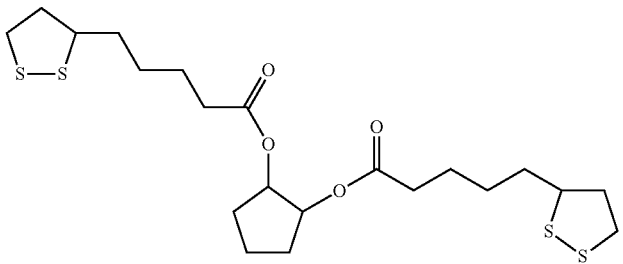 [SMILES: O=C(CCCCC1CCSS1)OC1CCCC1OC(=O)CCCCC1CCSS1] |
| 39a | 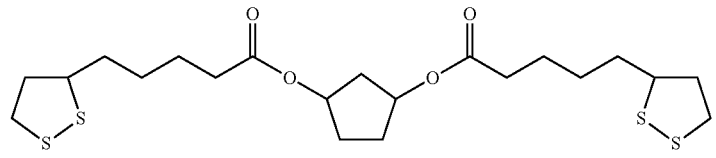 [SMILES: O=C(CCCCC1CCSS1)OC1CCC(OC(=O)CCCCC2CCSS2)C1] |
| 40a | 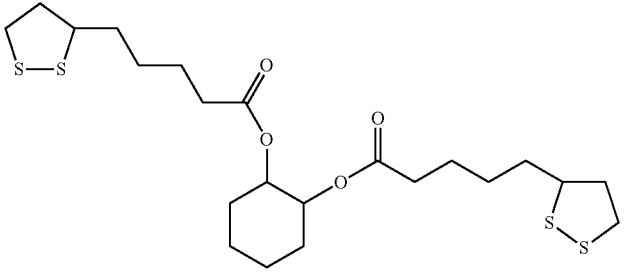 [SMILES: O=C(CCCCC1CCSS1)OC1CCCCC1OC(=O)CCCCC1CCSS1] |
| 41a | 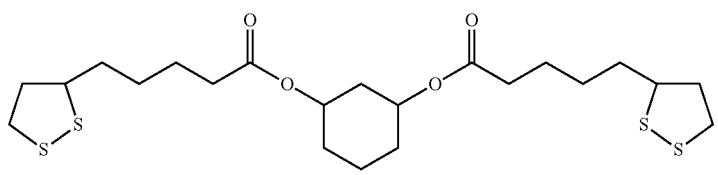 [SMILES: O=C(CCCCC1CCSS1)OC1CCCC(OC(=O)CCCCC2CCSS2)C1] |

TABLE 12-continued

| Compound | Structure |
| --- | --- |
| 42a | 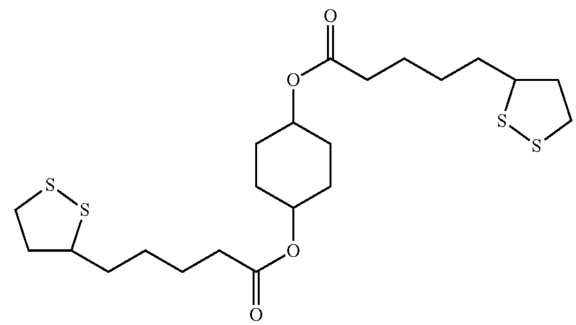 [SMILES: O=C(CCCCC1CCSS1)OC1CCC(OC(=O)CCCCC2CCSS2)CC1] |
| 43a | 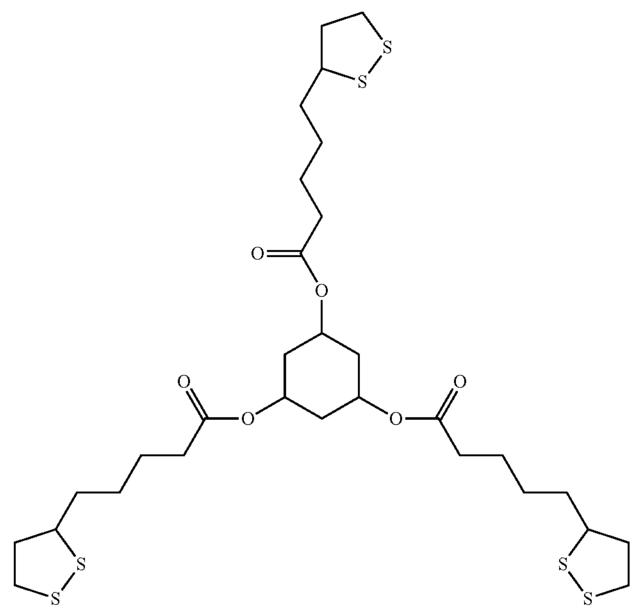 [SMILES: O=C(CCCCC1CCSS1)OC1CC(OC(=O)CCCCC2CCSS2)CC(OC(=O)CCCCC2CCSS2)C1] |
| 44a | 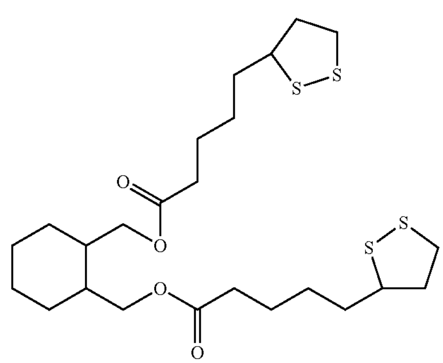 [SMILES: O=C(CCCCC1CCSS1)OCC1CCCCC1COC(=O)CCCCC1CCSS1] |
| 45a | 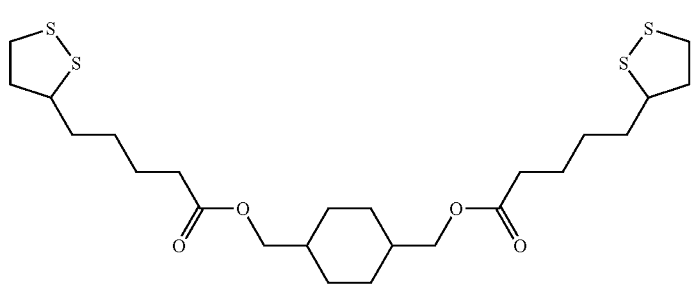 [SMILES: O=C(CCCCC1CCSS1)OCC1CCC(COC(=O)CCCCC2CCSS2)CC1] |

TABLE 12-continued

| Compound | Structure |
|---|---|
| 46a | 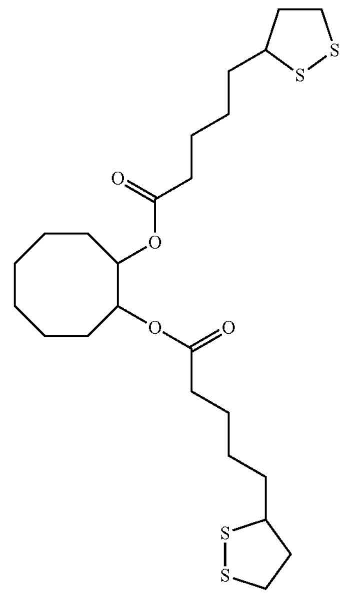 [SMILES: O=C(CCCCC1CCSS1)OC1CCCCCCC1OC(=O)CCCCC1CCSS1] |
| 47a | 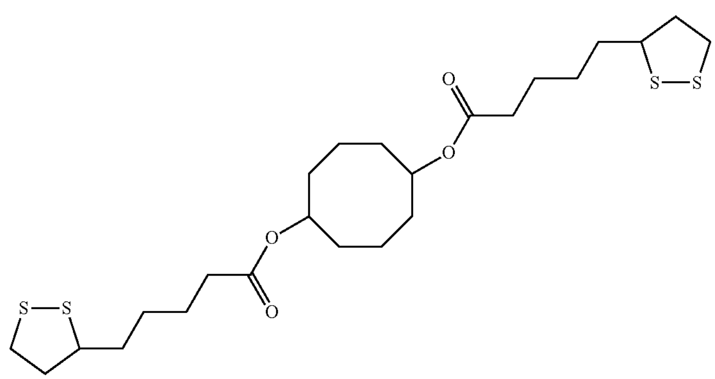 [SMILES: O=C(CCCCC1CCSS1)OC1CCCC(OC(=O)CCCCC2CCSS2)CCC1] |
| 48a | 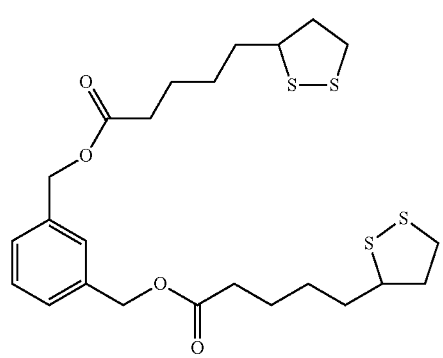 [SMILES: O=C(CCCCC1CCSS1)OCc1cccc(COC(=O)CCCCC2CCSS2)c1] |

TABLE 12-continued

| Compound | Structure |
| --- | --- |
| 49a | 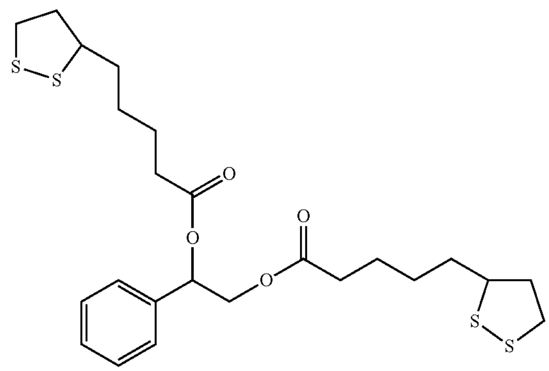 [SMILES: O=C(CCCCC1CCSS1)OCC(OC(=O)CCCCC1CCSS1)c1ccccc1] |
| 50a | 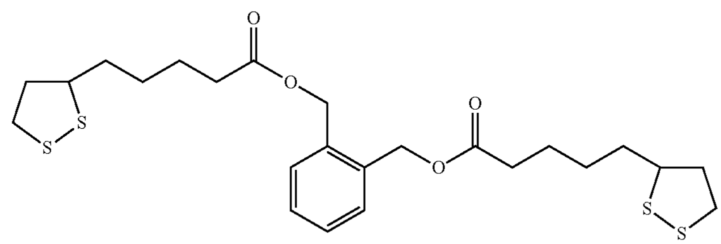 [SMILES: O=C(CCCCC1CCSS1)OCc1ccccc1COC(=O)CCCCC1CCSS1] |
| 51a | 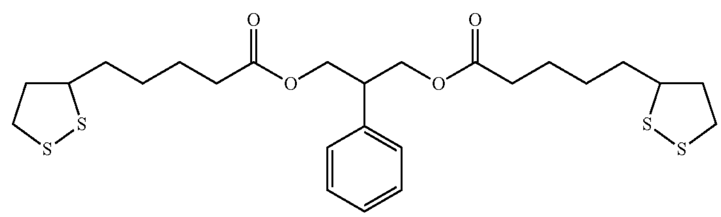 [SMILES: O=C(CCCCC1CCSS1)OCC(COC(=O)CCCCC1CCSS1)c1ccccc1] |
| 52a | 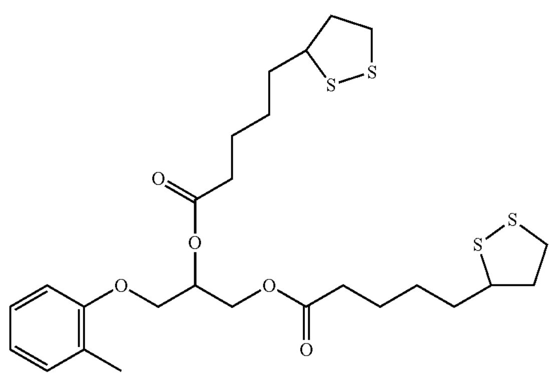 [SMILES: Cc1ccccc1OCC(COC(=O)CCCCC1CCSS1)OC(=O)CCCCC1CCSS1] |
| 53a | 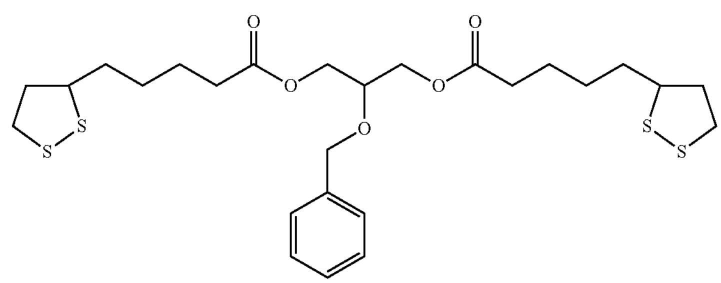 [SMILES: O=C(CCCCC1CCSS1)OCC(COC(=O)CCCCC1CCSS1)OCc1ccccc1] |

TABLE 12-continued

| Compound | Structure |
| --- | --- |
| 54a | 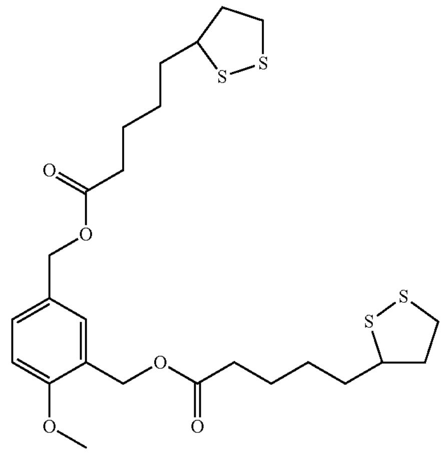 [SMILES: COc1ccc(COC(=O)CCCCC2CCSS2)cc1COC(=O)CCCCC1CCSS1] |
| 55a | 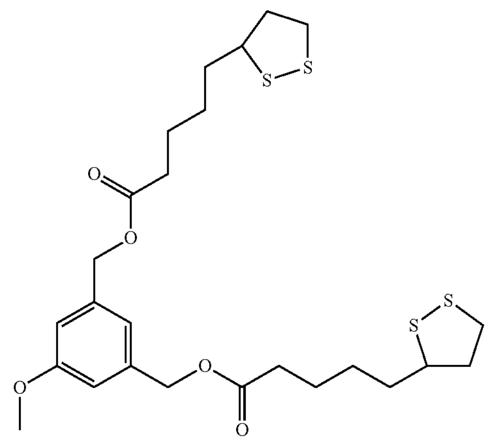 [SMILES: COc1cc(COC(=O)CCCCC2CCSS2)cc(COC(=O)CCCCC2CCSS2)c1] |
| 56a | 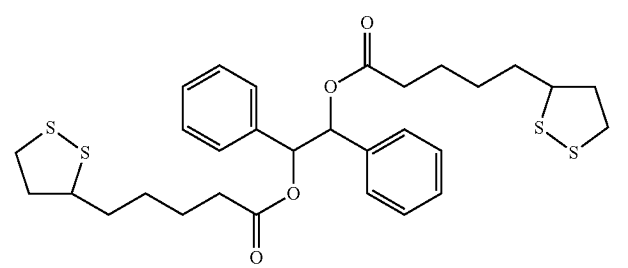 [SMILES: O=C(CCCCC1CCSS1)OC(c1ccccc1)C(OC(=O)CCCCC1CCSS1)c1ccccc1] |
| 57a | 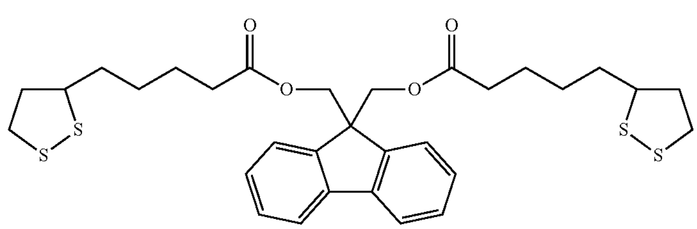 [SMILES: O=C(CCCCC1CCSS1)OCC1(COC(=O)CCCCC2CCSS2)c2ccccc2-c2ccccc21] |
| 58a | 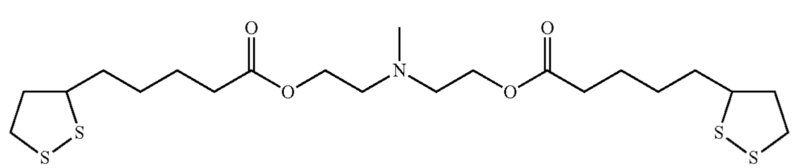 [SMILES: CN(CCOC(=O)CCCCC1CCSS1)CCOC(=O)CCCCC1CCSS1] |

TABLE 12-continued

| Compound | Structure |
| --- | --- |
| 59a | 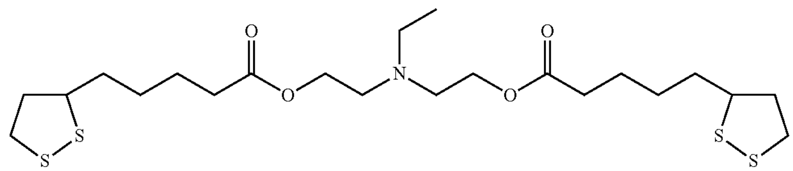 [SMILES: CCN(CCOC(=O)CCCCC1CCSS1)CCOC(=O)CCCCC1CCSS1] |
| 60a | 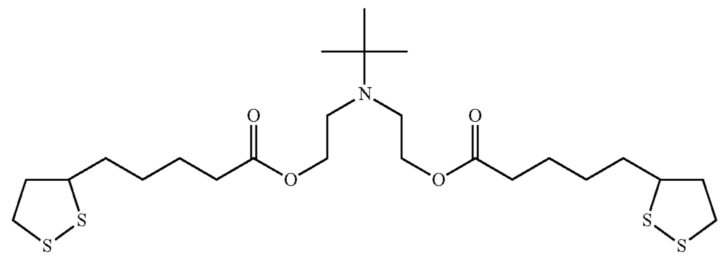 [SMILES: CC(C)(C)N(CCOC(=O)CCCCC1CCSS1)CCOC(=O)CCCCC1CCSS1] |
| 61a | 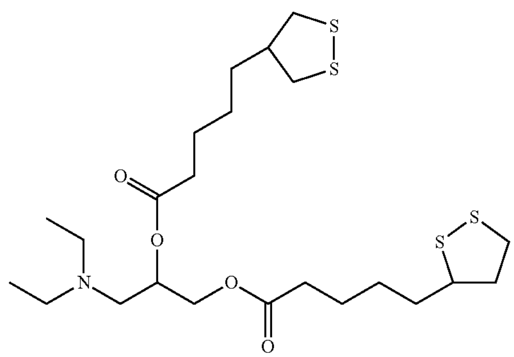 [SMILES: CCN(CC)CC(COC(=O)CCCCC1CCSS1)OC(=O)CCCCC1CSSC1] |
| 62a | 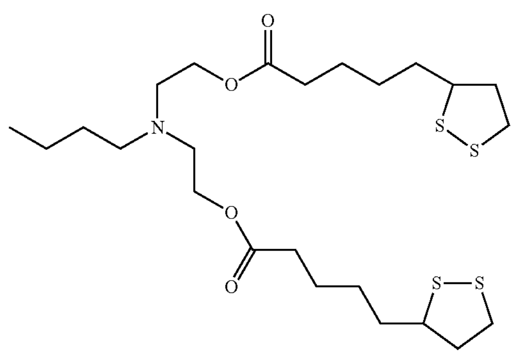 [SMILES: CCCCN(CCOC(=O)CCCCC1CCSS1)CCOC(=O)CCCCC1CCSS1] |
| 63a | 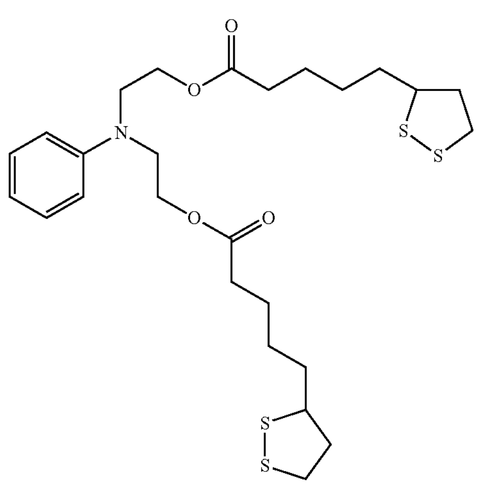 [SMILES: O=C(CCCCC1CCSS1)OCCN(CCOC(=O)CCCCC1CCSS1)c1ccccc1] |

TABLE 12-continued

| Compound | Structure |
|---|---|
| 64a | 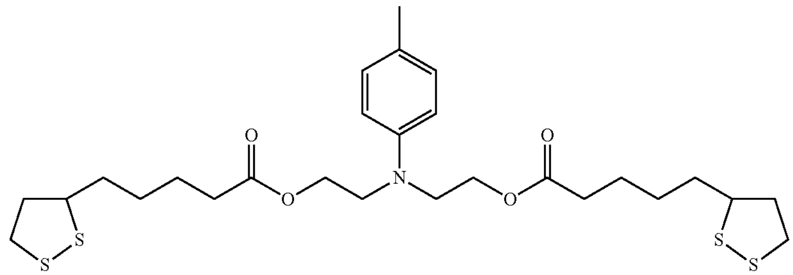 [SMILES: Cc1ccc(N(CCOC(=O)CCCCC2CCSS2)CCOC(=O)CCCCC2CCSS2)cc1] |
| 65a | 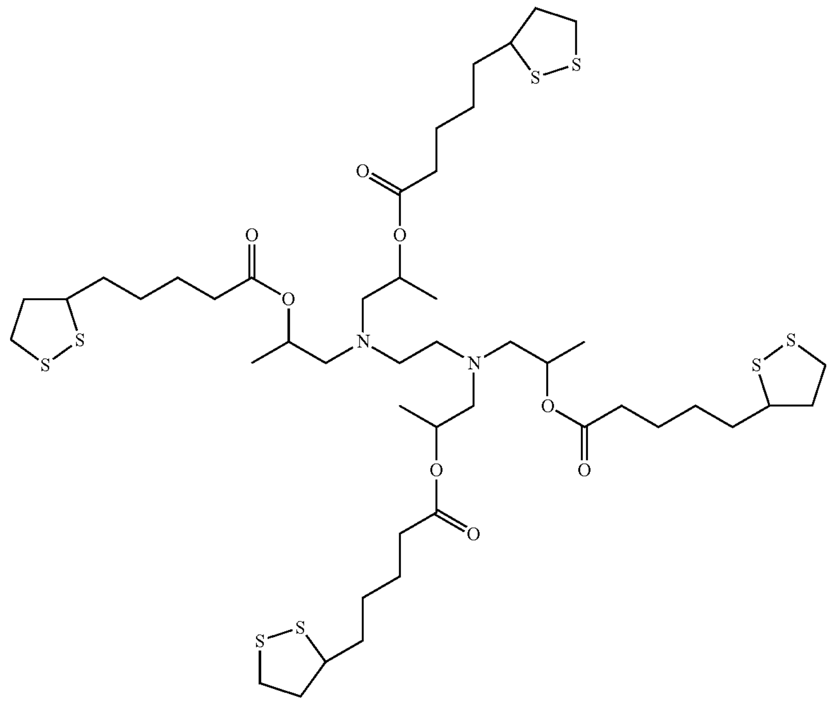 [SMILES: CC(CN(CCN(CC(C)OC(=O)CCCCC1CCSS1)CC(C)OC(=O)CCCCC1CCSS1)CC(C)OC(=O)CCCCC1CCSS1)OC(=O)CCCCC1CCSS1] |

The present invention also provides for methods of producing the antioxidant molecules of the present invention. The method comprises providing at least two [1,2]-dithiolane moieties; providing a polyol; and reacting the at least two [1,2]-dithiolane moieties with the polyol to produce the antioxidant molecule. In one embodiment, the [1,2]-dithiolane moieties may be α-lipoic acid molecules. In particular embodiments, the polyol may be selected from compounds 1-65 as described above. Thus, in specific embodiments, the method produces antioxidant molecules (compounds 1a-65a) as described above.

The present invention also provides an antioxidant nanosphere, which comprises the antioxidant molecules of the present invention.

The present invention further provides a method of producing the antioxidant nanosphere. In one embodiment, the antioxidant nanosphere is prepared by spontaneous emulsification (Bouchemal, K. et al., SYNTHESIS AND CHARACTERIZATION OF POLYURETHANE AND POLY(ETHER URETHANE) NANOCAPSULES USING A NEW TECHNIQUE OF INTERFACIAL POLYCONDENSATION COMBINED TO SPONTANEOUS EMULSIFICATION. *Int. J. Pharm.* 269, 89-100 (2004); Bouchemal, K. et al., NANO-EMULSION FORMULATION USING SPONTANEOUS EMULSIFICATION: SOLVENT, OIL AND SURFACTANT OPTIMISATION. *Int. J. Pharm.* 280, 241-251 (2004); Fessi, H. et al., NANOCAPSULE FORMATION BY INTERFACIAL POLYMER DEPOSITION FOLLOWING SOLVENT DISPLACEMENT. *Int. J. Pharm.* 55, R1-R4 (1989); each of which is incorporated herein by references though fully set forth.)

The method of spontaneous emulsification may comprise providing a quantity of antioxidant molecules of the present invention; dissolving the quantity of antioxidant molecules in an organic solvent to produced an organic solution, stirring the organic solution into an aqueous phase comprising a quantity of poloxamers (e.g., Pluronic F68); removing the organic solvent to produce a nanosphere; and filtering the nanosphere. The method of spontaneous emulsification may further comprise purifying the nanosphere. In one embodiment the organic solvent may be acetone.

The antioxidant molecules and nanospheres of the present invention are capable of acting as scavengers of free radicals. The antioxidant molecules and nanospheres of the present invention are also capable of serving as a vehicle for the delivery of pharmaceutical and biological therapies. Additionally, the antioxidant molecules and nanospheres of the present invention are also capable of enhancing the cytotoxicity of an antineoplastic drug. Accordingly, additional embodiments of the present invention provide for methods of using the antioxidant molecules and nanospheres of the present invention.

In one embodiment, the antioxidant molecules and nanospheres are used for treating diseases or disease conditions that are caused by oxidative stress or other free radical mediated diseases or disease conditions. The method comprises providing a composition comprising an antioxidant molecule or nanosphere of the present invention and administering a therapeutically effective amount of the composition a subject in need of treatment. In a further embodiment, the composition comprises a dermatologically acceptable carrier.

In one particular embodiment, the antioxidant molecules and nanospheres are used to treat inflammation of the skin mediated by free radicals. The method comprises providing a composition comprising an antioxidant molecule or nanosphere of the present invention and administering a therapeutically effective amount of the composition to areas of the skin in need of treatment. In a further embodiment, the composition comprises a dermatologically acceptable carrier.

In another particular embodiment, the antioxidant molecules and nanospheres are used to treat skin aging that is mediated by free radicals. The method comprises providing a composition comprising an antioxidant molecule or nanospheres of the present invention and administering a therapeutically effective amount of the composition to areas of the skin in need of treatment. In a further embodiment, the composition comprises a dermatologically acceptable carrier.

In another embodiment, the antioxidant molecules and nanospheres are used to prepare antioxidant particulate delivery vehicles for therapeutic agents. The therapeutic agents may be delivered to tissues, organs, cells, and the like.

Thus, the present invention also provides for a delivery vehicle composition comprising an antioxidant molecule or nanosphere of the present invention and a therapeutic agent. The present invention further provides a method to deliver the therapeutic agent to a location in or on the body (e.g., tissue, organ, cell). The method comprises providing a composition comprising an antioxidant molecule or nanospheres of the present invention and a therapeutic agent; and administering the composition to a subject in need of treatment.

In one particular embodiment, the antioxidant molecules and nanospheres are used as a gene delivery vehicle to carry and deliver genetic molecules to a subject. The genetic molecule may be DNA, RNA, oligonucleotide, polynucleotide and the like. Thus, an embodiment of the present invention provides for a genetic molecule delivery vehicle composition comprising an antioxidant molecule or nanosphere of the present invention and a genetic molecule. In another embodiment, the present invention provides a method of delivering a genetic molecule to a subject in need thereof, comprising providing a composition comprising an antioxidant molecule or nanosphere of the present invention and a genetic molecule; and administering the composition to a subject in need of treatment.

In another particular embodiment, the antioxidant molecules and nanospheres may be used as a carrier for peptides or proteins; for example, for antigens used in vaccination therapies. Thus, an embodiment of the present invention provides for a peptide or protein delivery vehicle composition comprising an antioxidant molecule or nanosphere of the present invention and a peptide or protein. In another embodiment, the present invention provides a method of delivering a peptide or protein to a subject in need thereof, comprising providing a composition comprising an antioxidant molecule or nanosphere of the present invention and a peptide or protein; and administering the composition to a subject in need of treatment. In one particular embodiment, the peptide is an antigen.

In another embodiment, the antioxidant nanospheres may be used as a carrier of a therapeutic agent. In one embodiment, the therapeutic agent is a small molecule or a chemotherapeutic agent, which may be useful for cancer treatment. Thus, an embodiment of the present invention provides for a carrier composition comprising an antioxidant molecule of the present invention and a therapeutic agent.

It has been discovered that antioxidants induce cell cycle arrest, and are thus useful to enhance the efficacy of antineoplastic drugs for the treatment of abnormal cell proliferation. It has been also discovered that antioxidants not only increase the cytotoxicity of antineoplastic agents to abnormally proliferating cells, but they also decrease the toxicity of antineoplastic agents to normal cells. Therefore, the present invention also provides a method to increase the cytotoxicity of an antineoplastic agent to abnormally proliferating cells and/or to decrease the toxicity of antineoplastic agents to normal cells. The method comprises administering the antioxidant molecule or antioxidant nanosphere of the present invention prior to, with, or following the antineoplastic treatment.

In one embodiment, the method comprises providing a composition comprising an antioxidant molecule or nanosphere of the present invention and an antineoplastic drug; and administering a therapeutically effective amount of the composition to a subject in need of treatment. In another embodiment, the method comprises providing a composition comprising an antioxidant molecule or a nanosphere of the present invention; administering a therapeutically effective amount of the antineoplastic drug to a subject in need of the treatment; and administering a therapeutically effective amount of the composition to the subject. Antineoplastic drugs are known to one skilled in the art. Examples include but are not limited to, paclitaxel, camptothecin and temozolomide. Antineoplastic that are hydrophobic and lipophilic can also be used in accordance with embodiments of the present invention.

In various embodiments, the present invention provides pharmaceutical compositions of the present invention including a pharmaceutically acceptable excipient along with a therapeutically effective amount of an antioxidant molecule or nanosphere of the present invention. In one embodiment, the pharmaceutical composition further comprises a therapeutic agent as described herein. "Pharmaceutically acceptable excipient" means an excipient that is useful in preparing a pharmaceutical composition that is generally safe, nontoxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

A general scheme for the synthesis of the multiple α-lipoic acid-containing hydrophobic compounds and preparation of the antioxidant nanospheres are described herein. The synthetic procedure is both simple and versatile and leads to the synthesis of the multiple ALA-containing compounds varying in size and hydrophobicity. The nanospheres showed remarkable physical and chemical stability over a two week period of incubation at 37° C. The antioxidant activity of the nanospheres has been demonstrated by HOCl scavenging assay. Upon HOCl scavenging, the nanospheres were converted into a transparent solution. These findings support the application of the nanospheres as a ROS-responsive controlled release system.

The nanospheres prepared from the mixture of the multiple α-lipoic acid-containing compounds and α-tocopherol showed unique radical scavenging capability in the aqueous phase, against particulate DPPH free radical, and their effect far exceeds those of nanosphere prepared from α-tocopherol, ascorbic acid, and/or Trolox. For applications where antioxidants are needed to neutralize particulate and/or water-insoluble oxidants in an aqueous environment, the antioxidant nanospheres of the present invention offer a unique opportunity.

The nanospheres and molecules containing [1,2]-dithiolane moieties (e.g., multiple α-lipoic acid containing hydrophobic compounds) may be useful for such treatments. The nanospheres and molecules containing [1,2]-dithiolane moieties may be useful to treat or delay the onset of conditions and disease conditions caused by oxidative damage (e.g., skin aging, wrinkle formation), for the protection of skin from damage caused by ultraviolet radiation and dessication, and for cancer therapy.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

General Procedures and Materials

Unless otherwise noted, solvents and chemicals were obtained as highest purity from Sigma-Aldrich Chemical Co. (St Louis, Mo., USA) and used without further preparation. $\alpha_1$-Antiproteinase ($\alpha_1$-AP, code A9024) and elastase (code E6883) were obtained from Sigma-Aldrich Chemical Co. Chromatographic purification of all newly synthesized compounds was performed using silica gel (60 Å, 200-400 mesh). The compounds were analyzed by thin layer chromatography (TLC): silicagel plates (Merck 60 F254); compounds were visualized by irritation by treatment with a solution of 1.5 g of KMnO$_4$, 10 g K$_2$CO$_3$, and 1.25 mL 10% NaOH in 200 mL of H$_2$O, followed by gentle heating. $^1$H and $^{13}$C NMR spectra were conducted on a Varian 400 MHz spectrometer and chemical shifts (δ) are given in ppm relative to TMS. The spectra were recorded in CDCl$_3$ as solvent at room temperature. HPLC analysis was performed on Merck-Hitachi analytical LaChrom D-7000 HPLC/UV detector system with CAPCELL PAK, Type SG 120 (phenomenex) C$_{18}$ reversed phase column (250/4.6 mm, 5 μm).

Example 2

Synthesis of Compounds 1a-12a

α-Lipoic acid (2.48 g, 12 mmol, 1.2 equiv.) and the core compounds 1-12 containing two to five hydroxyl groups (10 mmol OH, 1.0 equiv.) in 20 mL of anhydrous dichloromethane (DCM) were reacted with 4-(dimethylamino)-pyridine (DMAP, 1.47 g, 12 mmol, 1.2 equiv.) in the presence of molecular sieve (60 Å, 10-20 mesh beads) for 10 min at room temperature. N-(3-Dimethylaminopropyl)-N-ethylcarbodiimide hydrochloride (EDCl, 2.3 g, 12 mmol, 1.2 equiv.) was added portion wise over 10 min and the reaction mixture was stirred for 12 h at room temperature in the dark, filtered, and then concentrated under vacuum to reduce the volume. The resulting reaction mixture was purified using silica gel by direct loading onto the column without further preparation. The solvent was removed under reduced pressure to give the products. The same procedure was used for the synthesis of the compounds 1a-12a (See Scheme 1). $^1$H NMR and $^{13}$C NMR spectra of compounds 1a-12a are provided.

2×Lipoic Acid/Ethylene Glycol: Compound 1a

The column chromatography on silica gel (CHCl$_3$/MeOH 90:1) gave the compound 1a as a yellow oil (1.6 g, 73%). TLC (CHCl$_3$) R$_f$ 0.34; $^1$H NMR (400 MHz, CDCl$_3$): δ=1.46 (m, 4H, 2×Ha), 1.67 (m, 8H, 2×Hb), 1.92 (m, 2H, 2×Hc), 2.35 (t, J=7.5 Hz, 4H, 2×Hd), 2.46 (m, 2H, 2×He), 3.14 (m, 4H, 2×Hf+Hg), 3.56 (m, 2H, 2×Hh), 4.23 (s, 4H, O—CH$_2$—CH$_2$—O). $^{13}$C NMR (100 MHz, CDCl$_3$): δ=24.6, 28.7, 33.9, 34.6, 38.5, 40.2, 56.3, 62.1, 173.2.

2×Lipoic Acid/Diethylene Glycol: Compound 2a

The column chromatography on silica gel (CHCl$_3$/MeOH 90:1) gave the compound 2a as a yellow oil (1.5 g, 62%). TLC (CHCl$_3$/MeOH 100:0.5) R$_f$ 0.65; $^1$H NMR (400 MHz, CDCl$_3$): δ=1.46 (m, 4H, 2×Ha), 1.67 (m, 8H, 2×Hb), 1.91 (m, 2H, 2×Hc), 2.36 (t, J=7.5 Hz, 4H, 2×Hd), 2.46 (m, 2H, 2×He), 3.14 (m, 4H, 2×Hf+Hg), 3.57 (m, 2H, 2×Hh), 3.70 (t, J=4.8 Hz, 4H, O—CH$_2$—O—CH$_2$—O). 4.23 (t. J=4.8 Hz, 4H, 2×CO—O—CH$_2$—). $^{13}$C NMR (100 MHz, CDCl$_3$): δ=24.6, 28.7, 33.9, 34.6, 38.5, 40.2, 56.3, 63.3, 69.0, 173.3.

2×Lipoic Acid/Triethylene Glycol: Compound 3a

The column chromatography on silica gel (CHCl$_3$/MeOH 90:1) gave the compound 3a as a yellow oil (1.75 g, 66%). TLC (CHCl$_3$/MeOH 100:0.5) R$_f$ 0.32; $^1$H NMR (400 MHz, CDCl$_3$): δ=1.46 (m, 4H, 2×Ha), 1.68 (m, 8H, 2×Hb), 1.91 (m, 2H, 2×Hc), 2.35 (t, J=7.5 Hz, 4H. 2×Hd), 2.46 (m, 2H, 2×He), 3.16 (m, 4H, 2×Hf+Hg), 3.57 (m, 2H, 2×Hh), 3.66 (s, 4H, O—CH$_2$—CH$_2$—O), 3.70 (t, J=4.8 Hz, 4H, 2×O—CH$_2$—CH$_2$—OCO), 4.23 (t, J=4.8 Hz, 4H, 2×CO—O—CH$_2$—). $^{13}$C NMR (100 MHz, CDCl$_3$): δ=24.6, 28.7, 33.9, 34.6, 38.5, 40.2, 56.3, 63.4, 69.2, 70.5, 173.4.

2×Lipoic Acid/Tetraethylene Glycol: Compound 4a

The column chromatography on silica gel (CHCl$_3$/MeOH 90:1) gave the compound 4a as a yellow oil (2.1 g, 74%). TLC (CHCl$_3$/MeOH 100:0.5) R$_f$ 0.24; $^1$H NMR (400 MHz, CDCl$_3$): δ=1.48 (m, 4H, 2×Ha), 1.67 (m, 8H, 2×Hb), 1.92 (m, 2H, 2×Hc), 2.35 (t, J=7.5 Hz, 4H, 2×Hd),), 2.45 (m, 2H, 2×He), 3.11 (m, 4H, 2×Hf+Hg), 3.55 (m, 2H, 2×Hh), 3.66 (s, 8H, 2×O—CH$_2$—CH$_2$—), 3.69 (t, J=4.8 Hz, 4H, CO—O—CH$_2$—CH$_2$—O), 4.22 (t, J=4.8 Hz, 4H, CO—O—CH$_2$). $^{13}$C NMR (100 MHz, CDCl$_3$): δ=24.6, 28.7, 33.9, 34.5, 38.5, 40.2, 56.3, 63.4, 69.1, 70.5, 70.6, 173.4.

2×Lipoic Acid/1,6-Hexanediol: Compound 5a

The column chromatography on silica gel (CHCl$_3$/MeOH 95:0.5) gave the compound 5a as a yellow oil (1.85 g, 75%). TLC (CHCl$_3$) R$_f$ 0.34; $^1$H NMR (400 MHz, CDCl$_3$): δ=1.38 (quintett, J=3.7 Hz, 4H, CH$_2$—CH$_2$—CH$_2$—CH$_2$), 1.46 (m, 4H, 2×Ha), 1.64 (m, 4H, 2×CH$_2$—CH$_2$—OCO), 1.68 (m, 8H, 2×Hb), 1.92 (m, 2H, 2×Hc), 2.32 (t, J=7.5 Hz, 4H, 2×Hd), 2.46 (m, 2H, 2×He), 3.15 (m, 4H, 2×Hf+Hg), 3.57 (m, 2H, 2×Hh), 4.07 (t, J=6.7 Hz, 4H, 2×CO—O—CH$_2$—). $^{13}$C NMR (100 MHz, CDCl$_3$): δ=24.6, 25.6, 28.5, 28.7, 34.1, 34.6, 38.5, 40.2, 56.3, 64.2, 173.5.

2×Lipoic Acid/1,4-Benzenedimethanol (BDM): Compound 6a

The column chromatography on silica gel (CHCl$_3$) gave compound 6a as a yellow oil (2.05 g, 80%). TLC (CHCl$_3$) R$_f$ 0.44; $^1$H NMR (400 MHz, CDCl$_3$): δ=1.47 (m, 4H, 2×Ha), 1.70 (m, 8H, 2×Hb), 1.89 (m, 2H, 2×Hc), 2.37 (t, J=7.5 Hz, 4H, 2×Hd), 2.44 (m, 2H, 2×He), 3.13 (m, 4H, 2×Hf+Hg), 3.55 (m, 2H, 2×Hh), 5.11 (s, 4H, 2×COO—CH$_2$—), 7.35 (s, 4H, aromat.) $^{13}$C NMR (100 MHz, CDCl$_3$): δ=24.6, 28.7, 34.0, 34.6, 38.5, 40.2, 56.3, 65.8, 128.4, 136.1, 173.2.

2×Lipoic acid/1,4-Bis(2-hydroxyethyl)-piperazine: Compound 7a

The column chromatography on silica gel (CHCl$_3$/MeOH 90:1) gave the compound 7a as a yellow oil (1.85 g, 67%). TLC (CHCl$_3$/MeOH 95:1) R$_f$ 0.48; $^1$H NMR (400 MHz, CDCl$_3$): δ=1.48 (m, 4H, 2×Ha), 1.66 (m, 8H, 2×Hb), 1.92 (m, 2H, 2×Hc), 2.33 (t, J=7.5 Hz, 4H, 2×Hd), 2.46 (m, 2H, 2×He), 3.15 (m, 4H, 2×Hf+Hg), 3.56 (m, 2H, 2×Hh), 2.53 (t, 8H, 2×N—CH$_2$—CH$_2$—N), 2.62 (t, 4H, N—CH$_2$—CH$_2$O), 4.19 (t, J=5.9 Hz, 4H, N—CH$_2$—CH$_2$O). $^{13}$C NMR (100 MHz, CDCl$_3$): δ=24.6, 28.7, 33.9, 34.5, 38.4, 40.2, 53.2, 56.3, 56.6, 61.6, 173.4.

3×Lipoic Acid/Glycerol: Compound 8a

The column chromatography on silica gel (CHCl$_3$/MeOH 95:0.5) gave the compound 8a as a yellow oil (1.76 g, 80%). TLC (CHCl$_3$) R$_f$ 0.20; $^1$H NMR (400 MHz, CDCl$_3$): δ=1.41 (m, 6H, 3×Ha), 1.61 (m, 12H, 3×Hb), 1.84 (m, 3H, 3×Hc), 2.28 (m, 6H, 3×Hd), 2.40 (m, 3H, 3×He), 3.10 (m, 6H, 3×Hf+Hg), 3.50 (m, 3H, 3×Hh), 4.09 (dd, J=12.1, 6.2 Hz, 2H, O—CH$_2$—CH—CH$_2$—O—), 4.25 (dd, J=12.3, 4.4 Hz, 2H, O—CH$_2$—CH—CH$_2$—O—), 5.19 (m, 1H, CH—). $^{13}$C NMR (100 MHz, CDCl$_3$): δ=24.6, 28.6, 33.9, 34.6, 38.5, 40.2, 56.3, 62.1, 69.0, 173.4.

3×Lipoic Acid/Triethanolamine: Compound 9a

The column chromatography on silica gel (CHCl$_3$/MeOH 95:0.5) gave the compound 9a as a yellow oil (1.75 g, 74%). TLC (CHCl$_3$/MeOH 100:0.5) R$_f$ 0.80; $^1$H NMR (400 MHz, CDCl$_3$): δ=1.48 (m, 6H, 3×Ha), 1.68 (m, 12H, 3×Hb), 1.92

(m, 3H, 3×Hc), 2.32 (t, J=7.5 Hz, 6H, 3×Hd), 2.48 (m, 3H, 3×He), 2.84 (t, J=6.1 Hz, 6H, 3×N—CH$_2$—), 3.14 (m, 6H, 3×Hf+Hg), 3.57 (m, 3H, 3×Hh), 4.12 (t, J=6.1 Hz, 6H, CH$_2$—OCO). $^{13}$C NMR (100 MHz, CDCl$_3$): δ=24.6, 28.8, 34.0, 34.6, 38.5, 40.2, 53.3, 56.3, 62.5, 173.3.

3×Lipoic Acid/Triisopropanolamine: Compound 10a

The column chromatography on silica gel (CHCl$_3$/MeOH 95:0.5) gave the compound 10a as a yellow oil (1.67 g. 66%). TLC (CHCl$_3$) R$_f$ 0.21; $^1$H NMR (400 MHz, CDCl$_3$): δ=1.19 (m, 9H, 3×CH$_3$), 1.48 (m, 6H, 3×Ha), 1.68 (m, 12H, 3×Hb), 1.92 (m, 3H, 3×Hc), 2.28 (t, J=7.5 Hz, 6H, 3×Hd), 2.48 (m, 6H, 3×N—CH$_2$—), 2.65 (m, 3H, 3×He), 3.17 (m, 6H, 3×Hf+Hg), 3.58 (m, 3H, 3×Hh), 4.94 (m, 3H, 3×CH—OCO). $^{13}$C NMR (100 MHz, CDCl$_3$): δ=18.3, 24.7, 28.8, 34.3, 34.6, 38.5, 40.2, 56.3, 60.4, 68.9, 173.3.

4×Lipoic Acid/Pentaerythritol: Compound 11a

The column chromatography on silica gel (CHCl$_3$/MeOH 95:0.5) gave the compound 11a as a yellow oil (1.8 g, 81%). TLC (CHCl$_3$) R$_f$ 0.22; $^1$H NMR (400 MHz, CDCl$_3$): δ=1.46 (m, 8H, 4×Ha), 1.66 (m, 16H, 4×Hb), 1.91 (m, 4H, 4×Hc), 2.34 (t, J=7.5 Hz, 8H, 4×Hd), 2.46 (m, 4H, 4×He), 3.14 (m, 8H, 4×Hf+Hg), 3.56 (m, 4H, 4×Hh), 4.11 (s, 8H, 4×C—CH$_2$—O), $^{13}$C NMR (100 MHz, CDCl$_3$): δ=24.5, 28.6, 33.8, 34.5, 38.5, 40.2, 41.9, 56.2, 62.0, 172.6.

5×Lipoic Acid/Bis-Tris: Compound 12a

The column chromatography on silica gel (CHCl$_3$/MeOH 95:0.5) gave the compound 12a as a yellow oil (1.9 g, 83%). TLC (CHCl$_3$) R$_f$ 0.18; $^1$H NMR (400 MHz, CDCl$_3$): δ=1.48 (m, 10H, 5×Ha), 1.68 (m, 20H, 5×Hb), 1.92 (m, 5H, 5×Hc), 2.35 (t, J=7.5 Hz, 10H, 5×Hd), 2.47 (m, 5H, 5×He), 3.00 (t, J=6.6 Hz, 4H, 2×N—CH$_2$—), 3.16 (m, 10H, 5×Hf+Hg), 3.58 (m, 5H, 5×Hh), 4.05 (t, J=6.6 Hz, 4H, 2×CH$_2$CH$_2$—OCO), 4.17 (s, 6H, 3×CCH$_2$—OCO). $^{13}$C NMR (100 MHz, CDCl$_3$): δ=32.2, 36.4, 41.6, 42.3, 46.2, 47.9, 57.0, 64.0, 69.0, 70.8, 71.6, 180.6.

Scheme 1

Synthesis of the compounds 1a-12a containing two to five α-lipoic acid molecules

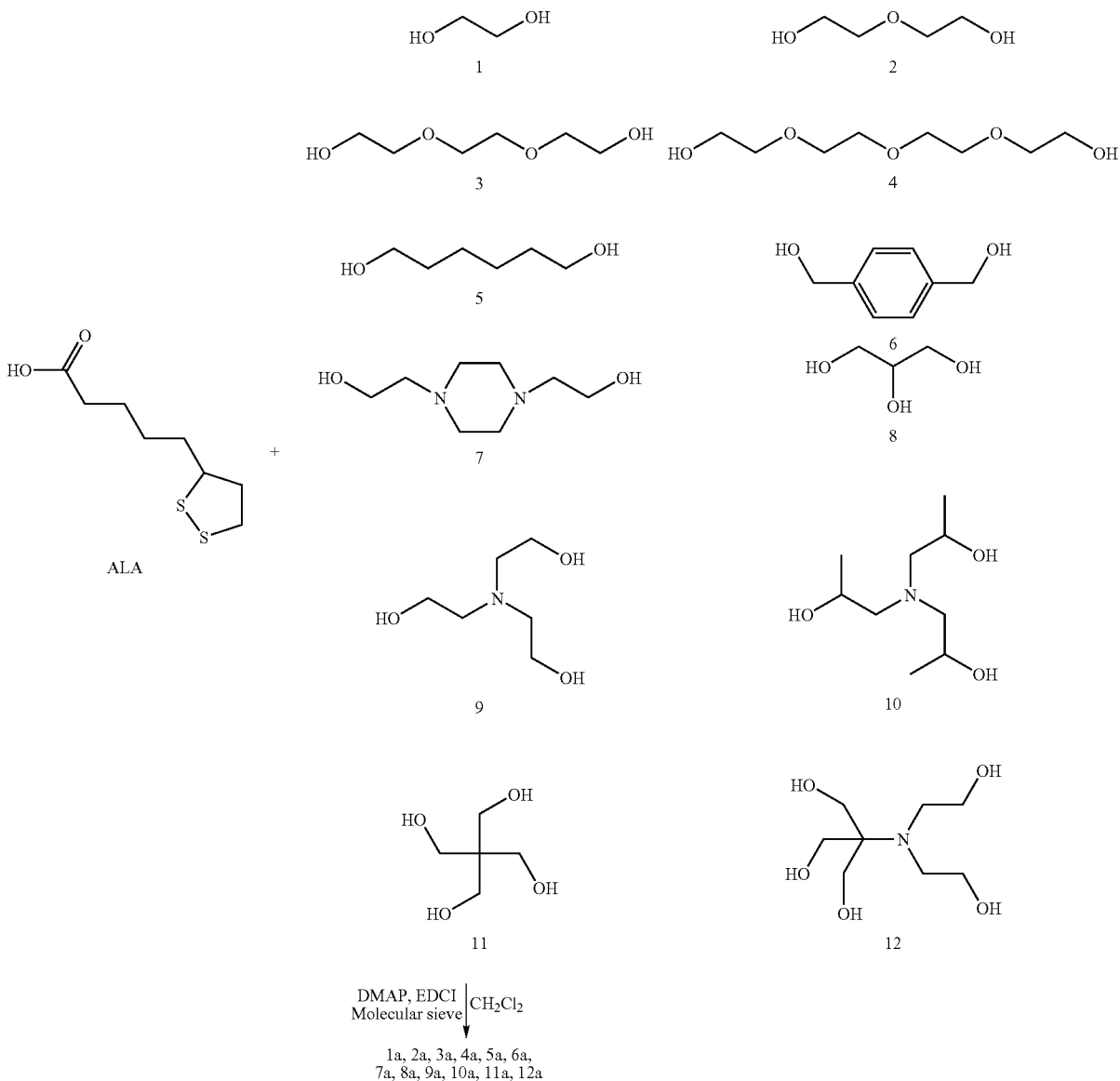

TABLE 10
Chemical structures of compounds 1a-12a
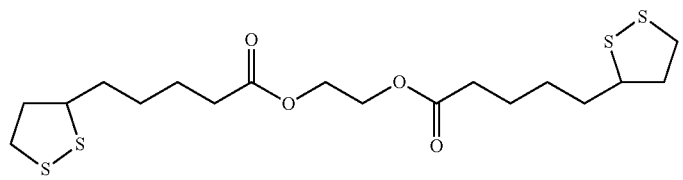 [SMILES: O=C(CCCCC1CCSS1)OCCOC(=O)CCCCC1CCSS1]
1a
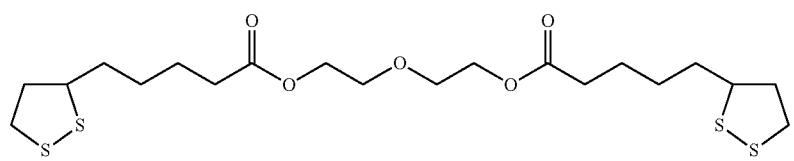 [SMILES: O=C(CCCCC1CCSS1)OCCOCCOC(=O)CCCCC1CCSS1]
2a
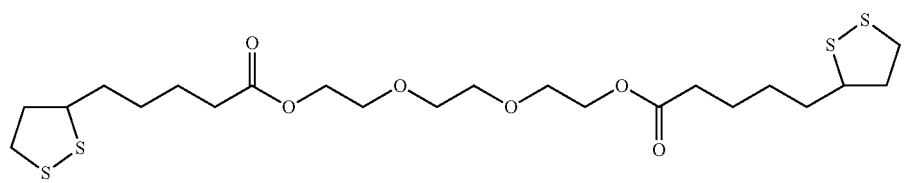 [SMILES: O=C(CCCCC1CCSS1)OCCOCCOCCOC(=O)CCCCC1CCSS1]
3a
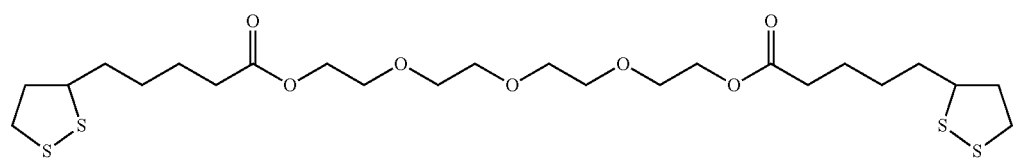 [SMILES: O=C(CCCCC1CCSS1)OCCOCCOCCOCCOC(=O)CCCCC1CCSS1]
4a
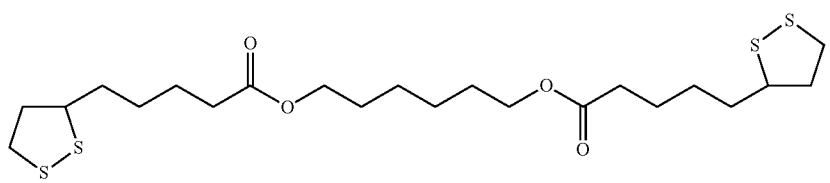 [SMILES: O=C(CCCCC1CCSS1)OCCCCCCOC(=O)CCCCC1CCSS1]
5a
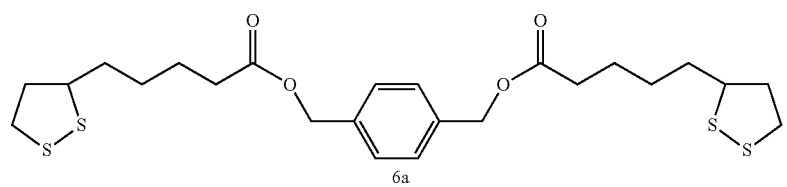
6a
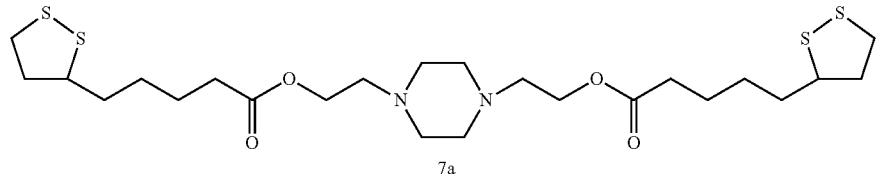
7a

TABLE 10-continued
Chemical structures of compounds 1a-12a
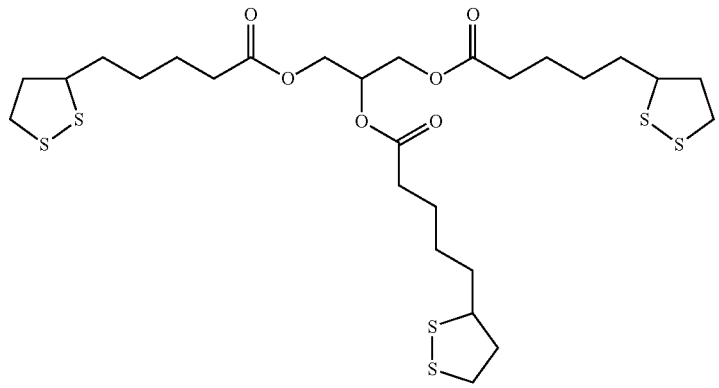 [SMILES: O=C(CCCCC1CCSS1)OCC(COC(=O)CCCCC1CCSS1)OC(=O)CCCCC1CCSS1]
8a
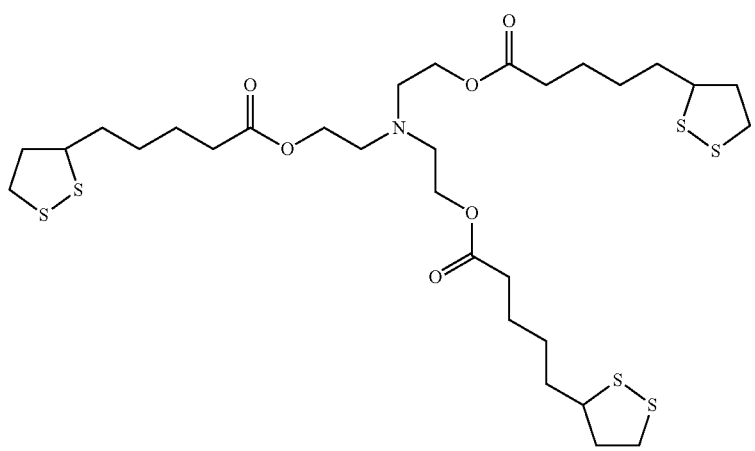 [SMILES: O=C(CCCCC1CCSS1)OCCN(CCOC(=O)CCCCC1CCSS1)CCOC(=O)CCCCC1CCSS1]
9a
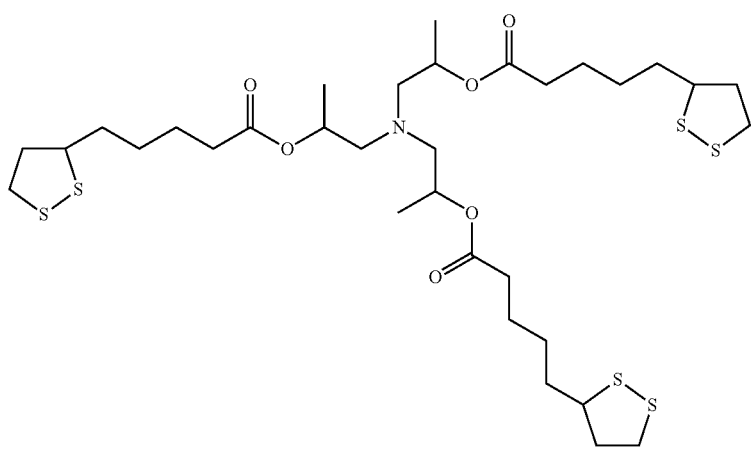 [SMILES: CC(CN(CC(C)OC(=O)CCCCC1CCSS1)CC(C)OC(=O)CCCCC1CCSS1)OC(=O)CCCCC1CCSS1]
10a TABLE 10-continued Chemical structures of compounds 1a-12a

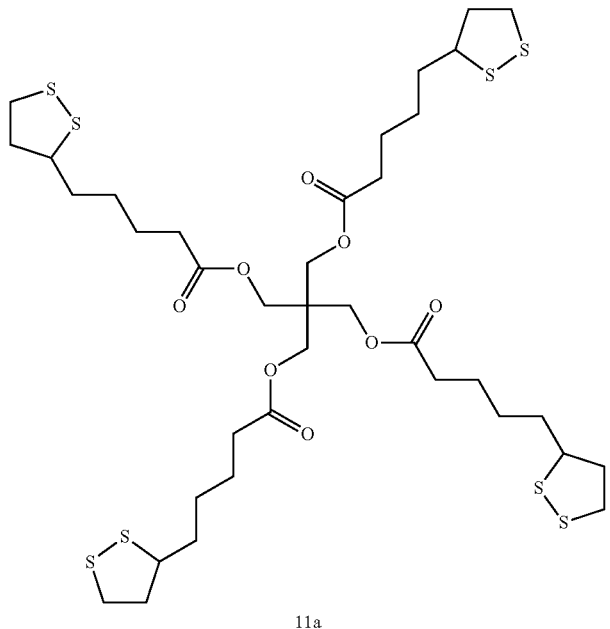

11a

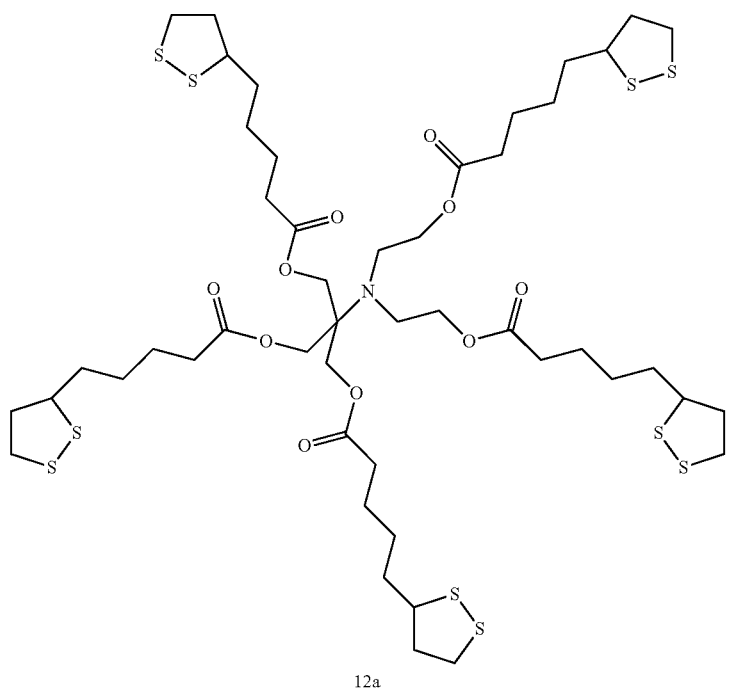

12a

The twelve hydrophobic compounds containing multiple ALA molecules were designed with the goal of constructing nanometer-sized antioxidants. The synthesis of the compounds by the coupling of α-lipoic acid molecules with the core molecules via ester bond is straightforward as described in Scheme 1. The commercially available molecules 1-12 with two to five hydroxyl groups were reacted with two to five α-lipoic acid to afford the compounds 1a-12a. The purity of the compounds was analyzed by TLC and RP-HPLC. The elution time of the compounds 1a-12a are summarized in Table 1. The HPLC analysis was performed with $C_{18}$ RP column under isocratic condition with 80% acetonitrile-0.1% TFA. Compound 7a contains two tertiary amines and the compounds 9a, 10a, and 12a contain one tertiary amine which can be ionized under the elution condition. The influence of the nitrogen atoms on the elution time was clearly shown for the compounds 7a, 9a, and 10a. While nitrogen atoms in the compounds 7a, 9a, and 10a are apparently accessible for ionization, the nitrogen atom in the compound 12a may be completely shielded by the five hydrophobic ALA units, resulting in the strongest retention of the compound. The four compounds 1a, 2a, 3a, and 4a contain two ALA units, but differ in number of ethylene glycol units ($—CH_2CH_2—O—$).

The stronger retention with decreasing number of ethylene glycol units shows that the increase in hydrophilicity due to the additional oxygen atom is larger than the increase in hydrophobicity due to the additional ethylene unit.

TABLE 1

RP-HPLC elution time for the compounds 1a-12a

| Multiple ALA-containing compounds | Number of ALA units | Elution time [min] |
|---|---|---|
| 7a: (ALA)$_2$/1,4-Bis(2-hydroxyethyl)-piperazine | 2 | 3.31 |
| 9a: (ALA)$_3$/Triethanolamine | 3 | 4.36 |
| 10a: (ALA)$_3$/Triisopropanolamine | 3 | 5.63 |
| 4a: (ALA)$_2$/Tetraethylene glycol | 2 | 6.07 |
| 3a: (ALA)$_2$/Triethylene glycol | 2 | 6.21 |
| 2a: (ALA)$_2$/Diethylene glycol | 2 | 6.42 |
| 1a: (ALA)$_2$/Ethylene glycol | 2 | 6.81 |
| 6a: (ALA)$_2$/1,4-Benzenedimethanol | 2 | 8.96 |
| 5a: (ALA)$_2$/1,6-Hexanediol | 2 | 11.35 |
| 8a: (ALA)$_3$/Glycerol | 3 | 12.39 |
| 11a: (ALA)$_4$/Pentaerythritol | 4 | 25.81 |
| 12a: (ALA)$_5$/Bis-Tris | 5 | 56.67 |

TABLE 2

Number of (-lipoic acid protons calculated from the integrated intensities of the $^1$H NMR peaks.

| Compounds | Number of ALA | Number of protons | | | | | | |
|---|---|---|---|---|---|---|---|---|
| | | a | b | c | d | e | f, g | h |
| 1a-7a | 2 | 4 | 8 | 2 | 4 | 2 | 4 | 2 |
| 8a-10a | 3 | 6 | 12 | 3 | 6 | 3 | 6 | 3 |
| 11a | 4 | 8 | 16 | 4 | 8 | 4 | 8 | 4 |
| 12a | 5 | 10 | 20 | 5 | 10 | 5 | 10 | 5 |

Example 3

Preparation and Characterization of the Inventive Antioxidant Nanospheres

Preparation of Nanospheres

Nanospheres were prepared according to the method using spontaneous emulsification with slight modification. Briefly, 25 mg of the compounds were dissolved in acetone (5 mL). The organic solution was poured under moderate stirring on a magnetic plate into an aqueous phase prepared by dissolving 25 mg of Pluronic F68 in 10 mL bidistilled water (0.25% w/v). Following 15 min of magnetic stirring, the acetone was removed under reduced pressure at room temperature. The nanospheres were filtered through 0.45 μm hydrophilic syringe filter and stored at 4° C. The hydrodynamic size measurement and size distribution of the nanospheres was performed by the dynamic light scattering (DLS) using a Coulter N4-Plus Submicron Particle Sizer (Coulter Corporation, Miami, Fla.). The nanospheres were purified by centrifuging three times at 20,000×g for 30 min at 25° C. and resuspending each time in the same volume of deionized water. Samples from the purified nanospheres were diluted in ultra-purified water and the analysis was performed at a scattering angle of 90° and at a temperature of 25° C. The size was assessed on three separate batches of the nanosphere formulation. The recovery yield was calculated as follows: RY (%)=(mass of the mALA-containing compounds recovered/mass of the mALA-containing compounds used in formulation)×100%. 500 μL of the purified nanospheres were centrifuged 20,000×g for 30 min at 25° C. The pellet was dried by rotatory evaporation under reduced pressure at 25° C. The dried pellet was dissolved in 500 μL of acetonitrile. The solution was analyzed for the compounds by RP-HPLC. Separation was performed using 80% acetonitrile (0.1% trifluoroacetic acid, TFA) as mobile phase and the eluent was monitored using UV detector at 330 nm. A standard curve in the concentration range of the compounds (0.1-2.0 μg/μL) was constructed to determine the concentration of the compounds in the solution. To assess the stability of the nanospheres in the physiological condition, 1 mL of the purified nanospheres was mixed with 9 mL of PBS and incubated at 37° C. for two weeks. The hydrodynamic size measurement and the recovery yield calculation after one week and two weeks of incubation were performed as described above.

Experiments were performed to investigate the formation of nanospheres from the twelve compounds and the influence of hydrophobicity of the compounds on the size and stability of the nanospheres. A preparation protocol which has been commonly followed was used (as described herein). Compounds 1a-12a were dissolved in acetone (25 mg/5 mL) and Pluronic F-68, the most commonly used surfactant in this technique, dissolved in 10 mL of water (0.25% w/v). Upon addition of the organic solution into the aqueous phase, nanospheres were formed instantaneously, except for the compound 4a (ALA$_2$/Tetraethylene glycol) and 7a (ALA$_2$/1,4-Bis(2-hydroxyethyl)-piperazine). The nanosphere size was within the range 200 and 600 nm and found to depend on the compounds used (Table 3). The smallest size was obtained in the formulation prepared with (ALA)$_5$/Bis-Tris, (ALA)$_4$/Pentaerythritol, and (ALA)$_3$/Triisopropanolamine, whereas more than a twofold larger size were produced with (ALA)$_2$/Ethylene glycol, (ALA)$_2$₁-Diethylene glycol, and (ALA)$_2$/Triethylene glycol. The increase in the size of the nanospheres prepared from these three ethylene glycol unit-containing compounds was also associated with lower RY, 44, 41, and 11%, respectively. It may be concluded that the nanosphere size is inversely dependent on the hydrophobicity of the compounds. The apparently more hydrophobic compounds (ALA)$_5$/Bis-Tris, (ALA)$_4$/Pentaerythritol, and (ALA)$_3$/Triisopropanolamine with five, four, and three ALA unit, respectively, were formed into the smaller nanosphere size. The failure of the compounds (ALA)$_2$/Tetraethylene glycol and (ALA)$_2$/1,4-Bis(2-hydroxyethyl)-piperazine to form stable nanospheres may be due to the insufficient hydrophobicity of the compounds leading to a decreased interfacial tension and rate of interfacial deposition.

TABLE 3

Recovery Yield (RY), Size, and Polydispersity Index (P.I.) of the Nanospheres (NS).

| Nanospheres | Multiple ALA-containing compounds | RY (%) | Size (nm) | P.I. |
|---|---|---|---|---|
| NS1 | (ALA)$_3$/Triisopropanolamine | 80 ± 11 | 190 ± 55 | 0.13 |
| NS2 | (ALA)$_5$/Bis-Tris | 59 ± 1 | 196 ± 59 | 0.14 |
| NS3 | (ALA)$_4$/Pentaerythritol | 60 ± 2 | 204 ± 59 | 0.12 |
| NS4 | (ALA)$_3$/Triethanolamine | 73 ± 2 | 242 ± 55 | 0.11 |
| NS5 | (ALA)$_3$/Glycerol | 63 ± 2 | 301 ± 80 | 0.10 |
| NS6 | (ALA)$_2$/1,4-Benzenedimethanol | 80 ± 8 | 316 ± 73 | 0.07 |
| NS7 | (ALA)$_2$/1,6-Hexanediol | 91 ± 6 | 341 ± 80 | 0.07 |
| NS8 | (ALA)$_2$/Ethylene glycol | 44 ± 5 | 505 ± 195 | 0.17 |
| NS9 | (ALA)$_2$/Diethylene glycol | 42 ± 10 | 544 ± 195 | 0.27 |
| NS10 | (ALA)$_2$/Triethylene glycol | 11 ± 2 | 568 ± 235 | 0.55 |

Stability of the Compounds in the Nanospheres

In order to maintain the antioxidant activity of the ALA units, thus of the nanospheres, the dithiolane ring moiety of the ALA should remain intact for a sufficiently prolonged time period. It is shown above that the compounds maintained their functional dithiolane ring structures during synthesis, purification, and storage.

Figure 2A:
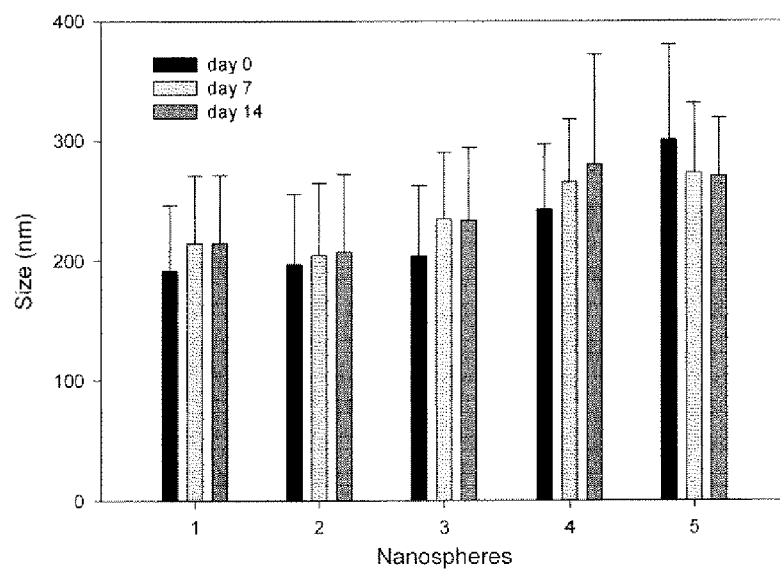
FIG. 2 depicts the size of the nanospheres after incubation at 37° C. for 7 and 14 days in accordance with an embodiment of the present invention. Error bar represents ±SD above and below the average size determined in triplicate.
Figure 2B:
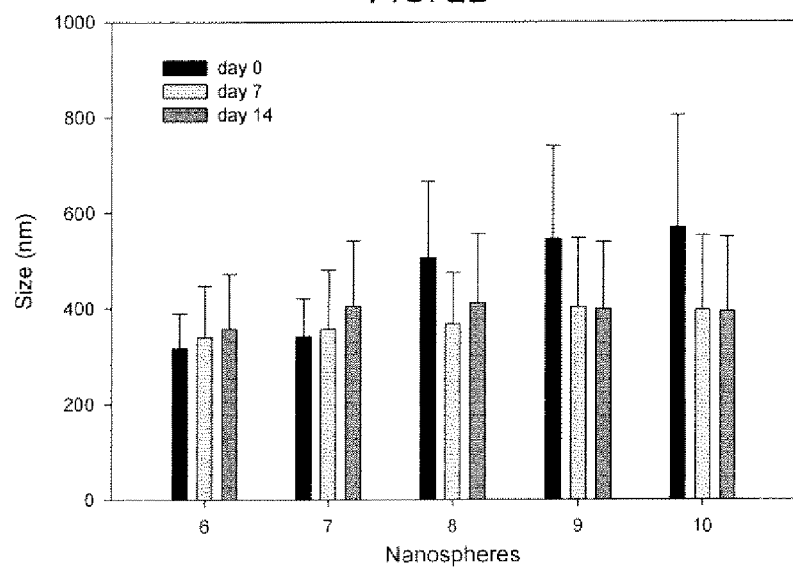

To assess the physical stability of the nanospheres, in physiological condition, the nanospheres were incubated in PBS at 37° C. for two weeks and the size was analyzed. The results demonstrate that the size and size distribution of the nanospheres remain substantially unchanged except for the nanospheres 8, 9, and 10, which were prepared from the relative hydrophilic compounds $(ALA)_2$/ethylene glycol, $(ALA)_2$/diethylene glycol, and $(ALA)_2$/triethylene glycol, respectively (Chart 1). (See FIG. 2.)

Figure 3A:
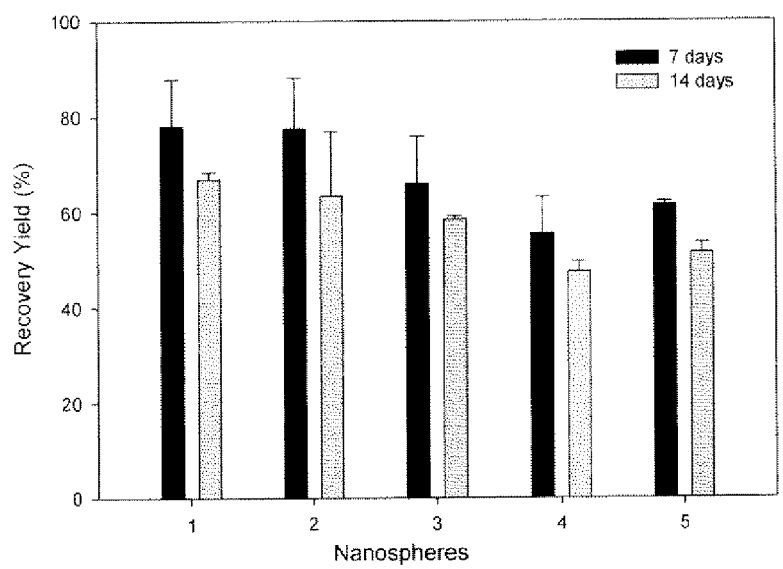
FIG. 3 depicts the recovery yields of the compounds after incubation of nanospheres 1-10 (see Table 3) in PBS at 37° C. in accordance with an embodiment of the present invention. 100% refers to the amount of the compounds determined before incubation. Error bar represents ±SD above and below the average recovery yield determined in duplicate.
Figure 3B:
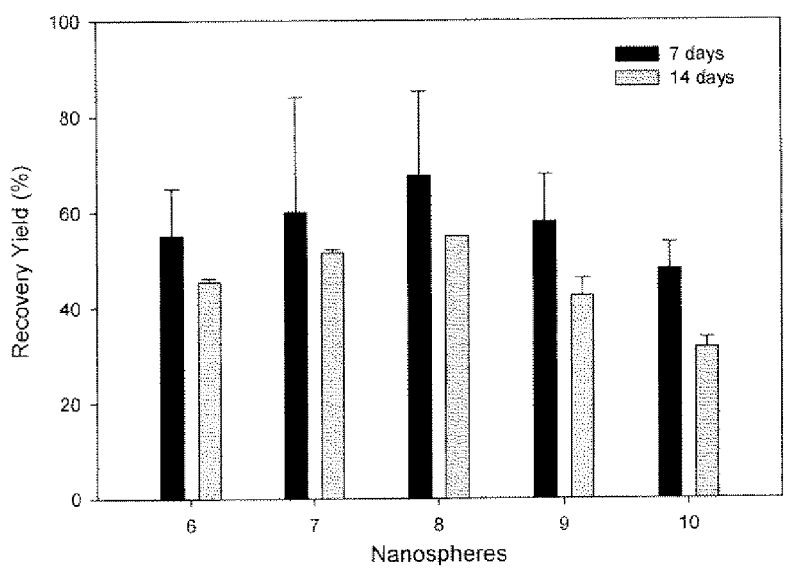

The functionality of the dithiolane ring moieties was quantified by the measuring the amount of intact compounds 1a-12a in the nanospheres after 7 and 14 days of incubation in PBS at 37° C. The compounds were analyzed using RP-HPLC as described herein. As shown in FIG. 3, 50-80% and 30-70% of the compounds remained intact after incubation of 7 and 14 days, respectively. (See FIG. 3.)

The long-term physical stability of the nanospheres along with the maintained functionality of the dithiolane ring moieties presents a particularly attractive basis for the development of a unique nanometer-sized antioxidant drug delivery device.

HOCl Scavenging Assay

The antioxidant activity of the nanospheres was assessed by their ability to scavenge hypochlorous acid. The HOCl scavenging activity of α-lipoic acid has been investigated. Hypochlorous acid is a powerful oxidizing agent that can react with many biological molecules. In the presence of physiological concentration of chloride ions, $H_2O_2$ is efficiently halogenated by the heme enzyme myeloperoxydase (MPO) to yield hypochlorous acid, by far the most abundant oxidant generated by activated phagocyte cells. Hypochlorous acid can chlorinate cytosolic proteins and nuclear DNA bases and also induces lipid peroxidation in phospholipid and lipoprotein. Importantly, the damages caused by HOCl to the intracellular glutathione and protein thiols are irreversible and can be replaced only by resynthesis. Furthermore, HOCl can be converted easily to the most damaging hydroxyl radical.

The HOCl-scavenging activity was determined by measuring the extent of $α_1$-antiproteinase ($α_1$-AP) inactivation by HOCl in the presence of nanospheres according to the assay described by Biewenga, et al. (Biewenga, G. Ph.; de Jong, J.; Bast, A. Arch. Biochem. Biophys. 1994, 312 (1), 114-120). The concentration of HOCl in the diluted commercial sodium hypochlorite solution was determined spectrophotometrically ($ε_{292}$=350 $M^{-1}$ $cm^{-1}$) (Morris, C. J. J. Phys. Chem. 1966, 70 (12), 3798-3805).

Figure 5:
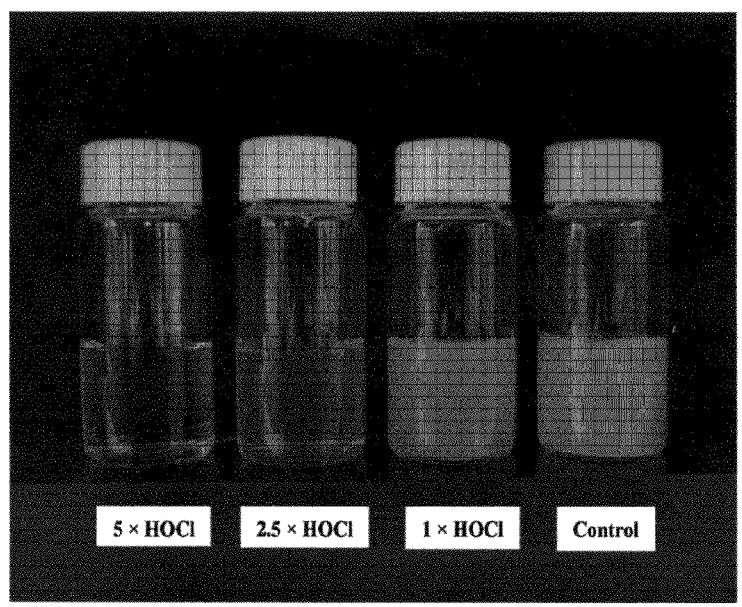
FIG. 5 depicts nanosphere 1 with 1 mM ALA units incubated with 5.0, 2.5 and 1.0 equivalent molar amount of HOCl in PBS at 37° C. for 30 min (with shaking) in accordance with an embodiment of the present invention. Control does not contain HOCl.

The HOCl scavenging activities of the nanospheres were compared with that of ALA. The results are calculated as the percentage of scavenging activity with 100% equal to the scavenging activity of ALA (50 μM). The results are the mean±S.D. of three experiments. The data reveal no significant differences in HOCl scavenging activities between the nanospheres made from different compounds and with different size (FIG. 4), indicating that the scavenging activity of the nanospheres are merely related to the amount of ALA units contained in the nanospheres. The 10 nanospheres transformed into clear solution on scavenging of HOCl (FIG. 5 shows a representative nanosphere 1) suggesting its potential application as a reactive oxygen species (ROS)-sensitive antioxidant therapeutic and as an antioxidant drug delivery vehicle.

Example 4

Scavenging of Solid Radical Nanoparticles in Aqueous Suspension with the Inventive Antioxidant Nanospheres Prepared from the Inventive Multiple α-Lipoic Acid Containing Compounds and α-Tocopherol as Model Biological Active Compound Nanospheres were prepared from mALAs (Lipo1-Lipo5), α-tocopherol (Taco), and from the mixture of mALAs 1-5 and α-tocopherol (LipoToco1-LipoToco5, Tables 4, 6, and 8). The recovered ratios of (mALAs/α-tocopherol) in the nanospheres did not considerably differ from the initial ratio (see Tables 6 and 8), and thus the initial ratio would be referred for further experiments. To assess the physical stability of the nanospheres in physiological condition, the nanospheres were incubated in PBS at 37° C. for two weeks. The results demonstrate that the nanospheres remains remarkably stable (Tables 5, 7, and 9).

Assessment of Antioxidant Activity of the Inventive Nanospheres DPPH Radical Scavenging Assay Method A: 5 mL of 100 μM DPPH solution in ethanol was mixed with 5 mL of water, resulting in a final concentration of 50 μM for DPPH. Trolox and ascorbic acid were dissolved in 100 mM sodium phosphate buffer (pH 7.5, 2.5 mM). The concentration of α-tocopherol in nanospheres was adjusted to 2.5 mM. The predetermined amount of Trolox, ascorbic acid solution and nanospheres were added to the DPPH solution using Hamilton syringe carefully to the bottom of 20 mL glass bottle to minimize the premature mixing. After gentle mixing, pictures were taken using digital camera (50000 pxitex).

Method B: 400 μL of 1.25 mM DPPH solution in ethanol was added to 9500 μL of water to give a fine dispersed DPPH suspension. Pictures were taken as described above.

TABLE 4

Size, polydispersity index (P.I.) and recovery yield (RY) of the nanospheres prepared from mALAs.

| Nanospheres[a] | mALAs | RY (%)[b] | Size (nm)[c] | P.I. |
|---|---|---|---|---|
| Lipo1 | $(ALA)_3$/Glycerol | 63 ± 2 | 301 ± 80 | 0.10 |
| Lipo2 | $(ALA)_3$/Triethanolamine | 73 ± 2 | 242 ± 55 | 0.11 |
| Lipo3 | $(ALA)_3$/Triisopropanolamine | 80 ± 11 | 190 ± 55 | 0.13 |
| Lipo4 | $(ALA)_4$/Pentaerythritol | 60 ± 2 | 204 ± 59 | 0.12 |
| Lipo5 | $(ALA)_5$/Bis-Tris | 59 ± 1 | 196 ± 59 | 0.14 |

[a]Nanospheres were prepared from mALAs (25 mg) dissolved in 5 mL of acetone.
[b]Recovery yield was determined in duplicate from two nanosphere formulations.
[c]Error represents ± SD above and below the average size determined in triplicate. Lipo1-Lipo5 correspond to nanospheres comprising compounds 8a-12a, respectively.

TABLE 5

Stability of the nanspheres prepared from mALAs.

| Nanospheres | mALAs | t = 1 week | | t = 2 weeks | |
|---|---|---|---|---|---|
| | | Size (nm)[a] | P.I | Size (nm)[a] | P.I |
| Lipo1 | (ALA)$_3$/Glycerol | 273 ± 59 | 0.06 | 270 ± 49 | 0.05 |
| Lipo2 | (ALA)$_3$/Triethanolamine | 250 ± 74 | 0.13 | 245 ± 77 | 0.16 |
| Lipo3 | (ALA)$_3$/Triisopropanolamine | 204 ± 64 | 0.16 | 200 ± 65 | 0.18 |
| Lipo4 | (ALA)$_4$/Pentaerythritol | 234 ± 56 | 0.08 | 233 ± 61 | 0.10 |
| Lipo5 | (ALA)$_5$/Bis-Tris | 204 ± 60 | 0.13 | 207 ± 65 | 0.16 |

[a]Size of the nanospheres after incubation at 37° C. for 7 and 14 days. Error bar represents ± SD above and below the average size determined in triplicate.

TABLE 6

Size, polydispersity index (P.I.), and recovery yield (RY) of nanospheres prepared from the 50:50 mixture of α-tocopherol and mALAs 1-5.

| Nanospheres[a] | mALAs | Size (nm)[b] | P.I. | RY (%)[c] | | RY (mg/10 mL)[c] | |
|---|---|---|---|---|---|---|---|
| | | | | mALAs | Toco | mALAs | Toco |
| LipoToco 1 | (ALA)$_3$/Glycerol | 233 ± 67 | 0.13 | 64 ± 6 | 65 ± 1 | 16.0 | 16.3 |
| LipoToco 2 | (ALA)$_3$/Triethanol-amine | 250 ± 66 | 0.10 | 64 ± 8 | 59 ± 1 | 16.0 | 14.8 |
| LipoToco 3 | (ALA)$_3$/Triisopropanolamine | 253 ± 79 | 0.16 | 69 ± 5 | 51 ± 3 | 17.3 | 12.8 |
| LipoToco 4 | (ALA)$_4$/Pentaerythritol | 206 ± 69 | 0.20 | 66 ± 4 | 64 ± 1 | 16.5 | 16.0 |
| LipoToco 5 | (ALA)$_5$/Bis-Tris | 229 ± 71 | 0.16 | 71 ± 13 | 58 ± 3 | 17.8 | 14.5 |

[a]Nanospheres were prepared from the mixture of mALAs (25 mg) and α-tocopherol (25 mg) dissolved in 5 mL of acetone.
[b]Error represents ± SD above and below the average size determined in triplicate.
[c]Recovery yield was determined in duplicate nanosphere formulations. LipoToco 1-LipoToco 2 correspond to nanospheres comprising compounds 8a-12a, respectively.

TABLE 7

Stability of the nanspheres prepared from the 50:50 mixture of α-tocopherol and mALAs 1-5 after incubation at 37° C. for two weeks.

| Nanospheres | mALAs | t = 0 | | t = 1 week | | t = 2 weeks | |
|---|---|---|---|---|---|---|---|
| | | Size (nm)[a] | P.I | Size (nm)[a] | P.I | Size (nm)[a] | P.I |
| LipoToco 1 | (ALA)$_3$/Glycerol | 233 ± 67 | 0.13 | 248 ± 60 | 0.08 | 246 ± 52 | 0.05 |
| LipoToco 2 | (ALA)$_3$/Triethanol-amine | 250 ± 66 | 0.10 | 261 ± 67 | 0.09 | 253 ± 69 | 0.07 |
| LipoToco 3 | (ALA)$_3$/Triisopropanolamine | 253 ± 79 | 0.16 | 271 ± 84 | 0.16 | 234 ± 66 | 0.12 |
| LipoToco 4 | (ALA)$_4$/Pentaerythritol | 206 ± 69 | 0.20 | 220 ± 57 | 0.09 | 219 ± 57 | 0.09 |
| LipoToco 5 | (ALA)$_5$/Bis-Tris | 229 ± 71 | 0.16 | 237 ± 69 | 0.13 | 237 ± 66 | 0.11 |

[a]Size of the nanospheres after incubation at 37° C. for 7 and 14 days. Error represents ± SD above and below the average size determined in triplicate.

TABLE 8

Size, polydispersity index (P.I.), and recovery yield of nanospheres prepared from the mixture of α-tocopherol and (ALA)$_4$/pentaerythritol with varying mass ratios

| Nanospheres | Lipo (mg/10 mL) | Toco (mg/10 mL) | Size (nm)[a] | P.I. | RY (%)[b] | |
|---|---|---|---|---|---|---|
| | | | | | mALAs | Toco |
| LipoToco 4A | 25 (16.5) | 25 (16.0) | 206 ± 69 | 0.20 | 66 ± 4 | 64 ± 1 |
| LipoToco 4B | 25 (16.8) | 15 (10.1) | 188 ± 61 | 0.18 | 67 ± 1 | 67 ± 5 |
| LipoToco 4C | 25 (16.5) | 7.5 (4.8) | 178 ± 62 | 0.24 | 66 ± 2 | 64 ± 13 |
| LipoToco 4D | 15 (10.8) | 25 (16.5) | 227 ± 71 | 0.16 | 72 ± 4 | 66 ± 1 |

TABLE 8-continued

Size, polydispersity index (P.I.), and recovery yield of nanospheres
prepared from the mixture of α-tocopherol and (ALA)$_4$/pentaerythritol
with varying mass ratios

| Nanospheres | Lipo (mg/10 mL) | Toco (mg/10 mL) | Size (nm)$^a$ | P.I. | RY (%)$^b$ mALAs | Toco |
|---|---|---|---|---|---|---|
| LipoToco 4E | 7.5 (5.9) | 25 (17.3) | 218 ± 66 | 0.15 | 78 ± 8 | 69 ± 1 |
| Toco | 0 | 25 (18.0) | 212 ± 69 | 0.18 | — | 72 ± 3 |

$^a$Size of the nanospheres after incubation at 37° C. for 7 and 14 days. Error represents ± SD above and below the average size determined in triplicate.
$^b$Recovery yield was determined in duplicate from two nanosphere formulations.

TABLE 9

Stability of nanospheres prepared from the mixture of α-tocopherol and (ALA)$_4$/pentaerythritol with varying mass ratios.

| Nanospheres | t = 0 Size (nm)$^a$ | P.I. | t = 1 week Size (nm)$^a$ | P.I | t = 2 weeks Size (nm)$^a$ | P.I |
|---|---|---|---|---|---|---|
| LipoToco 4A | 206 ± 69 | 0.20 | 220 ± 57 | 0.09 | 219 ± 57 | 0.09 |
| LipoToco 4B | 188 ± 61 | 0.18 | 201 ± 52 | 0.09 | 200 ± 54 | 0.10 |
| LipoToco 4C | 178 ± 62 | 0.24 | 240 ± 51 | 0.09 | 199 ± 53 | 0.10 |
| LipoToco 4D | 227 ± 71 | 0.16 | 245 ± 57 | 0.07 | 249 ± 59 | 0.08 |
| LipoToco 4E | 218 ± 66 | 0.15 | 229 ± 57 | 0.08 | 231 ± 58 | 0.09 |
| Toco | 212 ± 69 | 0.18 | 223 ± 56 | 0.09 | 222 ± 60 | 0.10 |

$^a$Size of the nanospheres after incubation at 37° C. for 7 and 14 days. Error bar represents ± SD above and below the average size determined in triplicate.

Example 5

Figure 6A:
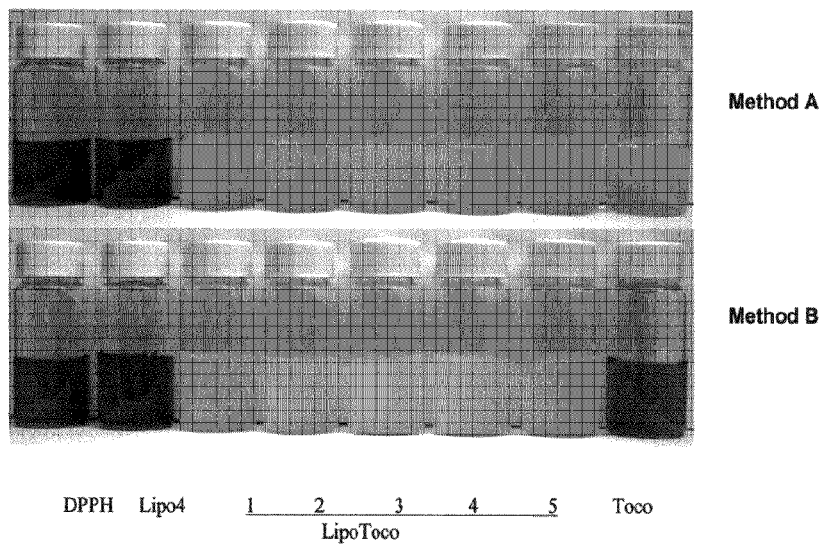
FIG. 6 depicts DPPH radical scavenging by nanospheres in accordance with an embodiment of the present invention. Toco: Nanosphere prepared from α-tocopherol only; Lipo4: Nanosphere prepared from 4((ALA)$_4$/Penta-erythritol) only (see table 4). LipoToco1-LipoToco5: Nanospheres prepared from a mixture of α-tocopherol (25 mg) and the multiple ALA-containing compounds (25 mg) (see table 6). (a) concentrations of α-tocopherol in Toco, LipoToco1-LipoToco5 was adjusted to 50 µM. The picture for Lipo4 is representative of the all nanospheres prepared from mALAs only. (b) concentration-dependent scavenging activity of LipoToco4 and Toco. (c) concentration-dependent scavenging activity Trolox and ascorbic acid. (d) comparison of the scavenging activity between LipoToco4, Trolox, and ascorbic acid.

The antioxidant capability of the nanospheres was assessed by the scavenging activity of DPPH free radical. The DPPH radical scavenging assay is often used as a model for the measurement of lipid radial scavenging activity of antioxidant compounds. DPPH radical solution is characterized by the intense violet color due to absorption at 520 nm, while its reduced form DPPH-H shows a pale yellow color. The DPPH radical scavenging assay is usually performed in a 50:50 mixture of water and organic solvents, commonly ethanol or dimethyl suloxide, in which the DPPH radical is completely dissolved. In this condition (Method A), the violet color of DPPH radical solution converted instantaneously to the pale yellow color, which is indicative of an instantaneous DPPH radical scavenging by the nanospheres (FIG. 6a, Method A).

The results show that there is no substantial difference between the nanospheres which are prepared from the mixture of α-tocopherol and different mALAs or from α-tocopherol only. The nanospheres not containing α-tocopherol (Lipo1) did not show any DPPH radical scavenging activity which indicates that the DPPH scavenging ability of the nanospheres is attributed to the α-tocopherol. In the method B (FIG. 6a), 400 µL of 1.25 mM DPPH solution in ethanol was added to 9500 µL of water to give a fine dispersed DPPH suspension with the particle size of 164±26 nm (polydispersity index 0.03). When the DPPH suspension is mixed with the nanospheres, the color changes occurred instantaneously for LipoToco1-5, which is indicative of the high reactivity of the nanospheres against solid DPPH radical nanoparticles.

There is no substantial difference between the nanospheres LipoToco1-LipoToco5 and Lipo1 did not show any scavenging activity. Taco showed only slight color changes, indicating that it is not an effective scavenger of the radical nanoparticles. A comparison of the images in FIG. 6a shows clearly the difference in DPPH scavenging activity of α-tocopherol nanosphere in Method A and Method B.

Usually, the DPPH radical scavenging activity of antioxidants is recorded as time-dependent disappearance of the odd electron of DPPH using electron spin relsonance (ESR) spectroscopy. In this study, the radical scavenging and the color changes occurred instantaneously without any lag phase, making the kinetic measurement unnecessary. In Method B, the DPPH radical exists as fine dispersed nanoparticles, which can not be measured by ESR.

Figure 6B:
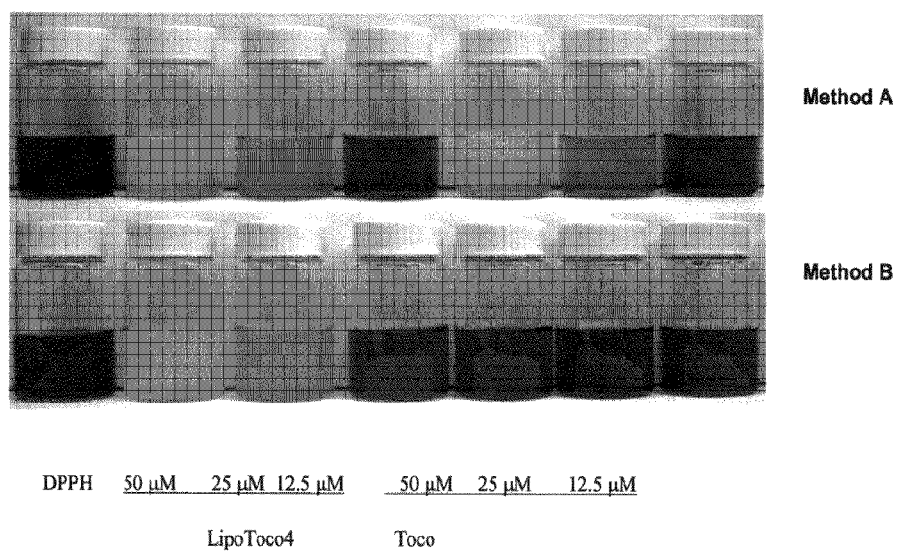

In order to assess the dependency of the scavenging activity on α-tocopherol concentration in the nanospheres, different amounts of LipoToco4 and Taco were added to give the final α-tocopherol concentration of 50, 25, and 12.5 µM. As shown in FIG. 6b, the color changes in Method A occurred instantaneously and revealed no substantial difference between LipoToco4 and Toco. No further color changes were observed indicating that the initial burst of the scavenging reaction exhausted DPPH radicals.

The difference between LipoToco4 and Toco was clearly shown in Method B. While the intensity of the color changes in LipoToco4 did not differ from those observed in Method A, Toco showed much less intense color changes. Furthermore, the dependency was not obvious as it was in Method A. The picture for LipoToco4 is representative of LipoToco1-5.

Figure 6C:
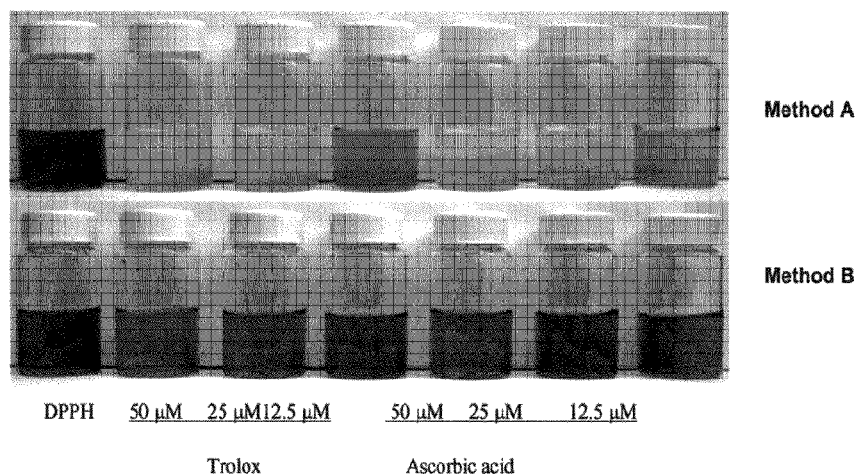
Figure 6D:
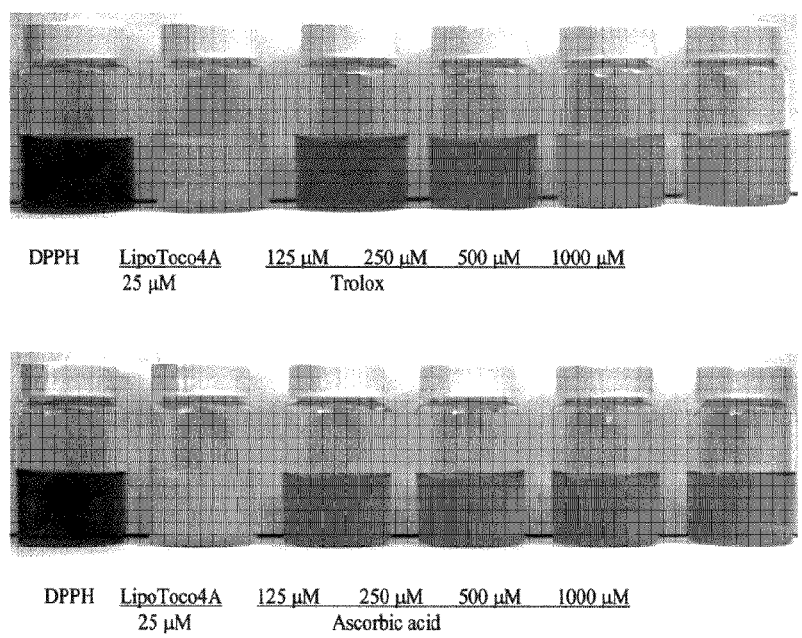

For comparison, the scavenging activity of water-soluble ascorbic acid (vitamin C) and the water-soluble derivative of α-tocopherol Trolox were demonstrated under the same condition. As shown in FIG. 6c in Method A, the color changes were complete and occurred instantaneously by ascorbic acid and Trolox in three different concentrations. In contrast, in Method B, ascorbic acid and Trolox caused much less color changes, even with a 40:1 molar excess, indicating that the water-soluble antioxidants are not as effective against particulate water-insoluble DPPH radicals as they are against dissolved DPPH radicals in the organic solvent/water mixture.

Figure 7A:
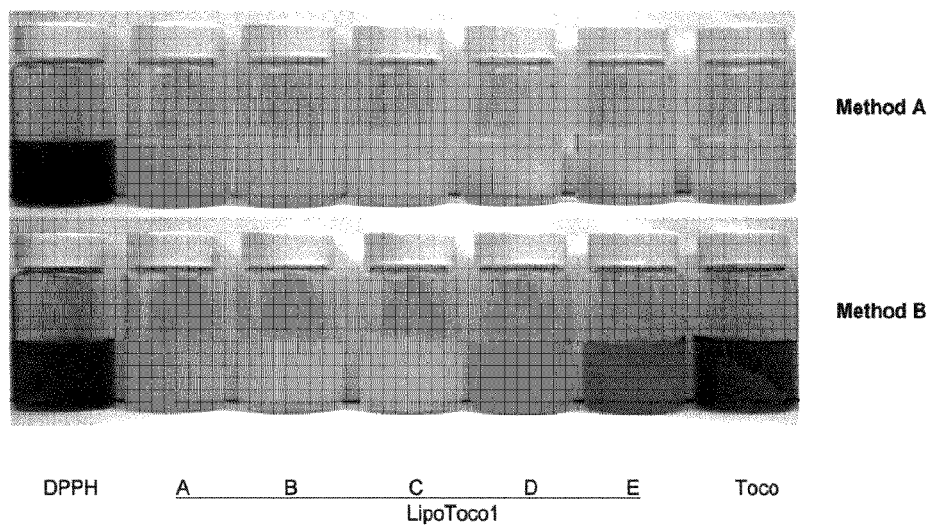
FIG. 7 depicts DPPH radical scavenging by the nanospheres prepared from the mixture with varying ratios of mALA4 and α-tocopherol in accordance with an embodiment of the present invention. (a) concentration of α-tocopherol in the nanospheres TocoLipo4A-TocoLipo4E and Toco was adjusted to 50 µM. (b) concentrations of α-tocopherol in the nanospheres TocoLipo4E and Toco were adjusted to 50, 100, and 250 Concentration of α-tocopherol in the nanosphere LipoToco4C was 25 µM.
Figure 7B:
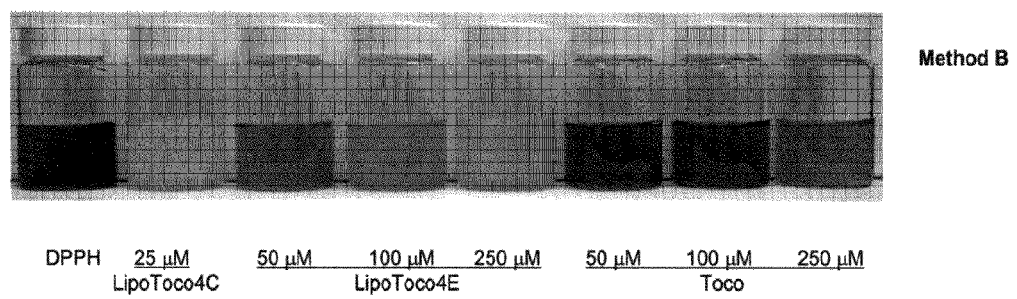

To further investigate the difference between the nanospheres prepared from α-tocopherol only and from the mixture of mALAs and α-tocopherol, the connection between the ratios of (mALAs)/(α-tocopherol) and the intensity of the color changes was illustrated by preparing a series of nanospheres with systematically varying compositions. The inventors chose the LipoToco 4 for this experiment. For each group, the ratio of (mALA)/(α-tocopherol) are: 25/25, 25/15, 25/7.5, 15/25, 7.5/25, and 0/25 for LipoToco4A, LipoToco4B, LipoToco4C, LipoToco4D, LipoToco4E, and Toco, respectively (see Table 8). In Method A (FIG. 7), there was no difference in the intensity of color changes between the nanospheres. In Method B (FIG. 7), it was obvious that the intensity of the color change decreased with decreasing ratio of (mALA)/(α-tocopherol) in the nanospheres.

Figure 8A:
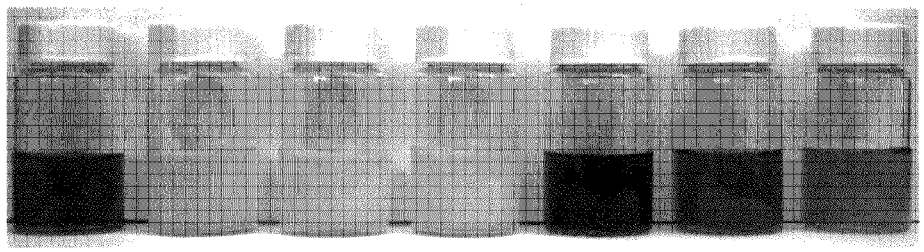
FIG. 8 depicts DPPH radical scavenging by the nanospheres in accordance with an embodiment of the present invention. Nanospheres were prepared with varying α-tocopherol contents (see Table 5), Concentrations of α-tocopherol in the nanospheres, Trolox, and ascorbic acid were adjusted to 25 µM. a, comparison of the time-dependent radical scavenging activity between LipoToco4A and Toco. b, comparison of the time-dependent radical scavenging activity between TocoLipo4A and TocoLipo4E. c, Time-dependent radical scavenging activity of Trolox and ascorbic acid.
Figure 8B:
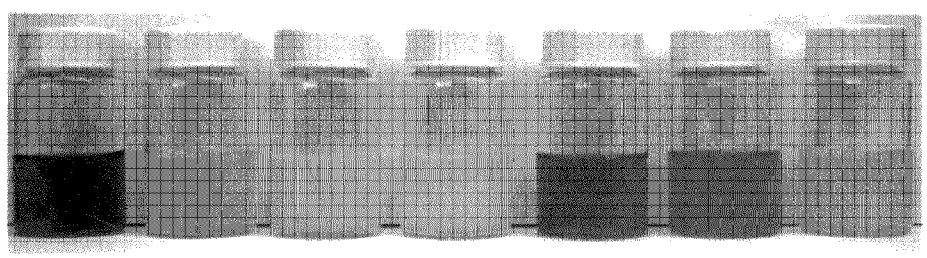
Figure 8C:
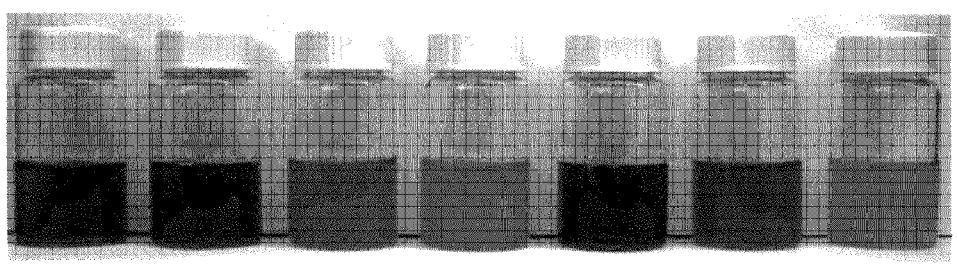

To further demonstrate the advantage of the increased ratio of (mALAs)/(α-tocopherol), two pairs of nanospheres (LipoToco4A vs. Toco, and LipoToco4A vs. LipoToco4E) were compared in the time course of 40 min. Color changes occurred instantaneously in LipoToco4A, and no further substantial changes were observed. In the case of Toco and LipoToco4E, the color changes were much less intense and proceeded further during the incubation period. A comparison between Toco and LipoToco 4E in FIG. 8a and FIG. 8b clearly showed the effect of the mALA in the nanosphere. Also shown is the less effective scavenging activity of the two water-soluble antioxidants in the time course of 40 min (FIG. 8c).

To explain the results presented, the relevant observations are summarized as follows:

First, in Method A, the nanospheres are as effective DPPH radical scavenger as Trolox and ascorbic acid. Second, nanospheres prepared from the mixture of α-tocopherol and mALAs showed more effective radical scavenging in Method B than the nanosphere prepared from α-tocopherol only, ascorbic and, Trolox. Third, the scavenging activity of the nanospheres in Method B increases with increasing ratio of (mALAs)/(α-tocopherol).

In Method A, DPPH radical, ascorbic acid, and Trolox were completely dissolved while the nanospheres were suspensions. A similar observation has been reported where the surface-modified nanoparticles with Trolox are even more reactive DPPH radical scavenger than Trolox. The increased scavenging reactivity was attributed to the preconcentrating effect of the DPPH radical around the nanoparticles. Because the rate of reaction between DPPH radicals and antioxidants is much slower than diffusion control, the concentrated DPPH radical may have favored the reaction rate.

Keeping the overall α-tocopherol content equal, the enlarged reactive surface area with an increase in the number of nanospheres with increasing ratio of (mALAs)/(α-tocopherol) would be a rational explanation for the more effective scavenging activity with larger ratio of (mALAs)/(α-tocopherol). The increase of the reactive surface area may not be due to the decrease of the nanosphere size because all the nanospheres tested do not differ so much in the hydrodynamic size range (see Tables 6 and 8). However, the increase of the reactive surface area may not explain the increasing scavenging reactivity of the nanospheres in the order of Toco, LipoToco4E, 4D, and 4C with the ratio of 0/25, 7.5/25, 15/25, and 25/25, respectively, where the same amount of α-tocopherol were used. While not wishing to be bound by any particular theory, the inventors believe that the apparently more effective scavenging activity of the nanospheres with increasing ratio of (mALAs)/(α-tocopherol) in Method B may be related to spatial distribution and orientation of the α-tocopherol molecules in the nano-droplets. First, α-tocopherol may be forced to position on the surface area of the nano-droplet during the droplet formation resulting a pseudo core-shell structure. The driving force for this special separation may be the stronger interaction between the mALAs to each other than the interaction between α-tocopherol and the mALAs.

Figure 9:
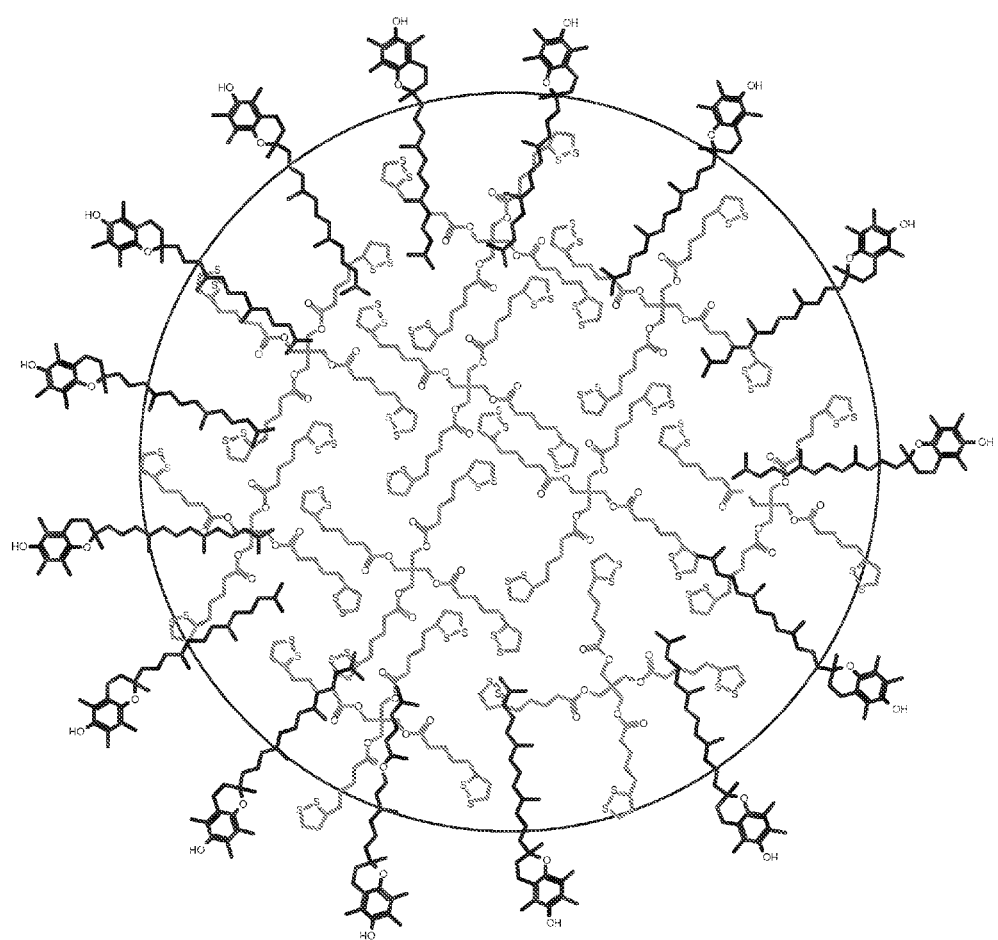
FIG. 9 depicts the proposed schematic orientation of α-tocopherol and mALA-containing compounds in the nanospheres in accordance with an embodiment of the present invention.
Figure 10:
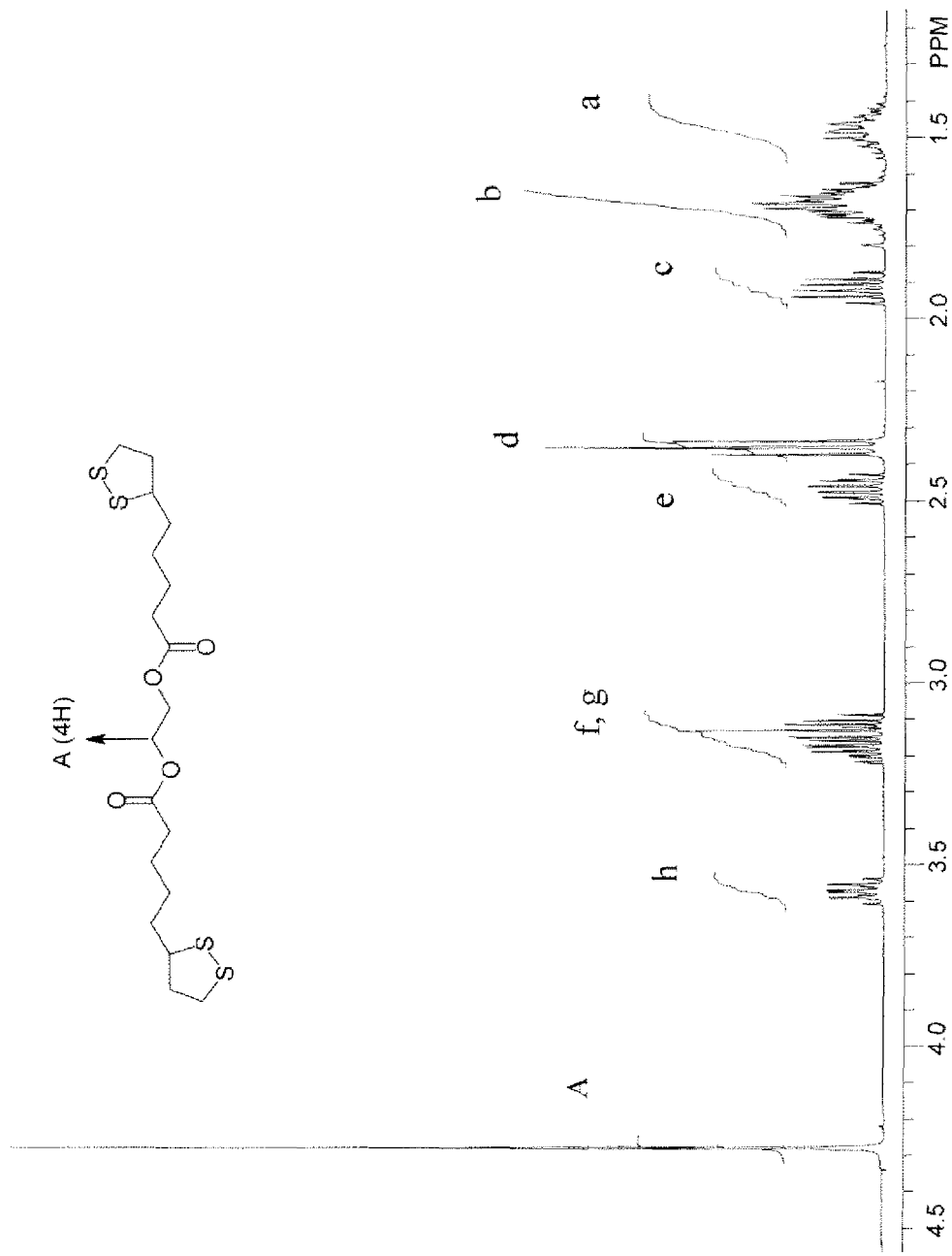
FIG. 10 depicts a $^1$H NMR spectrum of Compound 1a (ALA$_2$/ethyleneglycol) in accordance with an embodiment of the present invention.
Figure 11:
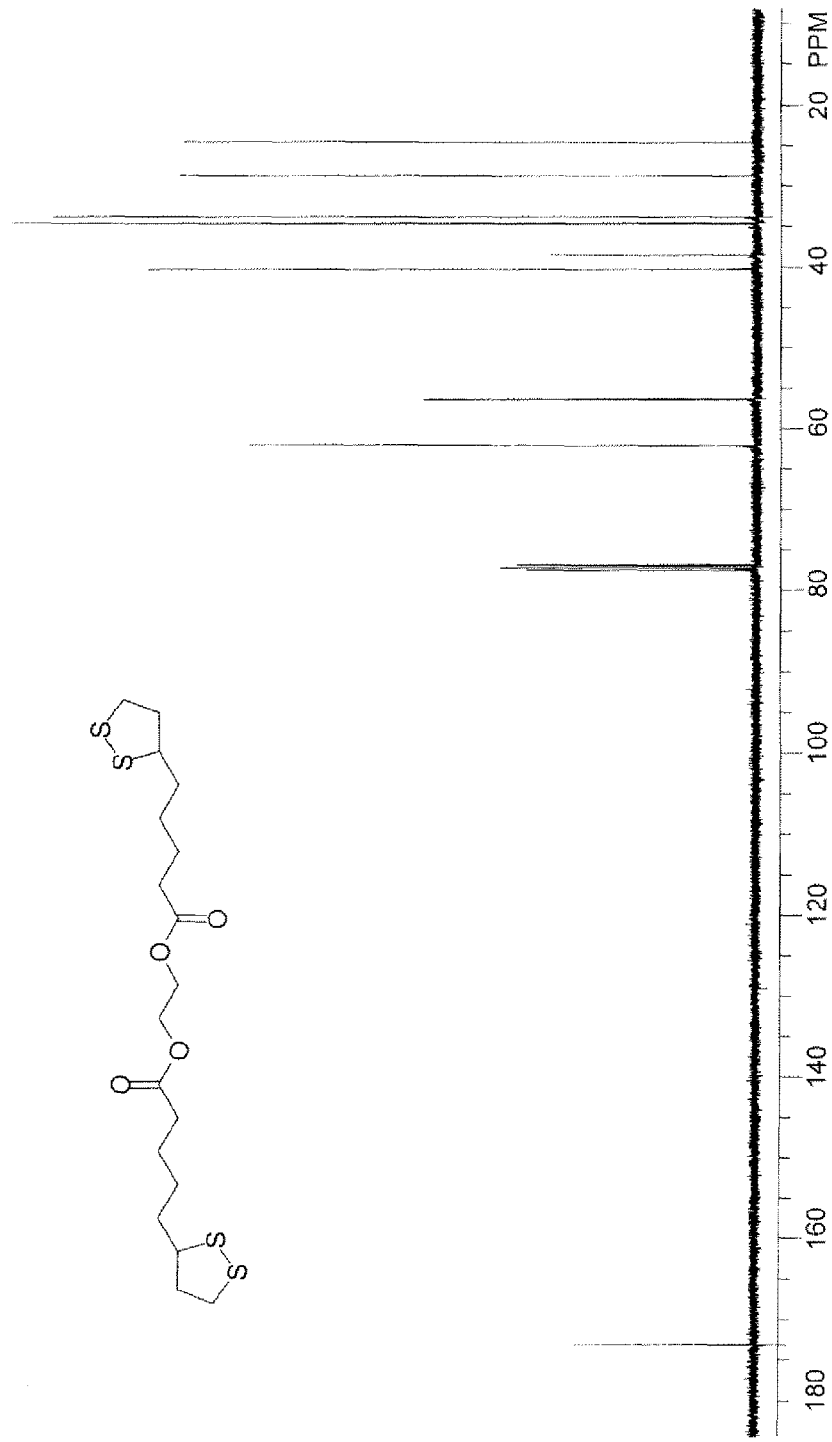
FIG. 11 depicts a $^{13}$C NMR spectrum of Compound 1a (ALA$_2$/ethyleneglycol) in accordance with an embodiment of the present invention.
Figure 12:
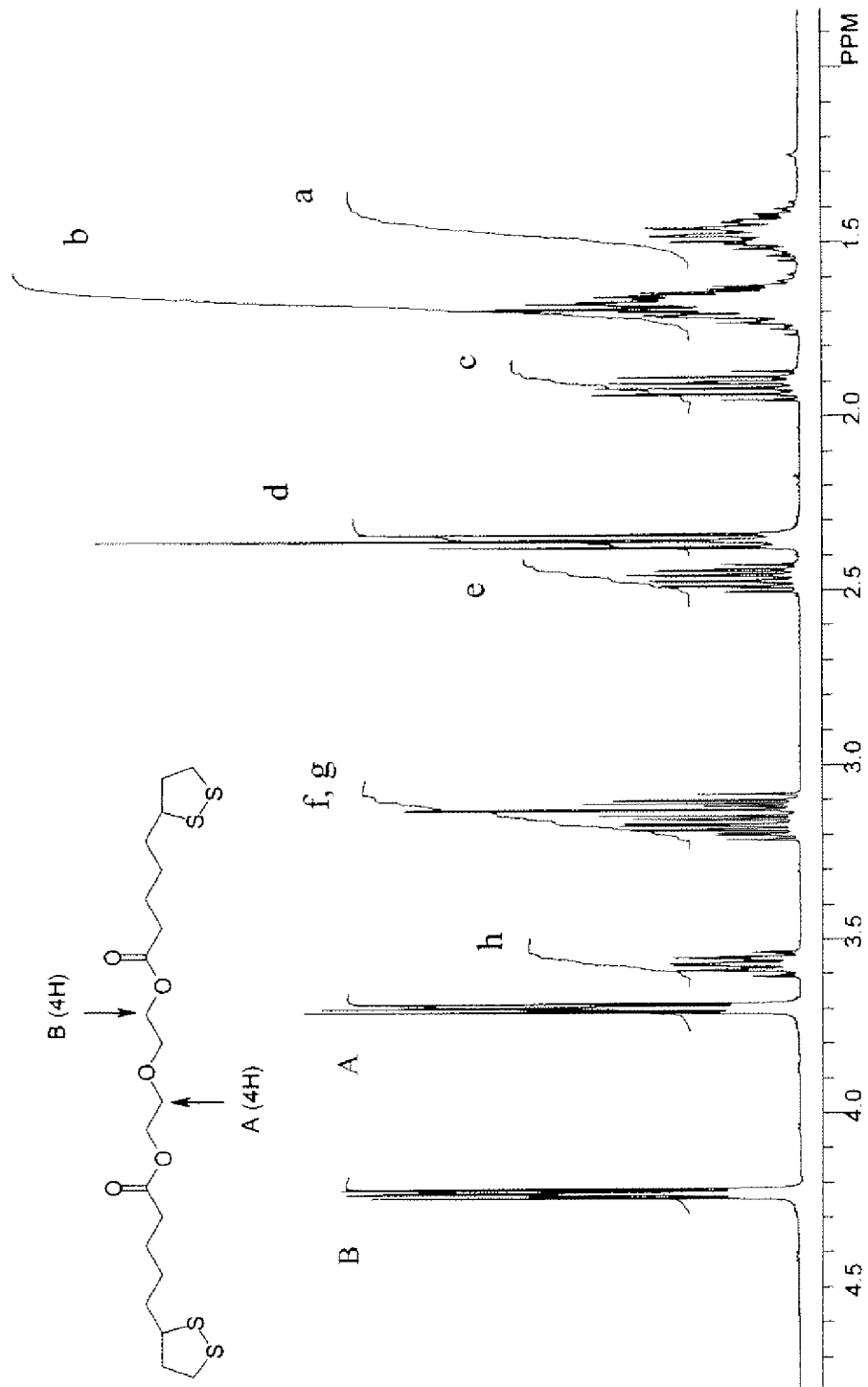
FIG. 12 depicts a $^1$H NMR spectrum of Compound 2a (ALA$_2$/diethyleneglycol) in accordance with an embodiment of the present invention.
Figure 13:
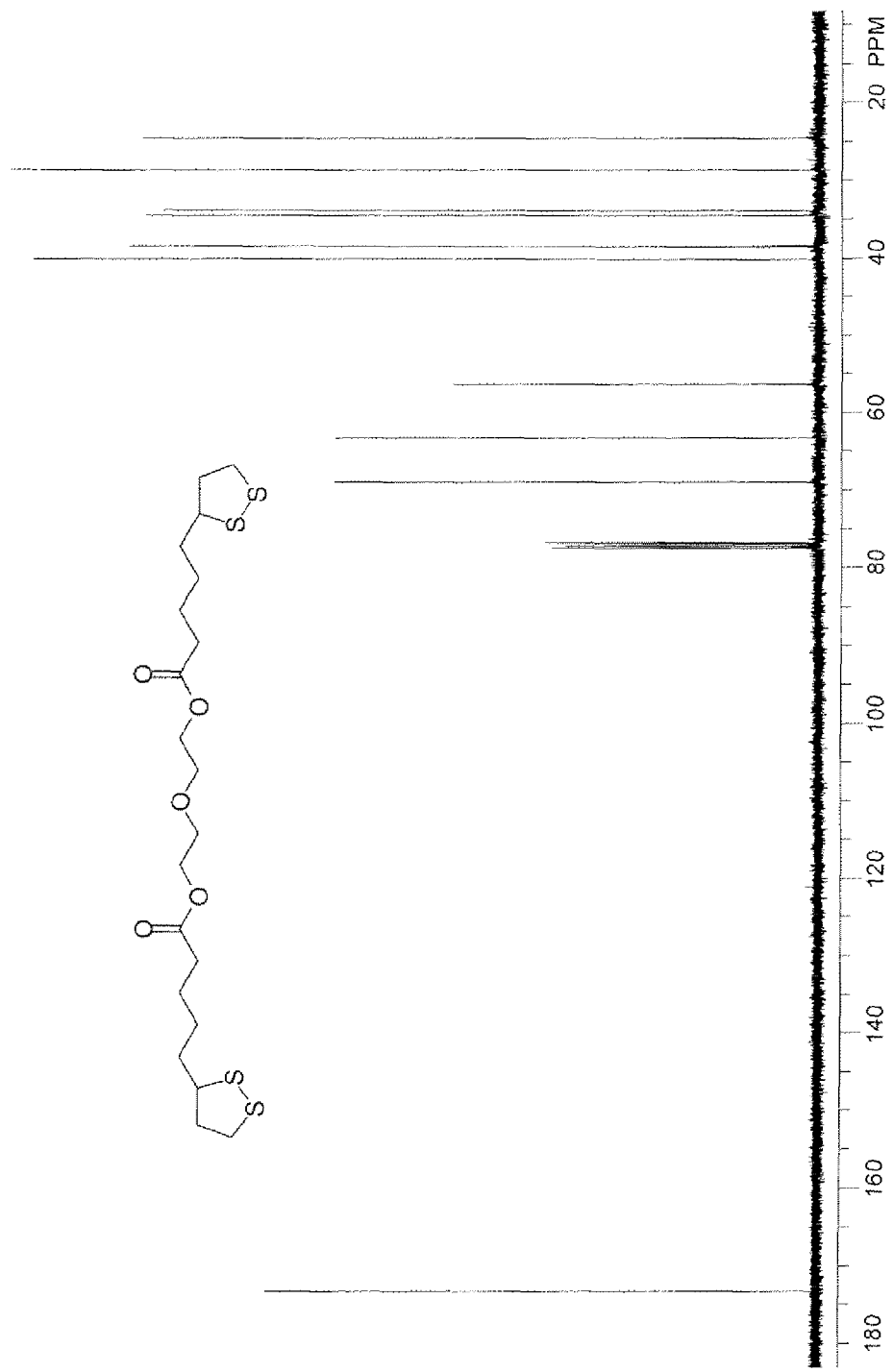
FIG. 13 depicts a $^{13}$C NMR spectrum of Compound 2a (ALA$_2$/diethyleneglycol) in accordance with an embodiment of the present invention.
Figure 14:
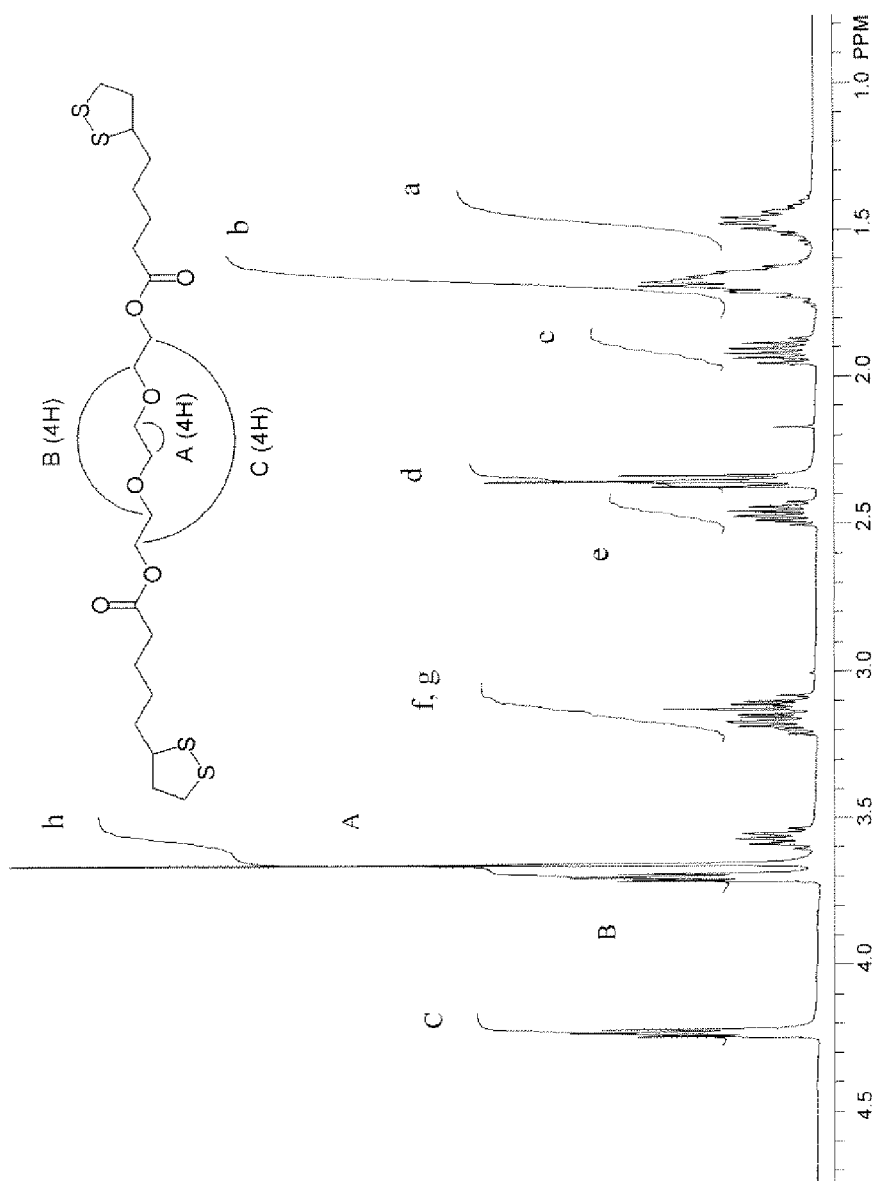
FIG. 14 depicts a $^1$H NMR spectrum of Compound 3a (ALA$_2$/triethyleneglycol) in accordance with an embodiment of the present invention.
Figure 15:
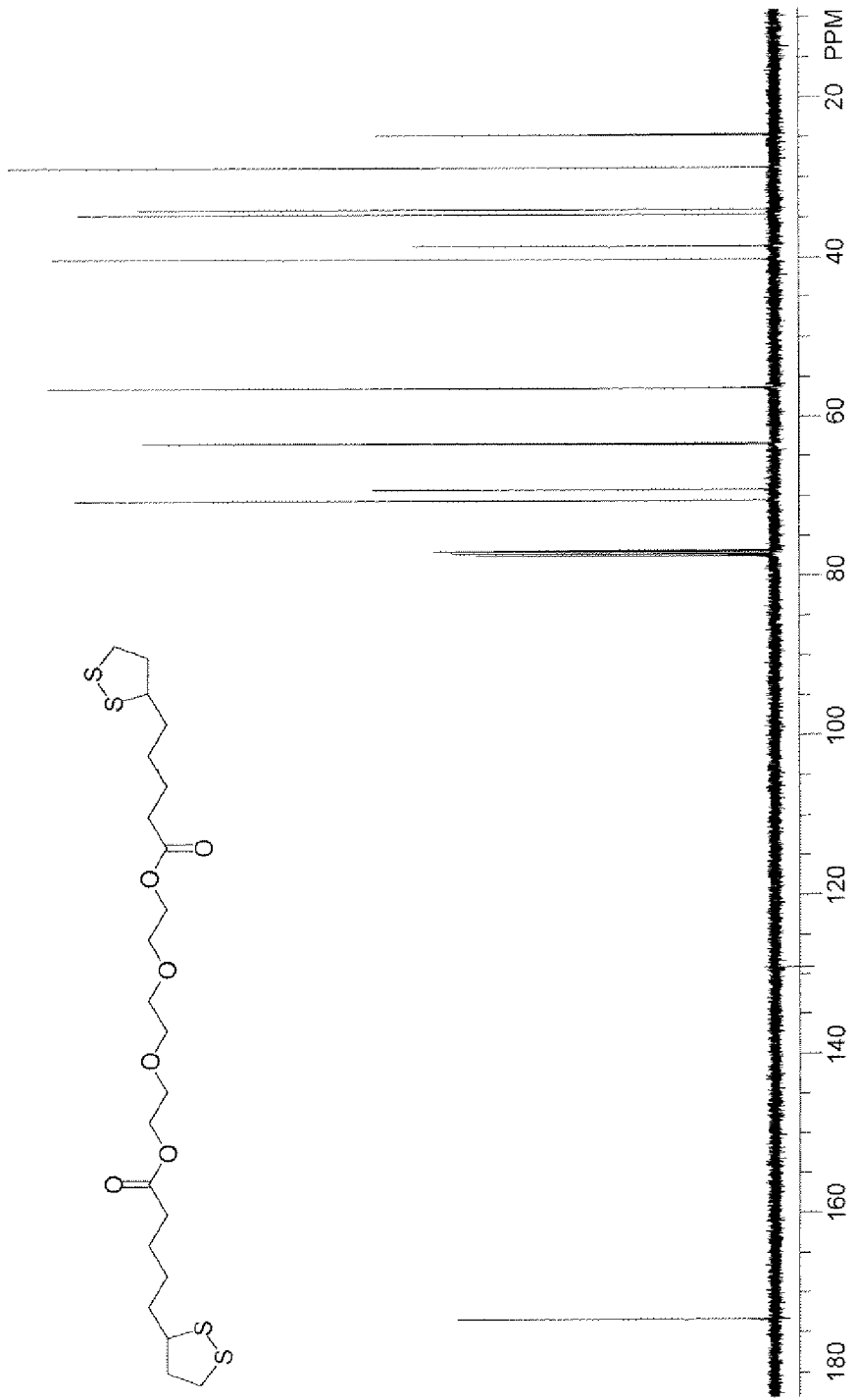
FIG. 15 depicts a $^{13}$C NMR spectrum of Compound 3a (ALA$_2$/triethyleneglycol) in accordance with an embodiment of the present invention.
Figure 16:
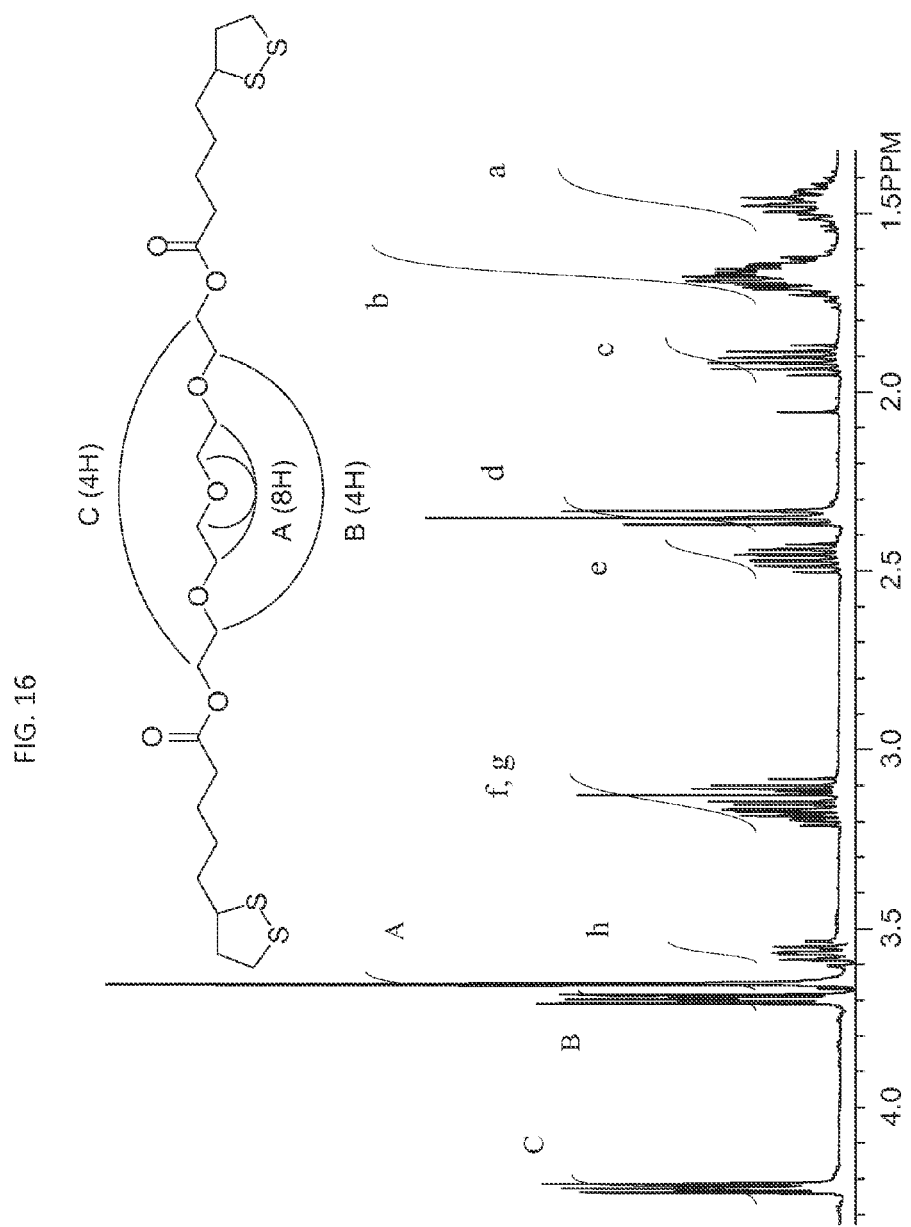
FIG. 16 depicts a $^1$H NMR spectrum of Compound 4a (ALA$_2$/tetraethyleneglycol) in accordance with an embodiment of the present invention.
Figure 17:
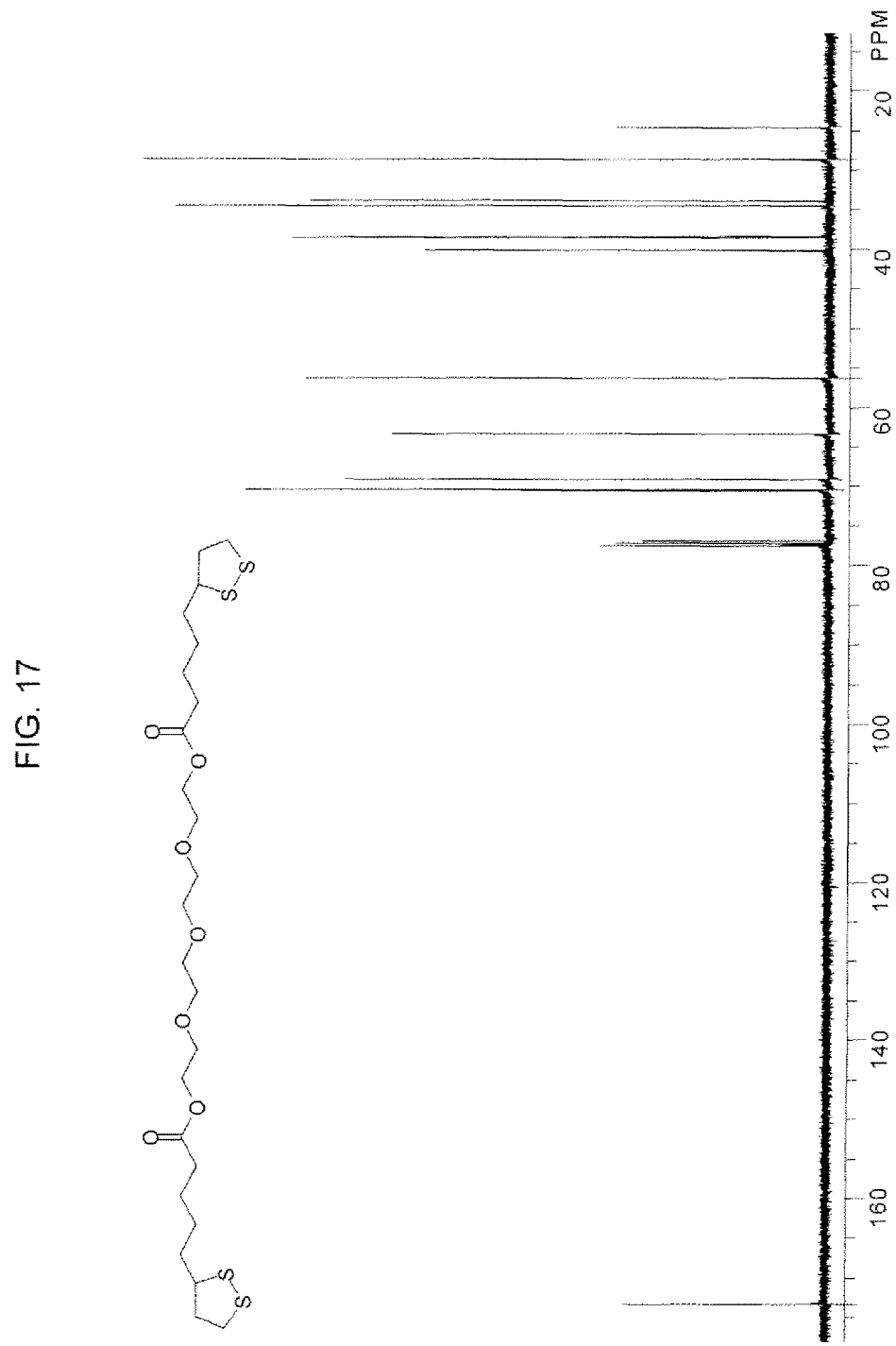
FIG. 17 depicts a $^{13}$C NMR spectrum of Compound 4a (ALA$_2$/tetraethyleneglycol) in accordance with an embodiment of the present invention.
Figure 18:
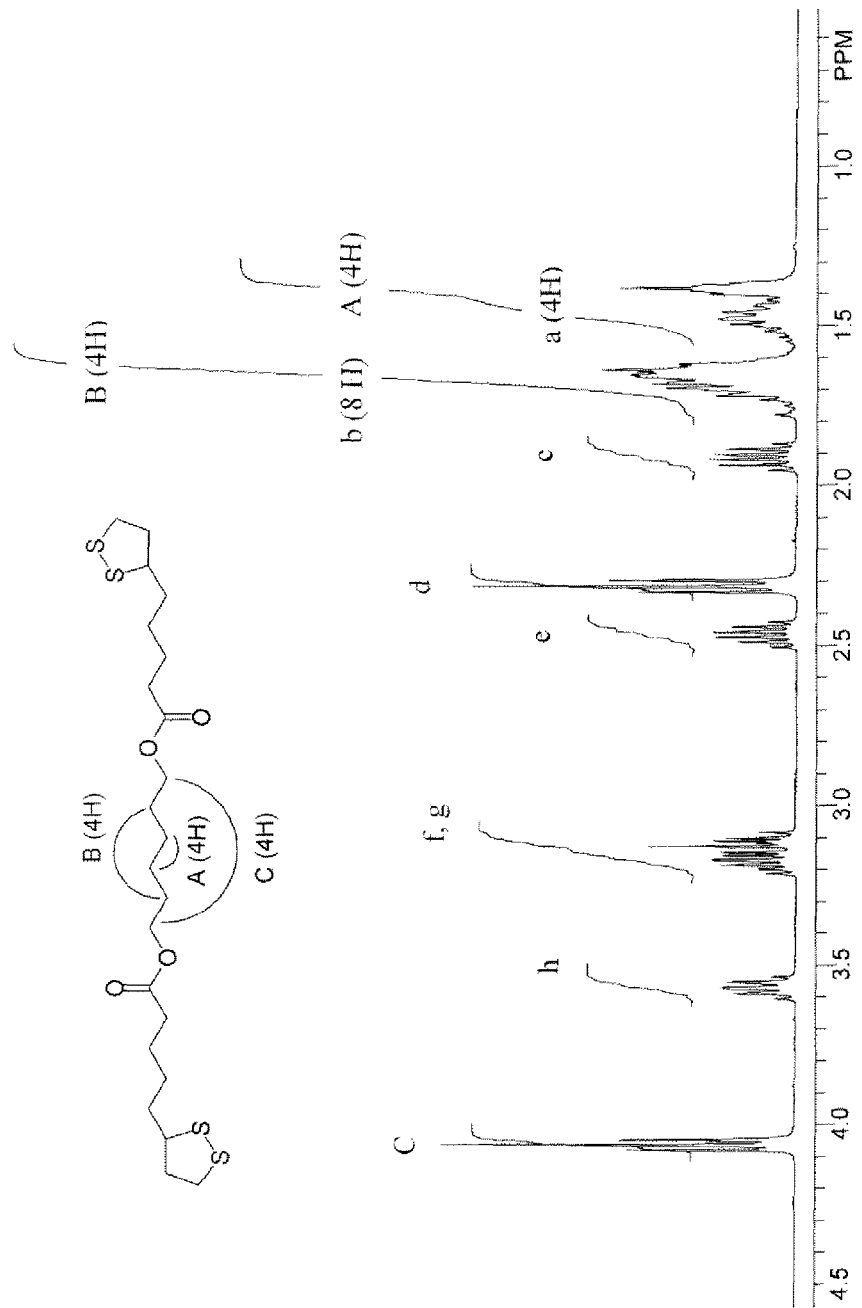
FIG. 18 depicts A $^1$H NMR spectrum of Compound 5a (ALA$_2$/1,6-hexanediol) in accordance with an embodiment of the present invention.
Figure 19:
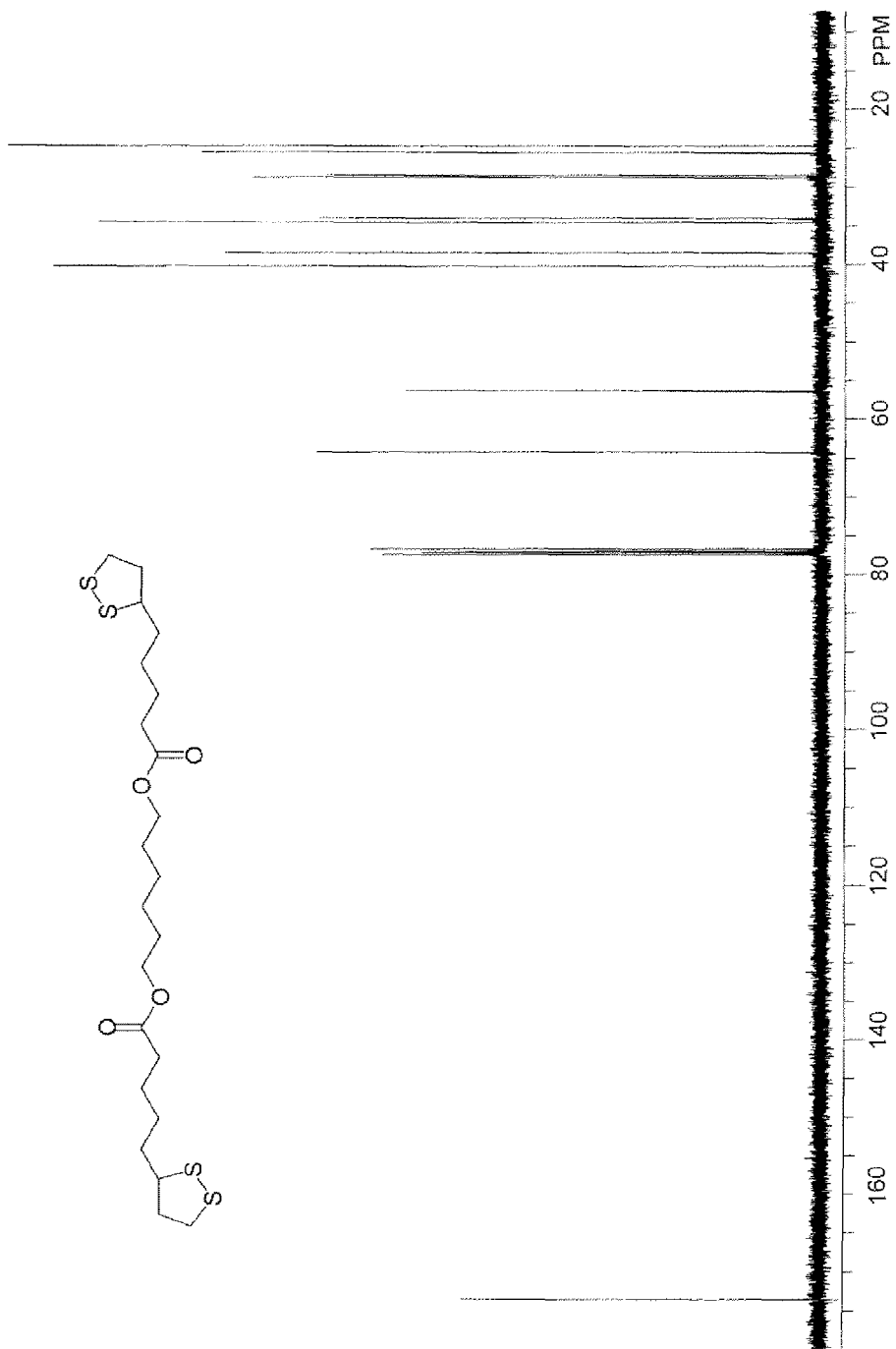
FIG. 19 depicts a $^{13}$C NMR spectrum of Compound 5a (ALA$_2$/1,6-hexanediol) in accordance with an embodiment of the present invention.
Figure 20:
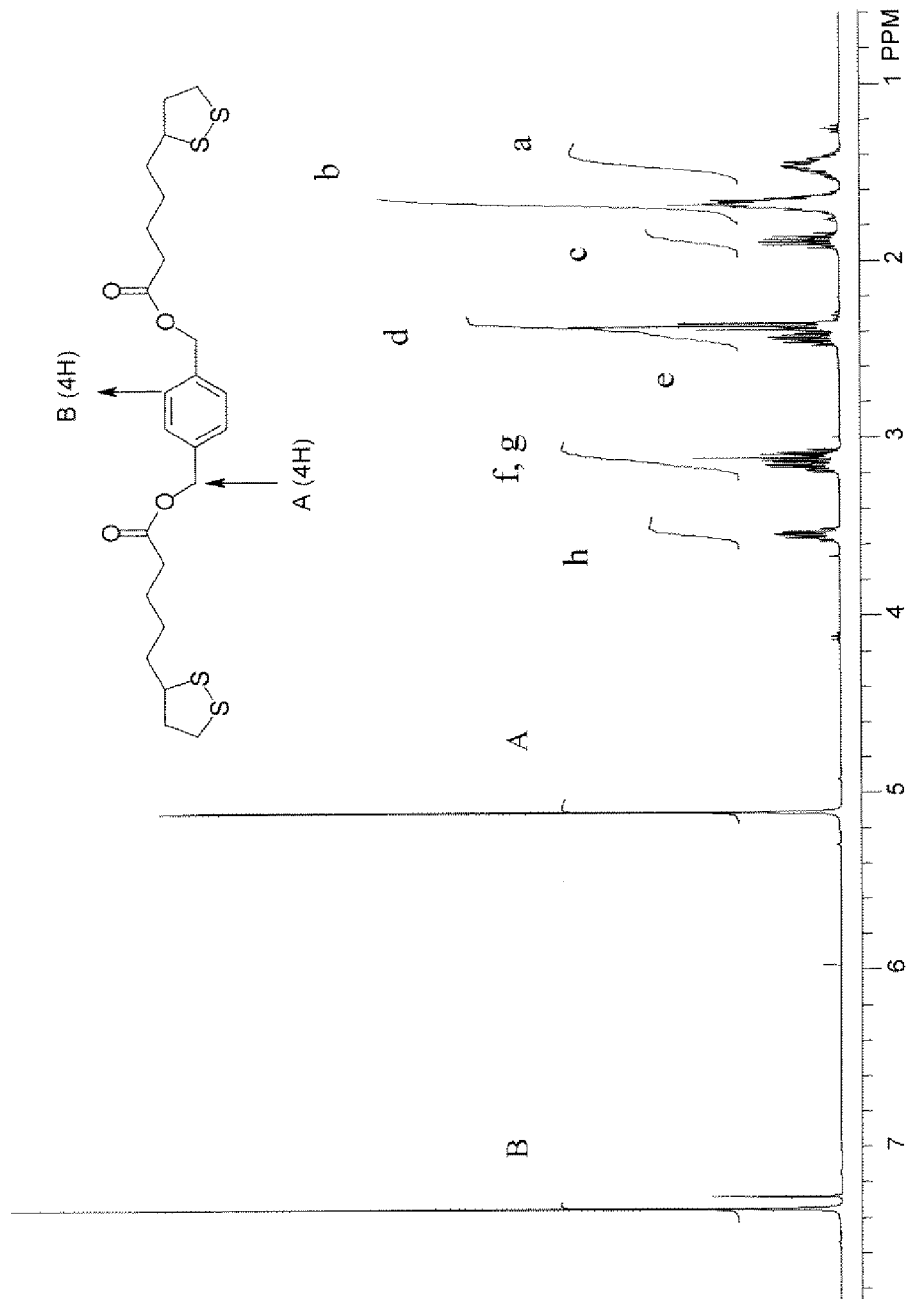
FIG. 20 depicts a $^1$H NMR spectrum of Compound 6a (ALA$_2$/1,4-benzenedimethanol) in accordance with an embodiment of the present invention.
Figure 21:
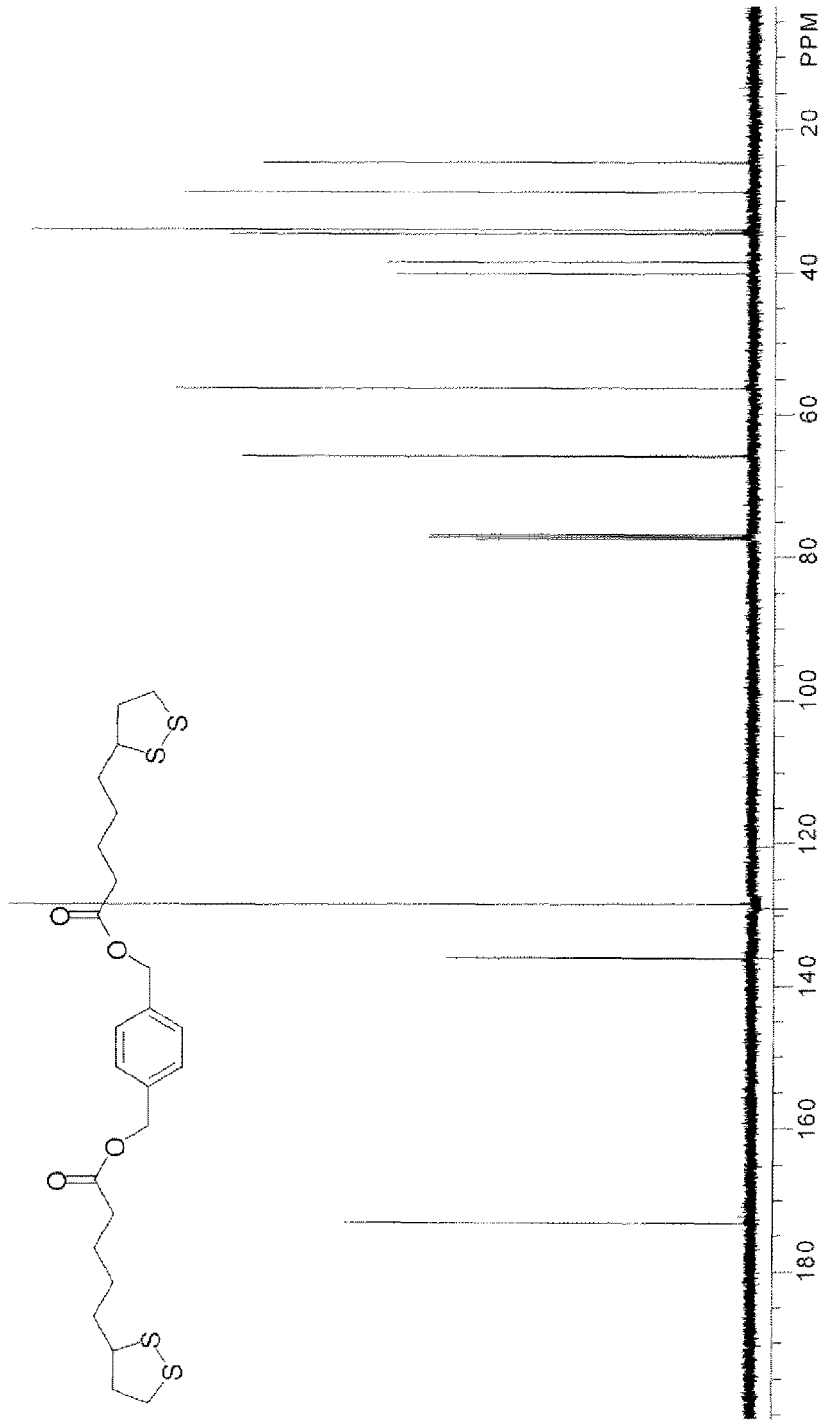
FIG. 21 depicts a $^{13}$C NMR spectrum of Compound 6a (ALA$_2$/1,4-benzenedimethanol) in accordance with an embodiment of the present invention.
Figure 22:
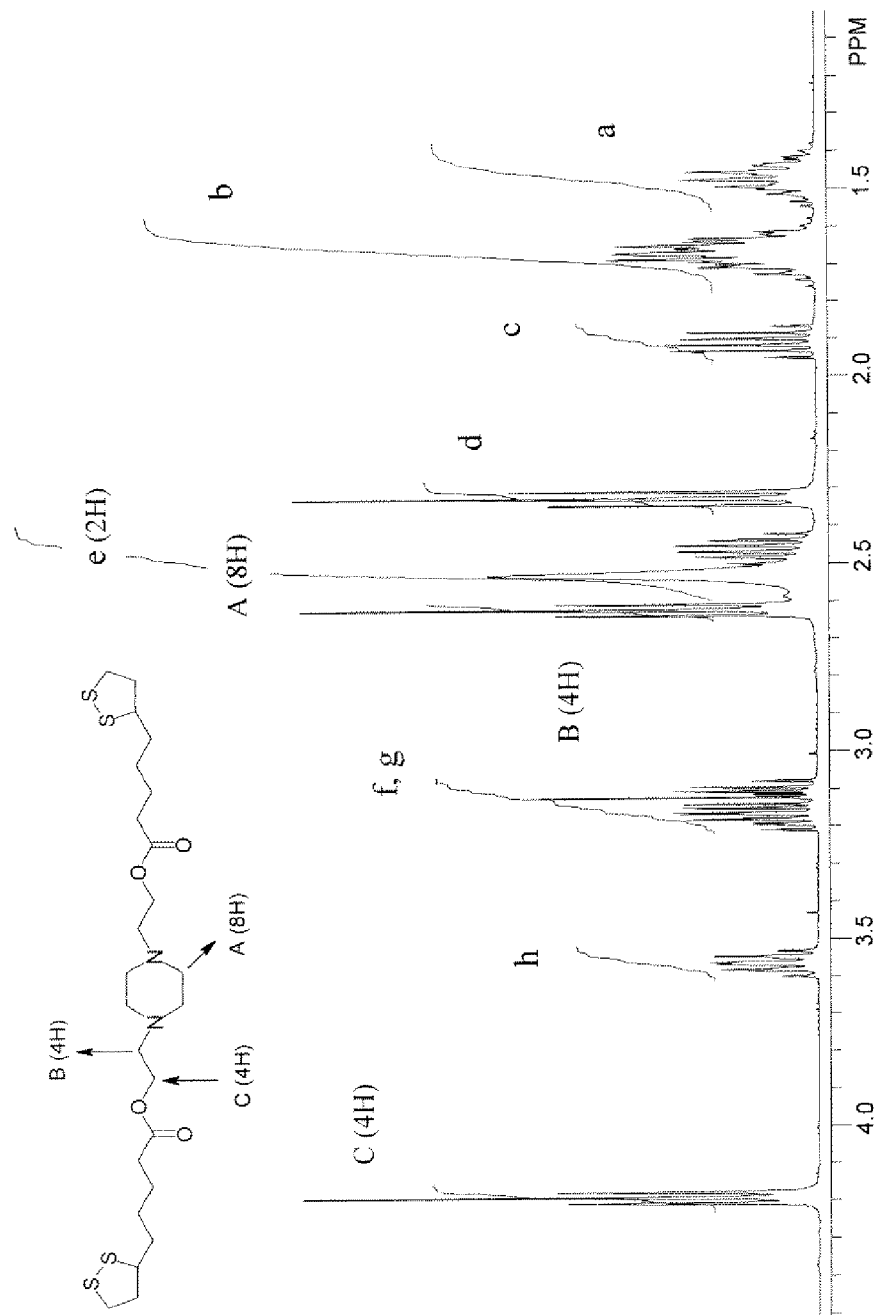
FIG. 22 depicts a $^1$H NMR spectrum of Compound 7a (ALA$_2$/1,4-bis(2-hydroxyethyl)-piperazine) in accordance with an embodiment of the present invention.
Figure 23:
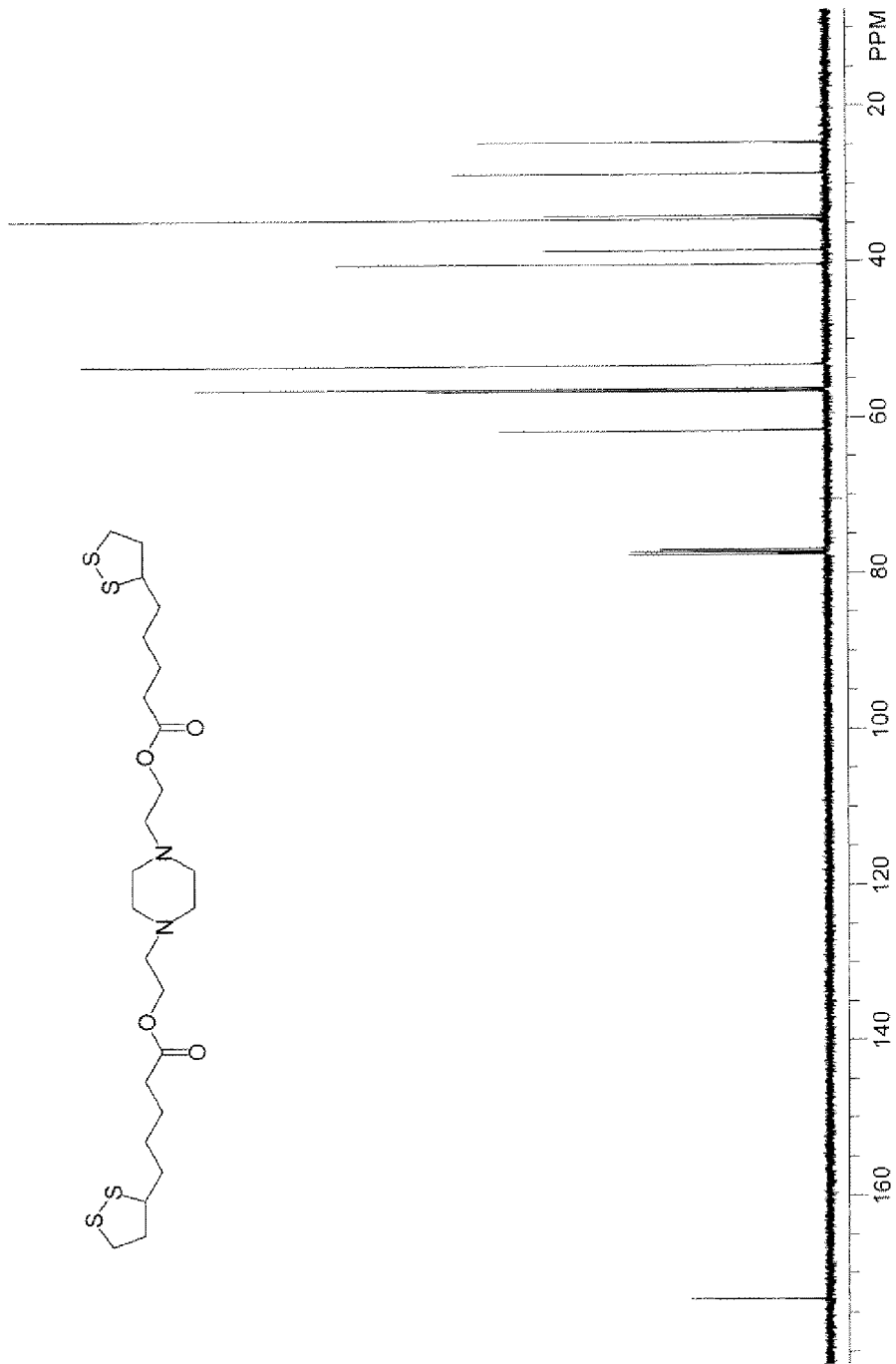
FIG. 23 depicts a $^{13}$C NMR spectrum of Compound 7a (ALA$_2$/1,4-bis(2-hydroxyethyl)-piperazine) in accordance with an embodiment of the present invention.
Figure 24:
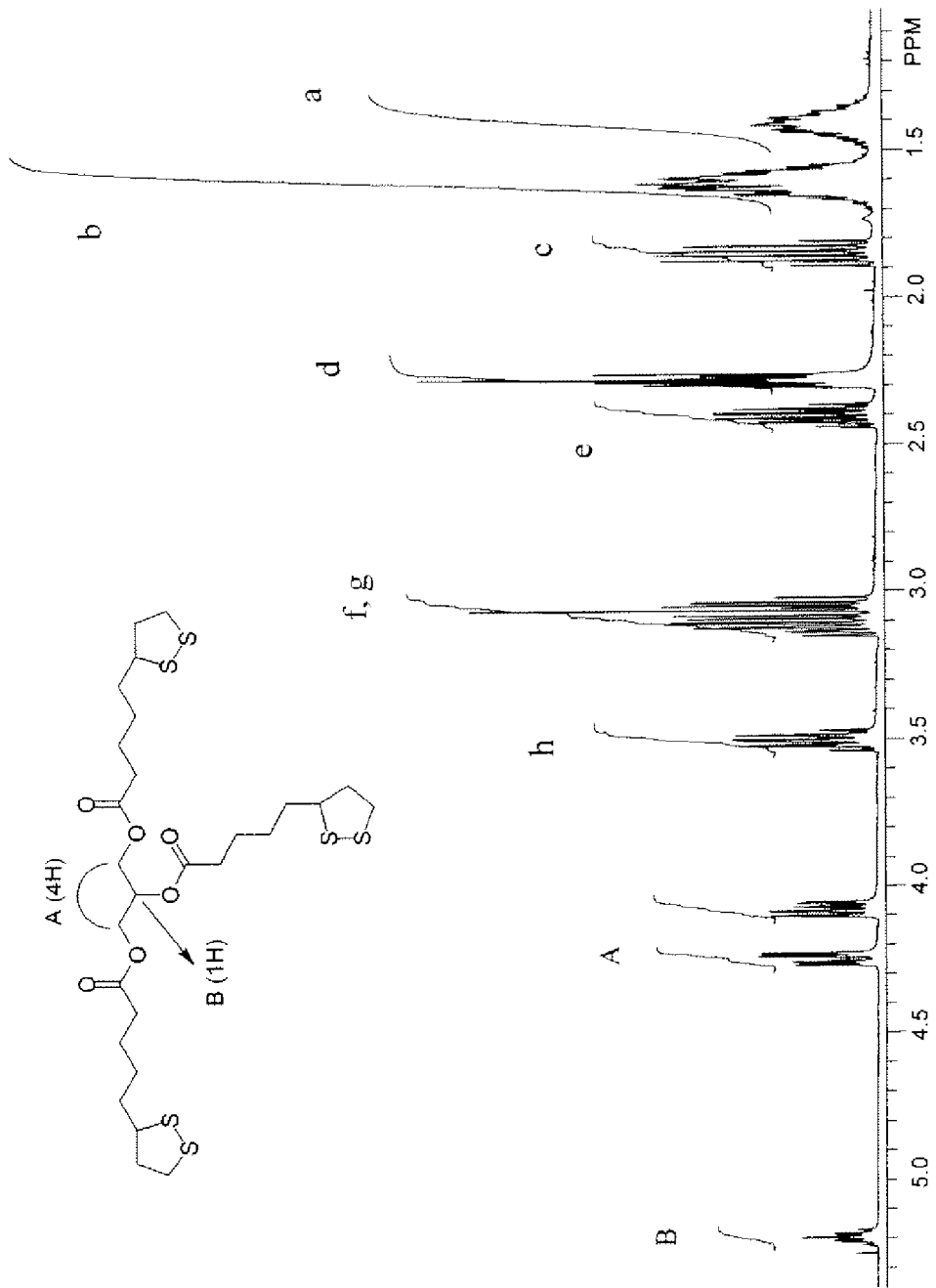
FIG. 24 depicts a $^1$H NMR spectrum of Compound 8a (ALA$_3$/glycerol) in accordance with an embodiment of the present invention.
Figure 25:
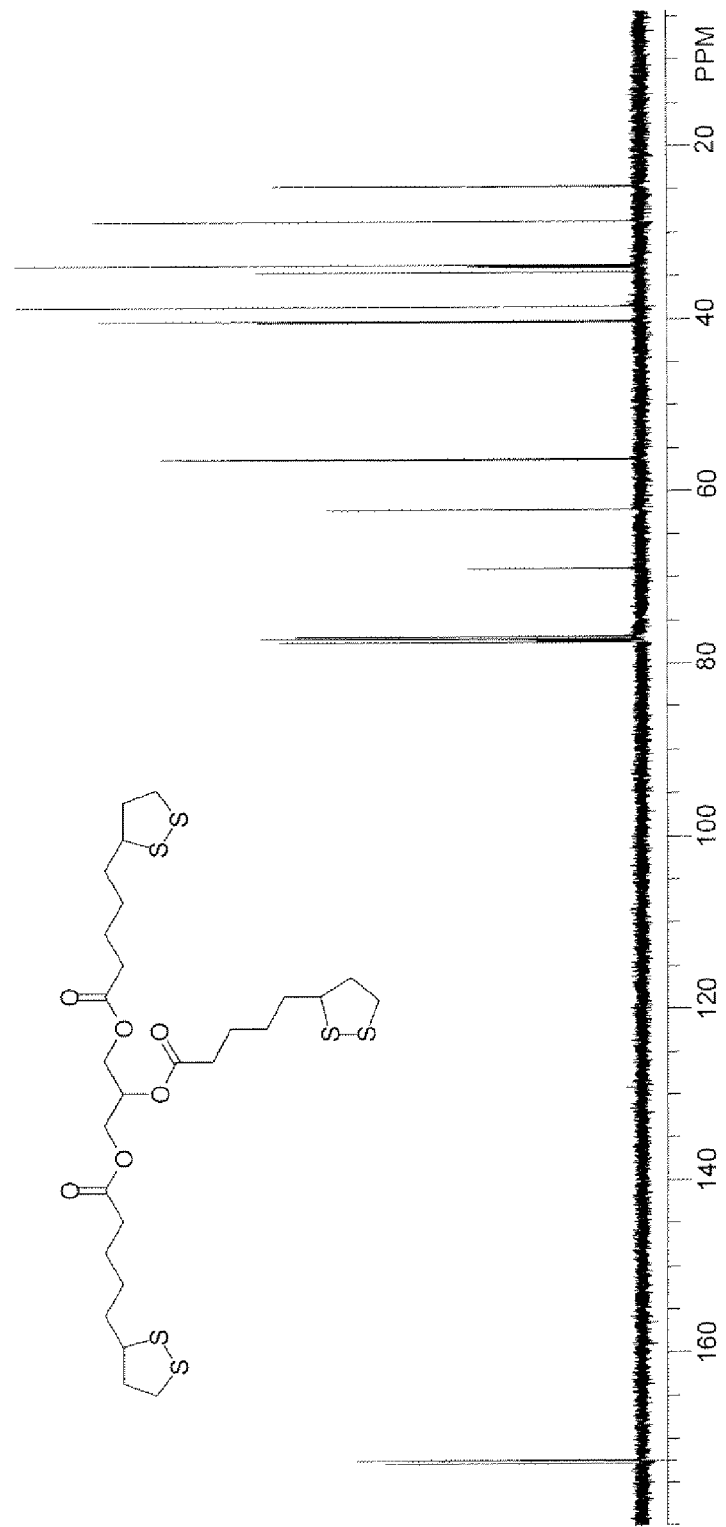
FIG. 25 depicts a $^{13}$C NMR spectrum of Compound 8a (ALA$_3$/glycerol) in accordance with an embodiment of the present invention.
Figure 26:
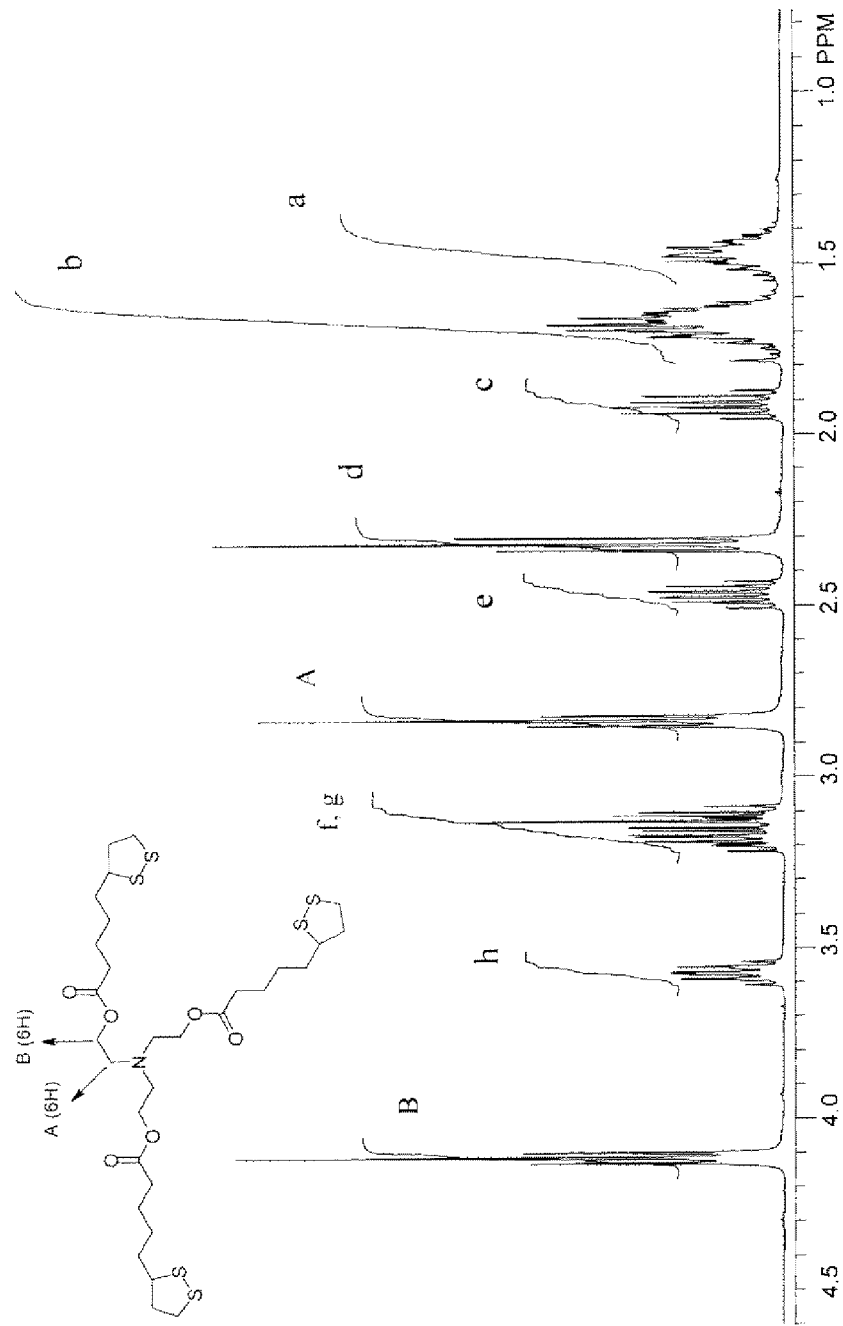
FIG. 26 depicts a $^1$H NMR spectrum of Compound 9a (ALA$_3$/triethanolamine) in accordance with an embodiment of the present invention.
Figure 27:
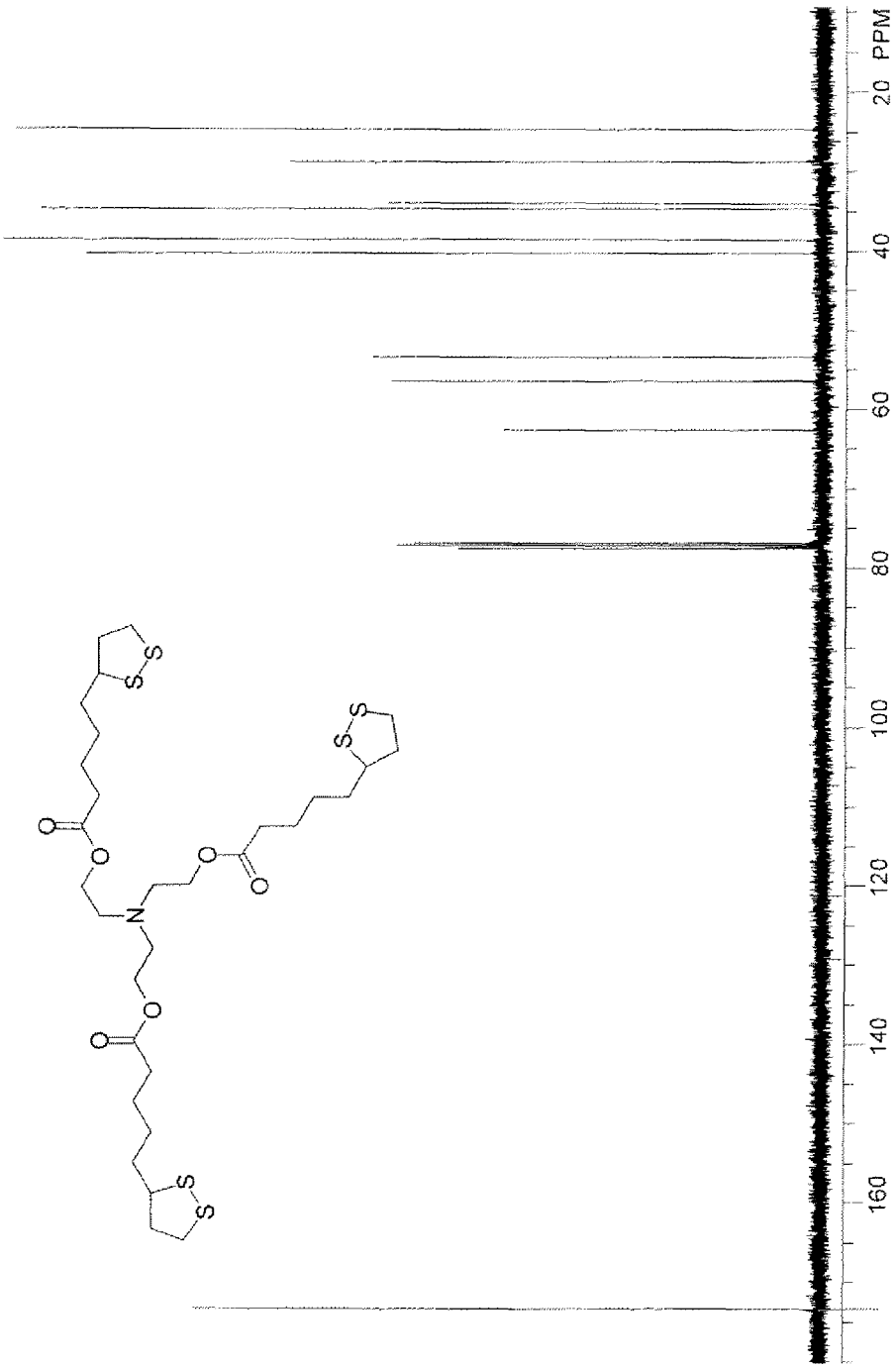
FIG. 27 depicts a $^{13}$C NMR spectrum of Compound 9a (ALA$_3$/triethanolamine) in accordance with an embodiment of the present invention.
Figure 28:
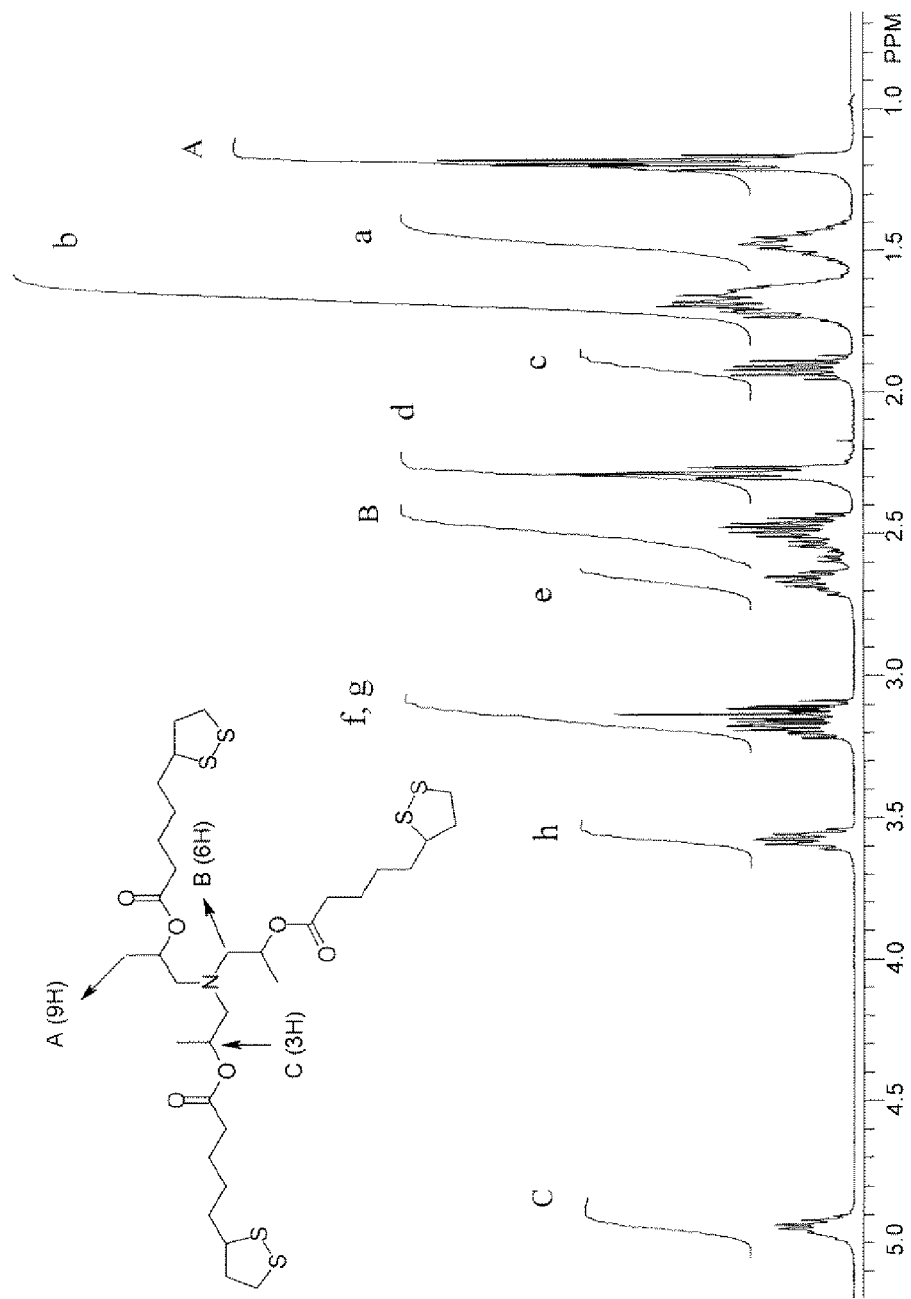
FIG. 28 depicts a $^1$H NMR spectrum of Compound 10a (ALA$_3$/triisoproanolamine), in accordance with an embodiment of the present invention.
Figure 29:
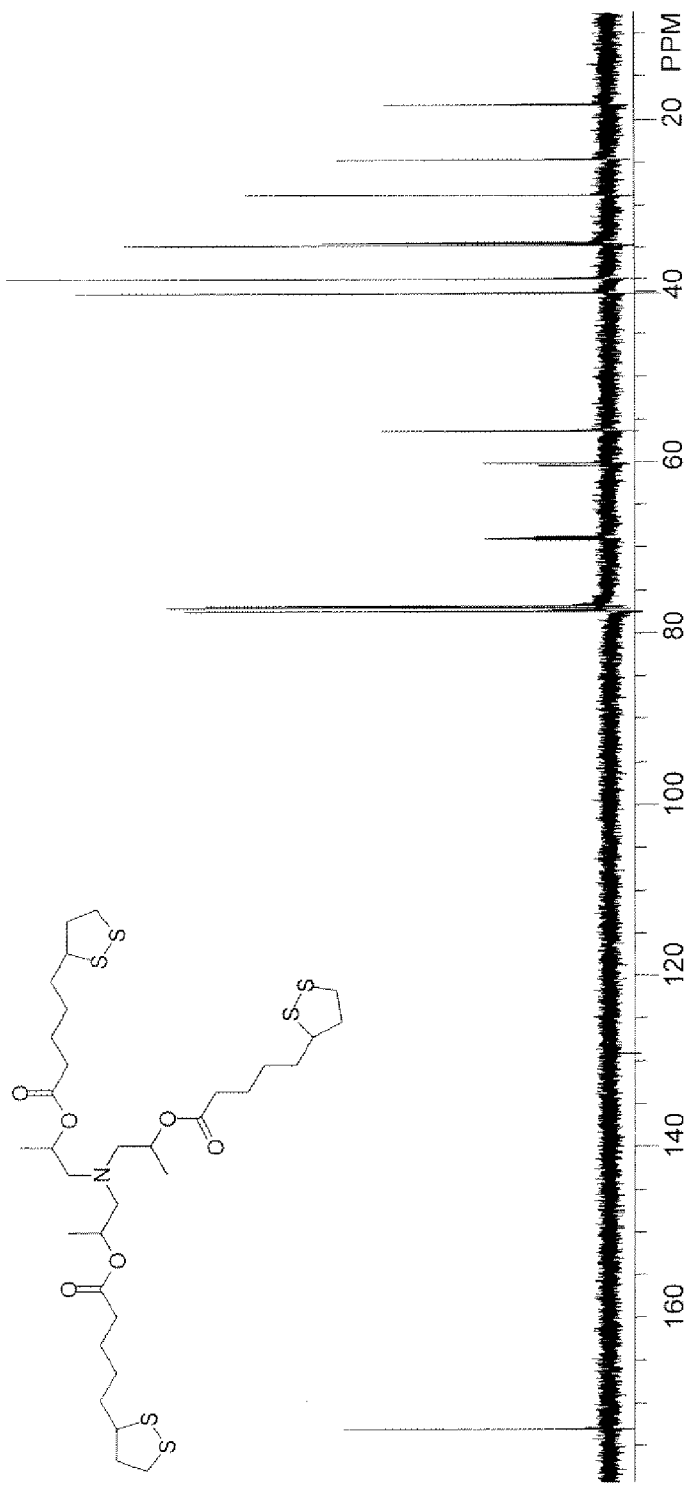
FIG. 29 depicts a $^{13}$C NMR spectrum of Compound 10a (ALA$_3$/triisoproanolamine) in accordance with an embodiment of the present invention.
Figure 30:
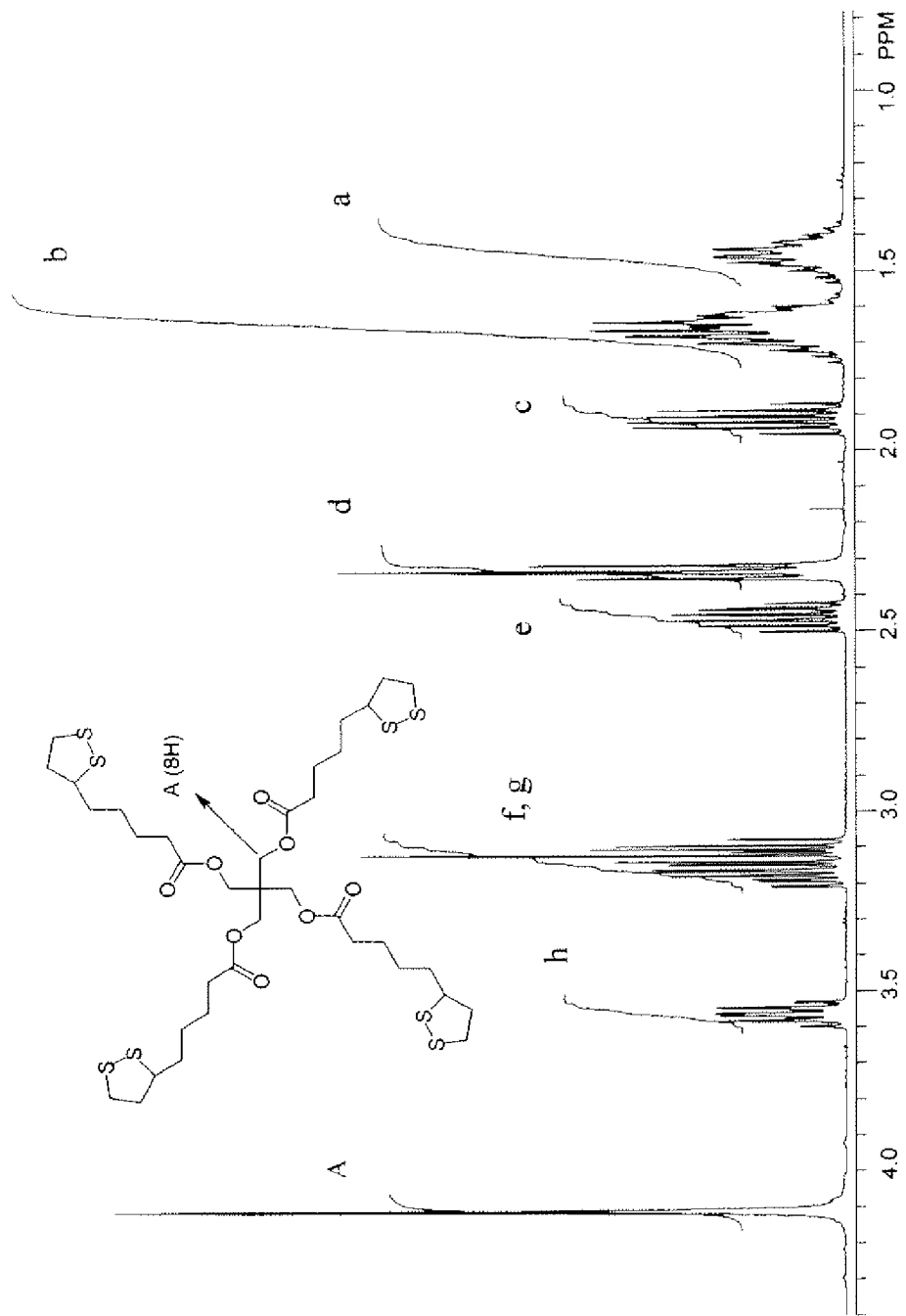
FIG. 30 depicts a $^1$H NMR spectrum of Compound 11a (ALA$_4$/pentaerythritol) in accordance with an embodiment of the present invention.
Figure 31:
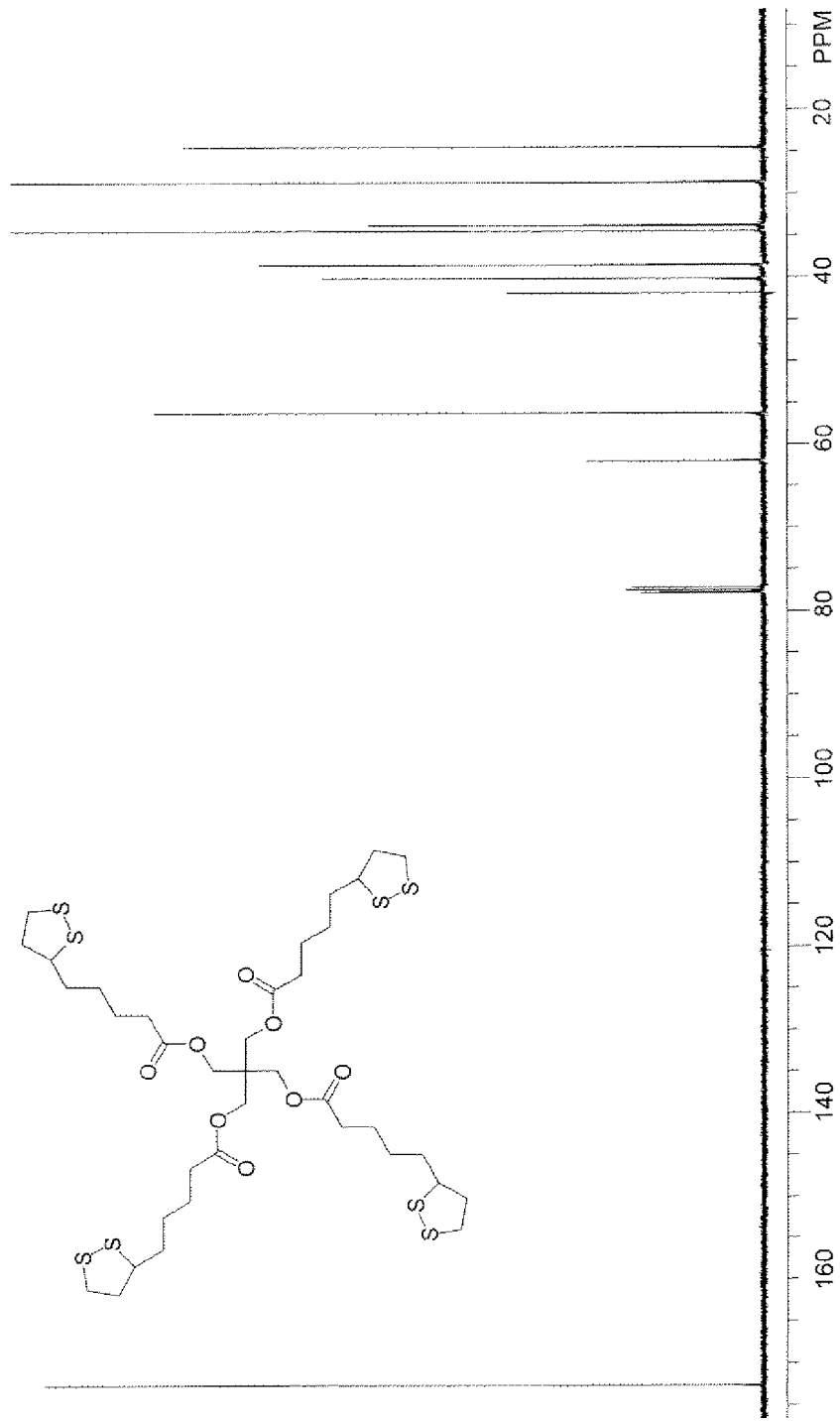
FIG. 31 depicts a $^{13}$C NMR spectrum of Compound 11a (ALA$_4$/pentaerythritol) in accordance with an embodiment of the present invention.
Figure 32:
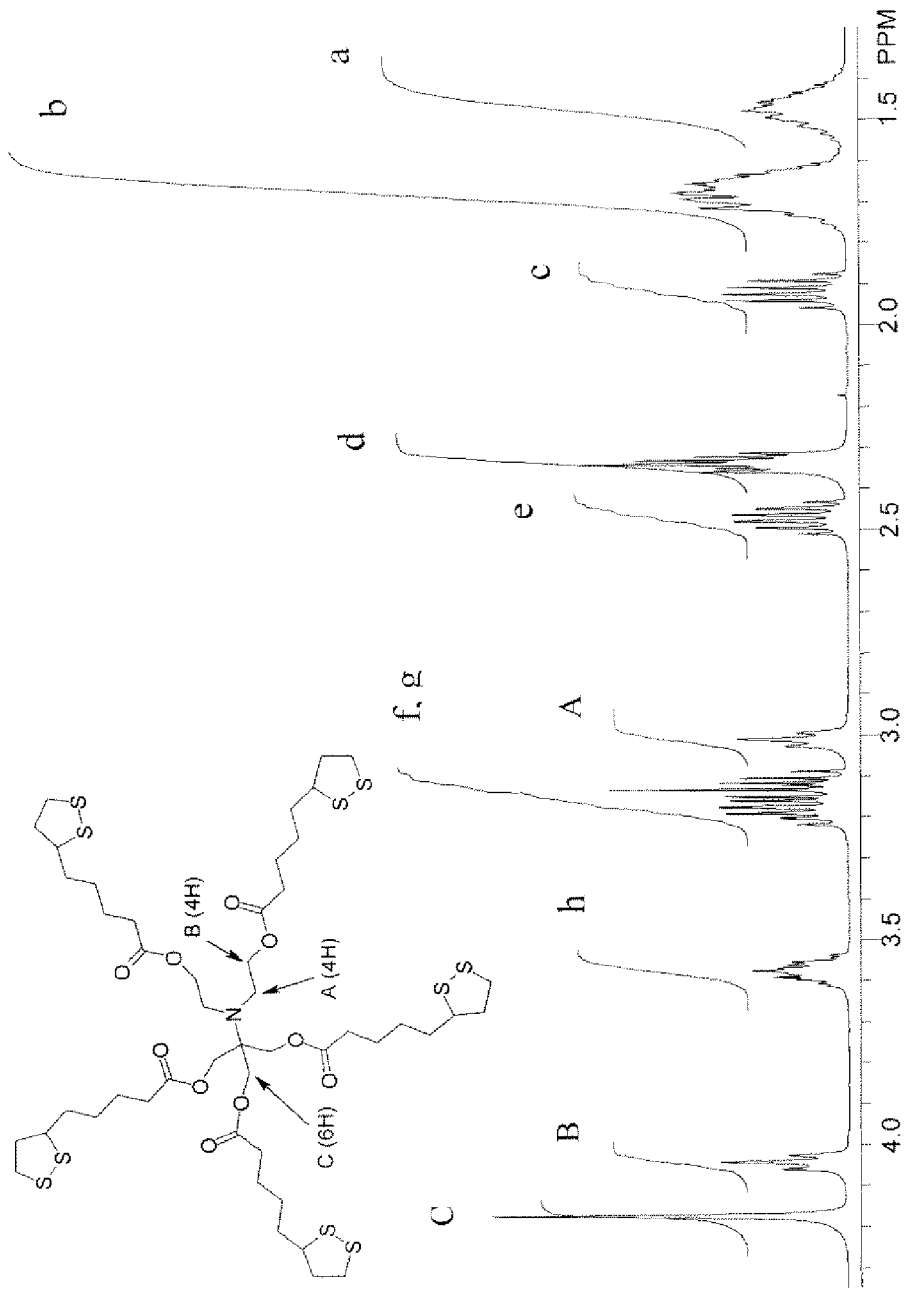
FIG. 32 depicts a $^1$H NMR spectrum of Compound 12a (ALA$_5$/Bis-Tris) in accordance with an embodiment of the present invention.
Figure 33:
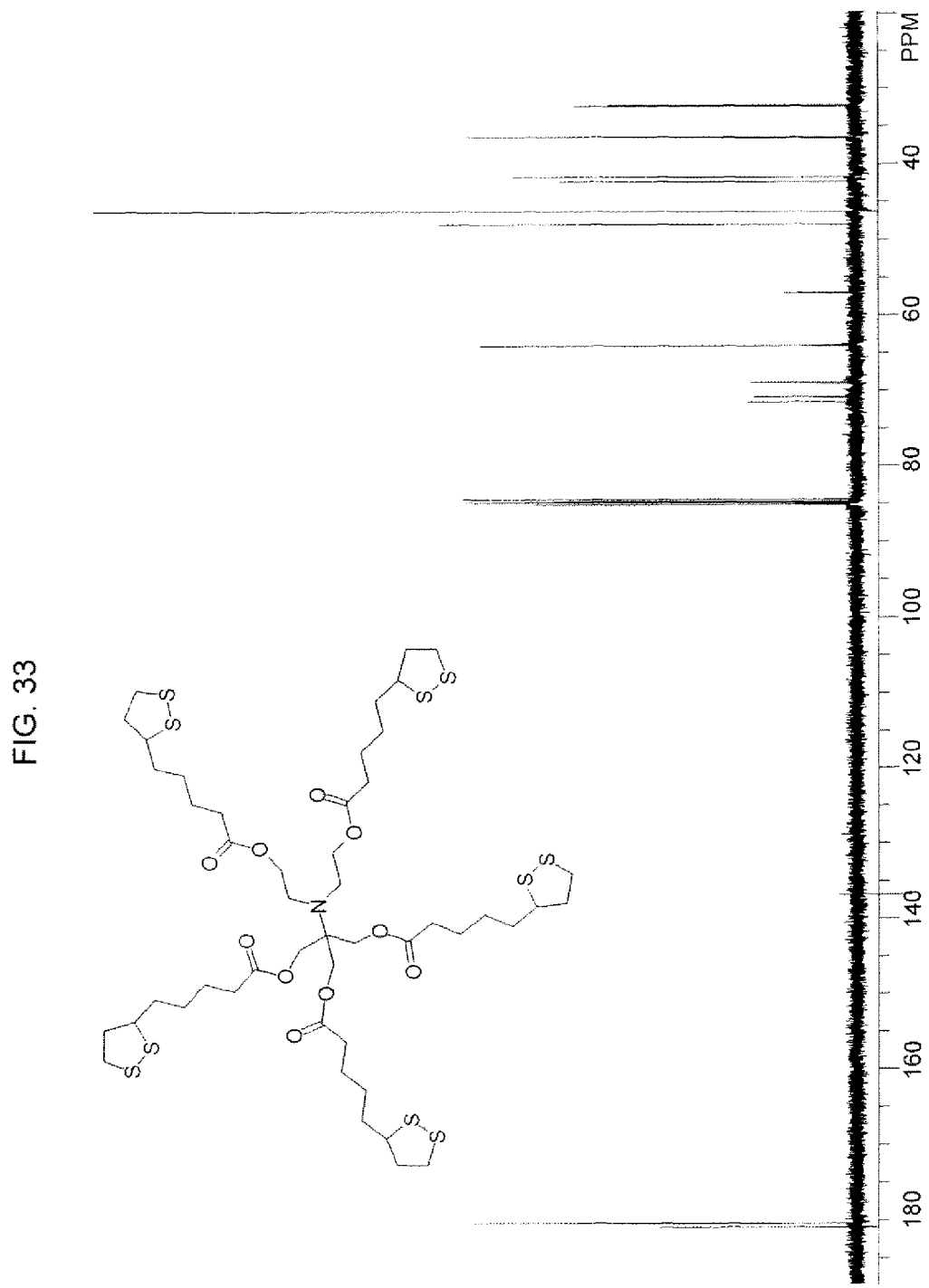
FIG. 33 depicts a $^{13}$C NMR spectrum of Compound 12a (ALA$_5$/Bis-Tris) in accordance with an embodiment of the present invention.

Second, the α-tocopherol may be forced to be oriented so that the functional chromanol rings are directed to the outside and the alkyl chains are directed inside, as depicted schematically in FIG. 9. The driving force for this formation may be the strong hydrophobic interaction between the alkyl chains of α-tocopherol and mALAs. In the case of nanosphere prepared from α-tocopherol only, the orientation may be rather random except for the utmost surface area where the hydroxyl group of chromanol ring seeks to contact the external aqueous phase. The high reactivity of the on the surface localized α-tocopherol may explain the observation that the color changes occurred instantaneously for the TocoLipo4A (FIG. 8a,b) and no further changes were observed. In the case of Toco and TocoLipo 4E (FIG. 8a,b) with the ratio of 0/25 and 7.5/25, respectively, the initial color changes were much less. The observation that the color changes in the case of LipoToco4E proceeded further during the incubation period and the final intensity was similar to that of the initial color change caused by TocoLipo4A indicated that the scavenging reaction kept going until α-tocopherols in the nanospheres were used.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention. While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. An antioxidant molecule represented by Formula I

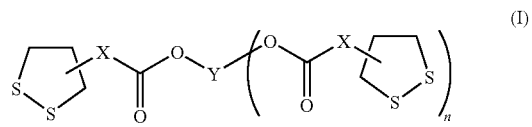

wherein X is selected from the group consisting of a substituted, unsubstituted, branched or unbranched chain of carbon atoms, and may optionally contain a heteroatom;

Y is a moiety formed by esterification of the hydroxyl groups of a polyol selected from the group consisting of $$HO-[\!-O-\!]_n\!\!-H,$$

wherein n is an integer between 1 and 4, (6) HOCH₂-C₆H₄-CH₂OH, (7) HOCH₂CH₂-N(piperazine)N-CH₂CH₂OH, (8) glycerol (HOCH₂-CH(OH)-CH₂OH), (9) triethanolamine N(CH₂CH₂OH)₃,

(10) triisopropanolamine N(CH₂CH(OH)CH₃)₃,

(11) pentaerythritol C(CH₂OH)₄,

(12) (HOCH₂)₃C-N(H)-CH₂CH₂OH type structure,

(13) CH₃-CH(OH)-CH(OH)-,

(14) CH₃CH₂-CH(OH)-CH₂OH,

(15) CH₃-CH(OH)-CH₂-CH₂OH,

(16) CH₃-CH(OH)-CH₂-CH(OH)-CH₃,

(17) CH₃-CH(OH)-CH₂-CH₂-OH (isomer),

(18) HOCH₂-C(CH₃)₂-CH₂OH,

(19) CH₃CH₂CH₂-CH(OH)-CH₂OH,

(20) CH₃(CH₂)₂-CH(OH)-CH₂OH (hexane diol),

(21) CH₃-CH(OH)-CH₂-CH(OH)-CH₃ (isomer),

(22) HOCH₂-CH₂-CH(CH₃)-CH₂-CH₂OH,

(23) CH₃-CH(OH)-CH₂-CH₂-CH₂-OH,

(24) 2-ethyl-hexane-1,3-diol,

(25) 2-ethyl-2-butyl-propane-1,3-diol,

(26) HO-CH₂-CH₂-CH₂-CH(OH)-CH₂OH,

(27) CH₃(CH₂)₄-CH(OH)-CH₂OH,

(28) long chain alkyl diol,

(29) longer chain alkyl diol,

(30) HOCH₂-C(CH₃)(CH₂OH)-CH₂OH,

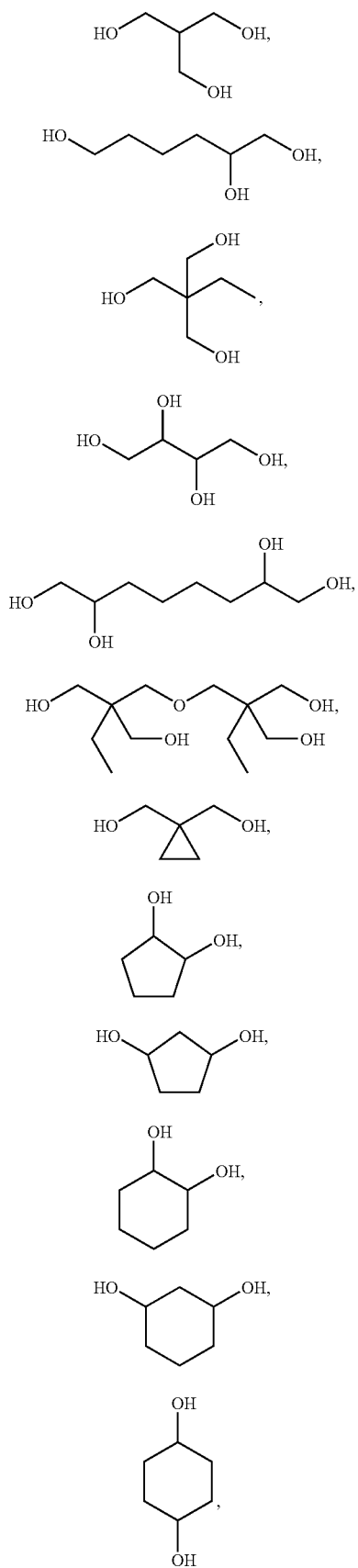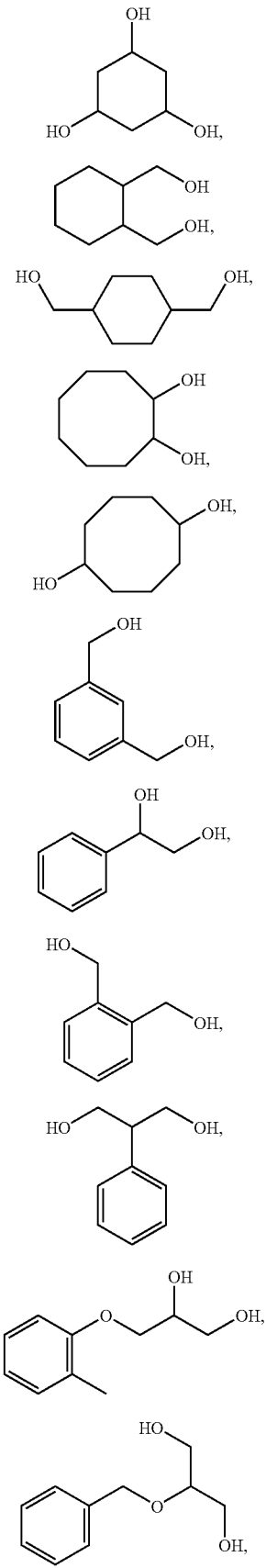

-continued
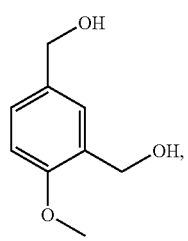 (54)
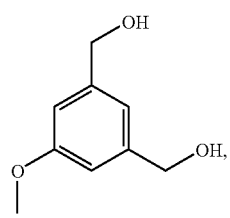 (55)
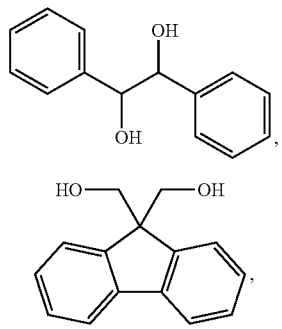 (56)
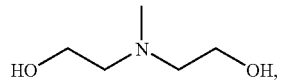 (57)
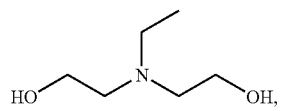 (58)
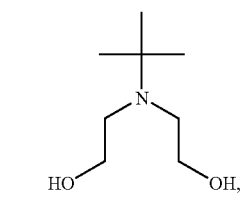 (59)
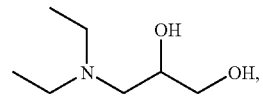 (60)
(61)
-continued
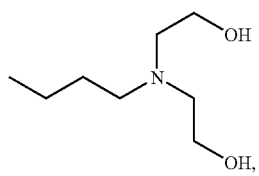 (62)
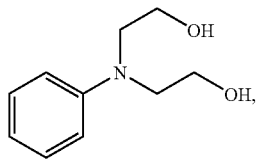 (63)
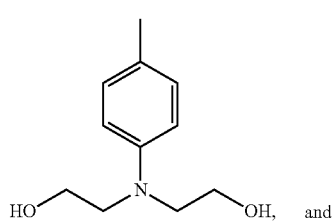 (64) and
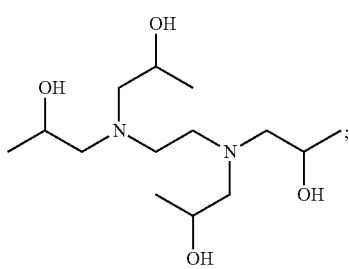 (65)
and
n is an integer of at least one.
2. The antioxidant molecule of claim 1, wherein X is an unsubstituted, unbranched chain of 1 to 6 carbon atoms.
3. The antioxidant molecule of claim 2, wherein the antioxidant molecule is represented by formula II
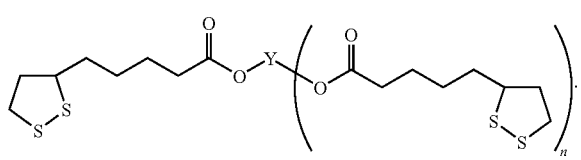 (II)
4. An antioxidant molecule selected from the group consisting of
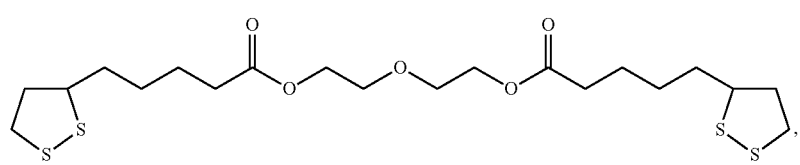 (2a)

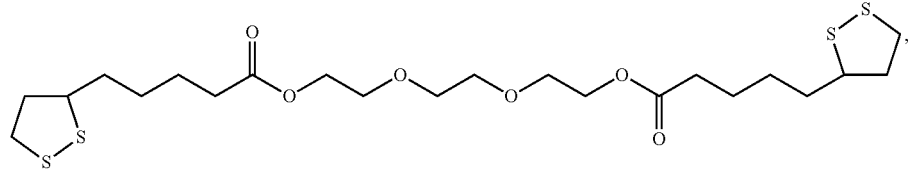
(3a)
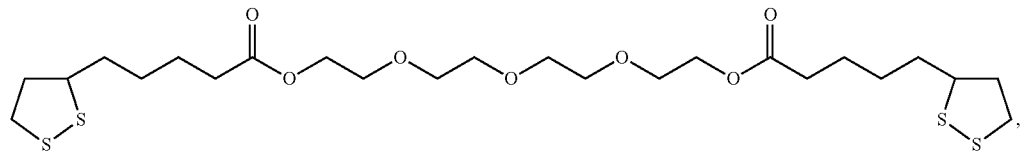
(4a)
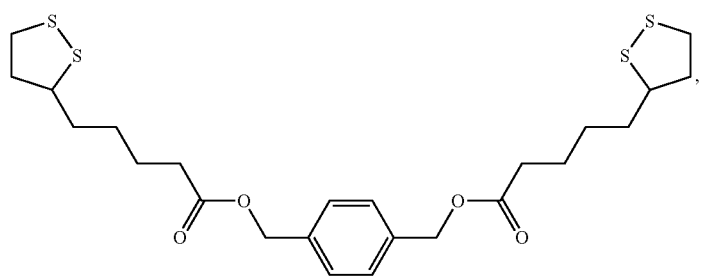
(6a)
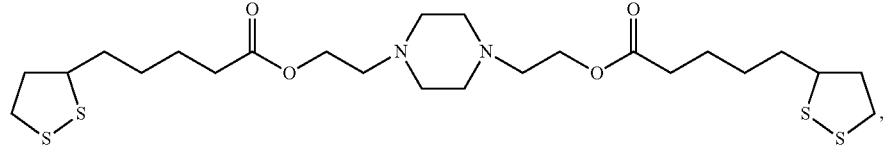
(7a)
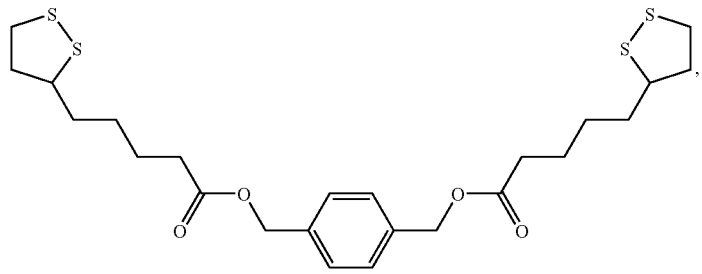
(6a)
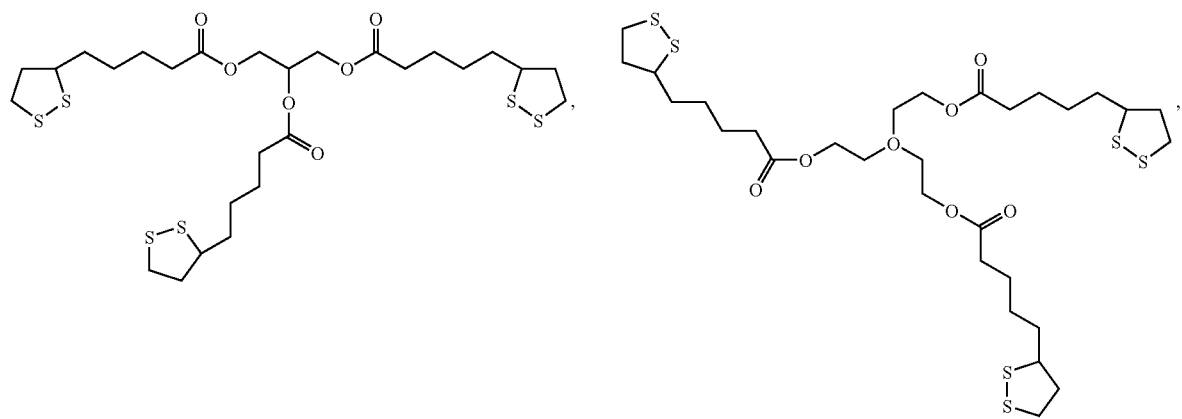
(8a) (9a)

(10a)
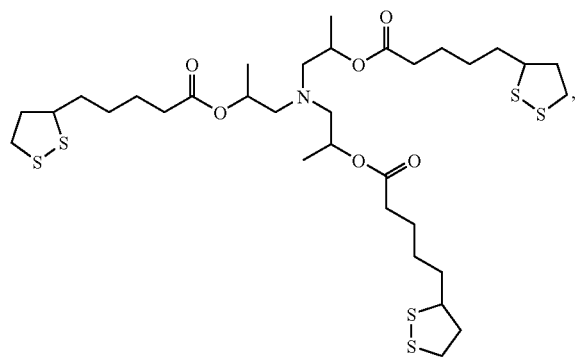
(11a)
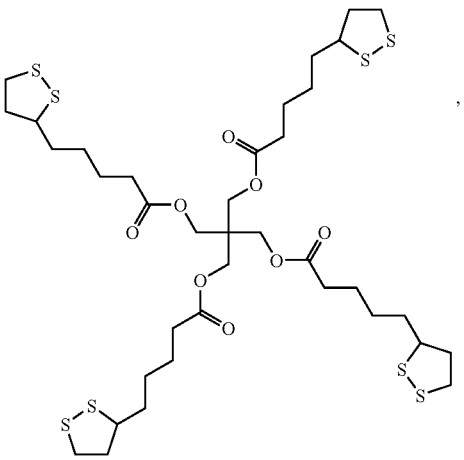
(12a)
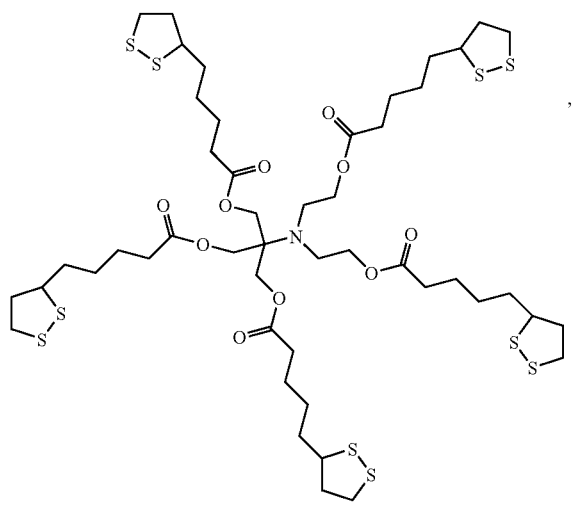
(13a)
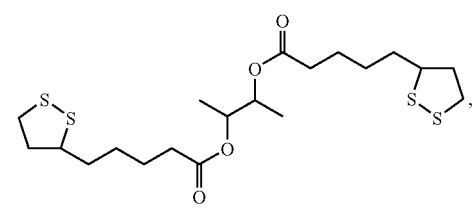
(14a)
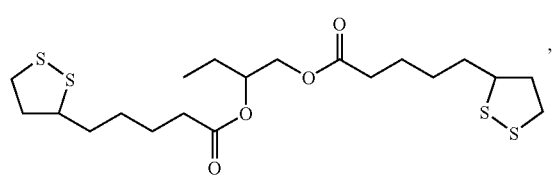
(15a)
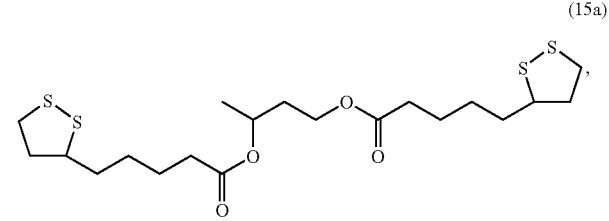
(16a)
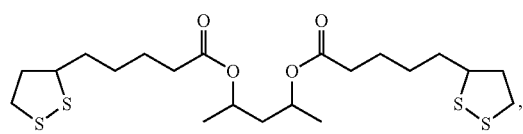
(17a)
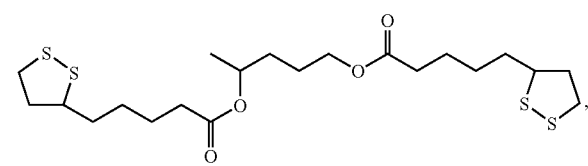
(18a)
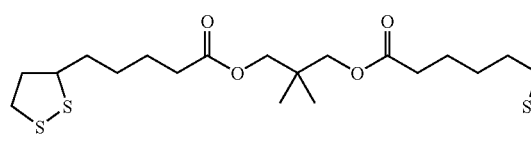
(19a)
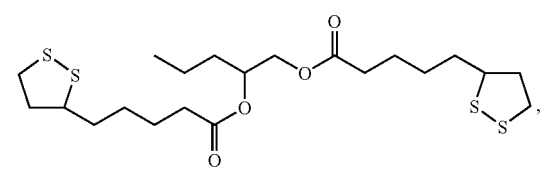

-continued
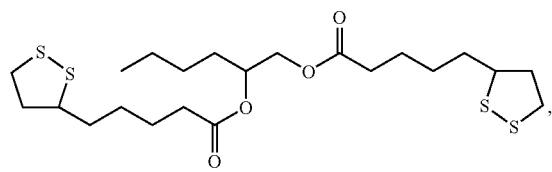
(20a)
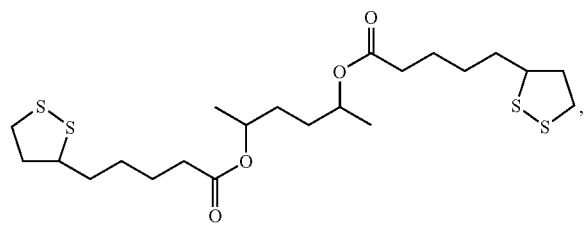
(21a)
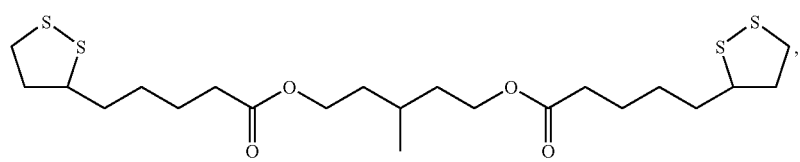
(22a)
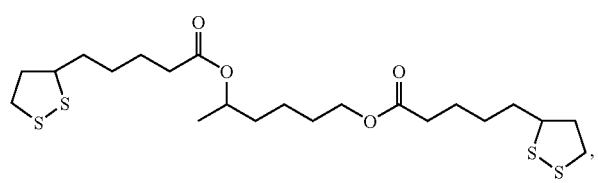
(23a)
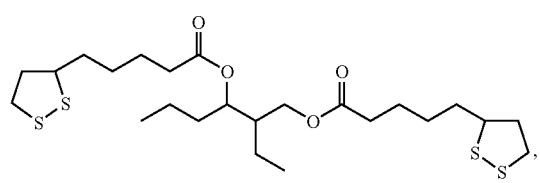
(24a)
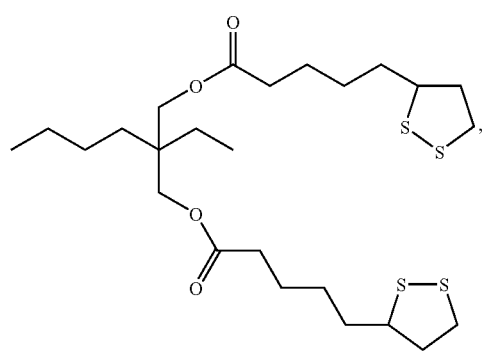
(25a)
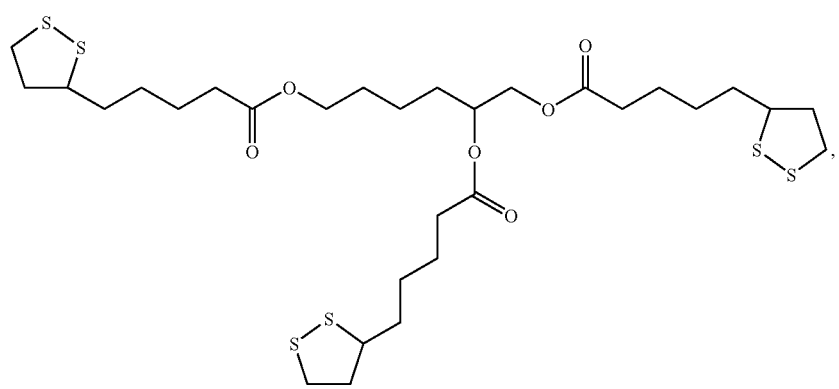
(26a)
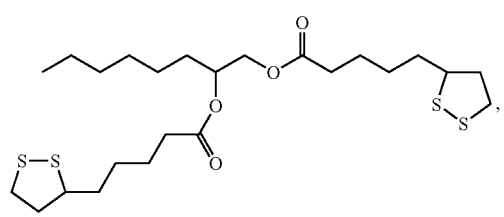
(27a)
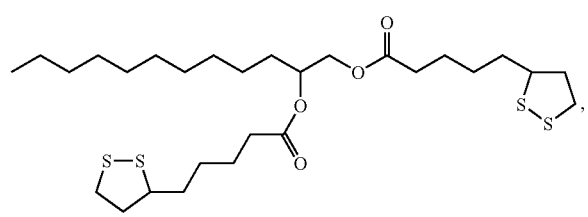
(28a)

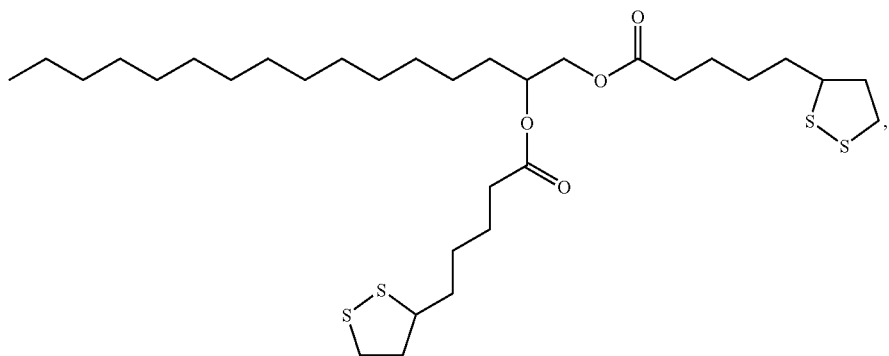
(29a)
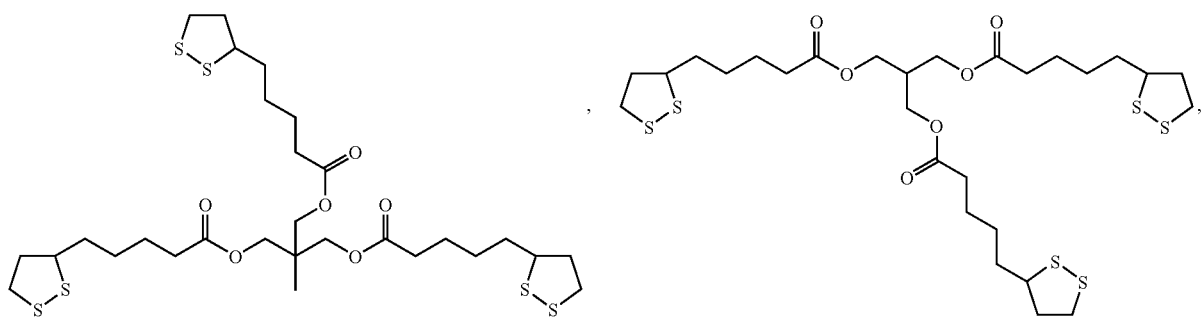
(30a) (31a)
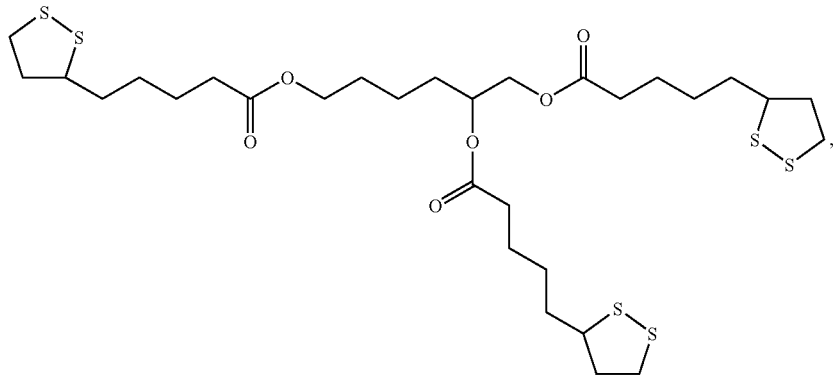
(32a)
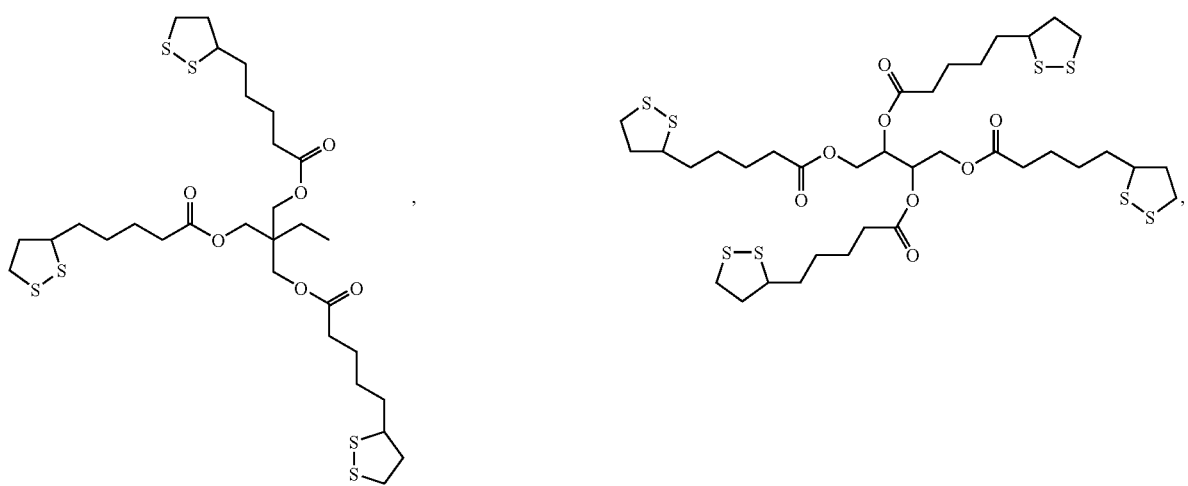
(33a) (34a)

(35a)
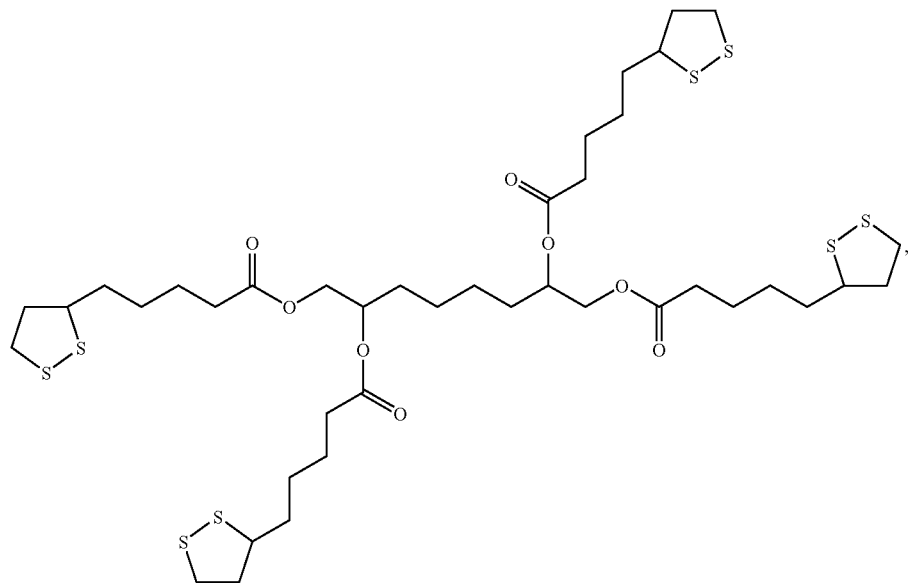
(36a)
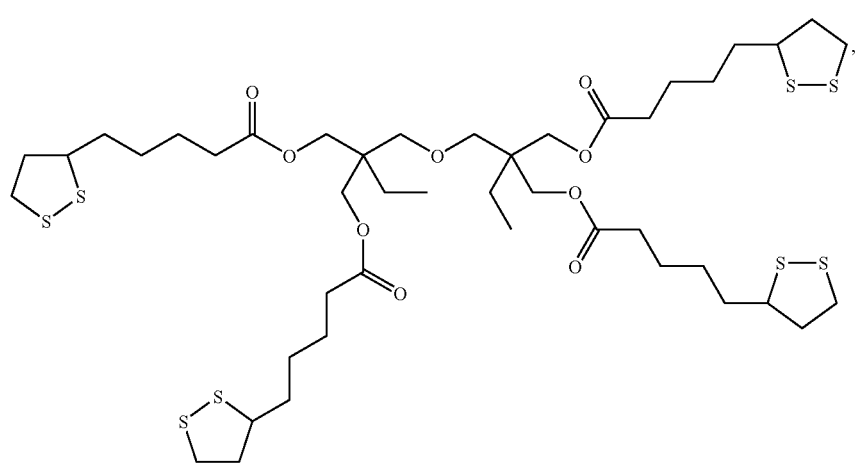
(37a)
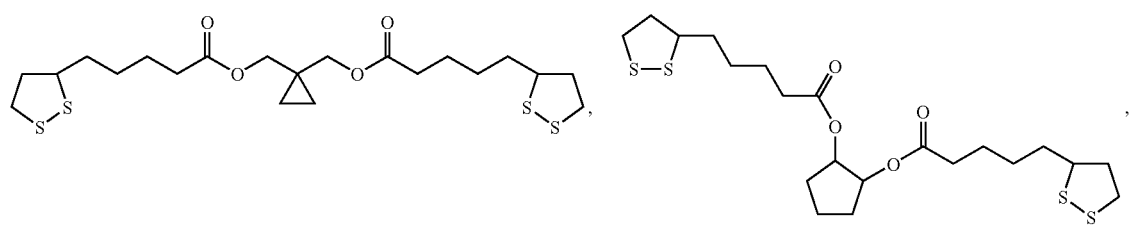
(38a)
(39a)
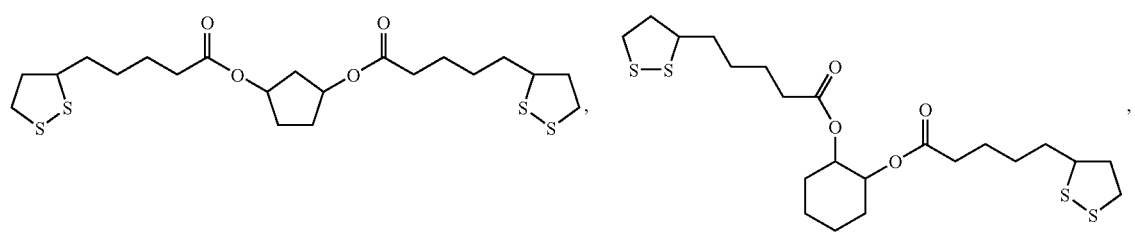
(40a)

-continued
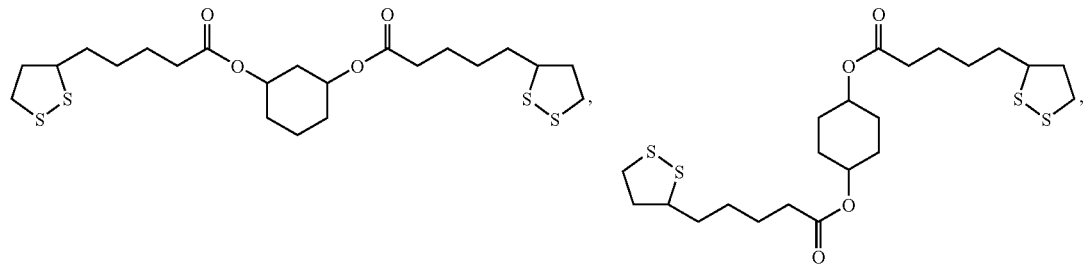
(41a) (42a)
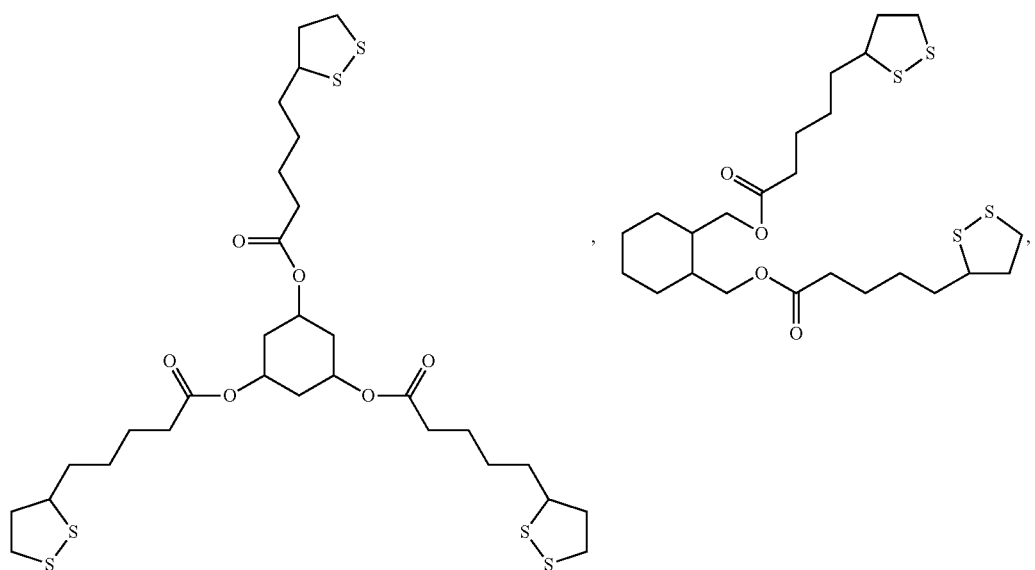
(43a) (44a)
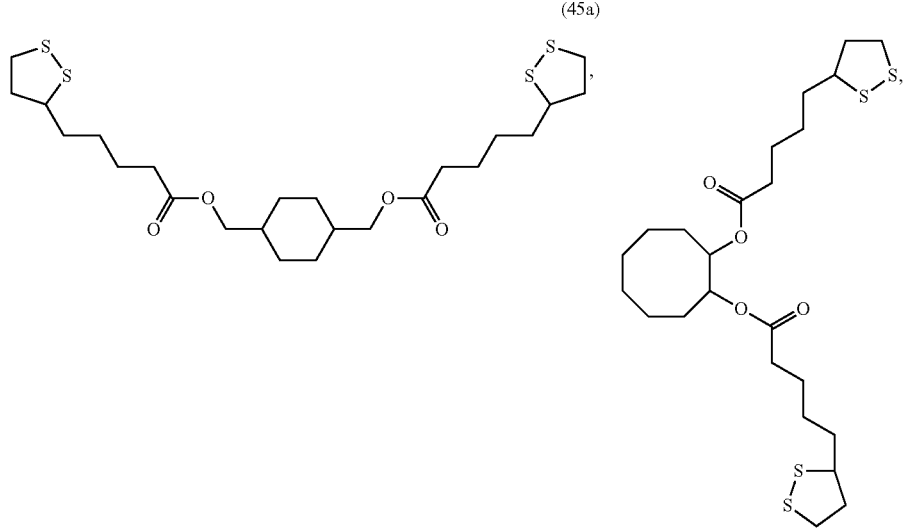
(45a) (46a)

-continued
(47a) (48a)
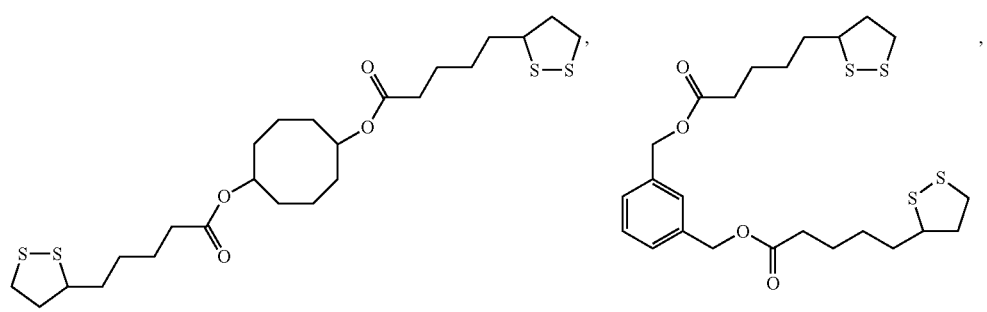
(49a) (50a)
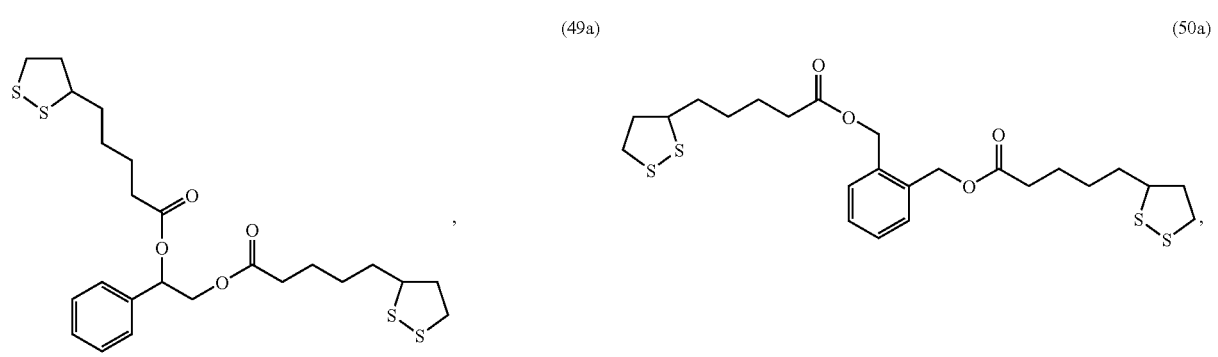
(51a) (52a)
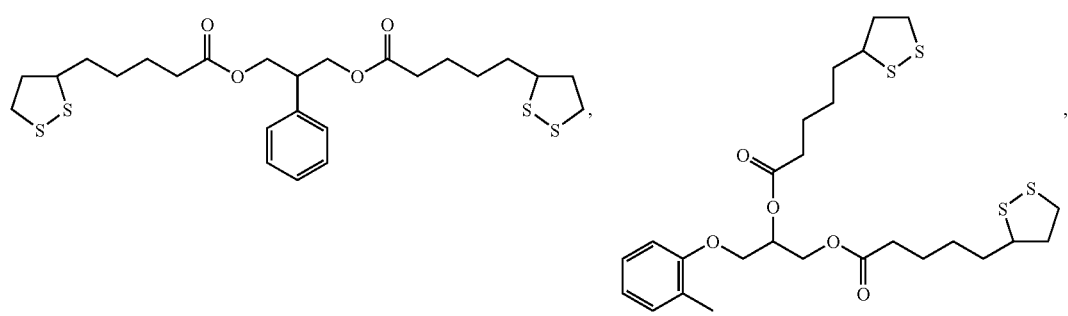
(53a) (54a)
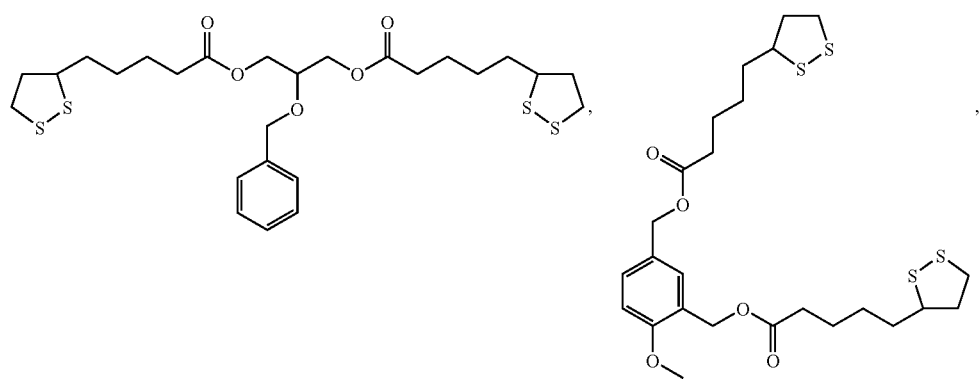

-continued
(55a)
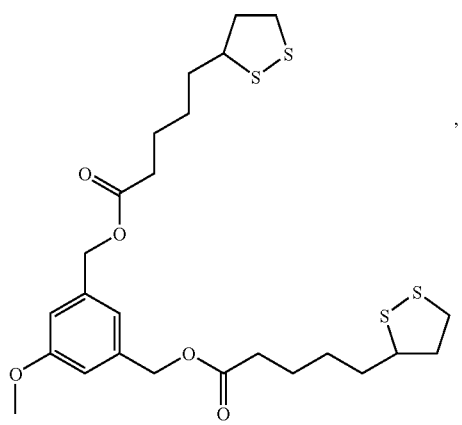
(56a)
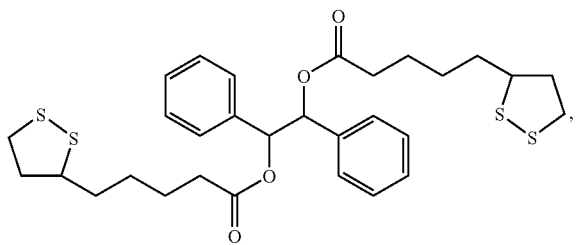
(57a)
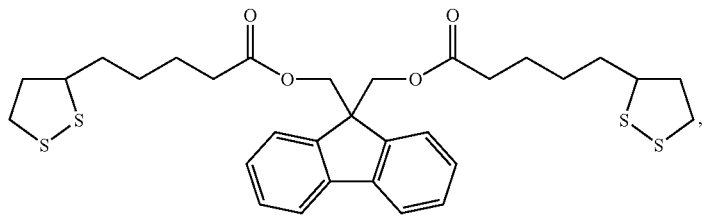
(58a)
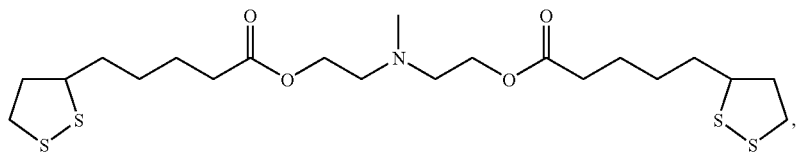
(59a)
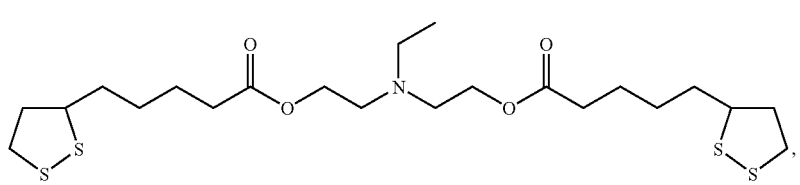
(60a)
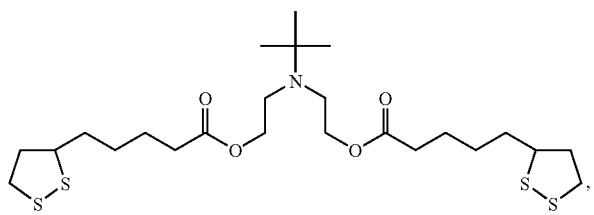
(61a)
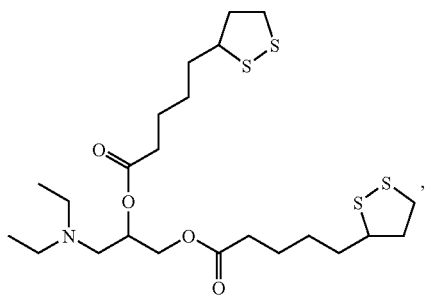

-continued
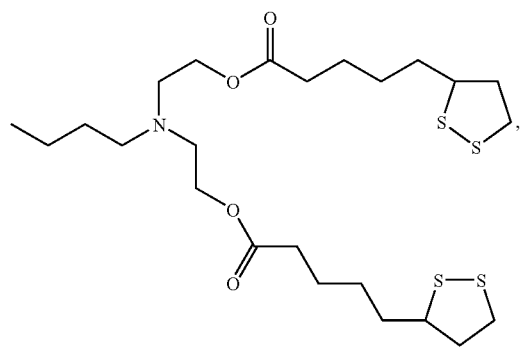
(62a)
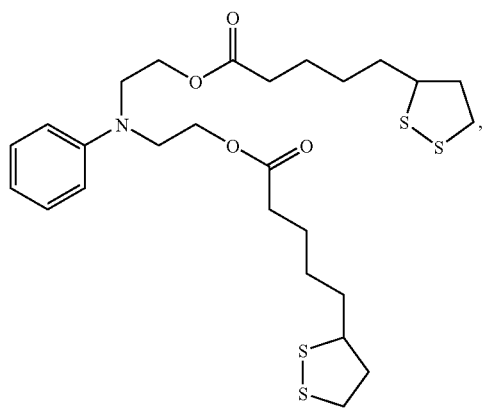
(63a)
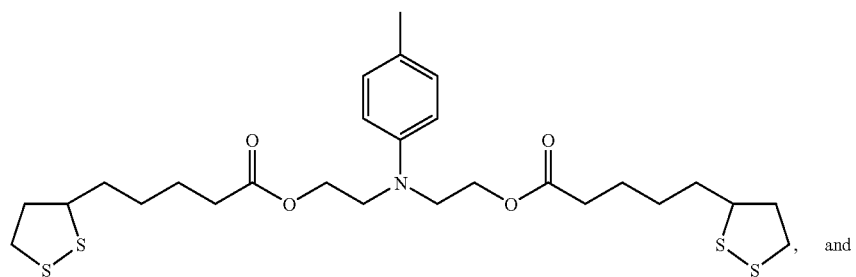, and
(64a)
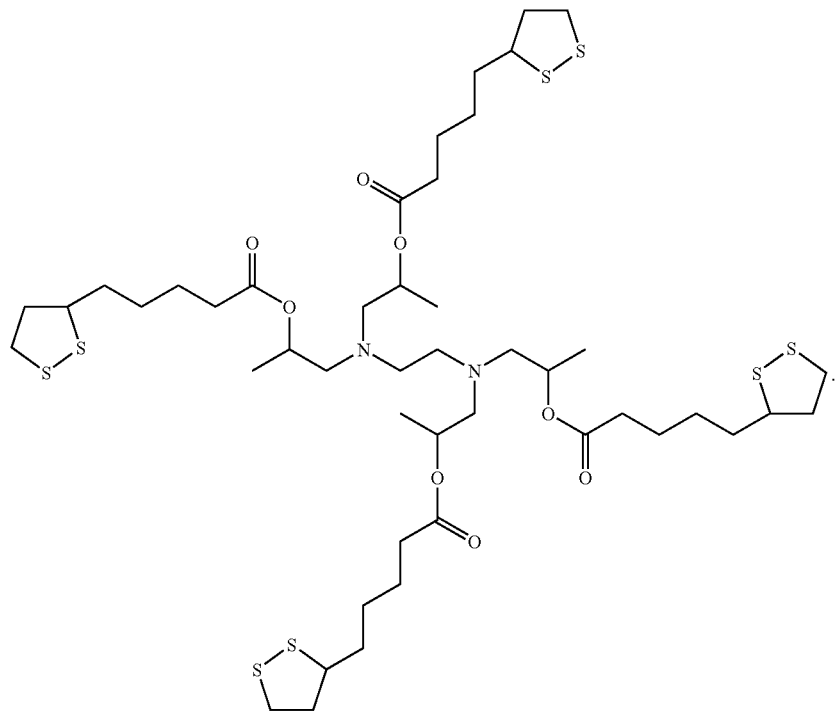
(65a)

5. A method of synthesizing an antioxidant molecule of claim 1, comprising:

providing at least two [1,2]-dithiolane moieties;

providing a polyol of claim 1 to conjugate the at least two [1,2]-dithiolane moieties; and reacting the at least two [1,2]-dithiolane moieties with the polyol to produce the antioxidant molecule.

6. The antioxidant molecule of claim 5 wherein the antioxidant molecule synthesized is represented by formula II

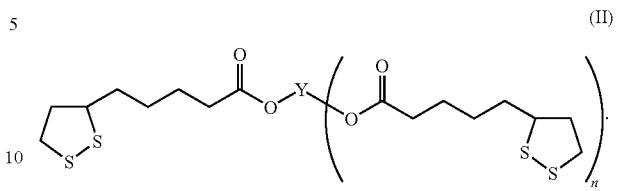

(II)

7. The method of claim 5, wherein the antioxidant molecule synthesized is selected from the group consisting of

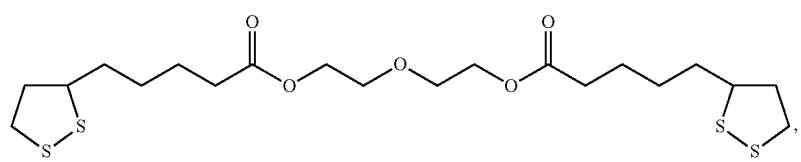

(2a)

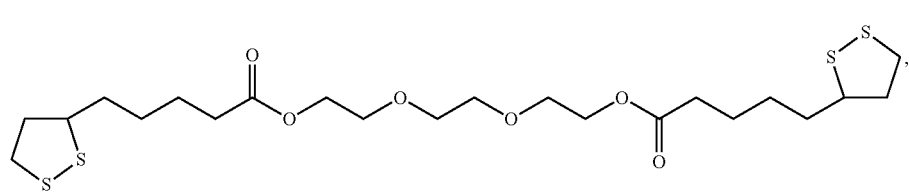

(3a)

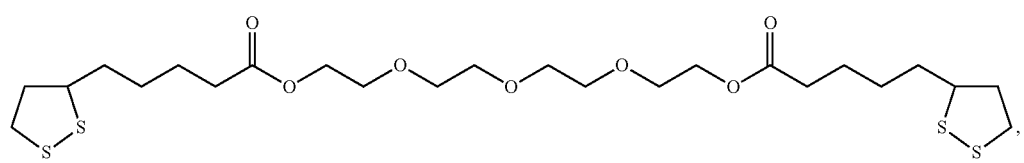

(4a)

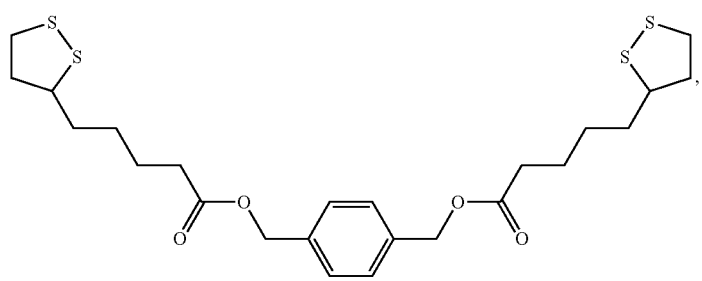

(6a)

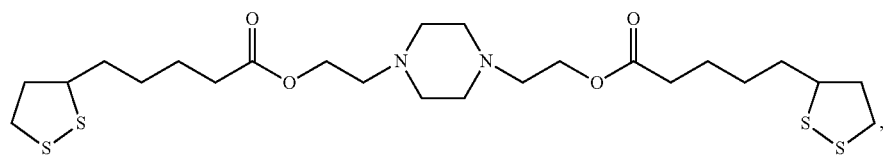

(7a)

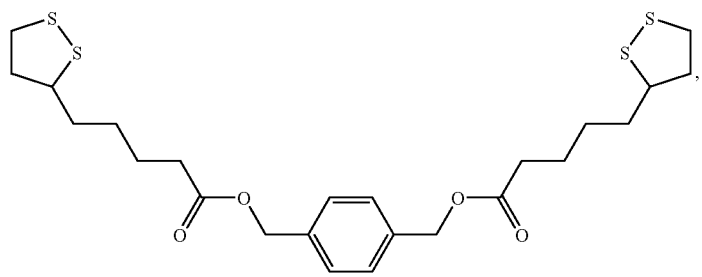

(6a)

-continued
(8a)
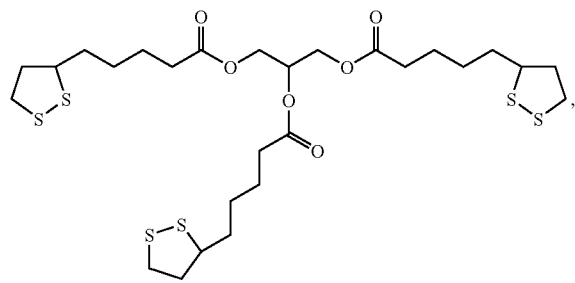
(9a)
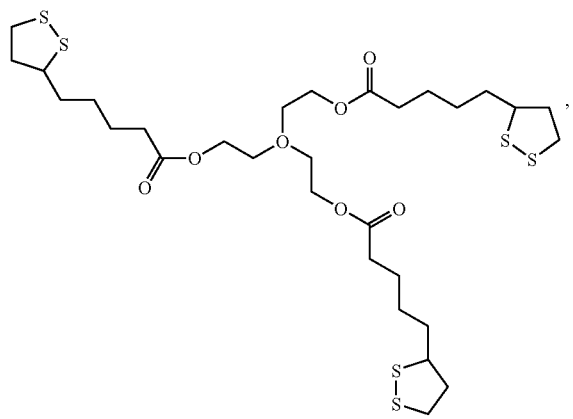
(10a)
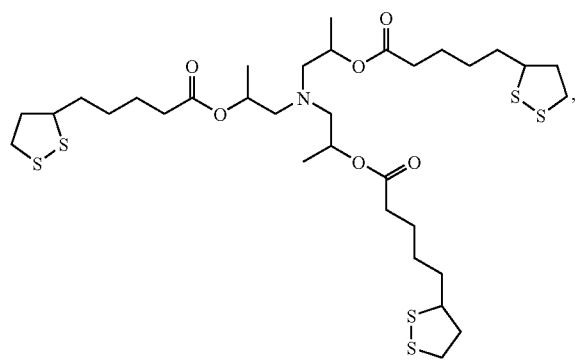
(11a)
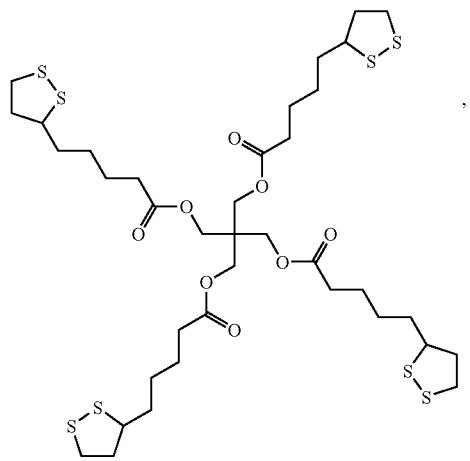
(12a)
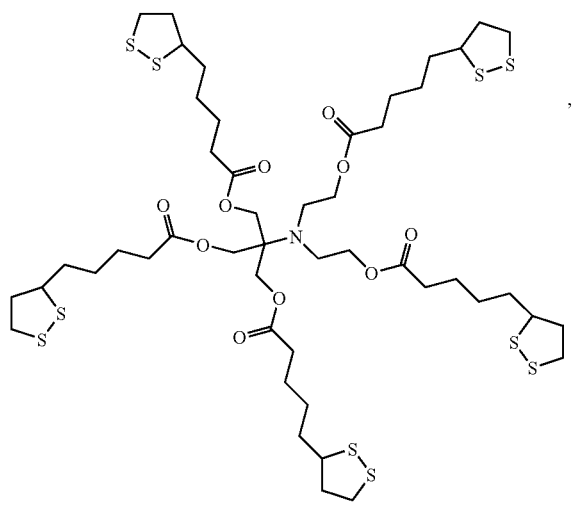
(13a)
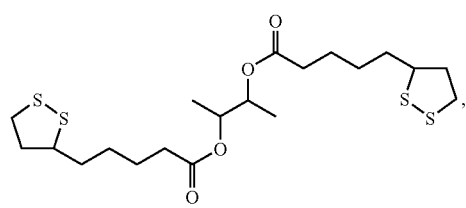
(14a)
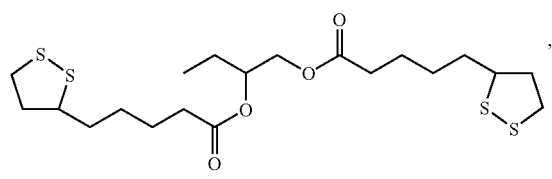
(15a)
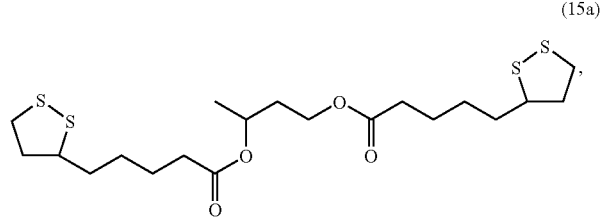

-continued
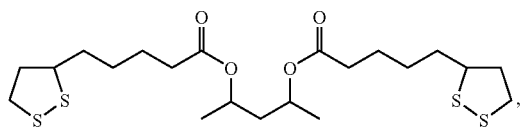 (16a)
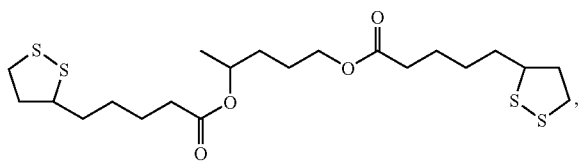 (17a)
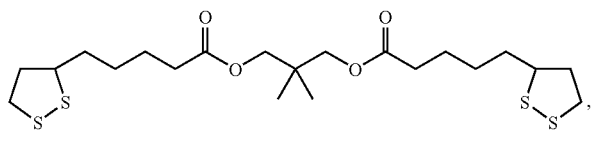 (18a)
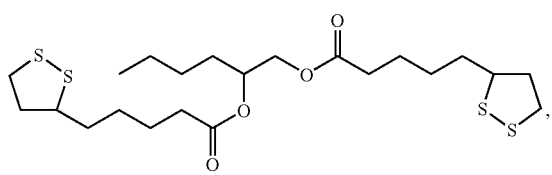 (19a)
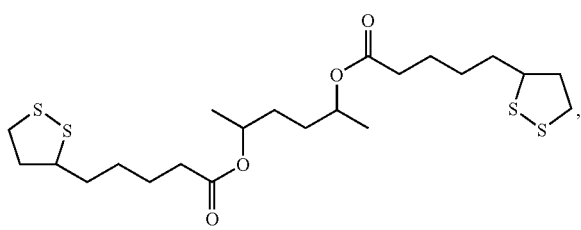 (20a) (21a)
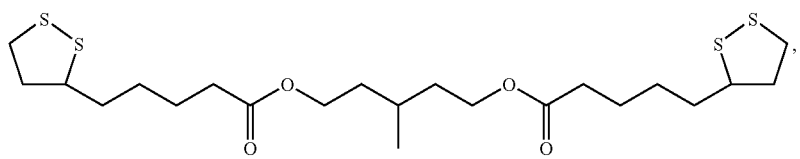 (22a)
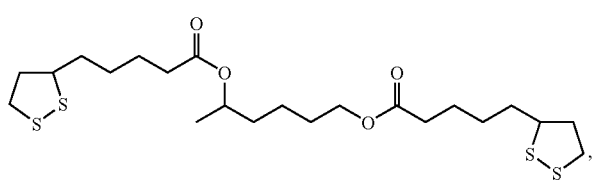 (23a) (24a)
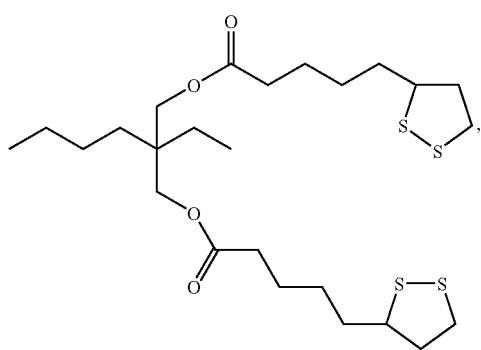 (25a)

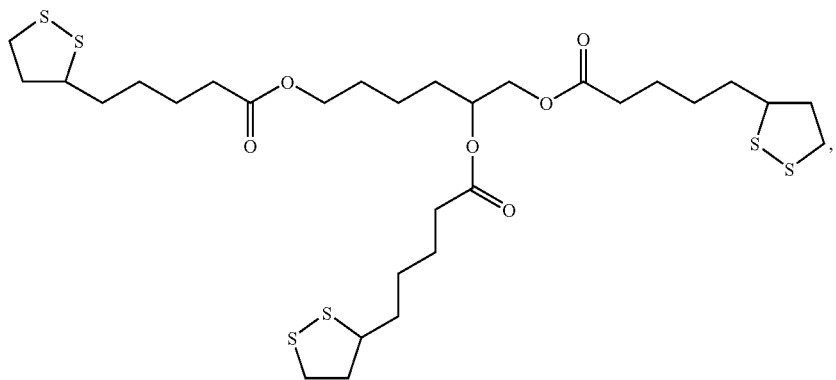
(26a)
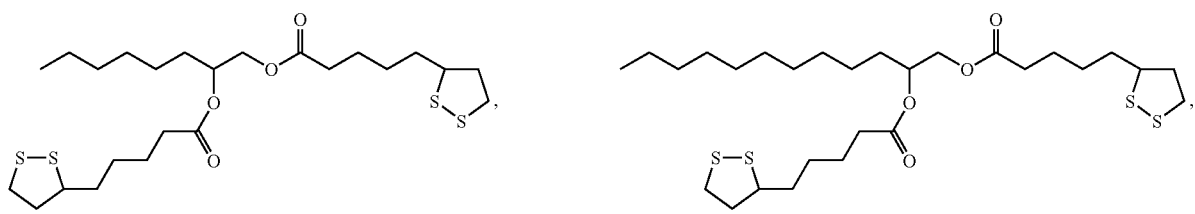
(27a) (28a)
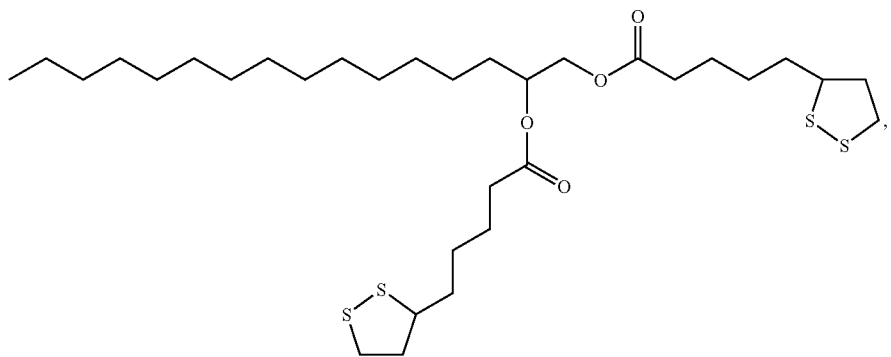
(29a)
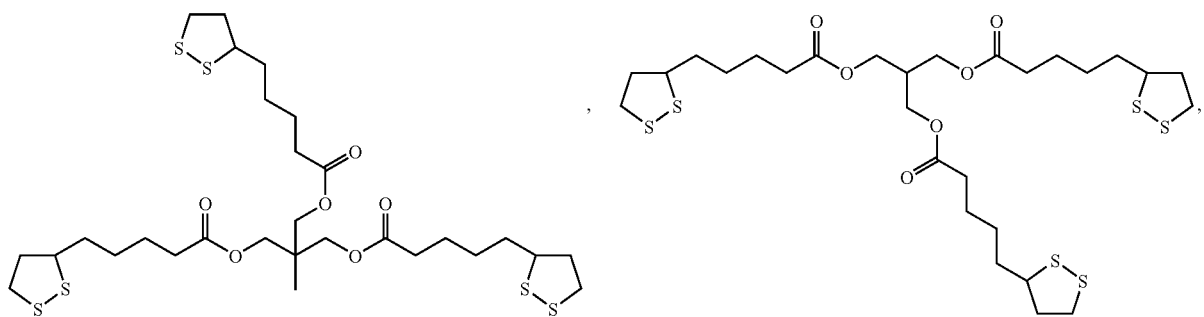
(30a) (31a)

-continued
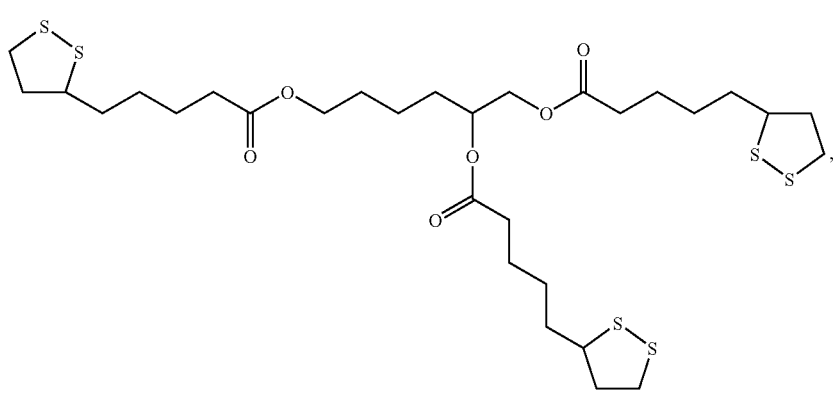
(32a)
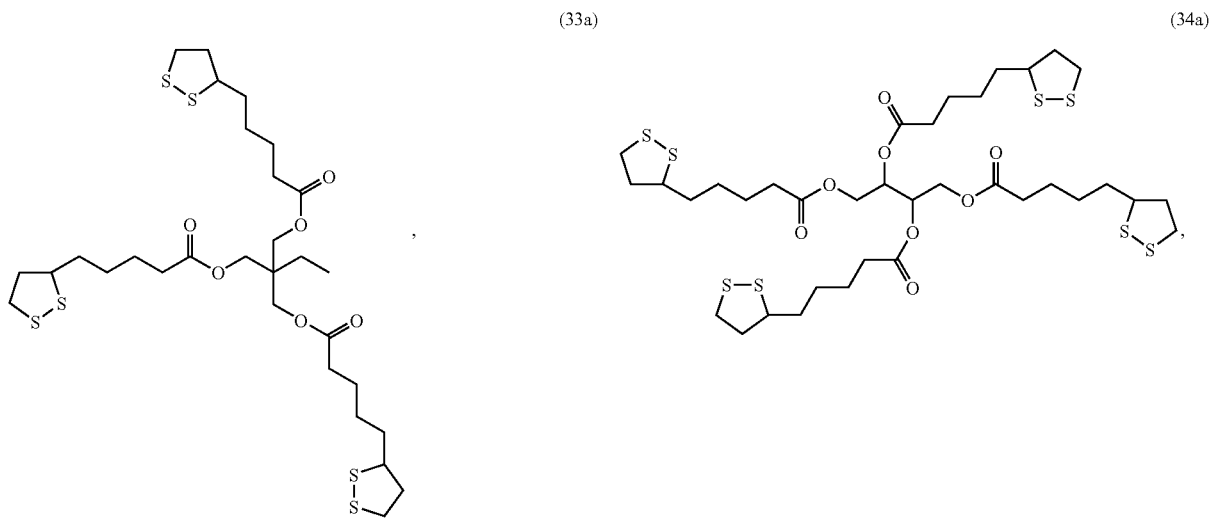
(33a) (34a)
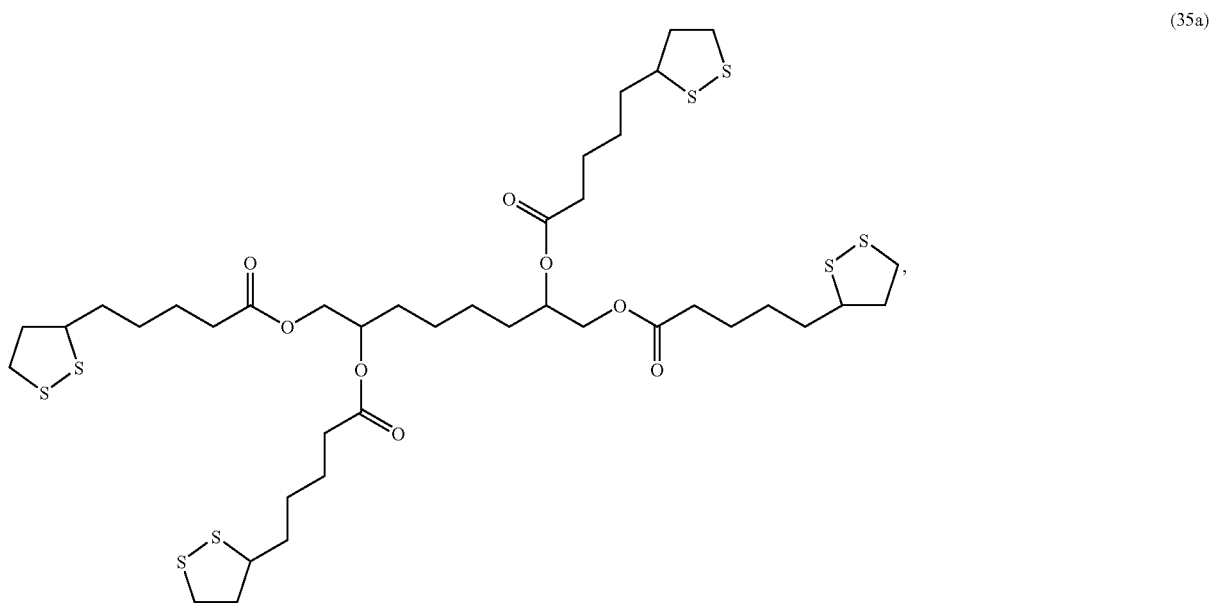
(35a)

-continued
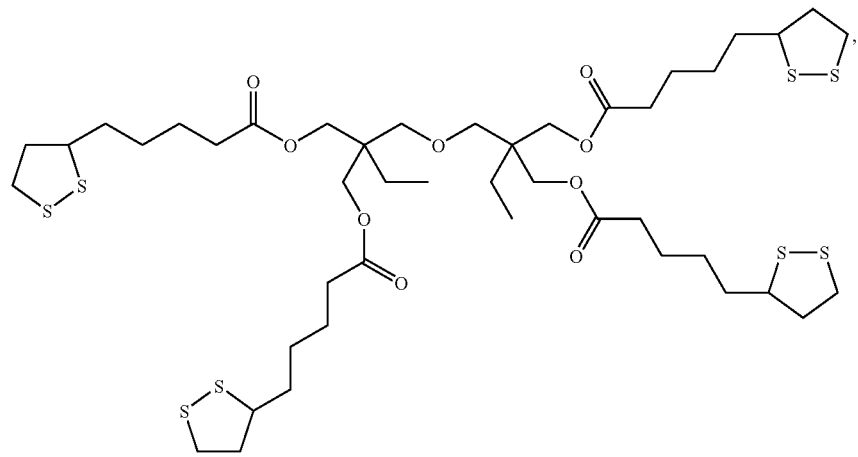
(36a)
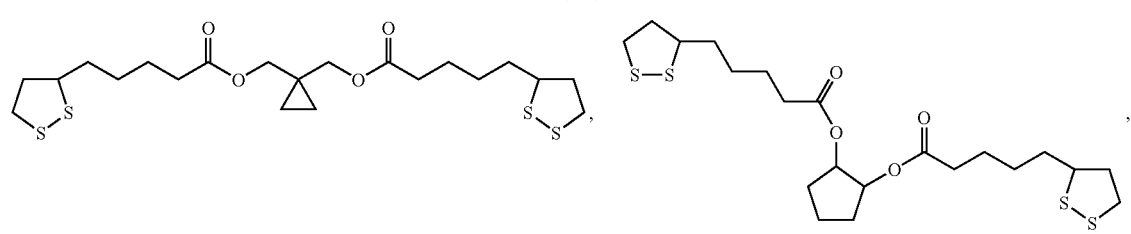
(37a) (38a)
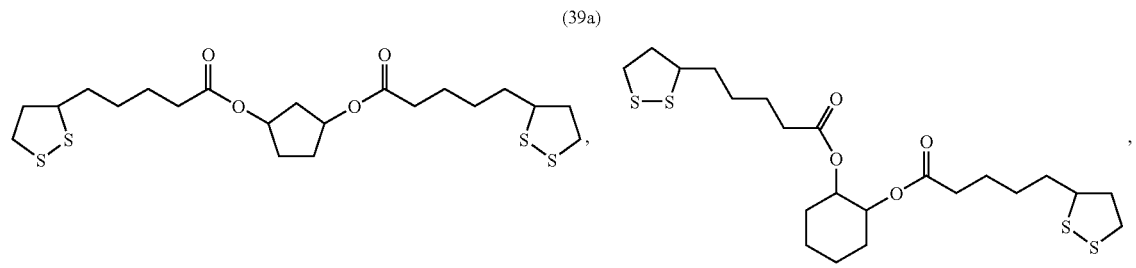
(39a) (40a)
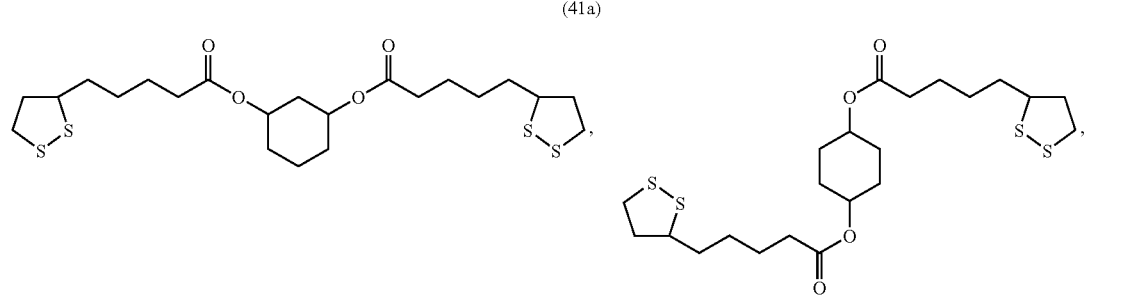
(41a) (42a)

-continued
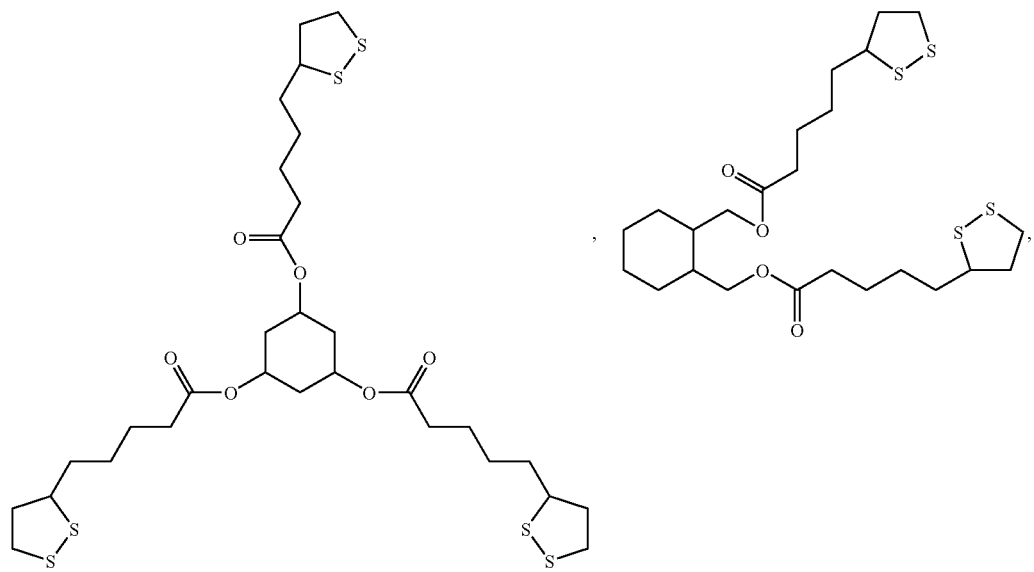
(43a)
(44a)
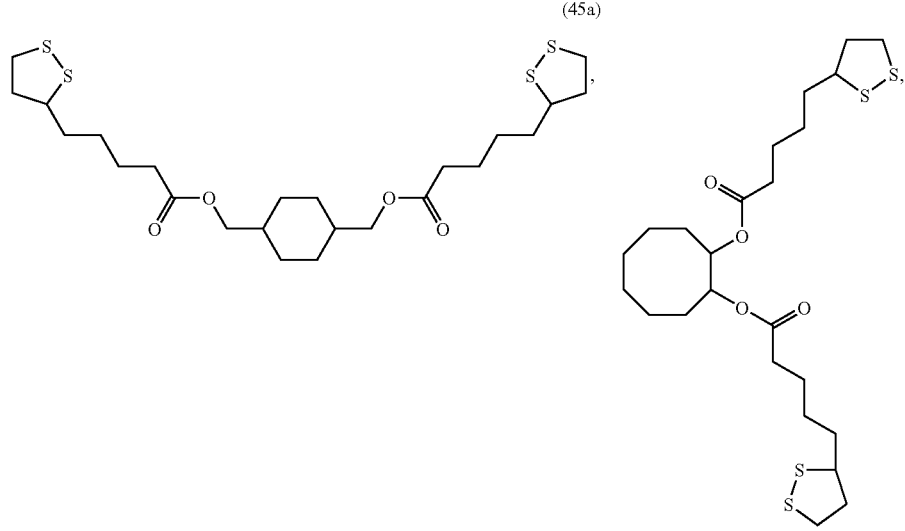
(45a)
(46a)
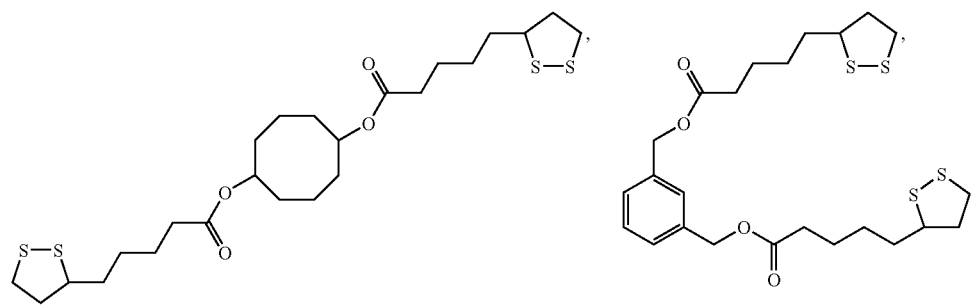
(47a)
(48a)

-continued
(49a)
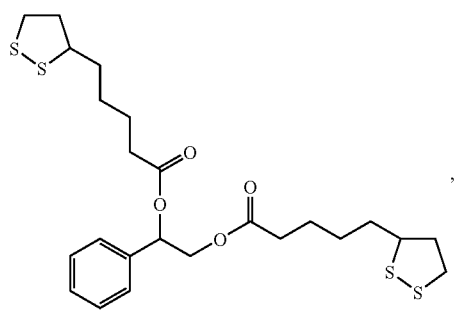
(50a)
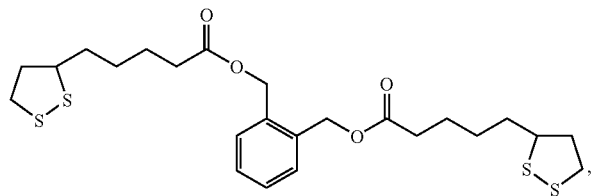
(51a)
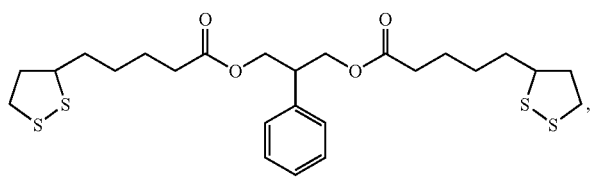
(52a)
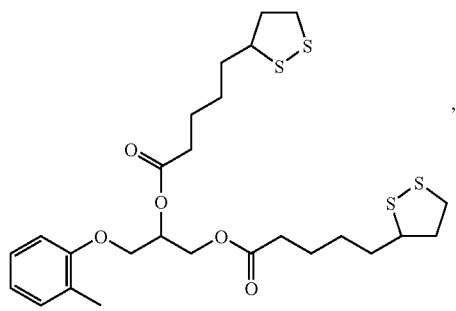
(53a)
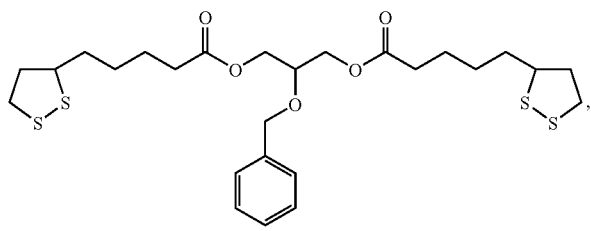
(54a)
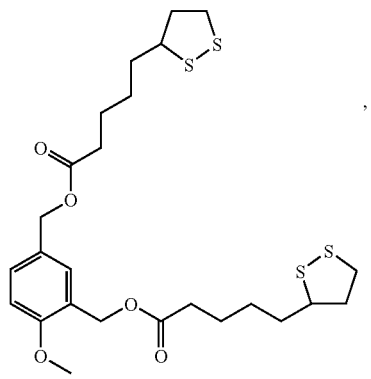
(55a)
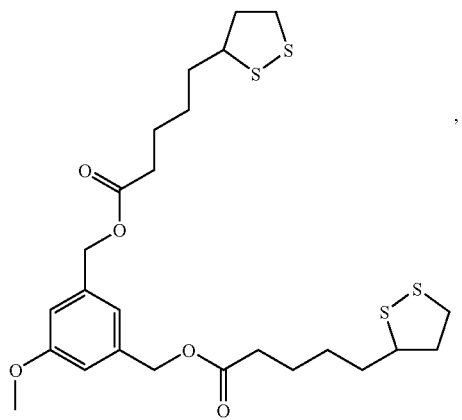
(56a)
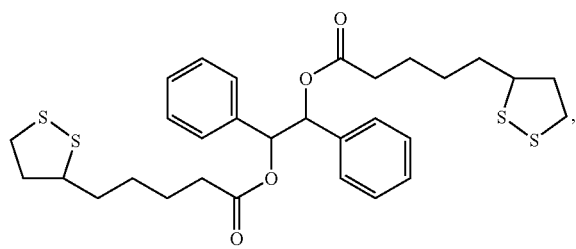

-continued
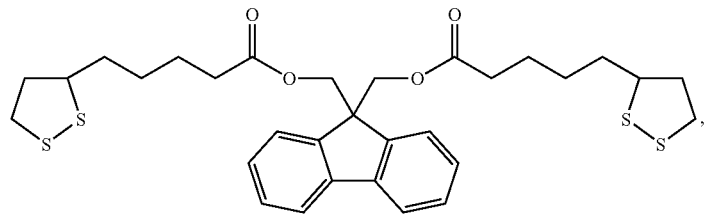
(57a)
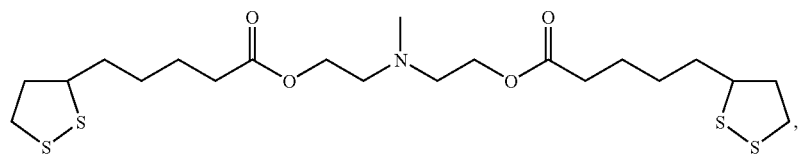
(58a)
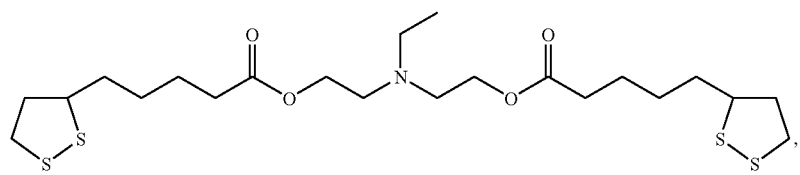
(59a)
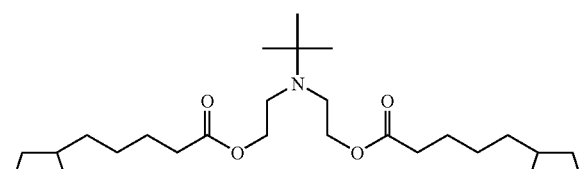
(60a)
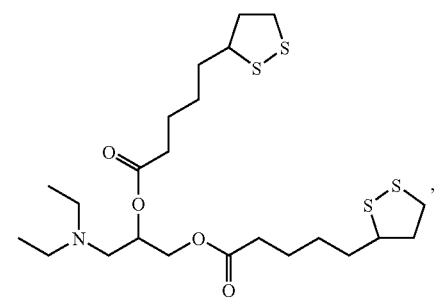
(61a)
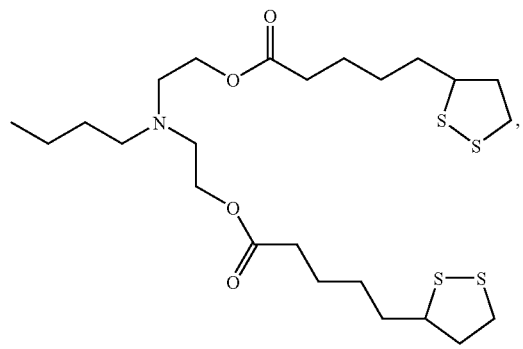
(62a)
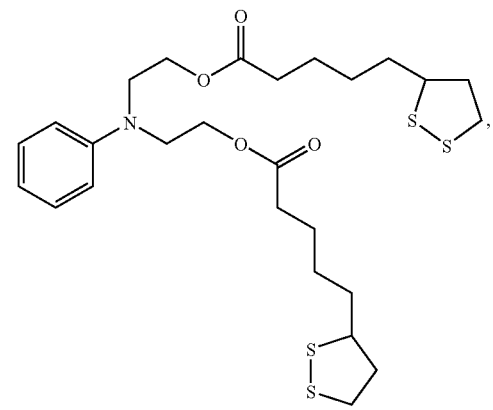
(63a)
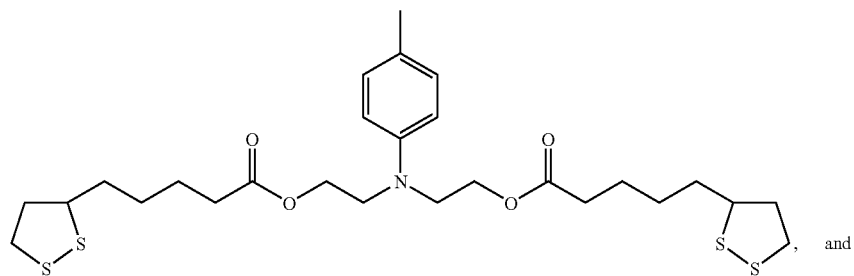
(64a)
, and -continued (65a)

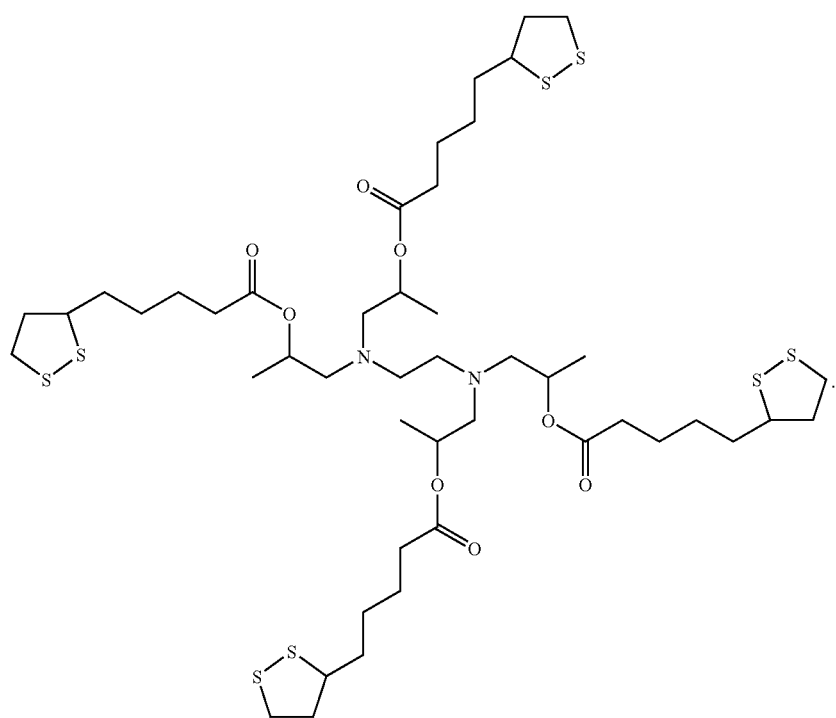

8. An antioxidant nanosphere, comprising:
an antioxidant molecule of Formula I

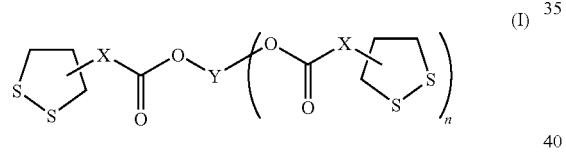
(I)

wherein X is selected from the group consisting of a substituted, unsubstituted, branched or unbranched chain of carbon atoms, and may optionally contain a heteroatom;
Y is a moiety formed by esterification of the hydroxyl groups of a polyol selected from the group consisting of

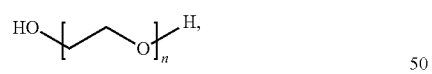

wherein n is an integer between 1 and 4,

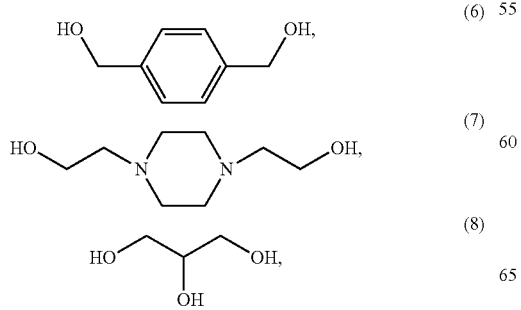
(6)
(7)
(8)

-continued

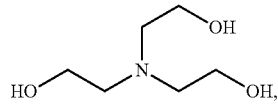
(9)

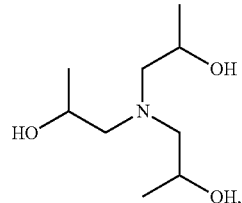
(10)

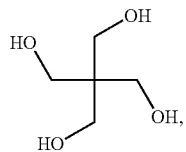
(11)

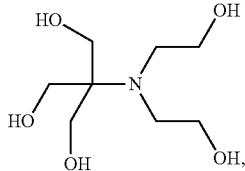
(12)

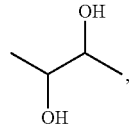
(13)

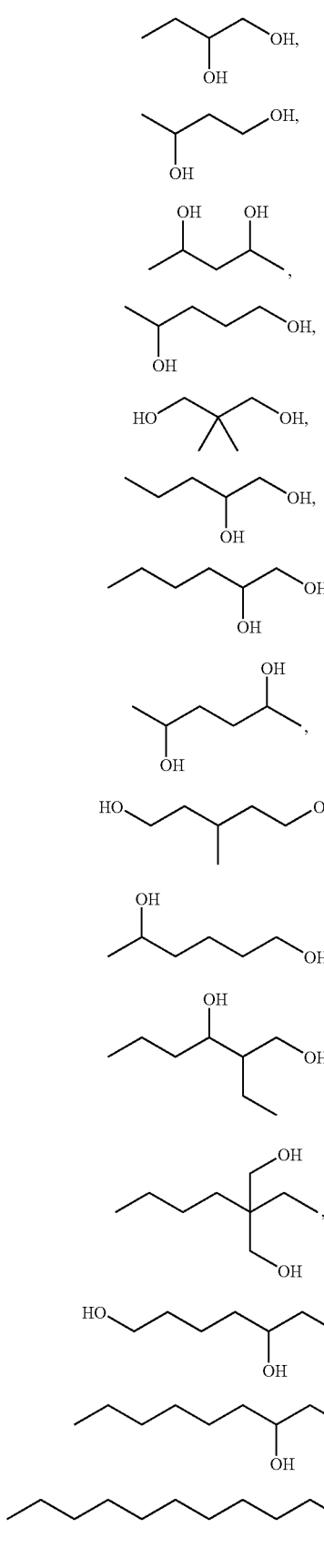
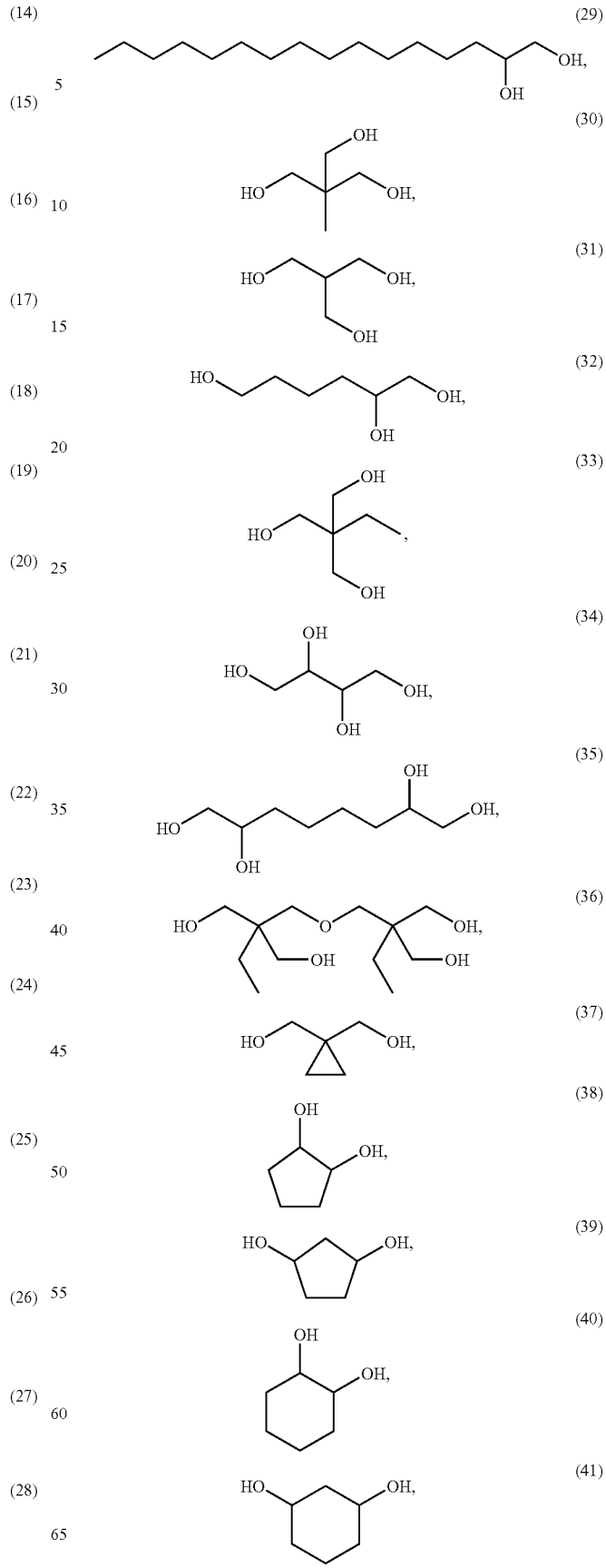

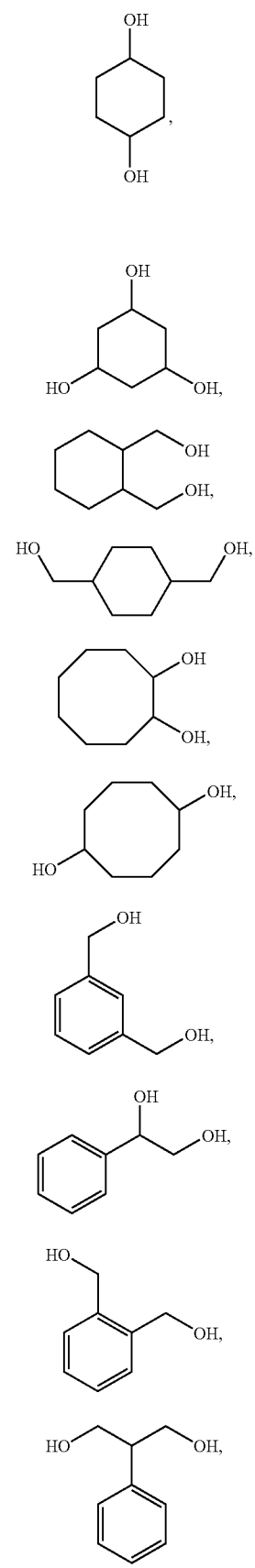
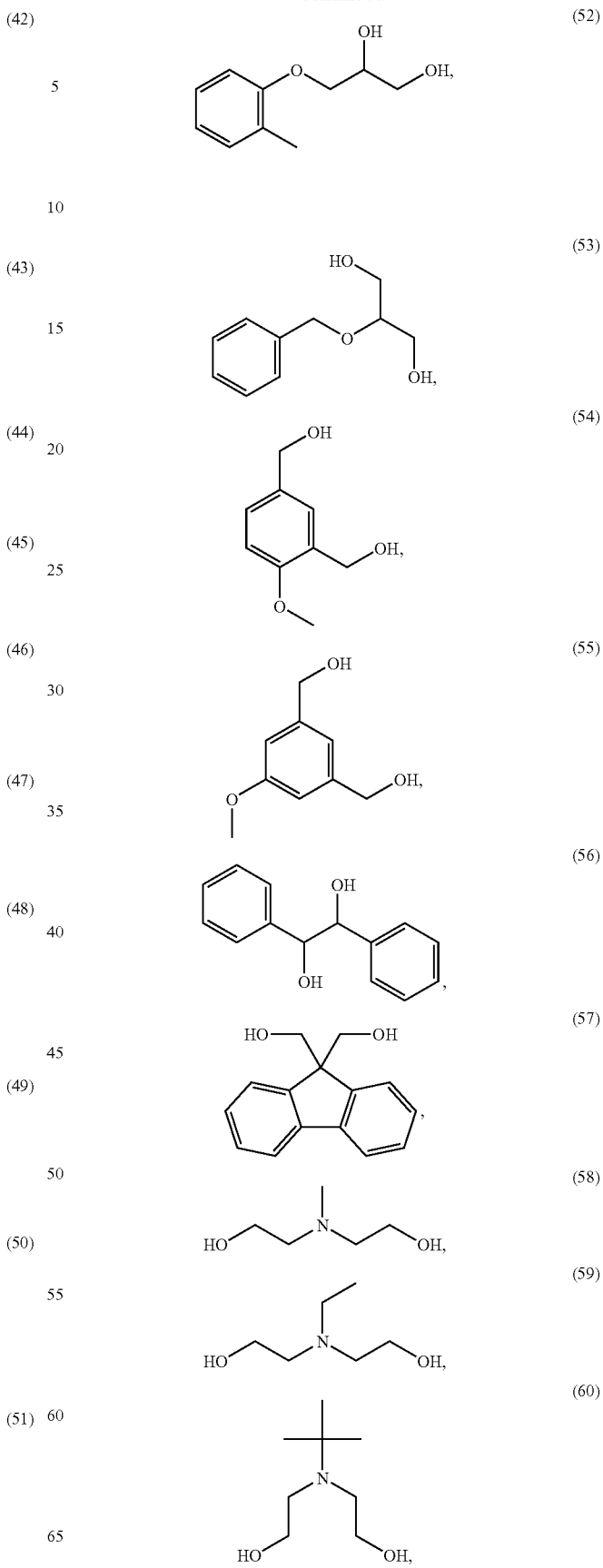

-continued

(61) 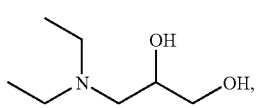

(62) 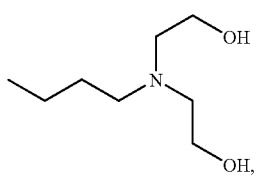

(63) 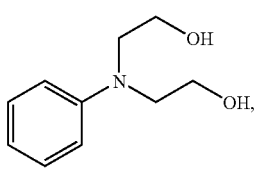

(64)

-continued

(65) 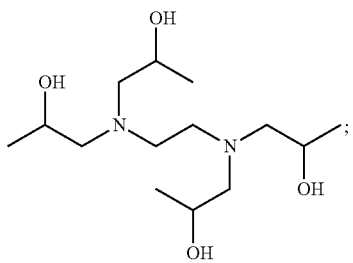

and n is an integer of at least one.

9. The antioxidant nanosphere of claim 8, wherein X is an unsubstituted, unbranched chain of 1 to 6 carbon atoms.

10. The antioxidant nanosphere of claim 9 wherein the antioxidant molecule is represented by formula II (II) 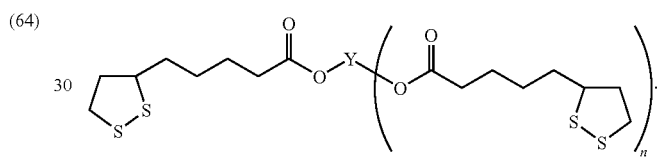

11. The antioxidant nanosphere of claim 8, wherein the antioxidant molecule selected from the group consisting of (2a) 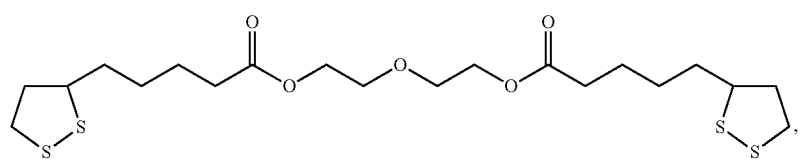

(3a) 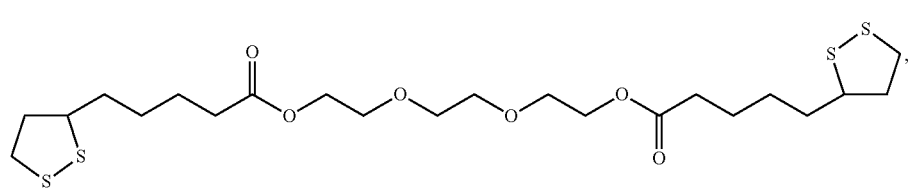

(4a) 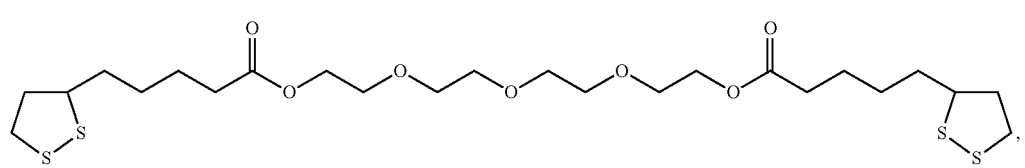

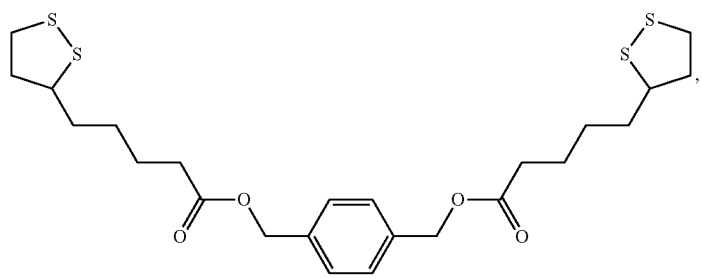
(6a)
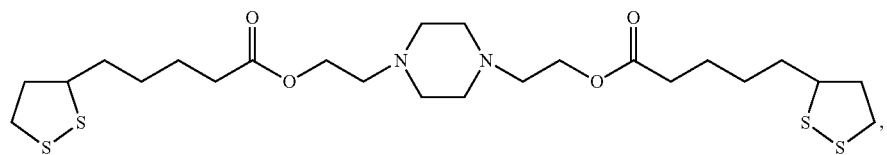
(7a)
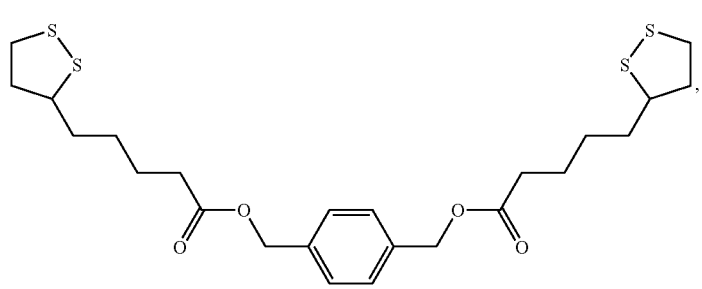
(6a)
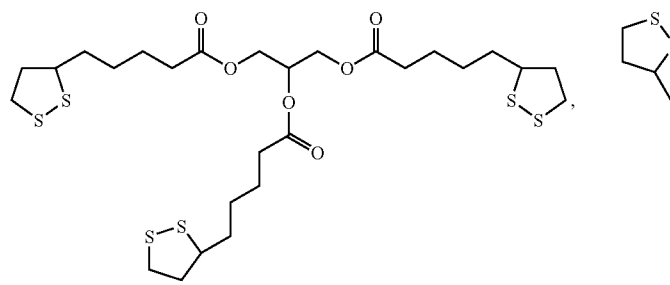
(8a)
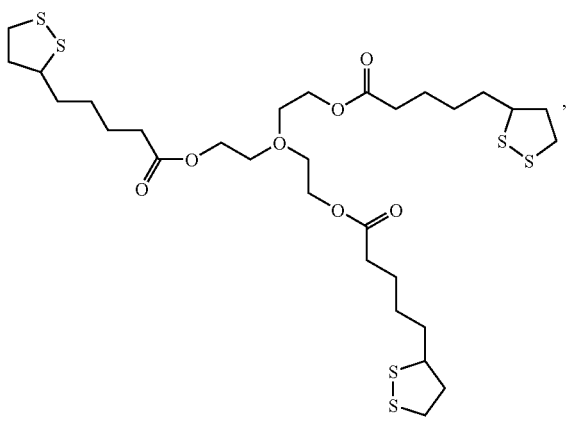
(9a)
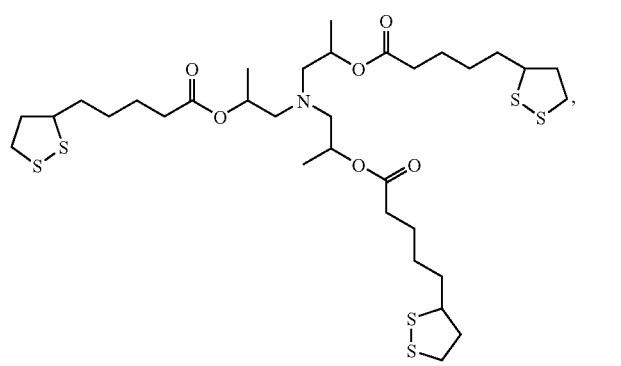
(10a)
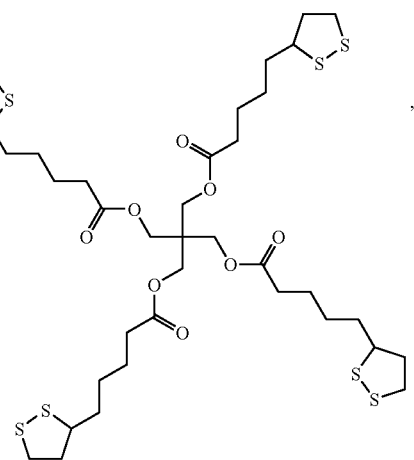
(11a)

-continued
(12a)
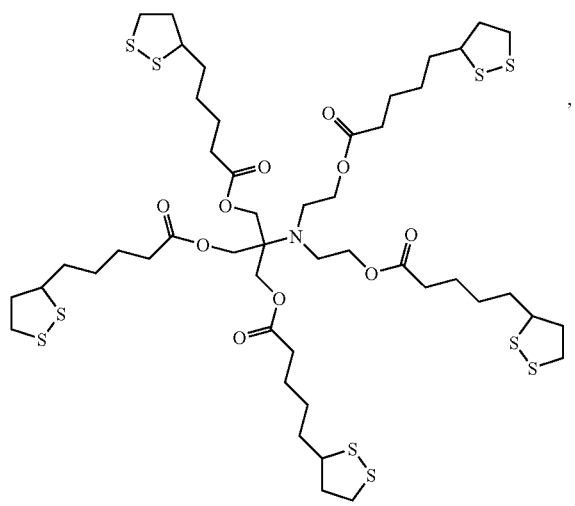
(13a)
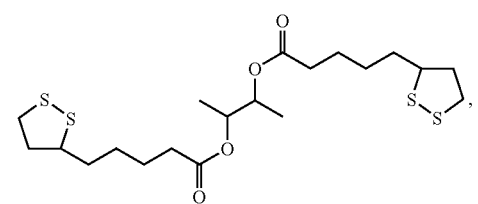
(14a)
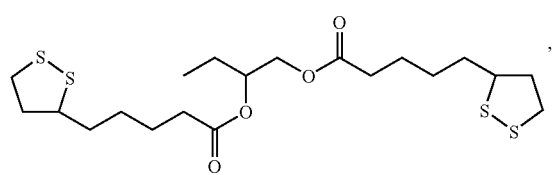
(15a)
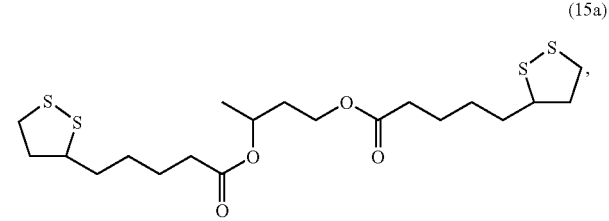
(16a)
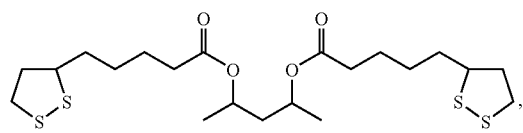
(17a)
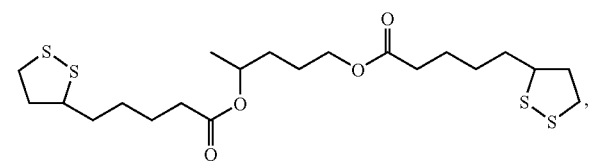
(18a)
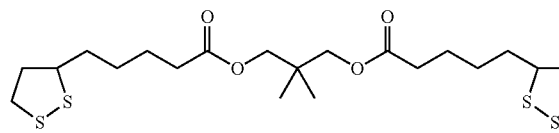
(19a)
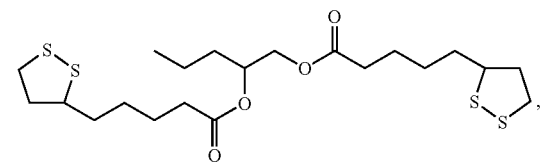
(20a)
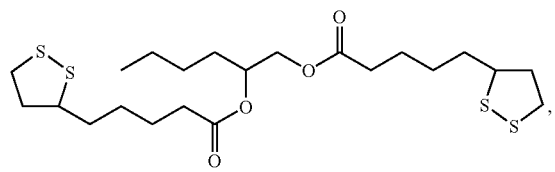
(21a)
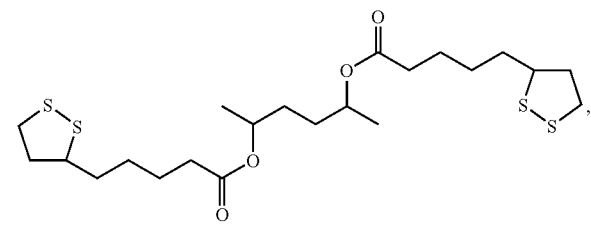
(22a)
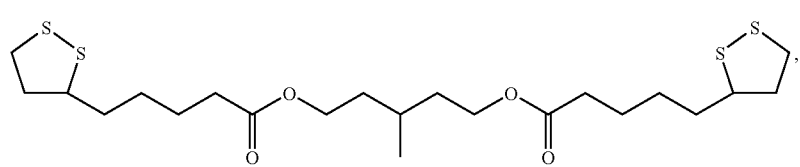

(23a)
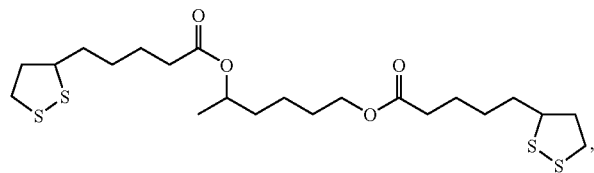
(24a)
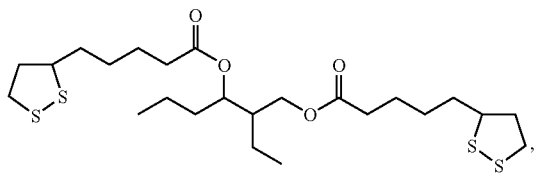
(25a)
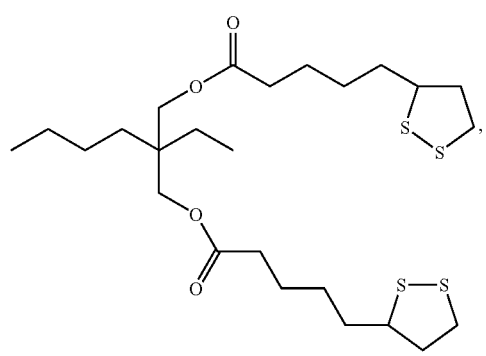
(26a)
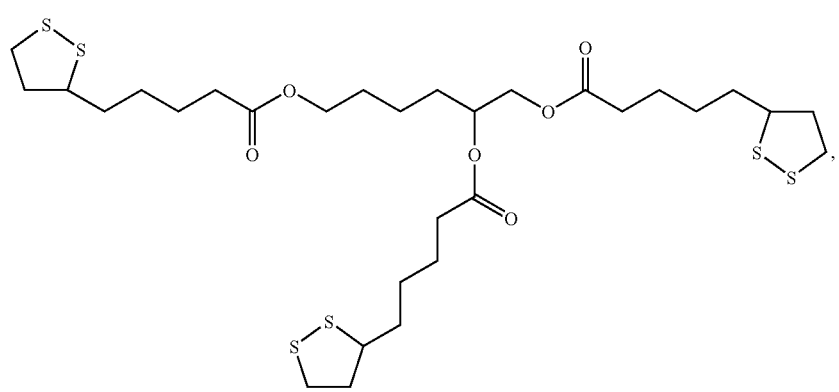
(27a)
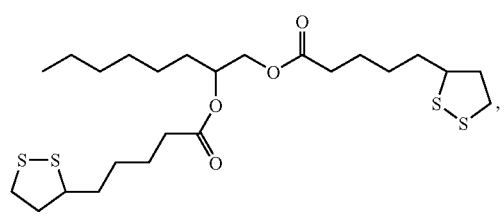
(28a)
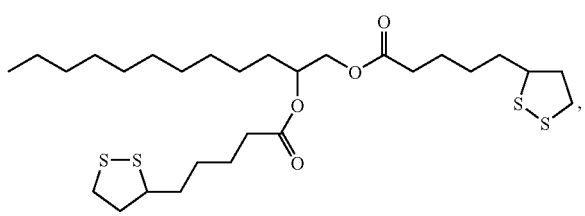
(29a)
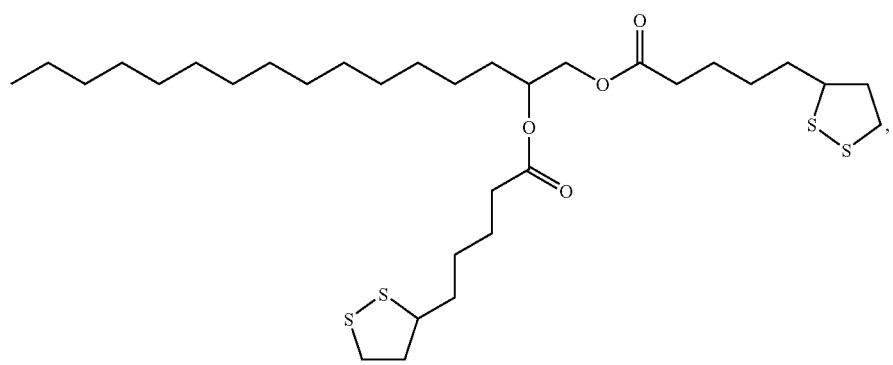

-continued
(30a)
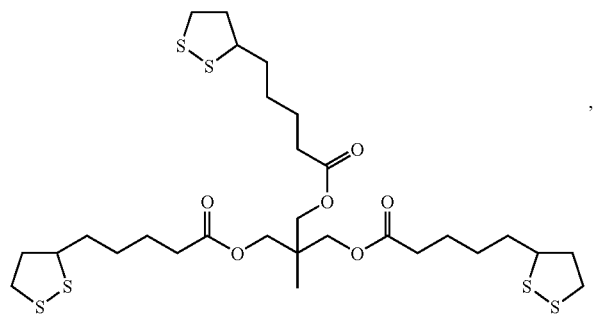
(31a)
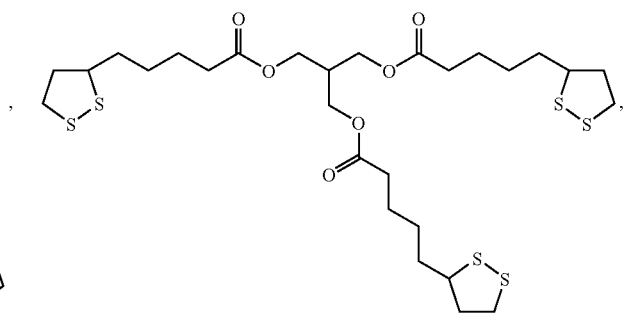
(32a)
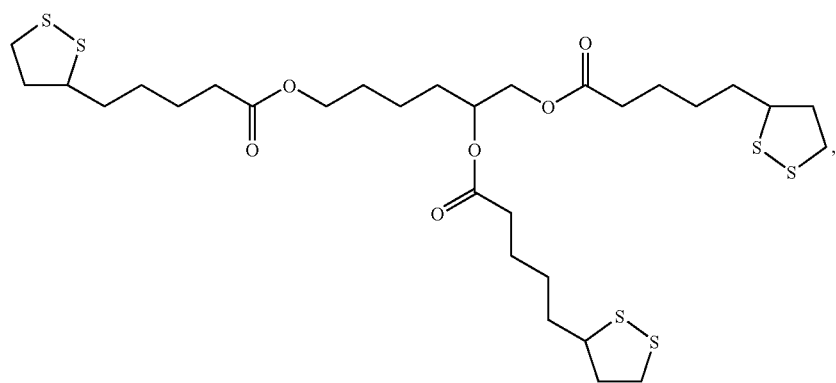
(33a)
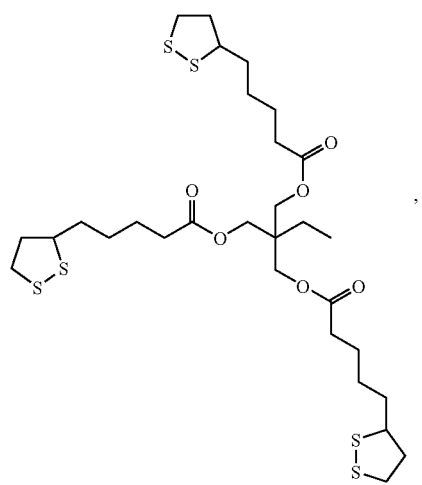
(34a)
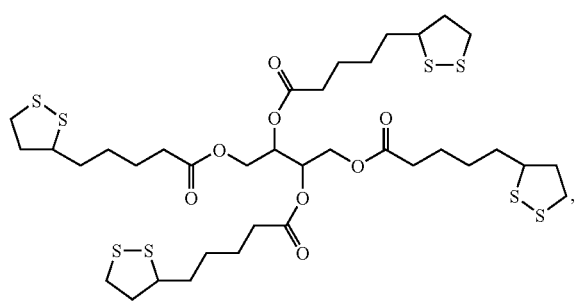

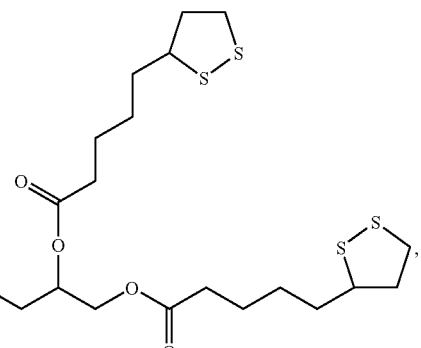
(35a)
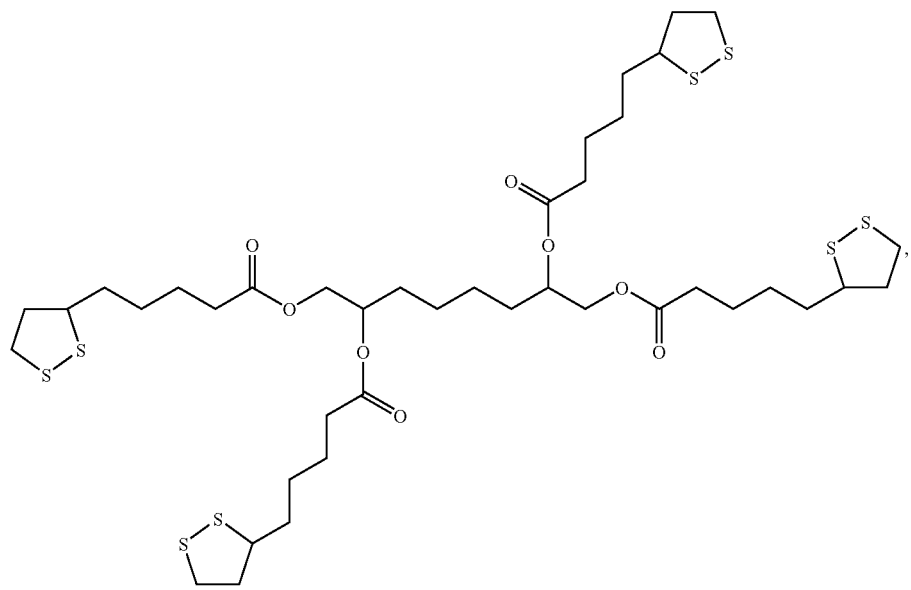
(36a)
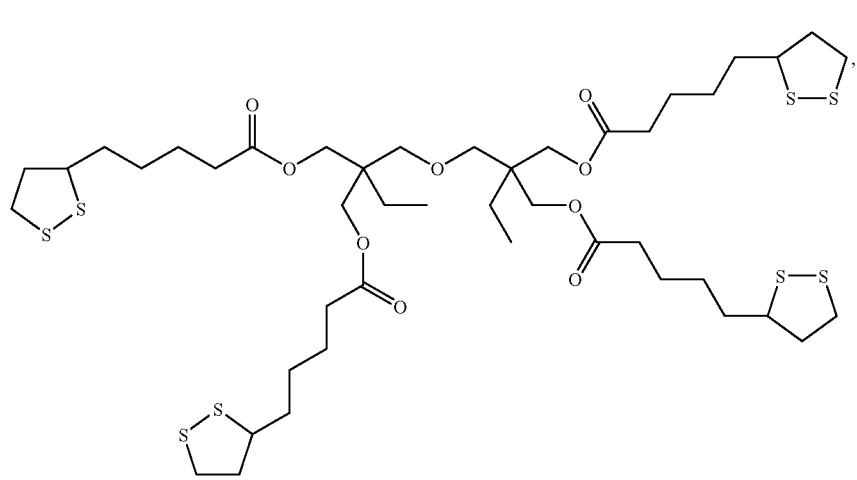
(37a)
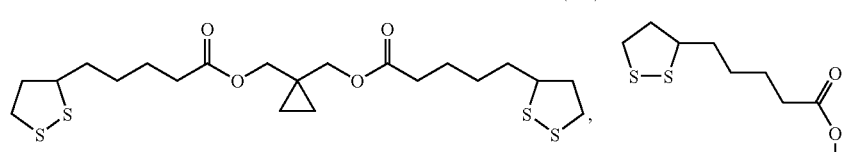
(38a)
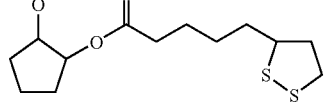
(39a)
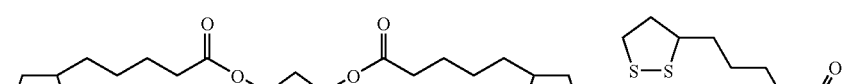
(40a)

-continued
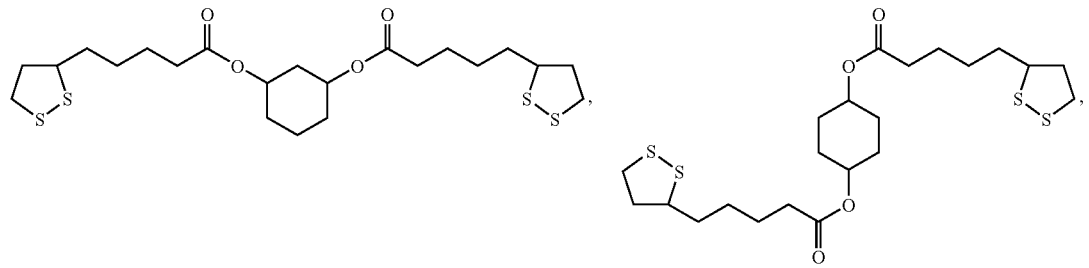
(41a) (42a)
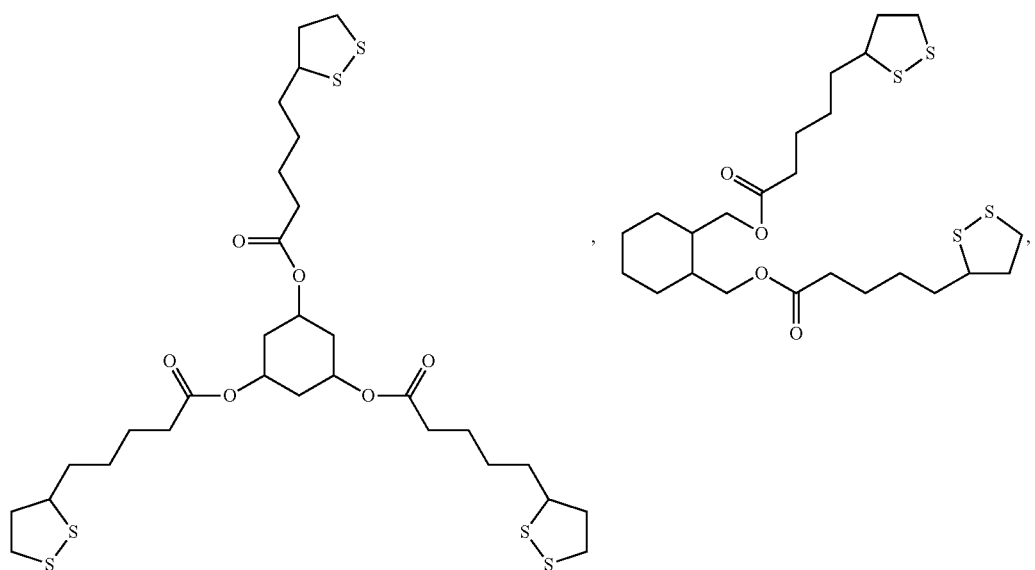
(43a) (44a)
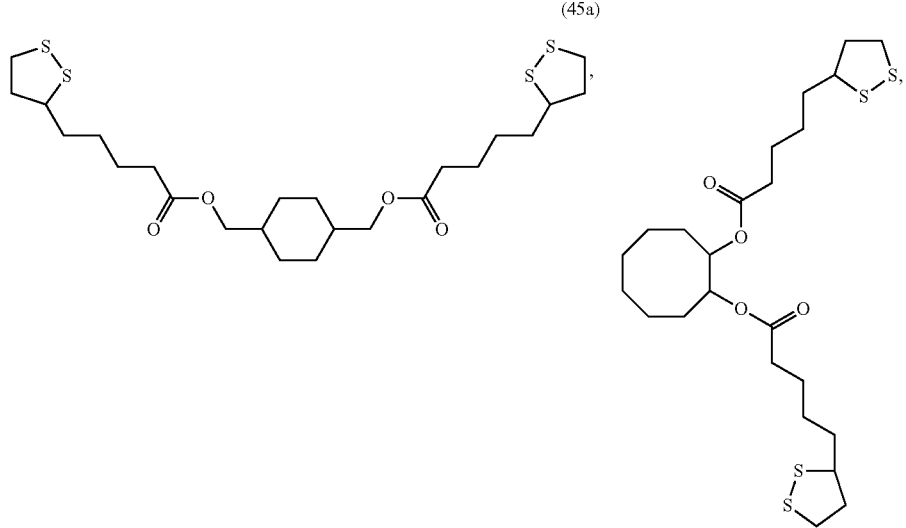
(45a) (46a)

-continued
(47a)
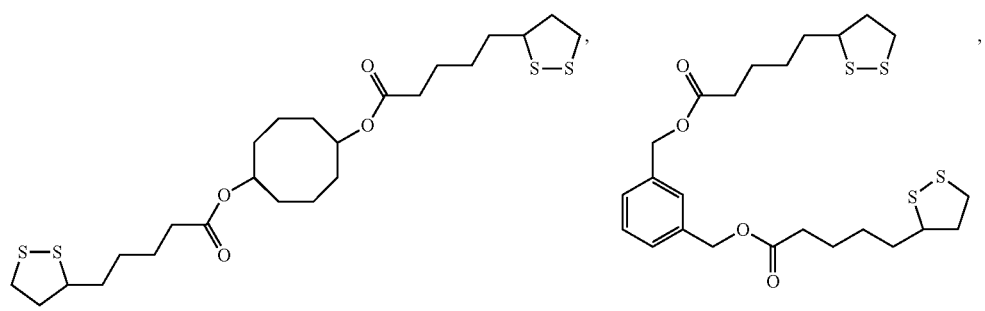
(48a)
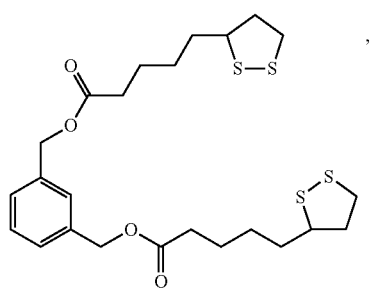
(49a)
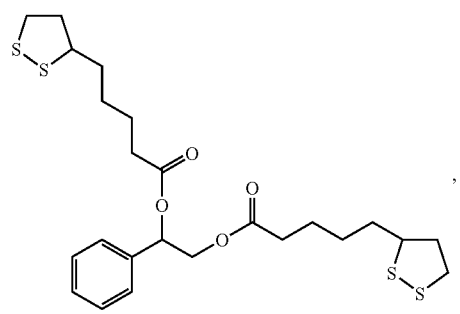
(50a)
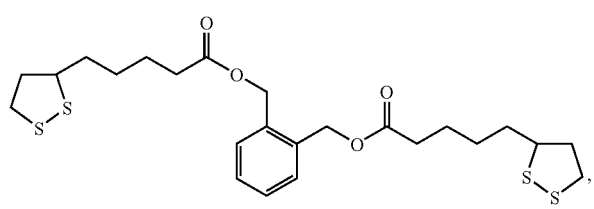
(51a)
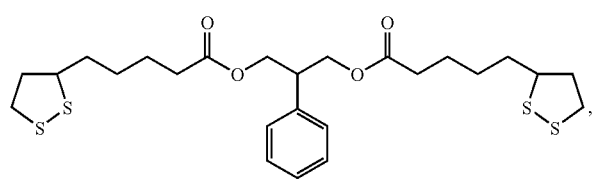
(52a)
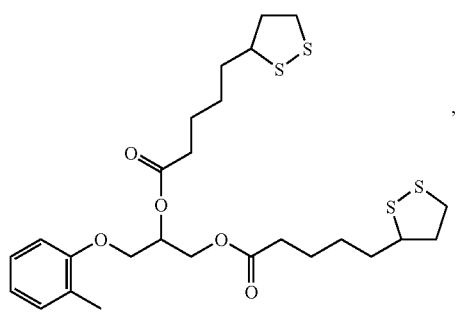
(53a)
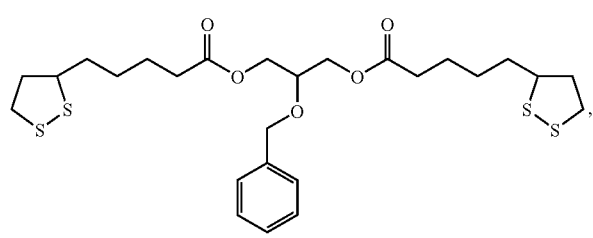
(54a)
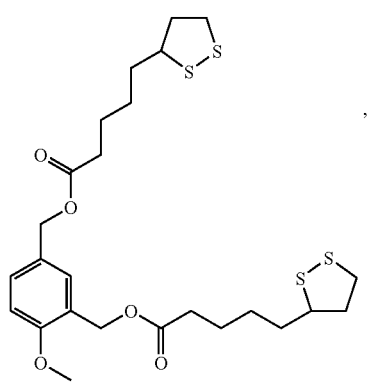

(55a)
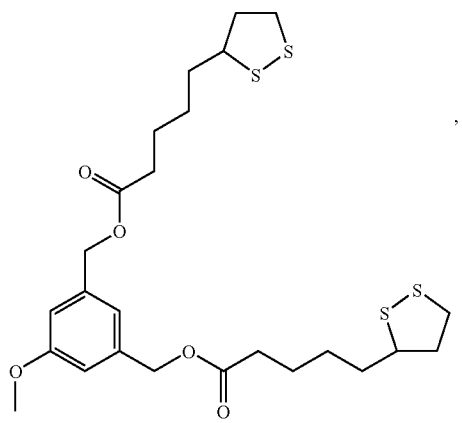
(56a)
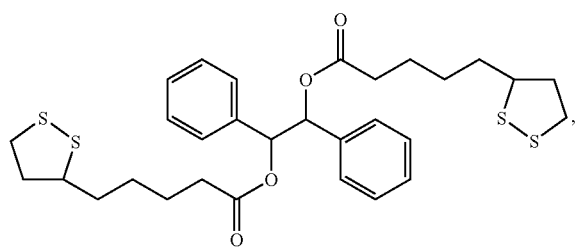
(57a)
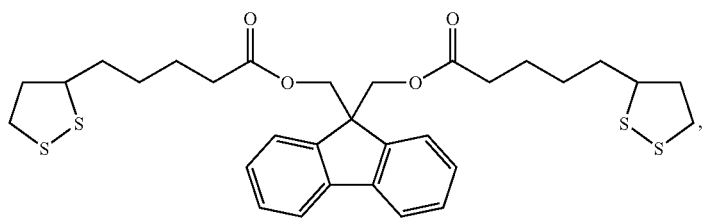
(58a)
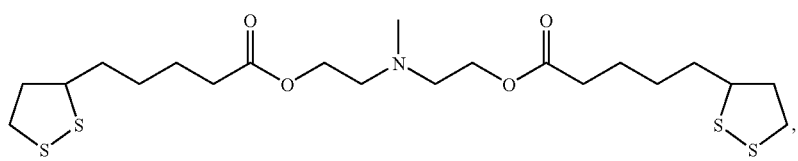
(59a)
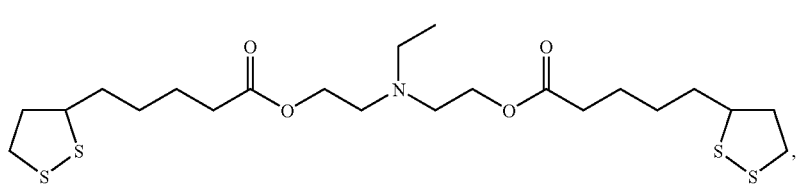
(60a)
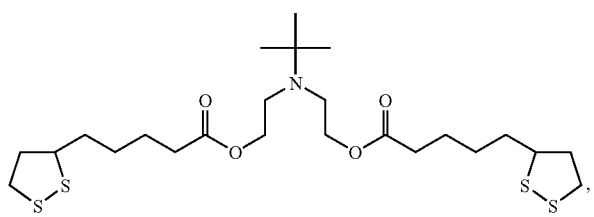
(61a)
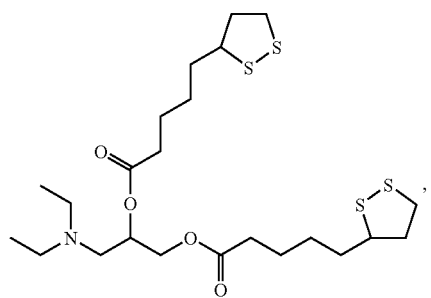

-continued

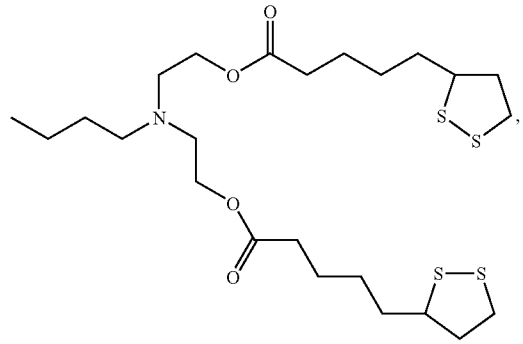
(62a)

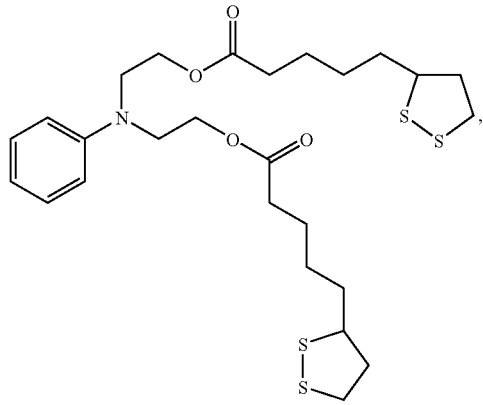
(63a)

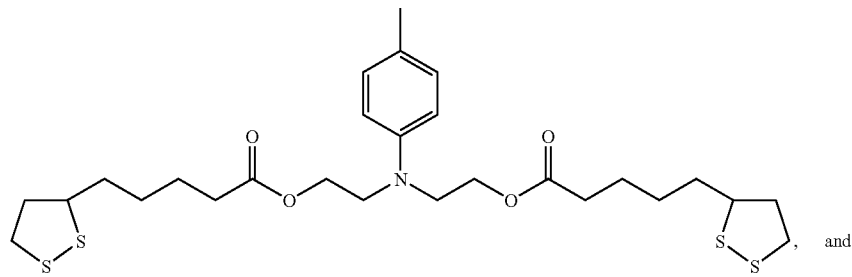
(64a)

, and

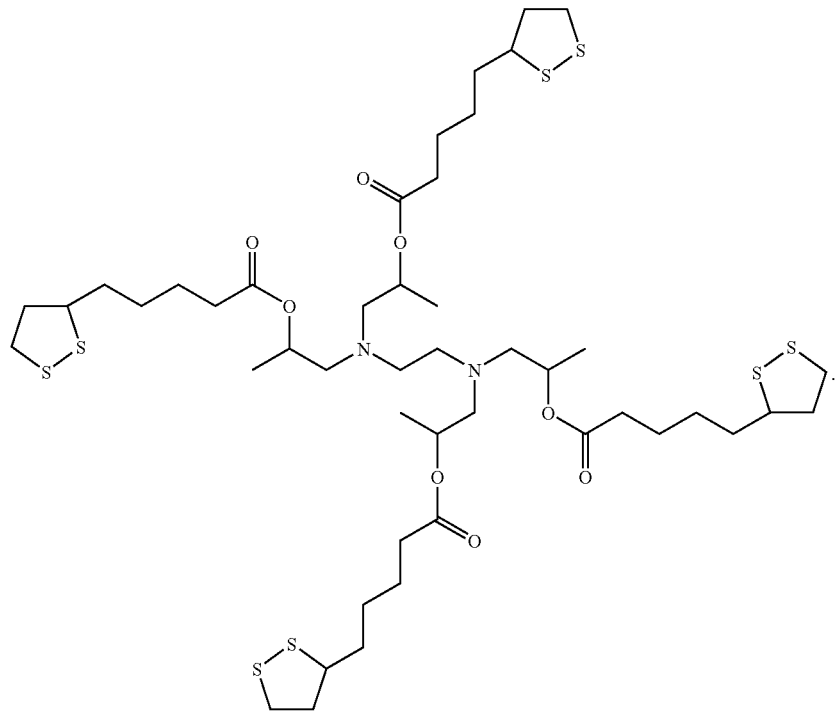
(65a)

12. A method of producing an antioxidant nanosphere, comprising:
providing a quantity of the antioxidant molecule of claim 1;
dissolving the quantity of antioxidant molecule in an organic solvent to produce an organic solution;
stirring the organic solution into an aqueous solution; and
removing the organic solvent to produce the antioxidant nanosphere.

13. The method of claim 12, further comprising a step selected from the group consisting of filtering the nanosphere, purifying the nanosphere and combinations thereof.

14. The method of claim 12, wherein the organic solvent is acetone.

15. The method of claim 12, wherein the aqueous solution comprises a quantity of poloxamers.

16. A method of treating a disease or disease condition in a subject in need thereof, comprising:

providing a composition comprising the antioxidant molecule of claim 1 and/or an antioxidant nanosphere comprising the antioxidant molecule; and administering a therapeutically effective amount of the composition to the subject.

17. The method of claim 16, wherein the disease or disease condition is selected from the group consisting of:
a disease or disease condition caused by oxidative stress, inflammation of the skin mediated by free radicals, aging of the skin mediated by free radicals, and combinations thereof.

18. A method of increasing the toxicity of an antineoplastic agent to abnormally proliferating cells and/or decreasing the toxicity of an antineoplastic agent to normal cells, in a subject in need thereof comprising:
providing a composition comprising the antioxidant molecule of claim 1 and/or an antioxidant nanosphere comprising the antioxidant molecule; and administering a therapeutically effective amount of the composition and the antineoplastic agent to the subject.

19. The method of claim 18, wherein the antineoplastic agent is selected from the group consisting of temozolomide, paclitaxel and camptothecin and combinations thereof.

20. A delivery vehicle composition, comprising:
an antioxidant molecule of claim 1 or an antioxidant nanosphere comprising the antioxidant molecule; and
a therapeutic agent.

21. The delivery vehicle composition of claim 20, wherein the therapeutic agent is selected from the group consisting of genetic molecule, peptide, protein, chemotherapeutic agent and combinations thereof.

22. A method of delivering a therapeutic agent to a location in or on the body, comprising:
providing a composition comprising a therapeutic agent, and the antioxidant molecule of claim 1 and/or an antioxidant nanosphere comprising the antioxidant molecule; and administering a therapeutically effective amount of the composition to the subject.

23. The method of claim 22, wherein the therapeutic agent is selected from the group consisting of a genetic molecule, a peptide, a protein and combinations thereof.

24. The method of claim 22, wherein the therapeutic agent is an antineoplastic drug.

25. The antioxidant molecule of claim 1, wherein Y is a moiety formed by esterification of the hydroxyl groups of

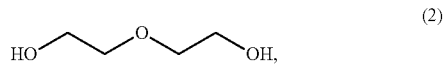

(2)

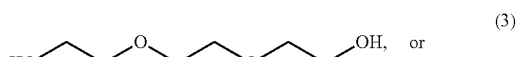

(3)

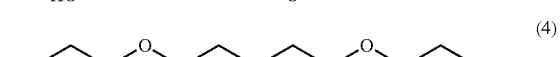

(4)

26. The antioxidant nanosphere of claim 8 wherein Y is a moiety formed by esterification of the hydroxyl groups of

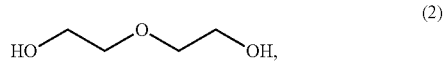

(2)

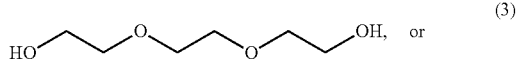

(3)

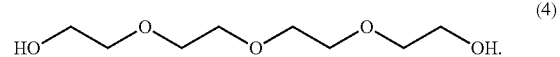

(4)

* * * * *